(12) United States Patent
Aime et al.

(10) Patent No.: US 8,540,966 B2
(45) Date of Patent: Sep. 24, 2013

(54) CONTRAST AGENTS ENDOWED WITH HIGH RELAXIVITY

(75) Inventors: Silvio Aime, Cariguauo (IT); Matteo Galli, Treviglio (IT); Luciano Lattuada, Bussero (IT); Pierfrancesco Morosini, Lodi (IT); Fulvio Uggeri, Codogno (IT); Kondareddiar Ramalingam, Dayton, NJ (US)

(73) Assignee: Bracco Imaging S.p.A., Milan (IT)

( * ) Notice: Subject to any disclaimer, the term of this patent is extended or adjusted under 35 U.S.C. 154(b) by 1324 days.

(21) Appl. No.: 11/630,600

(22) PCT Filed: Jun. 28, 2005

(86) PCT No.: PCT/EP2005/006956
§ 371 (c)(1), (2), (4) Date: Apr. 12, 2011

(87) PCT Pub. No.: WO2006/002873
PCT Pub. Date: Jan. 12, 2006

(65) Prior Publication Data
US 2011/0256067 A1     Oct. 20, 2011

Related U.S. Application Data

(60) Provisional application No. 60/585,181, filed on Jul. 2, 2004.

(51) Int. Cl.
*A61K 49/10* (2006.01)
*C07D 243/08* (2006.01)

(52) U.S. Cl.
USPC ........... 424/9.35; 540/467; 540/474; 540/475

(58) Field of Classification Search
USPC .......... 424/9.321, 9.35, 9.365, 450; 540/474, 540/475, 674
See application file for complete search history.

(56) References Cited

U.S. PATENT DOCUMENTS

| | | | |
|---|---|---|---|
| 5,330,743 A | 7/1994 | Gibby et al. | |
| 5,804,163 A | 9/1998 | Gibby et al. | |
| 6,440,956 B1 | 8/2002 | Port | |
| 6,509,324 B1 * | 1/2003 | Franzini et al. | 514/102 |
| 2007/0098643 A1 | 5/2007 | Nachman et al. | |

FOREIGN PATENT DOCUMENTS

| | | |
|---|---|---|
| EP | 0230893 A2 | 5/1987 |
| JP | H11-21279 A | 8/1987 |
| JP | S62-195388 A | 5/1989 |
| WO | 1989/00557 A1 | 1/1989 |
| WO | 92/08691 A1 | 5/1992 |
| WO | 93/12071 A1 | 6/1993 |
| WO | 93/16375 A1 | 8/1993 |
| WO | 96/04259 A1 | 2/1996 |
| WO | 00/75141 A1 | 12/2000 |
| WO | 01/46207 A1 | 6/2001 |
| WO | 03/074523 A2 | 9/2003 |

OTHER PUBLICATIONS

PCT Search Report for PCT/EP2005/006956, mail date Dec. 9, 2005.
PCT Written Opinion of the ISA for PCT/EP2005/006956, mail date Dec. 9, 2005.

* cited by examiner

*Primary Examiner* — Michael G Hartley
*Assistant Examiner* — Jagadishwar Samala
(74) *Attorney, Agent, or Firm* — M. Caragh Noone

(57) ABSTRACT

The present invention relates to a novel class of paramagnetic ion-based contrast agents of formula (I), wherein a chelating backbone moiety is highly functionalized by the presence of one or more polyhydroxylated chain, that show a pharmacokinetic profile analogous to that of the commonly used T1-general extravascular agents (NSA) but are further characterized by a higher relaxivity.

17 Claims, 5 Drawing Sheets

Figure 5bis
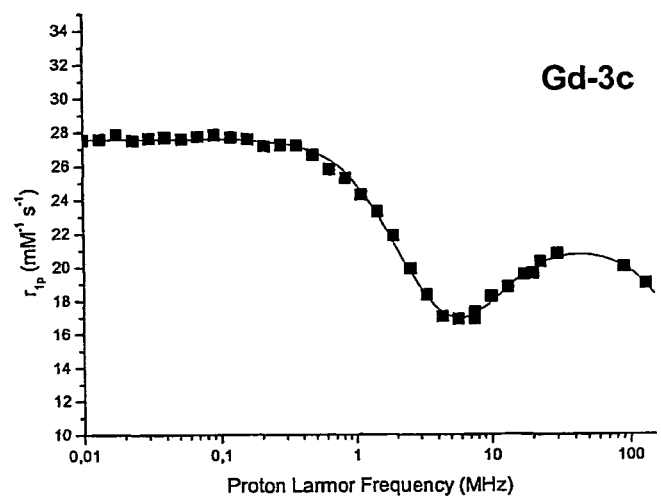
Figure 6
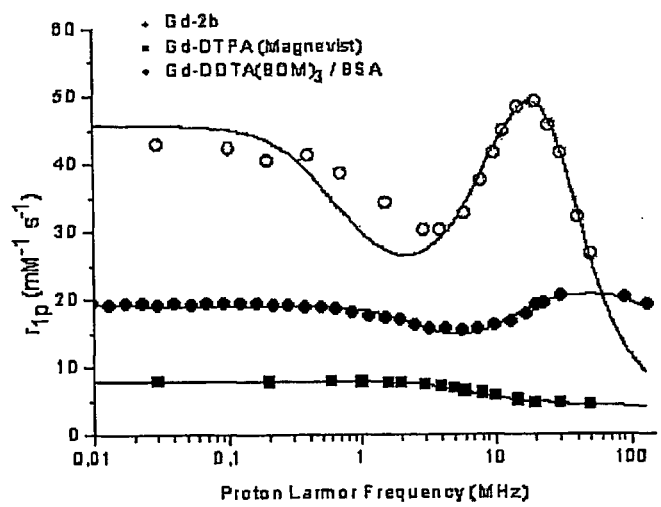

CONTRAST AGENTS ENDOWED WITH HIGH RELAXIVITY

This application is the national stage application of corresponding international application number PCT/EP2005/006956, filed Jun. 28, 2005, which claims priority to and the benefit of the U.S. provisional application U.S. Ser. No. 60/585,181, filed Jul. 2, 2004, all of which are hereby incorporated by reference.

The present invention relates to the field of diagnostic imaging and to novel contrast agents possessing high relativity. More in particular, it relates to compounds capable of chelating paramagnetic metal ions, to the chelated complexes thereof with said metal ions and to their use as non-specific contrast agents in Magnetic Resonance Imaging (MRI).

BACKGROUND OF THE INVENTION

Contrast in MRI is basically due to differences in relaxation times of water protons and it can be enhanced by the use of chemicals able to catalyse the relaxation processes of water protons. The most important class of MRI contrast agents is represented by the Gd(III) chelates which are currently used in about ⅓ of the clinical tests. To be considered as a potentially valuable MRI contrast agent, a Gd(III) complex must display a high thermodynamic (and possibly kinetic) stability in order to ensure against the release of free Gd(III) ions and ligands, both known to be toxic for living organisms. Therefore, known chelating compounds, including octa-coordinating ligands such as, for instance, diethylenetriaminopentaacetic acid (DTPA), 1,4,7,10-tetraazacyclododecane-1,4,7,10-tetraacetic acid (ROTA) and their derivatives, have been considered for the chelation of the Gd(III) ion. These ligands wrap around this lanthanide(III) ion and leave one binding site available for the coordination of one water molecule. Thus, the coordinated water protons display a very short relaxation time ($T_{1M}$) that is transferred to the "bulk" water molecules by the occurrence of a fast exchange process ($K_{ex}=1/\tau_M$). See, for a general reference, Aime S.; Botta M.; Fasano, M.; Terreno, E. Chem. Soc. Rev. 1998, 27, 19-29.

As far as the relaxation enhancement property is concerned, a paramagnetic Gd(III) complex is characterized by its relaxivity ($r_{1p}$) which represents the increase of the proton relaxation rate of an aqueous solution of the Gd(III) complex in comparison to the proton relaxation rate of neat water ($R_1°$). The relaxivity is usually measured at 298K and 20 MHz (0.5 T).

On the other side, when a different property such as the pharmacokinetic profile is considered for a Gd-complex or, more generally, for a paramagnetic chelate complex or a paramagnetic contrast agent, the following categories of diagnostics may be identified:

Non-Specific Agents (NSA) that freely and quickly distribute into the extracellular space after administration; Low Diffusion Agents (LDA) that may only diffuse slowly from the blood system into the extracellular space; and Blood Pool Agents that mainly distribute, if not completely, into the blood system.

Because of their biodistribution profile, the NSA are thus designed for general use. As an example, the NSA agents below which are currently used in clinical practice display almost identical relaxivity of approximately 4.7 mM$^{-1}$ s$^{-1}$ (measured at 298K and 20 MHz).

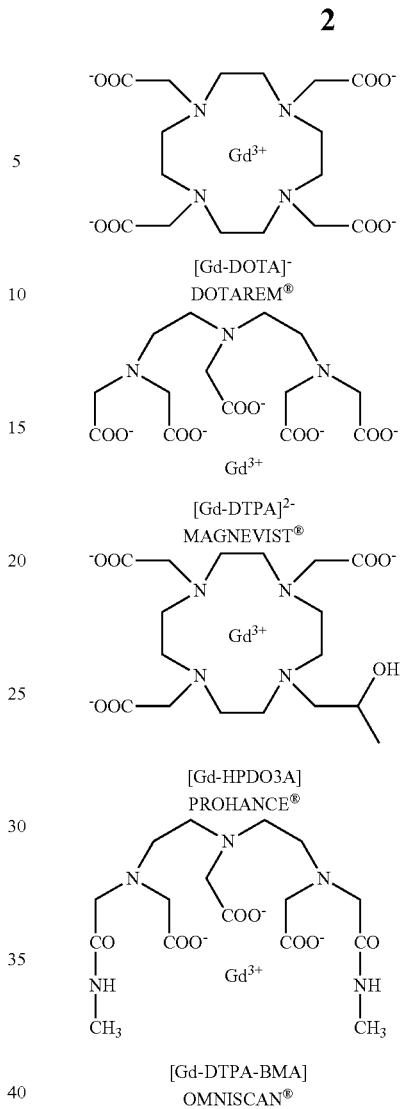

[Gd-DOTA]$^-$
DOTAREM®

[Gd-DTPA]$^{2-}$
MAGNEVIST®

[Gd-HPDO3A]
PROHANCE®

[Gd-DTPA-BMA]
OMNISCAN®

Since higher relaxivity leads to better contrast differentiation in MR images, much attention has been devoted in the last two decades to the search for systems with higher relaxivities than those found in commercial products.

In this respect, it was recognised that for Gd(III) complexes, which coordinated water molecules were in fast exchange with the "bulk" water, the $r_{1p}$ values increased linearly with the increase of their Molecular Weight (MW). This behaviour is fully consistent with the known dependence of $T_{1M}$ from the molecular reorientational time ($\tau_R$) (see the aforementioned reference).

On this basis, two pathways have been followed to lengthen the molecular reorientational time: i) the covalent route, consisting of binding bulky moieties on the surface of the ligand; and the non-covalent route, consisting of systems able to form supramolecular adducts with slowly moving substrates. For this latter approach, the most commonly used substrate is represented by Human Serum Albumin (HSA) and several Gd(III) chelates containing suitable substituents for a high affinity binding to the serum protein have been reported. Upon binding to HSA, these Gd(III) complexes display their maximum $r_{1p}$ value at observation frequencies of 25-30 MHz, i.e. at magnetic field strength close to 1 T. At higher fields, however, their $r_{1p}$ decreases quickly thus showing that the strong effect of $\tau_R$ on $T_{1M}$ is mostly important at imaging fields ranging between 0.5 and 1.5 T. See, for a general reference: Aime S., Botta M., Fasano, M.; Terreno, E. *Chem. Soc. Rev.* 1998, 27, 19-29; and Caravan P., Cloutier N. J., Matthew T., Lauffer R. B. et al. JACS, 2002, 124, 3152-3162.

For clinical applications the current trend is to move to tomographs operating at 3 T so as to obtain a better imaging resolution. Therefore, there is the need to identify new ways to attain high relaxivities over an extended range of magnetic field strength.

Moreover, in view of their increased size, these high MW Contrast agents have an almost unique localization in the body vascular system and this biodistribution pattern, characterizing them as "blood-pool" contrast agents, limit their use accordingly.

When considering MRI contrast agents with high relaxivity, some further compounds exist having MW lower than those of the blood pool agents but still exhibiting a relaxivity up to 25 mM$^{-1}$·s$^{-1}$ measured at 20 MHz and 37° C. (see, for instance, WO 00/75141; and J. Magn. Reson. Imaging 2000, 11:182-191).

These compounds are known as Low Diffusion Agents (LDA) because their MW, ranging from 5 to 10 kDa, is high enough to allow only their low diffusion into the extravascular space. Because of their pharmacokinetic profile, the diagnostic applications of these LDA are different from those of the already marketed NSA which, by freely diffusing from the vascular bed, are consequently designed for a general diagnostic application.

There is therefore the need for new and improved NSA able to combine free and rapid biodistribution, and consequent general usefulness, with high relaxivity.

The present invention thus relates to a novel class of contrast agents, essentially characterized by the presence of hydroxylated groups, that satisfy the above requirements.

SUMMARY OF THE INVENTION

The present invention relates to a new class of paramagnetic ion-based contrast agents of low molecular weight, that show a pharmacokinetic profile analogous to that of the commonly used T1-general extravascular agents but, when compared to said already marketed NSA, are further characterized by higher relaxivity. Moreover, the improved relaxivity is persistent without any significant decrease over an extended range of magnetic field strength.

Therefore, it is a first object of the present invention a paramagnetic ion-based, non-specific contrast agent (NSA) having low molecular weight characterized by a high relaxivity, which is substantially retained over a magnetic field strength varying from about 0.5 to about 3 MHz.

Preferably, with the term low molecular weight we intend a molecular weight lower than about 3.5 kDa.

In the present description, unless otherwise indicated, with the term non-specific contrast agent (NSA) we intend any contrast agent that, despite any of the above additional features, is rapidly and freely distributed into the extracellular space after administration, particularly intravascular administration.

The term paramagnetic ion-based contrast agent includes any chelated complex with a bi- or trivalent paramagnetic metal ion, preferably having atomic number ranging between 20 and 31, 39, 42, 43, 44, 49, and between 57 and 83 such as, for instance, Fe($^{2+}$), Fe($^{3+}$), Cu($^{2+}$), Cr($^{3+}$), Eu($^{3+}$), Dy($^{3+}$), La($^{3+}$), Yb($^{3+}$), Mn($^{2+}$), Mn($^{3+}$) and Gd($^{3+}$), this latter being preferred.

With the expression high relaxivity we intend, according to the present invention and unless otherwise provided, a relaxivity equal or higher than 8 mM$^{-1}$ s$^{-1}$ [when measured at 20 MHz (approx. 0.5 T), 298K and pH 7] and, even more preferably, higher than 10 mM$^{-1}$ s$^{-1}$, 12 mM$^{-1}$ s$^{-1}$, 15 mM$^{-1}$ s$^{-1}$ and 20 mM$^{-1}$ s$^{-1}$ for systems with MW of about 1500, 2000, 2500 and 3500 Da, respectively.

Furthermore, the high relaxivity should be retained without a significant decrease in the above range of magnetic field strength, that is from about 0.5 to about 3 MHz. In its turn, any non significant decrease may preferably comprise, for instance, possible variations of relaxivity not exceeding 40%.

According to a first embodiment, the contrast agents of the invention (which may also include the physiologically acceptable salts thereof) comprise a chelating backbone moiety being substituted by one or more highly hydrophilic aminopolyol moieties wherein said aminopolyol moieties are linked, directly or through a linker, to the said backbone chelating structure, in a way not altering the characteristics of the coordination cage of the said chelating moiety.

It is therefore an additional object of the invention to provide a chelating ligand of formula (I):

A(LR)$_v$      (I)

wherein:
A is a linear or cyclic chelating backbone moiety;
R is, independently, H or a C$_2$-C$_{70}$ aminopolyol moiety comprising a straight or branched alkyl chain substituted by from 2 to 30 hydroxyl groups, the said chain being optionally interrupted by one or more groups selected from —O—, —NH—, —N<, —CO—, —CONH—, —NHCO—, —CON< or >NCO—; and optionally substituted by one or more C$_4$-C$_{10}$ cyclic units;
L is, independently, a direct bond or a divalent straight or branched linker moiety between A and R, at most comprising 20 carbon atoms;
v is a positive integer from 1 to 7;
with the proviso that at least one of the R groups is other than H;
or a physiologically acceptable salt of such ligand.

Unless otherwise provided, with the term aminopolyol moiety we intend a group —NHR' or —NR'R", wherein the nitrogen atom is bonded to the backbone moiety A through the linker L and R' and R", the same or different, either alone or taken together, represent the above polyhydroxylated straight or branched alkyl chain.

The said aminopolyol moieties may be also optionally interrupted or substituted as above indicated (see, as an example, the experimental section).

Unless otherwise provided, with the term cyclic unit we refer to an optionally substituted 4 to 10 membered, either carbocyclic or heterocyclic ring, this latter comprising from 1 to 2 heteroatoms selected from N and O.

Preferably, the carbocyclic ring is a 6-membered ring substituted by one or more groups selected from hydroxy, hydroxymethyl and amino and, even more preferably, it is the amino-inositol derivative having the following formula:

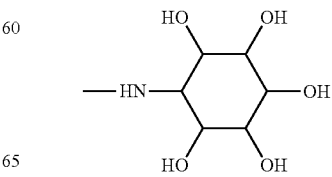

Preferably, the heterocyclic ring is a 5- or 6-membered pyranoside or piperidino ring optionally substituted by one or more hydroxy, hydroxymethyl and amino groups and, even more preferably, it is a pyranoside or piperidino derivative of formula:

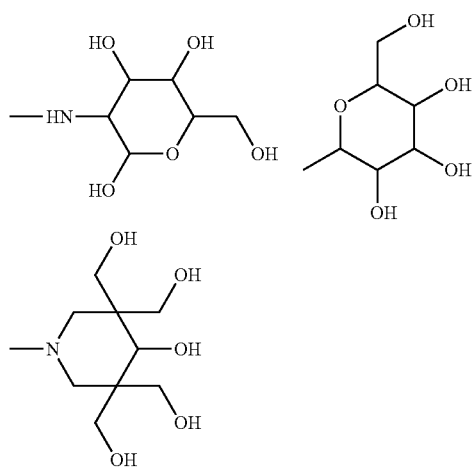

Clearly, within the compounds of formula (I) and unless otherwise provided, when one or more carbon atoms represent a centre of asymmetry, any optically active form, the racemates thereof as well as any mixture comprising a majority of any optically active form, are all to be intended as comprised within the scope of the present invention.

Depending upon the nature of the chelating backbone moiety A, a variety of compounds of formula (I) have been herewith identified.

According to a preferred aspect of the invention, the compounds of formula (I) may be thus selected, from the group consisting of:

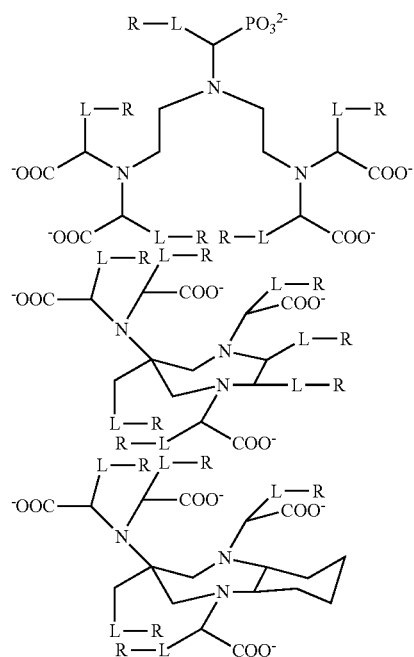

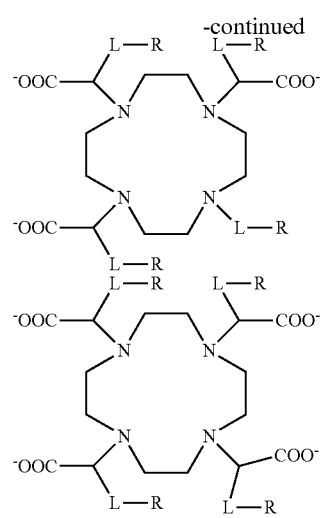

wherein L and R are, the same or different and independently in each occasion, as formerly indicated.

In the above formulae, and provided that at least one of the said R groups is other than H, the -L-R groups themselves are therein positioned as non-limiting examples of preferred binding sites with the rest of the molecule.

Unless otherwise provided, even if the negative charge in each of the above formulae has been herewith inserted to identify the carboxylate and phosphonate anions, for instance when the compounds are present as paramagnetic chelated complexes or salts, e.g. alkaline metal salts, the corresponding compounds bearing the carboxylic (—COOH) and the phosphonic (—PO$_3$H$_2$) group have also to be intended as comprised within the scope of the invention.

According to a first embodiment of the invention, particularly preferred are the chelating compounds of formula (II) below

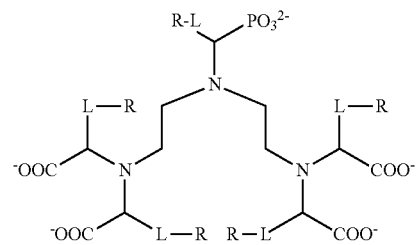

wherein R and L have the above-reported meanings.

Even more preferred, in this class, are the derivatives represented through formula (II) below

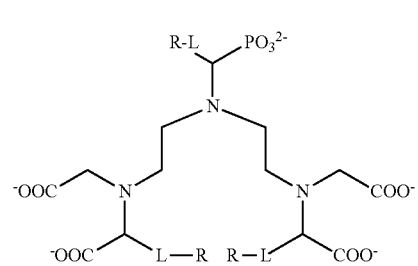

(II)

wherein R and L have the above-reported meanings.

Still more preferred are the compounds of formula (II) below

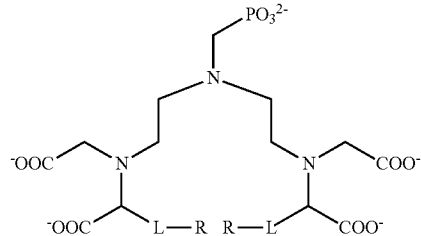
(II)

wherein R and L have the above-reported meanings.

Clearly, within the above sub-classes of compounds of formula (II), given -LR groups have been purposely replaced by H; in those same positions, therefore, L is a single bond and R is H. As far as the remaining -LR groups are concerned, instead, they may have the above reported meanings, hence also including H, provided that at least one of the said R groups is other than H.

According to another embodiment of the invention, also preferred are the chelating compounds of formula (III) and (IIIa) below

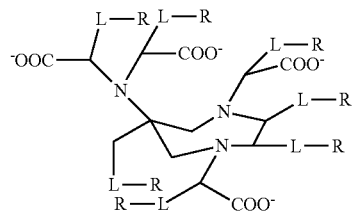

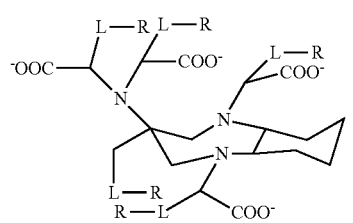

wherein R and L have the above-reported meanings.

Even more preferred, in this class, are the derivatives represented through formulae (III) and (IIIa) below

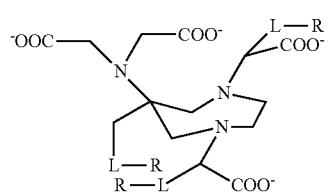
(III)

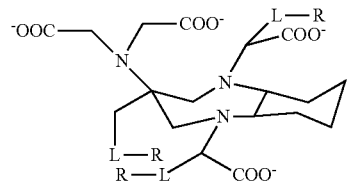
(IIIa)

wherein R and L have the above-reported meanings.

Still more preferred, in this class, are the derivatives of formula (III)

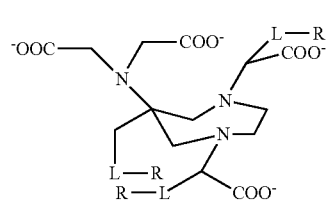
(III)

wherein R and L have the above-reported meanings.

As far as the -LR groups are concerned within the sub-classes of compounds of formula (III) or of formula (IIIa), and their possible replacement with H, see the aforementioned comments provided for the above compounds of formula (II).

According to another embodiment of the invention, also preferred are the derivatives represented through formulae (IV) and (V) below

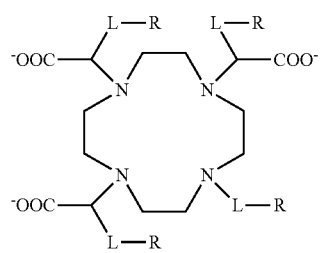
(IV)

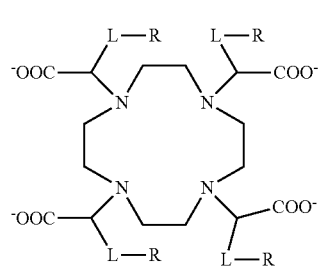
(V)

wherein R and L have the above-reported meanings.

From all of the above, it is clear to the person skilled in the art that any of the compounds of formula (II), (III), (IIIa), (IV) and (V), do represent specific embodiments of the invention and, hence, fall within the meanings of the above-reported formula (I).

According to another embodiment of the invention, the R groups within the compounds of formula (I), hence also encompassing the derivatives having formula from (II) to (V), are preferably selected, when other than H, from the groups consisting of:

—NH—$(CH_2)_{0-2}$—C[$(CH_2)_{1-2}$—O-Q]$_3$;
—NH—$(CH_2)_{1-2}$—CON[$(CH_2)_{1-3}$—CONH—C[$(CH_2)_{1-2}$—O-Q]$_3$]$_2$;
—N[$(CH_2)_{1-4}$—NHCO—$(CHOH)_{1-4}$—$CH_2OH$]$_2$;
—NH—$(CH_2)_{0-2}$—C[$(CH_2)_{1-4}$—NHCO—$(CHOH)_4$—$CH_2OH$]$_3$;
—N[$(CH_2)_{1-4}$—N[$(CH_2)_{1-4}$—COY]$_2$]$_2$;
—NH—C[$(CH_2)_{1-4}$—COY]$_3$;
—NH—C[$(CH_{1-2}$—O—$(CH_2)_{1-3}$—COY]$_3$;
—NH—CH(COY)[$(CH_2)_{1-2}$—COY];
—NH—$(CH_2)_{1-2}$—CH[$(CH_2)_{1-2}$—O—$(CH_2)_{0-2}$—C($R_1$)$(CH_2OH)_2$]$_2$;
—NH—$(CH_2)_{1-2}$—CH[$(CH_2)_{1-2}$—O—$(CH_2)_{1-2}$—CH[$(CH_2)_{1-2}$—O— cont. —$(CH_2)_{0-2}$—C($R_1$)$(CH_2OH)_2$]$_2$]$_2$;
—NH—$(CH_2)_{1-2}$—CH[$(CH_2)_{1-2}$—O—$(CH_2)_{1-2}$—CH[$(CH_2)_{1-2}$—O— cont. —$(CH_2)_{1-2}$—CH[$(CH_2)_{1-2}$—O—$(CH_2)_{0-2}$—C($R_1$)$(CH_2OH)_2$]$_2$]$_2$]$_2$;

wherein
Q is a group of formula

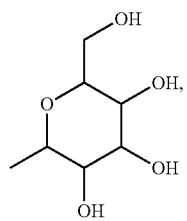

$R_1$ is H or methyl; and
Y is a group as set forth in the following table (a)

TABLE (a)

Y

[Structures shown:
- —HN—C(CH$_2$OH)$_3$ (tris)
- —HN—CH$_2$—C(CH$_2$OH)$_3$
- —HN—inositol (cyclohexane with OH groups)
- piperidine with four CH$_2$OH groups
- —HN—glucosamine-type sugar]

TABLE (a)-continued

Y

[Structures shown:
- H—N(Me)—CH$_2$—(CHOH)$_4$—CH$_2$OH
- Me—N(Me)—CH$_2$—(CHOH)$_4$—CH$_2$OH
- N[CH$_2$—(CHOH)$_4$—CH$_2$OH]$_2$
- —HN—CH$_2$—CH(OCH$_2$CH(OH)CH$_2$OH)—OCH$_2$CH(OH)CH$_2$OH
- —HN—CH$_2$—C(CH$_3$)(CH$_2$OH)—OCH$_2$C(CH$_3$)(CH$_2$OH)—OCH$_2$C(CH$_3$)(CH$_2$OH)$_2$
- N—(CH$_2$CH$_2$CONH—C(CH$_2$OH)$_3$)$_2$]

In a more preferred aspect, the invention relates to chelating compounds of formula from (II) to (V) wherein R is H or is selected among the following preferred aminopolyols being herewith identified by codes from A to G, as follows.

| 11 | 12 |
|---|---|
| 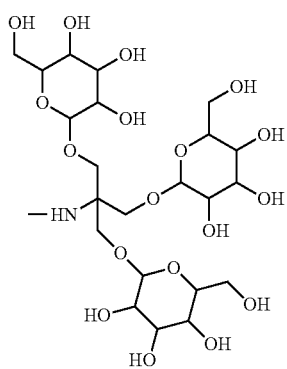 A1 | 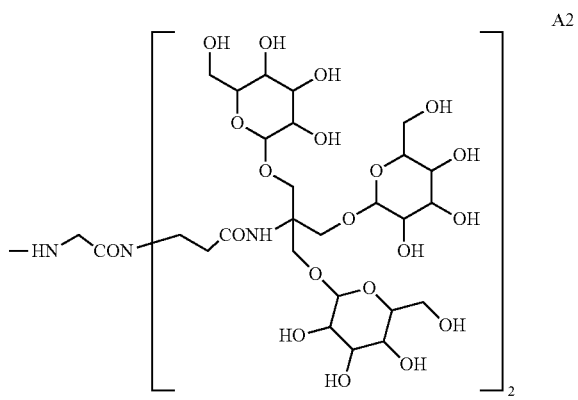 A2 |
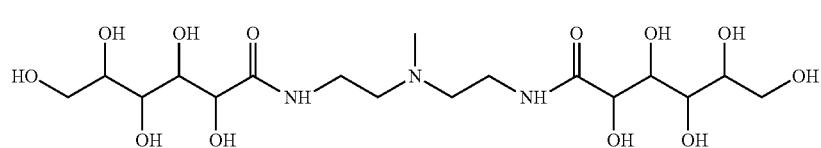
B1
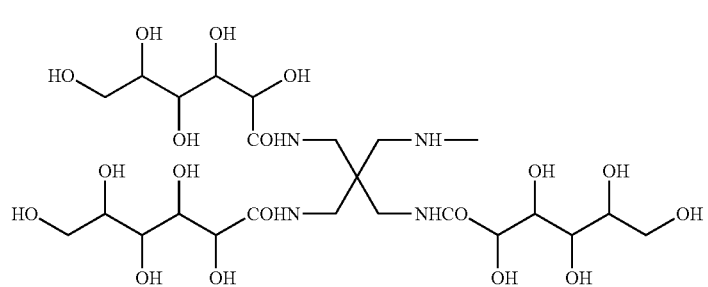
B2
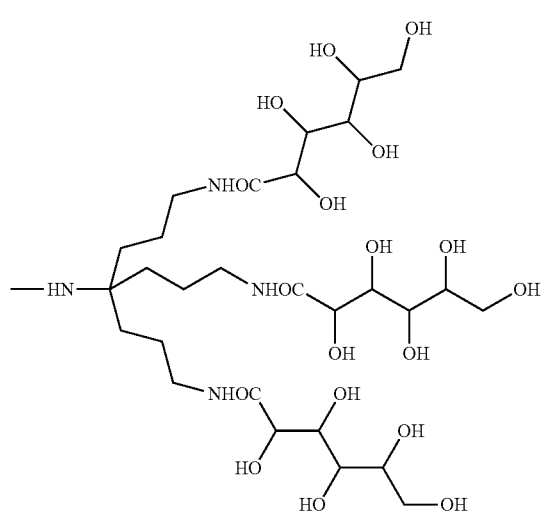
B3

TABLE (b)

| C | D | wherein Y is |
|---|---|---|
| C1 | D1 | HN-C(CH2OH)3 (tris) |
| C2 | D2 | HN-CH2-C(CH2OH)3 |
| C3 | D3 | aminocyclohexanepentol (HN-cyclohexyl with 4 OH and HO) |
| C4 | D4 | N-methylpiperidine tetrakis(hydroxymethyl) with OH |
| C5 | D5 | HN-glucosamine-like pyranose (HN on sugar ring with HO, OH, OH, OH, CH2OH) |
| C6 | D6 | MeHN-CH2-(CHOH)4-CH2OH (N-methylglucamine) |
| C7 | D7 | Me2N-CH2-(CHOH)4-CH2OH |
| C8 | D8 | N(CH2-(CHOH)4-CH2OH)2 with Me |

Header structures:
- C series: tetra-substituted tris(2-aminoethyl)amine-like core with four COY groups (N(CH2CH2N(CH2CH2COY)2)2 with N-Me)
- D series: HN-C(CH2CH2COY)3 (tetrahedral carbon with three CH2CH2COY arms)

TABLE (b)-continued
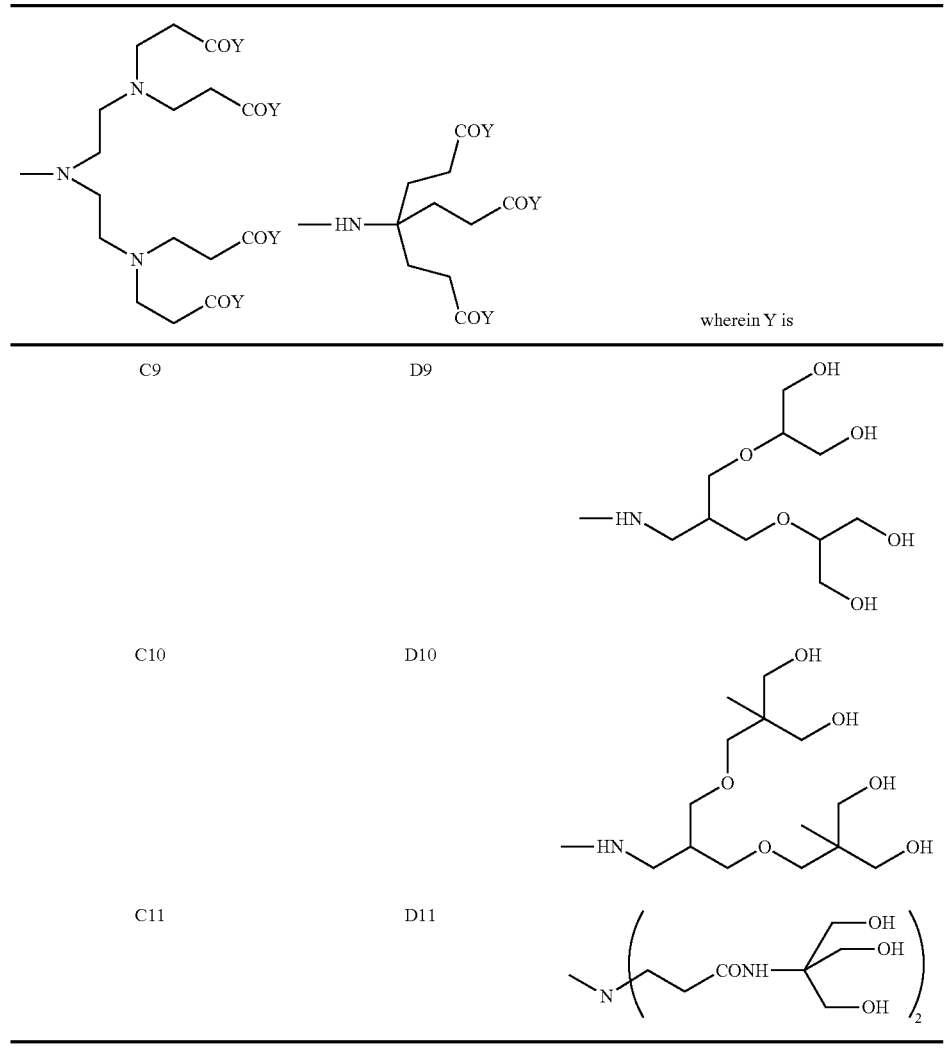
TABLE (c)
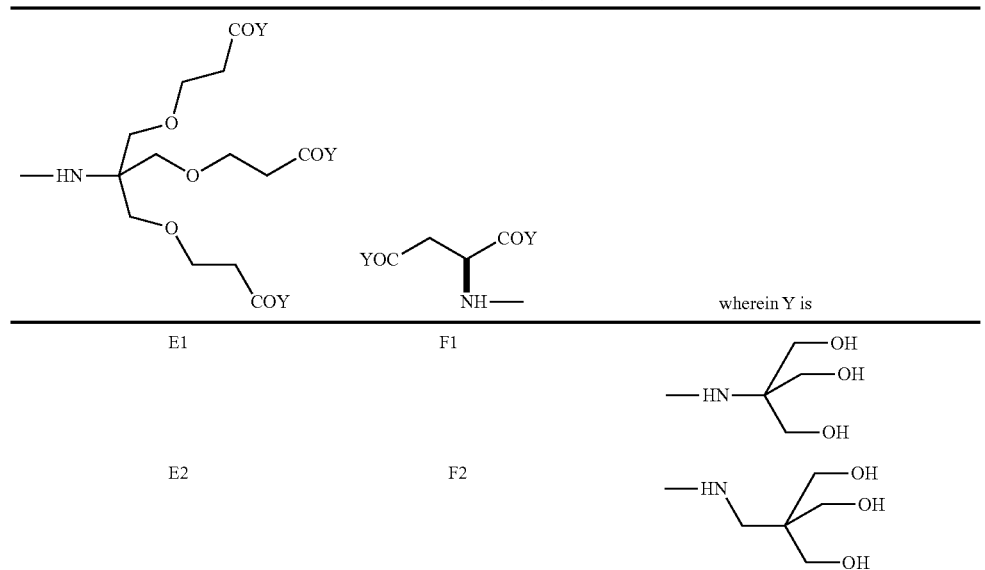

TABLE (c)-continued
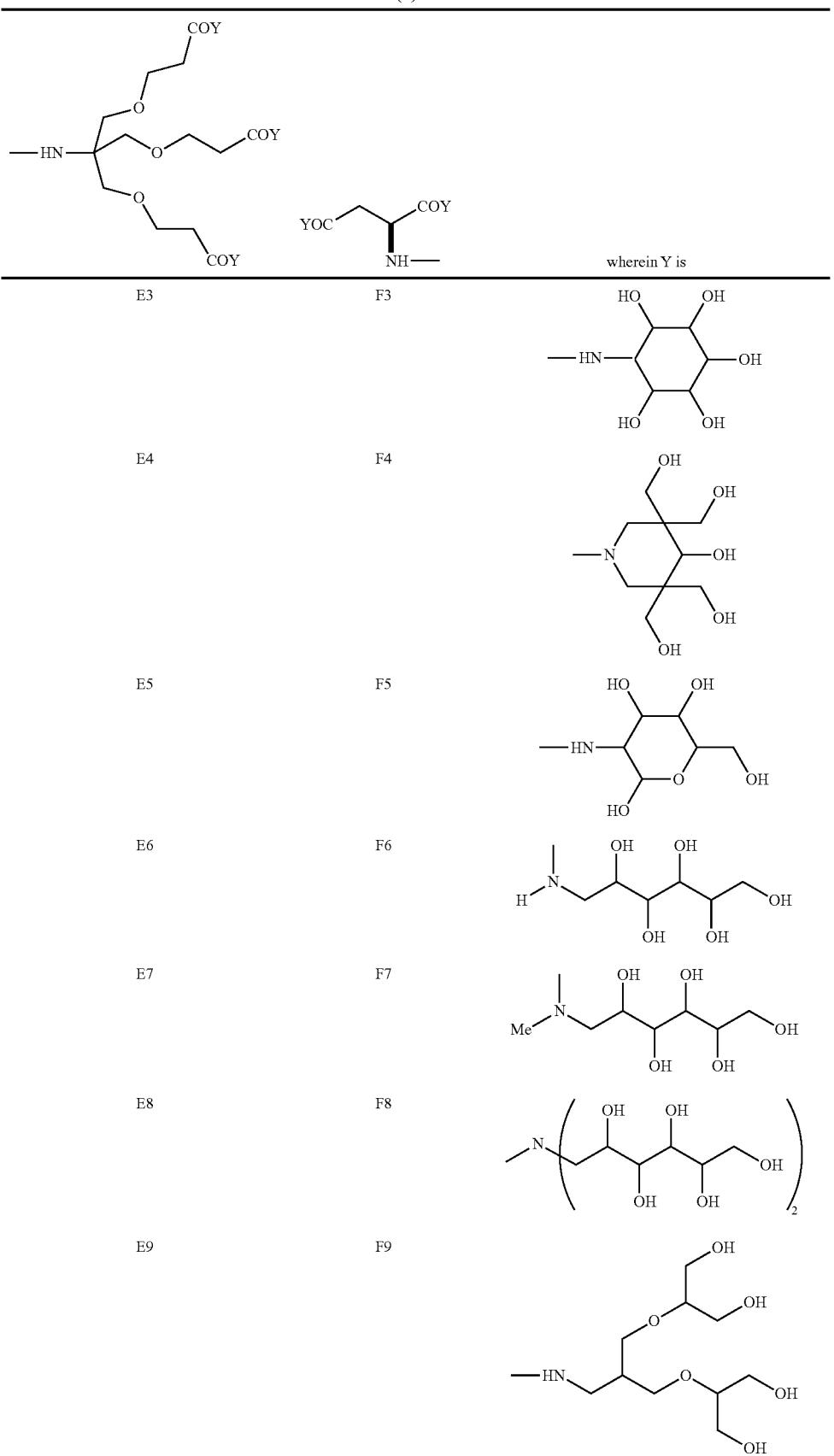

TABLE (c)-continued
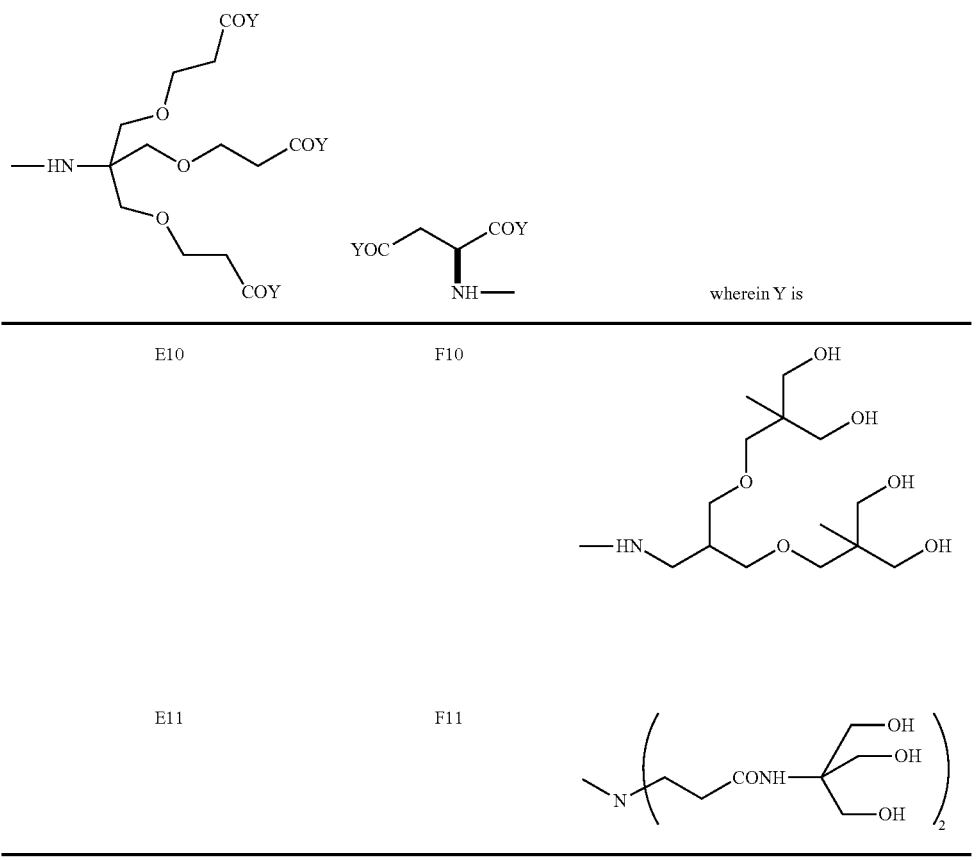
| E10 | F10 |
|---|---|
| E11 | F11 |
TABLE (d)
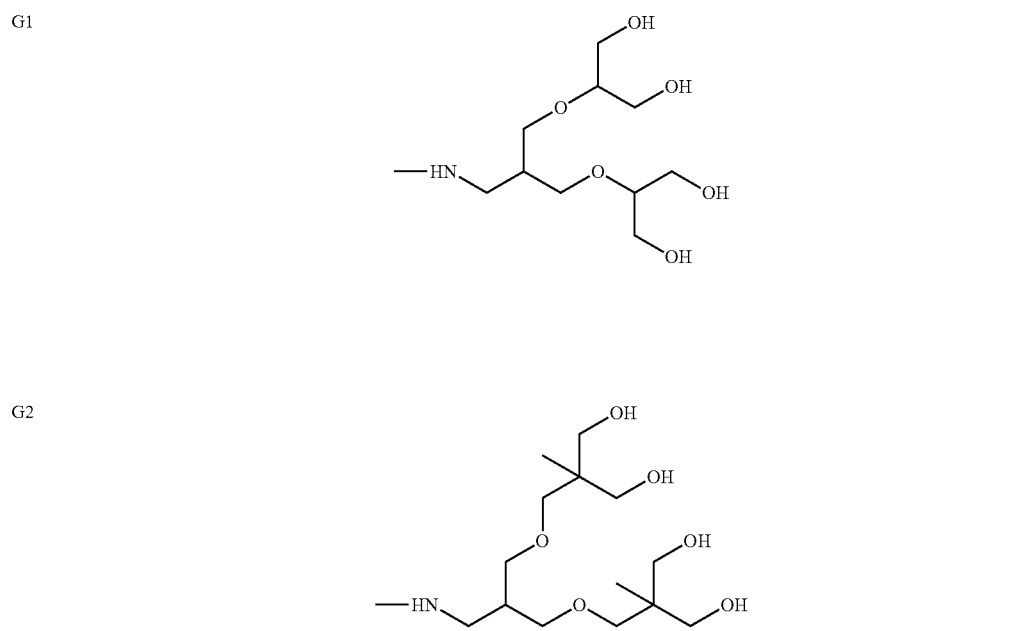
G1
G2

TABLE (d)-continued
G3
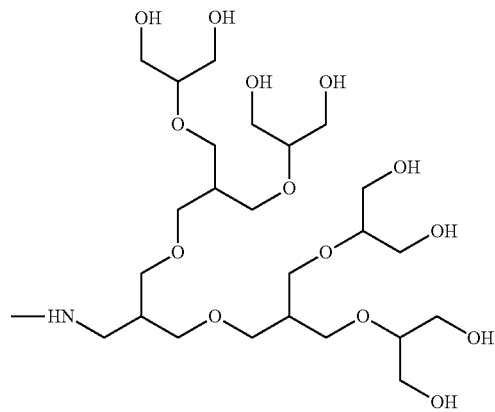 [SMILES: CNCC(COCC(COC(CO)CO)COC(CO)CO)COCC(COC(CO)CO)COC(CO)CO]
G4
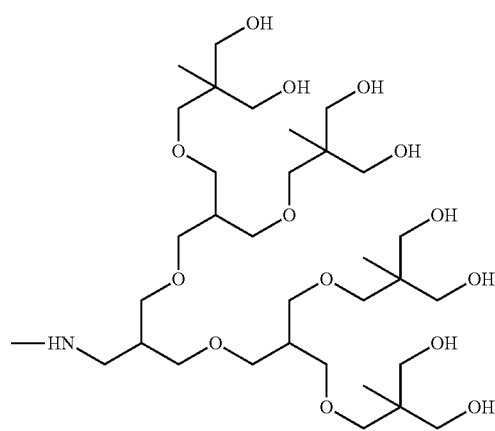 [SMILES: CNCC(COCC(COCC(C)(CO)CO)COCC(C)(CO)CO)COCC(COCC(C)(CO)CO)COCC(C)(CO)CO]
G5
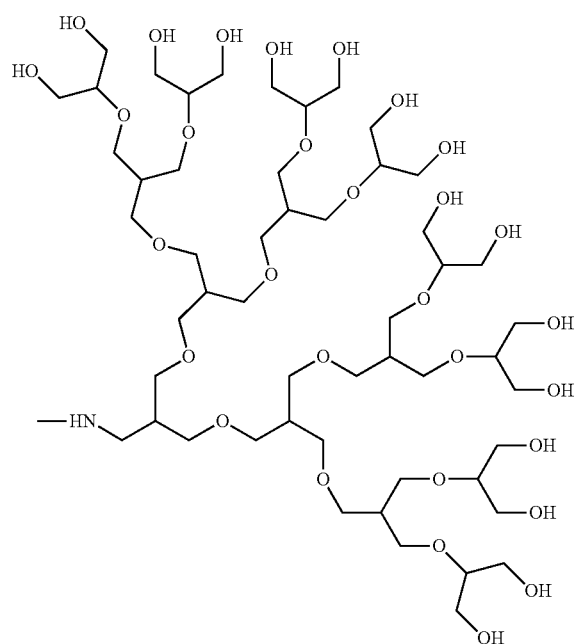 [SMILES: CNCC(COCC(COCC(COC(CO)CO)COC(CO)CO)COCC(COC(CO)CO)COC(CO)CO)COCC(COCC(COC(CO)CO)COC(CO)CO)COCC(COC(CO)CO)COC(CO)CO]

TABLE (d)-continued
G6
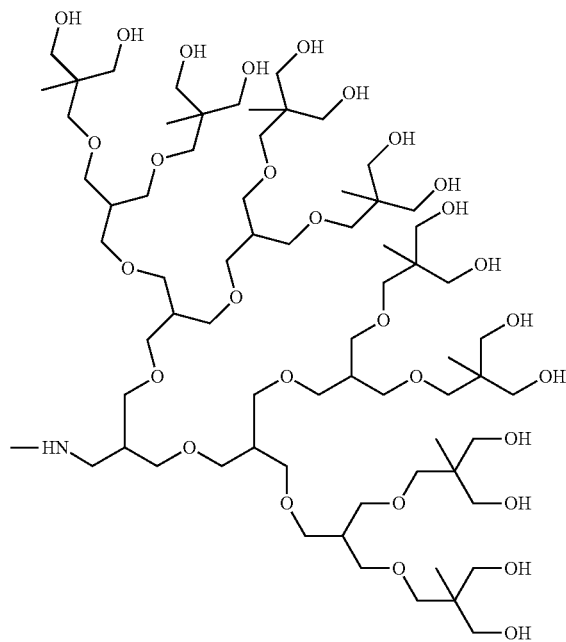 [SMILES: CNCC(COCC(COCC(COCC(C)(CO)CO)COCC(C)(CO)CO)COCC(COCC(C)(CO)CO)COCC(C)(CO)CO)COCC(COCC(COCC(C)(CO)CO)COCC(C)(CO)CO)COCC(COCC(C)(CO)CO)COCC(C)(CO)CO]
G7
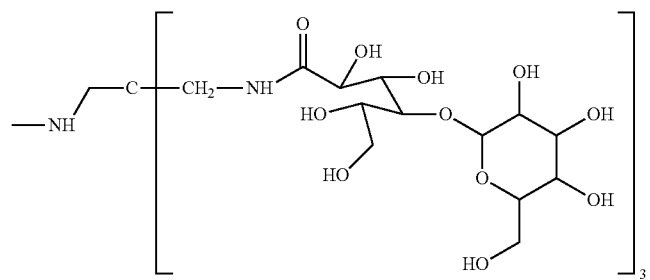
G8
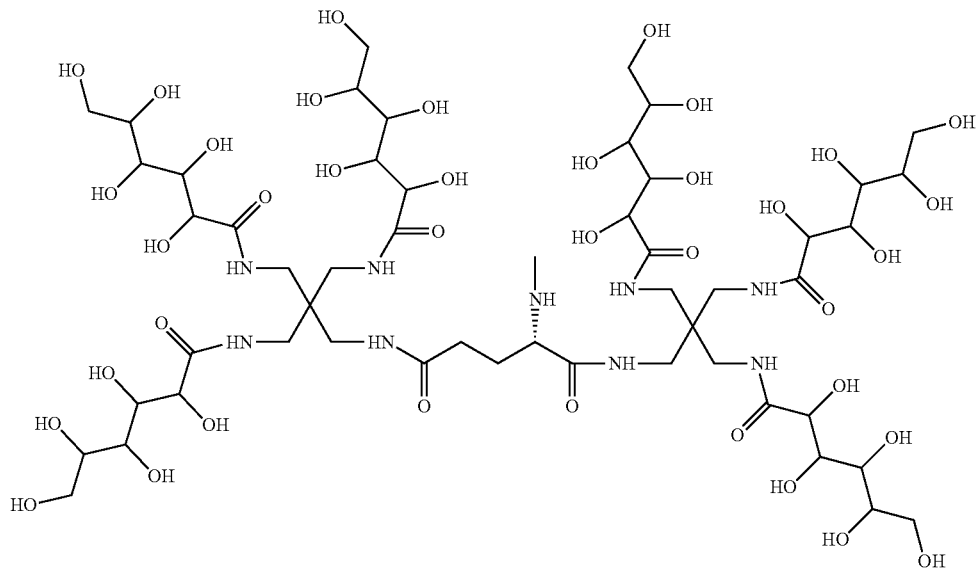 [SMILES: CN[C@@H](CCC(=O)NCC(CNC(=O)C(O)C(O)C(O)C(O)CO)(CNC(=O)C(O)C(O)C(O)C(O)CO)CNC(=O)C(O)C(O)C(O)C(O)CO)C(=O)NCC(CNC(=O)C(O)C(O)C(O)C(O)CO)(CNC(=O)C(O)C(O)C(O)C(O)CO)CNC(=O)C(O)C(O)C(O)C(O)CO]

TABLE (d)-continued

G9 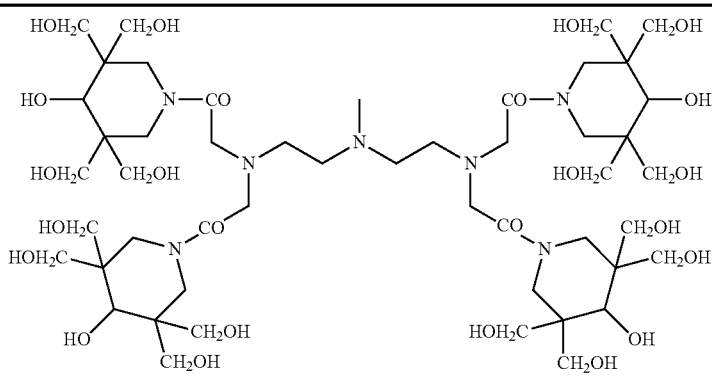

G10 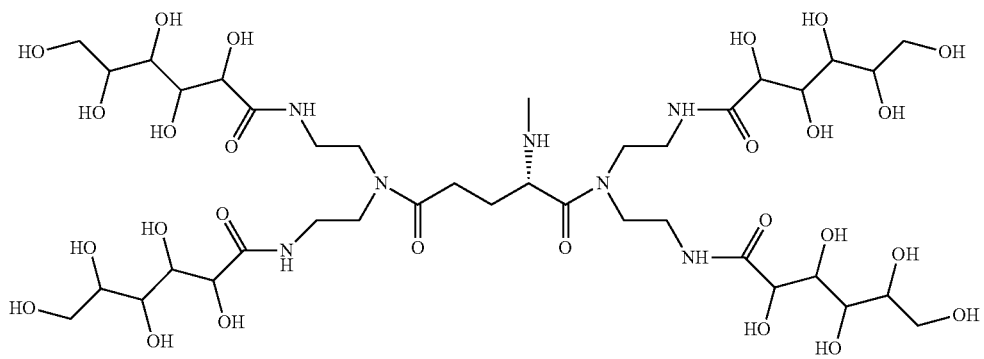 [SMILES: CN[C@@H](CCC(=O)N(CCNC(=O)C(O)C(O)C(O)C(O)CO)CCNC(=O)C(O)C(O)C(O)C(O)CO)C(=O)N(CCNC(=O)C(O)C(O)C(O)C(O)CO)CCNC(=O)C(O)C(O)C(O)C(O)CO]

G11 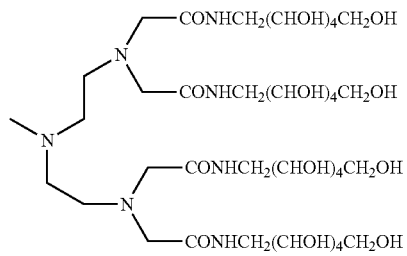

From all of the above, it should be clear to the skilled person that whilst any of the A, B and G aminopolyols is defined through the proper chemical formula, tables (b) and (c) are purposely construed so as to unambiguously define the C, D, E and F moieties through the formulae at the top of them, which moieties are then substituted by Y groups so as to give rise to a variety of R groups, each being exactly defined by the above coding system.

According to an additional embodiment of the invention, L represents a direct bond or a linker at most comprising 20 carbon atoms.

Preferably, L represents a direct bond or a linker at most comprising 15 carbon atoms; still more preferably, L represents a direct bond or a linker of formula

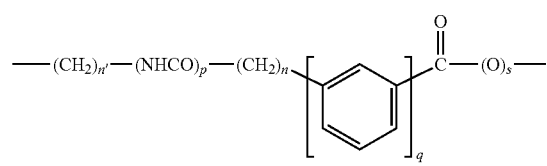

wherein n and n' are, the same or different and each independently, 0 or an integer from 1 to 4, p, q and s are selected, each independently, from 0 or 1.

Even more preferably, L represents a direct bond or a linker of formula

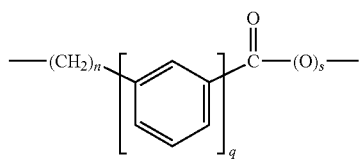

wherein n, q and s have the above-reported meanings.

From all of the above, particularly preferred compounds of formula (I) of the invention are those represented by formula (II) as per the following table 1; formula (III) as per the following table 2; formula (IV) as per the following table 3; and formula (V) as per the following table 4.

TABLE 1

| | $L_1$ is (in $A-L_1-R_1$) | $L_2$ is (in $A-L_2-R_2$) | $R_1$ | $R_2$ |
|---|---|---|---|---|
| 1b | $CH_2CO$ | Direct bond | B1 | H |
| 2b | $CH_2CO$ | Direct bond | B2 | H |
| 3b | $CH_2CO$ | $CH_2CO$ | B1 | B1 |
| 4b | $CH_2CO$ | $CH_2CO$ | B2 | B2 |
| 5b | $CH_2CO$ | Direct bond | G9 | H |
| 6b | $CH_2CO$ | Direct bond | G3 | H |
| 7b | $CH_2CO$ | Direct bond | C1 | H |
| 8b | $CH_2CO$ | Direct bond | E1 | H |
| 9b | $CH_2CO$ | Direct bond | G10 | H |
| 10b | Direct bond | $CH_2CH_2CO$ | H | G7 |
| 11b | $CH_2CO$ | Direct bond | G8 | H |

TABLE 2

| | $L_1$ is (in $A-L_1-R_1$) | $L_2$ is (in $A-L_2-R_2$) | $R_1$ | $R_2$ |
|---|---|---|---|---|
| 1a | direct bond | $CH_2CO$ | H | A2 |
| 2a | direct bond | $CH_2CO$ | H | B1 |
| 3a | direct bond | $CH_2CO$ | H | B2 |
| 4a | $CH_2CH_2CO$ | direct bond | B1 | H |
| 5a | $CH_2CH_2CO$ | direct bond | B2 | H |
| 6a | $CH_2CH_2CO$ | direct bond | G3 | H |
| 7a | $CH_2CH_2CO$ | $CH_2CO$ | B1 | B1 |
| 8a | $CH_2CH_2CO$ | $CH_2CO$ | G3 | G3 |
| 9a | $CH_2CO$ | direct bond | B1 | H |
| 10a | $CH_2CO$ | direct bond | B2 | H |
| 11a | $CH_2CH_2CO$ | $CH_2CO$ | B2 | B2 |
| 12a | direct bond | $CH_2CO$ | H | C1 |
| 13a | $CH_2CH_2CO$ | direct bond | B2 | H |
| 14a | direct bond | $CH_2CO$ | H | G7 |
| 15a | $CH_2CH_2CO$ | direct bond | C1 | H |

TABLE 3

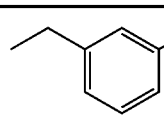

| | $L_1$ is (in $A-L_1-R$) | $L_2$ is (in $A-L_2-R$) | $R_1$ | $R_2$ |
|---|---|---|---|---|
| 1d | $CH_2CH_2COO$ | (m-phenylene-CH$_2$CH$_2$-CO—) | H | B2 |

TABLE 3-continued

| | Wherein in the sequence A—L$_1$—R L$_1$ is | Wherein in the sequence A—L$_2$—R L$_2$ is | R$_1$ | R$_2$ |
|---|---|---|---|---|
| 2d | CH$_2$CH$_2$CO | 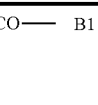 | B1 | B1 |
| 3d | CH$_2$CH$_2$COO | CH$_2$CH$_2$CO | H | B2 |
| 4d | CH$_2$CH$_2$CO | CH$_2$CH$_2$CO | B1 | B1 |
| 5d | CH$_2$CH$_2$CO | 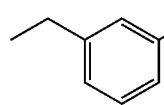 | B2 | B2 |

TABLE 4

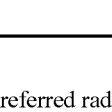

| | Wherein in the sequence A—L$_1$—R$_1$ L$_1$ is | R$_1$ |
|---|---|---|
| 1c | CH$_2$CH$_2$CO | G1 |
| 2c | CH$_2$CH$_2$CO | G2 |
| 3c | CH$_2$CH$_2$CO | G3 |
| 4c | CH$_2$CH$_2$CO | G4 |
| 5c | CH$_2$CH$_2$CO | G5 |
| 6c | CH$_2$CH$_2$CO | B1 |
| 7c | CH$_2$CH$_2$CO | A1 |

A further object of the invention is represented by the chelated complexes of the compounds of formula (I), hence encompassing those of formulae from (II) to (V), with a bivalent or trivalent paramagnetic metal ion and the physiologically acceptable salts thereof. Preferred chelate complexes are those wherein the chelated paramagnetic metal ion has atomic number ranging between 20 and 31, 39, 42, 43, 44, 49, and between 57 and 83 such as, for instance, Fe($^{2+}$), Fe($^{3+}$), Cu($^{2+}$), Cr($^{3+}$), Eu($^{3+}$), Dy($^{3+}$), La($^{3+}$), Yb($^{3+}$), Mn($^{2+}$), Mn($^{3+}$) and Gd($^{3+}$), this latter being even more preferred.

Compounds of formula (I), hence encompassing those of formula from (II) to (V) can also be complexed with radionuclides including: $^{203}$Pb, $^{67}$Ga, $^{68}$Ga, $^{72}$As, $^{111}$In, $^{113}$In, $^{90}$Y, $^{97}$Ru, $^{62}$Cu, $^{64}$Cu, $^{52}$Fe, $^{52m}$Mn, $^{140}$La, $^{175}$Yb, $^{153}$Sm, $^{166}$Ho, $^{149}$Pm, $^{177}$Lu, $^{142}$Pr, $^{159}$Gd, $^{212}$Bi, $^{47}$Sc, $^{149}$Pm, $^{67}$Cu, $^{111}$Ag, $^{199}$Au, $^{161}$Tb, $^{51}$Cr, $^{167}$Tm, $^{141}$Ce, $^{168}$Yb, $^{88}$Y, $^{165}$Dy, $^{166}$Dy, $^{97}$Ru, $^{103}$Ru, $^{186}$Re, $^{188}$Re, $^{99m}$Tc, $^{211}$Bi, $^{212}$Bi, $^{213}$Bi, $^{214}$Bi, $^{105}$Rh, $^{109}$Pd, $^{117m}$Sn, $^{177}$Sn and $^{199}$Au and oxides and nitrides thereof. The choice of radionuclide will be determined based on the desired therapeutic or diagnostic application. For example, for diagnostic purposes (e.g., to diagnose and monitor therapeutic progress using scintigraphic imaging), the preferred radionuclides include $^{64}$Cu, $^{67}$Ga, $^{68}$Ga, and $^{111}$In, with $^{111}$In being especially preferred. For therapeutic purposes (e.g., to provide radiotherapy), the preferred radionuclides include $^{64}$Cu, $^{90}$Y, $^{105}$Rh, $^{111}$In, $^{177m}$Sn, $^{149}$Pm, $^{153}$Sm, $^{161}$Tb, $^{166}$Dy, $^{166}$Ho, $^{175}$Yb, $^{177}$Lu, $^{186/188}$Re, and $^{199}$Au, with $^{177}$Lu and $^{90}$Y being particularly preferred.

Both the ligand and the paramagnetic or radioactive chelate can also be in the form of a salt, particularly as an addition salt with a physiologically compatible base or acid. Preferred cations of inorganic bases which can be suitably used to prepare a salt of the complexes or the ligands of the invention comprise, for instance, ions of alkali or alkaline-earth metals such as potassium, sodium, calcium or magnesium.

Preferred cations of organic bases comprise, for instance, those of primary, secondary and tertiary amines such as, for instance, ethanolamine, diethanolamine, morpholine, glucamine, N-methylglucamine, N,N-dimethylglucamine.

Preferred anions of inorganic acids which can be suitably used to prepare salts of the complexes of the invention comprise the ions of halo acids, for instance chlorides, bromides or iodides, as well as of other suitable ions such as sulfate.

Preferred anions of organic acids comprise those routinely used in pharmaceutical techniques for the preparation of salts of basic substances such as, for instance, acetate, succinate, citrate, fumarate, maleate or oxalate.

Preferred cations and anions of amino acids comprise, for instance, those of taurine, glycine, lysine, arginine, ornithine or of aspartic and glutamic acids.

The preparation of the compounds of formula (I), hence encompassing the compounds of formulae from (II) to (V), and of the chelate complexes thereof, either as such or in the form of physiologically acceptable salts, represent a further object of the invention.

In particular, the compounds of formula (I) and the chelated complexes thereof may be prepared through a general synthetic process comprising the following steps:

1) preparation of the aminopolyol moiety R in a suitable form wherein the amino group involved in the coupling reaction with the rest of the molecule (A-L) and the hydroxy groups can be suitably and independently protected or activated;

2) preparation of the linker L in a suitable form, in which any optional functional group being part of it can be independently and suitably protected or activated;

3) preparation of the backbone chelating moiety A in a suitable form wherein any functional group, either involved or not in the metal coordination and covalent binding with the rest of the molecule, can be suitably and independently protected or activated; and, optionally, wherein the chelating moiety A can be already complexed with the selected paramagnetic or radioactive metal ion;

4) coupling of groups A, L and R, in any suitable order, upon cleavage of any selected protecting group and/or activation of any selected functional group, in any of the A, L and R moieties;

5) cleavage of any protecting group and isolation of the compound of formula (I); and, optionally 6) complexation of the compound of formula (I) with the selected paramagnetic or radioactive metal ion, followed by isolation of the chelated complex and/or the salt thereof.

The above process, comprehensive of any variant thereof, particularly when referring to the steps of protection/deprotection and activation of known functional groups, or even in the order in which the above reaction steps may be accomplished, is carried out according to conventional methods known in the art.

From all of the above it should be clear to the skilled person that when the linker L represents a covalent bond, step (4) is carried out by direct coupling of group R with the rest of the molecule.

By analogy, in case L is other than a covalent bond, the preparation of the compounds of formula (I) and of the chelated complexes thereof may be accomplished by first coupling the moieties R and L and by subsequently reacting the obtained compound with moiety A or, alternatively, by first coupling the moieties A and L and by then reacting the resulting compound with moiety R.

In the present description, unless otherwise indicated, with the term functional group within a given molecule or moiety, we refer to the meaning commonly intended in the field of synthetic organic chemistry.

In the present case, in particular, with the term functional group we either intend any atom or group of atoms directly involved in the formation of a bond between A and L, R and L or even directly between A and R, as well as any other group which, being suitably protected with known methods, does not take part to the former reaction. From the above, functional groups taking part of a coupling reaction need to be properly activated or anyway be present as, or easily converted into, a reactive form. On the other side, any functional group which has not to be involved in the formation of a bond, despite its susceptibility to react, needs to be suitably protected so as to avoid the undesired formation of by-products; means for protecting and deprotecting functional groups are very well-known in the art.

According to the compounds of the invention and to their preparation process, said functional groups are essentially selected from amino, carboxamido, carbonyl, carboxyl, hydroxyl and phosphonic groups.

The starting materials of the process, which can be hereinafter conveniently identified by the groups A, R and L, as well as any precursor and reactant thereof, are known compounds or can be prepared by working according to conventional methods.

As a non limiting example, whilst several aminopolyols of the invention are commercially available per se, others may be easily prepared by methods known in the art:

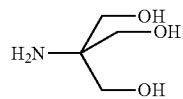

2-Amino-2-(hydroxymethyl)-1,3-propandiol, CAS number [77-86-1], commercially available;

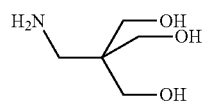

2-(Aminomethyl)-2-(hydroxymethyl)-1,3-propandiol, CAS number [7332-39-0]; Hiskey, M. A. et al. Propellants, Explosives, Pyrotechnics, 1991, 16, 40-42;

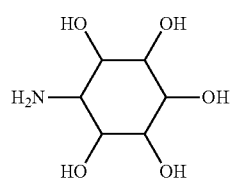

See Kitagawa, I. et al. Chem. Pharm. Bull. 1984, 32, 4858-4865;

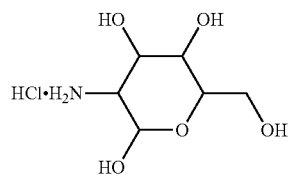

Glucosamine hydrochloride, [66-84-2], commercially available;

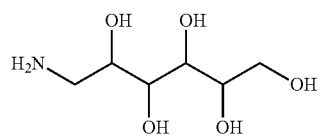 [SMILES: NCC(O)C(O)C(O)C(O)CO]

D-glucamine, [488-43-7], commercially available;

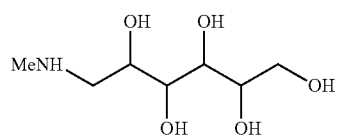

N-Methyl-D-glucamine, [6284-40-8], commercially available;

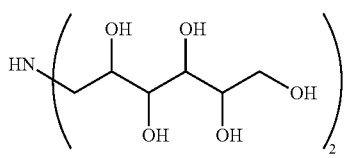

1,1'-Iminobis[1-deoxyglucitol], [15351-31-2], van Haveren, J. Et al. Carbohydrate Res. 1993, 243, 259-271.

In addition to the above, general bibliographic references are herewith provided for the preparation of the corresponding amines of the aminopolyols formerly indicated as A1 (Ashton, P. R. et al. Chem. Eur. J. 1996, 2, 1115-1128) and B1 (Tetrahedron Lett. 2000, 41, 8485-8488; CAS [55264-15-8]).

Some aminopolyols according to the invention, or the amines to which they refer, are new and thus constitute a further object of the present invention.

In particular, the said novel aminopolyols include the following compounds:

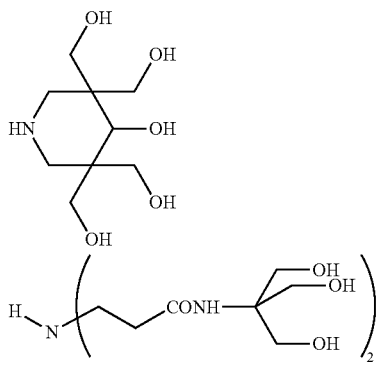

as well as those previously indicated as A2, B2, B3, from C1 to C11, from D1 to D11, from E1 to E11, from F1 to F11 and from G1 to G11.

The paramagnetic complexes of the invention and, particularly, the Gd(III) chelated may be prepared by stoichiometric addition of suitable Gd(III) derivatives; particularly Gd(III) salts or oxides.

Preferably, Gd(III) chloride or oxide is employed by working according to well known experimental methods, for instance as reported in EP 230893.

For a general reference to the operative conditions being employed in the process of the invention, as well as to the reaction schemes being employed, see the following experimental section.

Because of their high relaxivity, the NSA of the invention represent a significant improvement over the prior art, particularly in comparison to the NSA being used in the clinical practice.

Surprisingly, the high relaxivity is not only dependent on the MW (preferably lower than about 3.5 kDa). In fact, some tests have been performed to evaluate the correlation between relaxivity and MW for a number of Gd-based contrast agents.

In this respect, some representative compounds of the invention were tested, as set forth in the experimental section, in comparison to derivatives bearing the same backbone chelating structure but without the L-R groups of the invention. The obtained results clearly indicate that the Gd-chelated compounds of the invention provide an additional contribution to relaxivity of at least 3 $mM^{-1}$ $s^{-1}$, and in some cases even higher, and that the obtained relaxivity is higher than would have been expected for these same compounds on the basis of their MW (see FIG. 1 and example 34). Similar results have been obtained when a number of different Gd-chelated compounds of the invention, including either linear or cyclic backbone chelating structures, were compared with the relaxivity of some marketed NSA, well-known LDA and other compounds being prepared for comparative purposes.

The obtained relaxivity values were plotted versus the corresponding MW (see FIG. 2 and example 34). Also in this case, there was an additional contribution to the relaxivity for the compounds of the invention that is certainly unexpected in the light of their MW.

The relaxivity enhancement shown by the compounds of the invention is further magnified when the relaxivity values $r_{1p}$, measured at 20 MHz and 298K., are plotted against the molecular reorientational values $\tau_R$ of the same compounds (FIG. 3). This latter parameter $\tau_R$, used for this plotting, can be suitably obtained from the fitting of 1/T1 NMRD (Nuclear Magnetic Resonance Dispersion) profiles according to known procedures.

Even more interestingly, the improved relaxivity the compounds of the invention possess is unexpectedly maintained, substantially unchanged, by varying the magnetic field strength from about 0.01 to about 130 MHz (FIGS. 4, 5 and 5 bis).

As an example, the relaxivity profile of the gadolinium complex of the chelating ligand of the invention 2b (hereinafter referred to as Gd-2b), in the above magnetic field range, has been compared with that of a marketed NSA, i.e. Magnevist®, and that of a blood pool agent, i.e. the macromolecular adduct between Gd-DTPA(BOM)3 and BSA (Bovine Serum Albumin) (FIG. 6).

The analysis of the obtained profiles shows that while the relaxivity of Magnevist® from 0.2 to 3 MHz is quite stable though very low, the relaxivity exhibited by the compounds of the invention, under the same conditions, is substantially stable and significantly higher. The corresponding profile for the above blood pool agent is quite different. In fact, it shows an increase in the relaxivity at 25-30 MHz that, however, falls in a very short range of field strength. All of these results strongly support that the compounds of the invention may be advantageously used over an extended range of magnetic field strength and, hence, represent a valuable tool for the ongoing trend in the MRI field.

Some of the chelated compounds of the invention have been also examined for their pharmacokinetic profile. These compounds show a biodistribution profile analogous to that shown by typical NSA like ProHance®, Magnevist®, Dotarem® and Omniscan® (see examples 36-37).

The compounds of the invention have a wide range of applications as they can be used for intravasal, (for instance intravenous, intraarterial, intracoronaric, intraventricular administration and the like), intrathecal, intraperitoneal, intralymphatic and intracavital administrations. Furthermore, the compounds are suitable for the oral or parenteral administration and, therefore, specifically for the imaging of the gastrointestinal tract.

For parenteral administration they can be preferably formulated as sterile aqueous solutions or suspensions, whose pH can range from 6.0 to 8.5.

These aqueous solutions or suspensions can be administered in concentrations ranging between 0.002 and 1.0 M. These formulations can be lyophilized and supplied as they are, to be reconstituted before use.

For the gastrointestinal use or for injection in the body cavities, these agents can be formulated as a solution or suspension optionally containing suitable excipients in order, for example, to control viscosity.

For the oral administration they can be formulated according to preparation methods routinely used in the pharmaceutical technique or as coated formulations to gain additional protection against the stomach acidic pH, thus preventing the chelated metal ion from release, which takes place particularly at the typical pH values of gastric fluids.

Other excipients, for example including sweeteners and/or flavouring agents, can also be added, according to known techniques of pharmaceutical formulations.

The solutions or suspensions of the compounds of this invention can also be formulated as aerosol to be used in aerosol-bronchography and instillation.

Optionally, the compounds of the present invention can be chemically conjugated to suitable macromolecules or incorporated into, or encompassed within, suitable carriers.

For example, they can be also encapsulated into liposomes or even constitute the liposomes themselves, and thus can be used as uni- or multi-lamellar vesicles.

It is therefore a further object of the invention a chelated complex of a compound of formula (I), or a pharmaceutically acceptable salt thereof, with a bi- or trivalent paramagnetic metal ion, particularly gadolinium, for diagnostic use.

It is an additional object of the invention the use of a chelated complex of formula (I) with a paramagnetic metal ion, particularly gadolinium, or a physiologically compatible salt thereof, in the preparation of a pharmaceutical formulation for the diagnostic imaging of a human or animal body organ or tissue by use of M.R.I.

In a further aspect, the invention relates to a pharmaceutical composition for diagnostic use comprising a chelated compound of the invention. Preferably, the invention relates to a contrast-producing composition comprising at least one Gd-based NSA of the invention.

According to a further object, the present invention also refers to a method of imaging a human or animal body organ or tissue by use of MRI, said method comprising administering a pharmaceutical composition comprising a paramagnetic metal ion complex of the invention, or a pharmaceutically acceptable salt thereof, to the human or animal body.

A further object of the invention includes chelated complexes of a compound of formula (I) with a radionuclide or a physiologically compatible salt thereof.

For use as a diagnostic imaging agent (e.g. scintigraphic) compounds of formula (I) are complexed with a diagnostic radionuclide. For use in radiotherapy, compounds of formula (I) are complexed with a therapeutic radionuclide. Preferably, such chelated complexes include one or more appropriate targeting moieties and are thus able to localize to tissue of interest.

BRIEF DESCRIPTION OF THE DRAWINGS

FIG. 6: $^1$H 1/T1 NMRD profiles (25° C., 1 mM aqueous solutions) of Gd-2b (●), Gd-DTPA (Magnevist)® (■) and the non covalent adduct between Gd-DOTA(BOM)$_3$ and BSA (○).

EXPERIMENTAL SECTION

Figure 1:
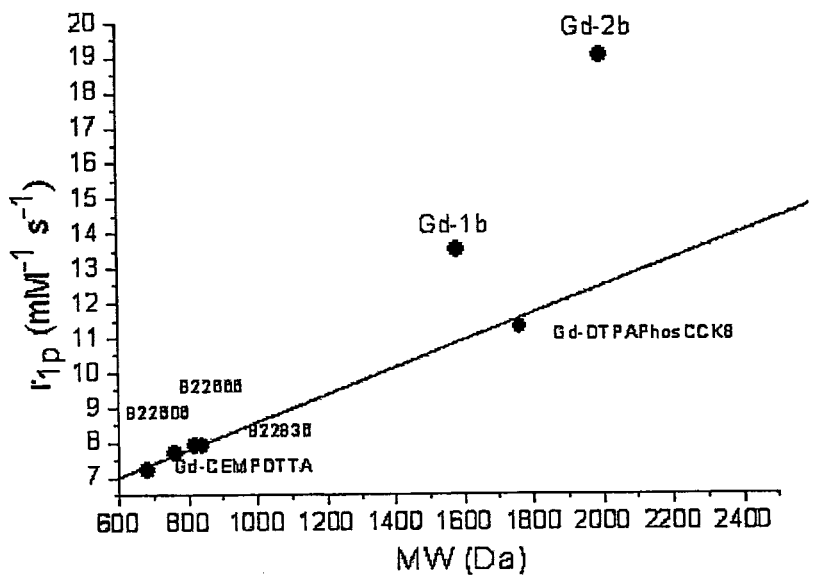
FIG. 1: Relaxivity values for q=1 Gd(III)-complexes of the invention bearing a phosphonate chelating group and comparative Gd-complex compounds, plotted against their molecular weight (25° C., neutral pH, 0.47 T).

A non-limiting list of preferred compounds of the invention and intermediates for their preparation is reported in the following section, to better exemplify the wide applicative potential of the present invention.

Herewith reported is a list of abbreviations being used in the following experimental section; several others are not herewith reported as being conventionally adopted.

| DBU | 1,8-diazabicyclo[5.4.0] undecene-7-ene | TMG | N,N,N',N'-tetramethyl-guanidine |
| --- | --- | --- | --- |
| DIEA | diisopropylethyl-amine | EDC | N-(3-dimethylaminopropyl)-N'-ethylcarbodiimide |
| DMF | N,N-dimethylformamide | HOBT | 1-hydroxybenozotriazole |
| TFA | trifluoroacetic acid | DIC | N,N'-diisopropyl-carbodiimide |
| DMAP | dimethylaminopyridine | TEA | triethylamine |
| HATU | O-(7-azabenzotriazol-1-yl)-N,N,N',N'-tetramethyluronium hexafluorphosphate | HBTU | O—(1H-benzotriazole-1-yl)-N,N,N',N'-tetramethyluronium hexafluorophosphate |
| 9-BBN | 9-borobicyclo[3.3.1]nonane | THF | tetrahydrofuran |
| DMSO | dimethyl sulfoxide | Tris | Tris(hydroxymethyl)aminomethane |
| DCC | N,N'-dicyclohexyl-carbodiimide | | |

Example 1

Preparation of the Compound 1a of Formula

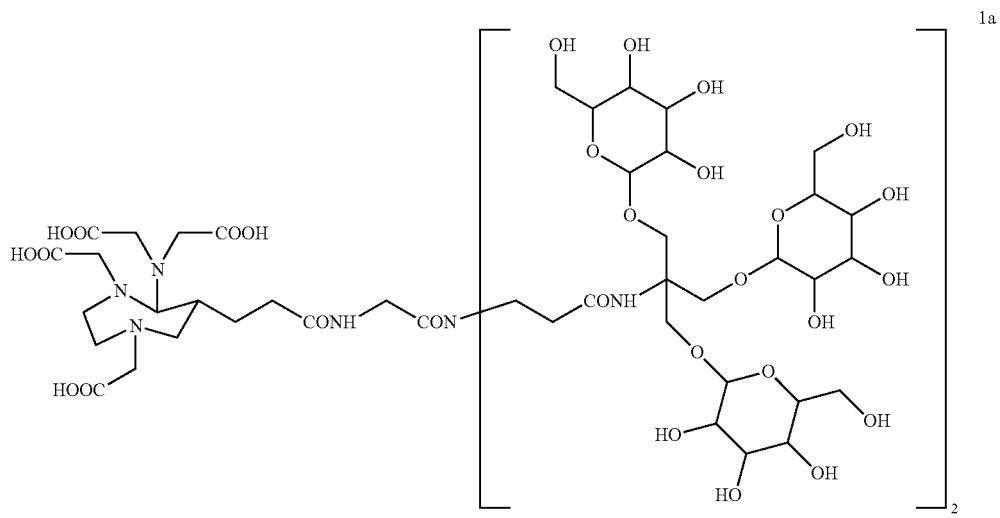

The preparation includes the following steps.
a) synthesis of the aminopolyol A2 according to the following scheme A;
b) synthesis of the backbone chelating structure suitably functionalized, as per scheme B;
c) coupling reaction according to the following scheme C.

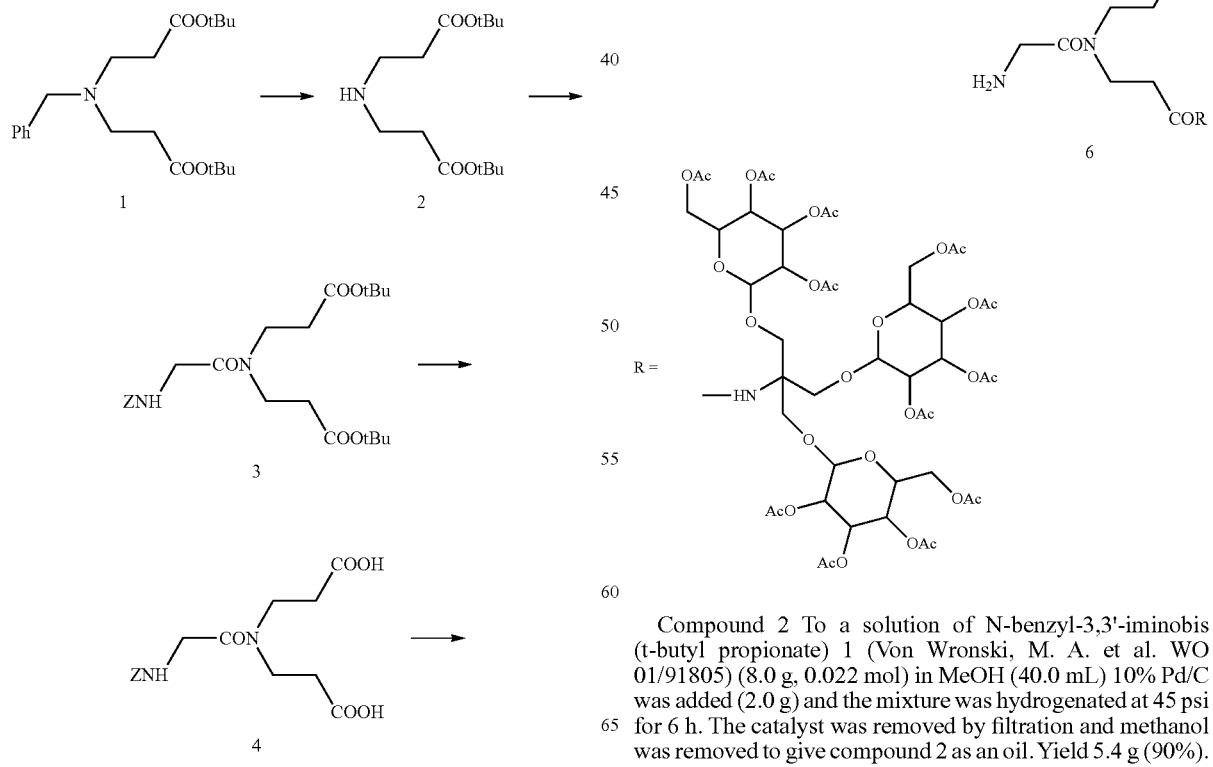

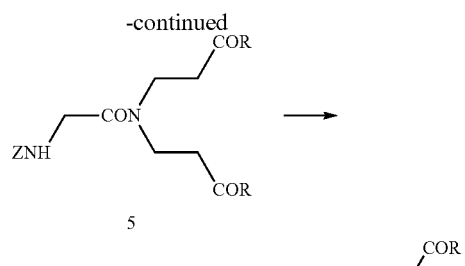

Compound 2 To a solution of N-benzyl-3,3'-iminobis (t-butyl propionate) 1 (Von Wronski, M. A. et al. WO 01/91805) (8.0 g, 0.022 mol) in MeOH (40.0 mL) 10% Pd/C was added (2.0 g) and the mixture was hydrogenated at 45 psi for 6 h. The catalyst was removed by filtration and methanol was removed to give compound 2 as an oil. Yield 5.4 g (90%). MS: 274 (M+H)

Compound 3 To a mixture of the amine 2 (5.46 g, 0.02 mol), Z-glycine (4.5 g, 0.0215 mol) and HATU (8.17 g, 0.0215 mol) in methylene chloride (25 mL) was added diisopropylethylamine (3.9 g, 5.41 mL, 0.03 mol) and the mixture was stirred for 6 h. Methylene chloride was removed and the residue was dissolved in ethyl acetate (150 mL) and washed with a saturated solution of sodium bicarbonate (2×100 mL), water (2×100 mL) and dried (Na$_2$SO$_4$). Evaporation of ethyl acetate gave a crude that was chromatographed over silica gel to give the Z-derivative 3 as a viscous oil. Yield 6.8 g (94%). MS: 487.2 (M+H)

Compound 4 TFA (15.0 mL) was added to compound 3 (2.32 g, 0.005 mol) and the solution was stirred for 6 h. TFA was removed to yield a viscous oil. This was dried under vacuum and then triturated with acetonitrile to yield compound 4 as a white solid. Yield 1.2 g (68%). MS: 353.4 (M+H)

Compound 5 To a solution of the di-acid 4 (0.1 g, 0.284 mmol) in DMF (2.0 mL) was added HOBT (0.1 g, 0.66 mmol) and DIC (0.1 mL). The mixture was stirred at RT for 2 h. Tris(2,3,4,6-O-acetyl-β-D-glucopyranosyl-oxymethyl)methylamine (Ashton, P. R; Boyd, S. E.; Brown C. L.; Jayaraman, N.; Nepogodiev, S. A.; Stoddart, J. F. *Chem. Eur. J.* 1996, 2, 1115-1128) (0.65 g, 0.58 mmol) was then added to the reaction mixture and stirred at 50° C. for 48 h. Then, DMF was removed under vacuum and the residue was dried under vacuum for 2 h. Water (5.0 mL) was added to the residue and the solution was decanted. This latter process was repeated (5×5 mL) and the obtained solid was filtered and air dried to give a pure product which was used in the subsequent hydrogenation step without further purification.

Compound 6 (aminopolyol A2 in protected form) To a solution of compound 5 (45 mg, 0.018 mmol) in MeOH (5 mL) 10% Pd/C was added (25 mg) and the mixture was hydrogenated at 15 psi for 6 h. The catalyst was removed and methanol was removed on a rotary evaporator to give a foamy solid. Yield 35 mg (81%). MS: 2407 (M+H).

Scheme B

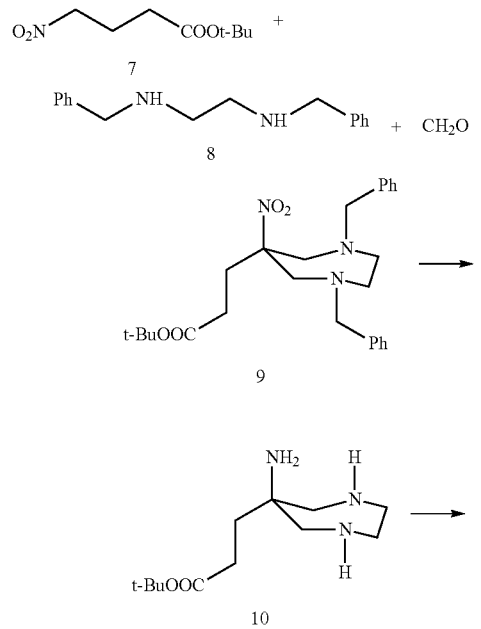

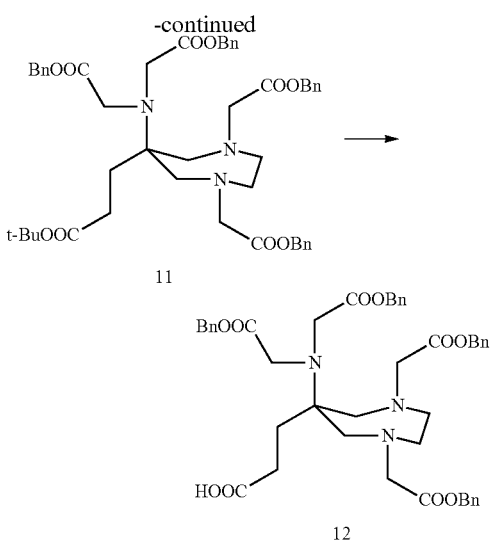

Compound 9 4-Nitrobutanoic acid 1,1-dimethylethyl ester 7 (Fuji, M.; Muratake, H.; Natsume, M. *Chem. Pharm. Bull.* 1992, 40 (9), 2338-2343) (3.00 g; 15.0 mmol) was added dropwise to a stirred solution of N,N-dibenzylethylendiamine acetate 8 (5.40 g; 15.0 mmol) in abs. EtOH (20 mL) and then heated to 60° C. Paraformaldehyde (1.50 g; 49.5 mmol) was added to the reaction mixture and, after 3 h, the solution was allowed to cool to room temperature. After 16 h the reaction mixture was evaporated under reduced pressure. The oily residue was dissolved in EtOAc (200 mL) and washed with sat. aq. NaHCO$_3$ (150 mL). The aqueous phase was extracted with EtOAc (200 mL). The organic phases were combined, dried (Na$_2$SO$_4$) and evaporated. The crude product was purified by flash chromatography to give 9 (6.00 g; 13.0 mmol) as a light yellow oil. Yield 86%. MS: 454.3 (M+H); 476.3 (M+Na)

Compound 10 10% Pd/C (1.00 g) was added to a solution of compound 9 (3.00 g; 6.62 mmol) in MeOH (110 mL). The reaction mixture was heated to 40° C. and stirred under a hydrogen atmosphere for 10 h. The mixture was filtered through a Millipore® apparatus (FH 0.5 μm) and evaporated to give 10 (1.46 g; 6.00 mmol) as a light yellow oil. Yield 97%. MS: 244.2 (M+H).

Compound 11 A solution of compound 10 (1.56 g; 6.40 mmol) in DMF (20 mL) was added dropwise to a mixture of K$_2$CO$_3$ (4.40 g; 32.0 mmol), Na$_2$SO$_4$ (2.70 g; 19.2 mmol) and benzyl-2-bromoacetate (7.33 g; 32.0 mmol) in DMF (20 mL). The reaction mixture was heated to 65° C. for 15 h under stirring, then filtered and evaporated. The residue was dissolved in EtOAc (300 mL) and washed with water (3×150 mL). The organic phase was dried (Na$_2$SO$_4$) and evaporated to a residue which was purified by column chromatography to give 11 (1.02 g; 1.22 mmol) as a yellow oil. Yield 19%. MS: 836.8 (M+H); 858.7 (M+Na).

Compound 12 A solution of compound 11 (0.74 g; 0.88 mmol) in TFA (5.0 mL) was stirred at room temperature for 4 h. The mixture was then evaporated, the residue taken up with CH$_2$Cl$_2$ (30 mL) and the solution evaporated under reduced pressure. The operation was repeated two more times. The crude oil was then purified by column chromatography. The fractions containing the product were pooled, evaporated, dissolved in 50 mL of H$_2$O/CH$_3$CN (80/20) and lyophilised to afford 12 (0.43 g; 0.55 mmol) as a white solid. Yield 62.5%. MS: 780.5 (M+H); 802.4 (M+Na).

Scheme C

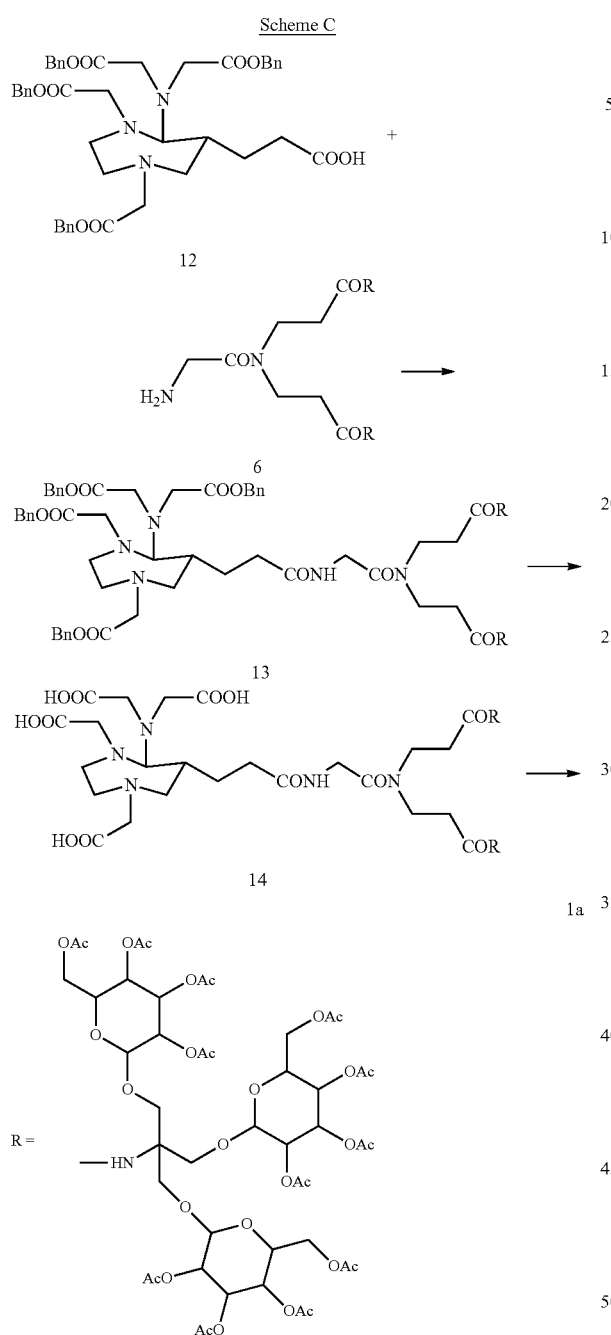

Compound 13 To a solution of compound 6 (0.58 g, 0.24 mmol), compound 12 (0.175 g, 0.225 mmol) and HATU (0.11 g, 0.29 mmol) in DMF (3.0 mL) was added diisopropylethylamine (0.3 mL) and the mixture was stirred for 24 h. DMF was removed under vacuum and the residue was dried under vacuum for 6 h. Water (5.0 mL) was added to the residue and the aqueous solution was decanted. Water (5.0 mL) was added again and the mixture was triturated. The solid formed was washed with water (6×5 mL) and filtered and dried. The crude product was purified by silica gel column chromatography using methylene chloride-methanol (95:5) to give product 13 as a foamy solid. Yield 0.22 g (31%). MS: 1584.3 (M+2H)/2.

Compound 14 To a solution of the benzyl ester 13 (0.35 g, 0.11 mmol) in methanol (10.0 mL) 10% Pd/C was added (150 mg) and the mixture was hydrogenated at 15 psi for 6 h. The catalyst was removed by filtration and the methanolic solution was concentrated to give an oil which was dried under vacuum to give compound 14 as a foamy solid. Yield 0.29 g (94%). MS: 1584.3 (M+2H)/2.

Compound 1a Methanol (10 mL) was saturated with ammonia at −20° C. Saturated methanolic ammonia (4.0 mL) was added to compound 14 (0.2 g, 0.07 mmol) and the reaction mixture was allowed to stand at 0° C. for 1 h and at RT for 48 h. A white solid was formed after 24 h. The methanolic solution was decanted and the solid obtained was then washed with methanolic ammonia (1.0 mL) and dried under vacuum to give product 1a. Yield. 98 mg (76.5%). MS: 1797 (M+H); 893.3 (M+2H)/2.

Example 2

Preparation of the Compound 3a of Formula

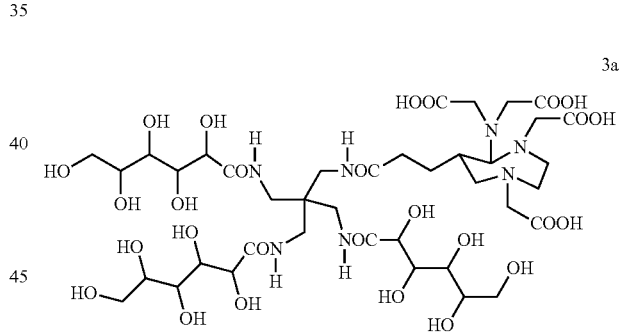

The preparation includes the following steps.
a) synthesis of the aminopolyol B2 according to the following scheme D;
b) coupling reaction according to the following scheme E Scheme D

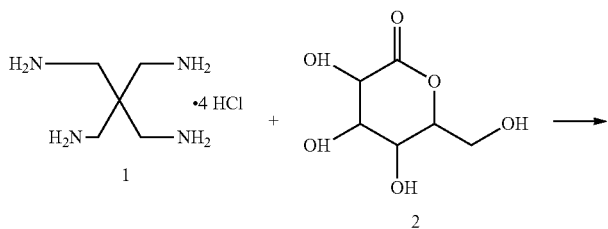

-continued
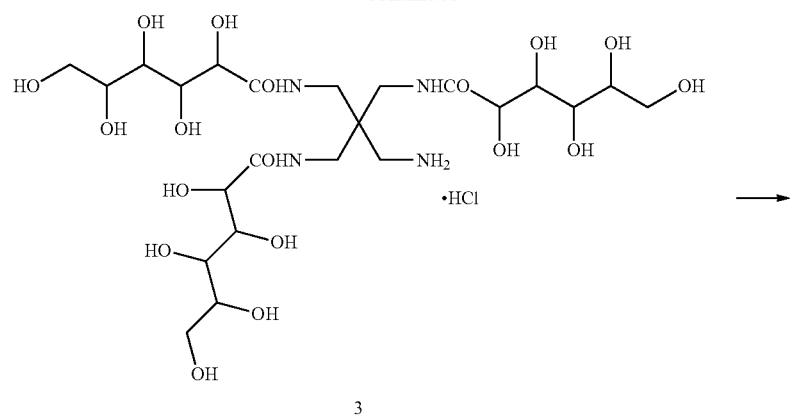
3
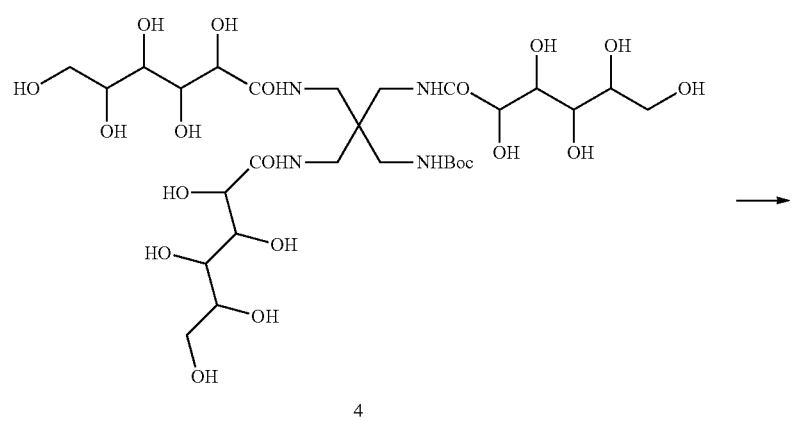
4
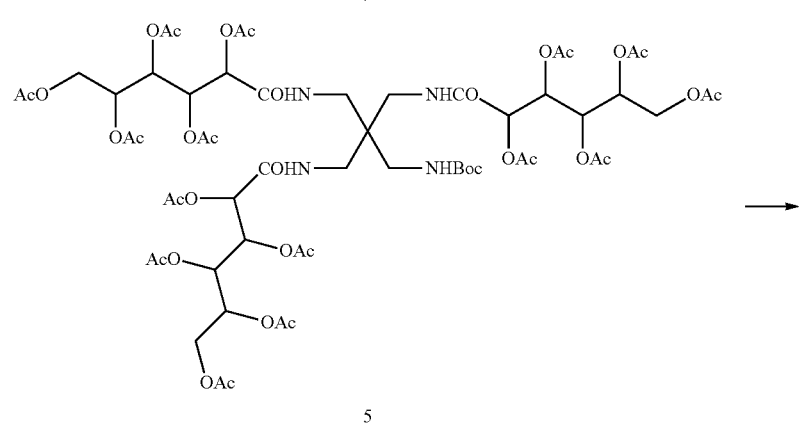
5
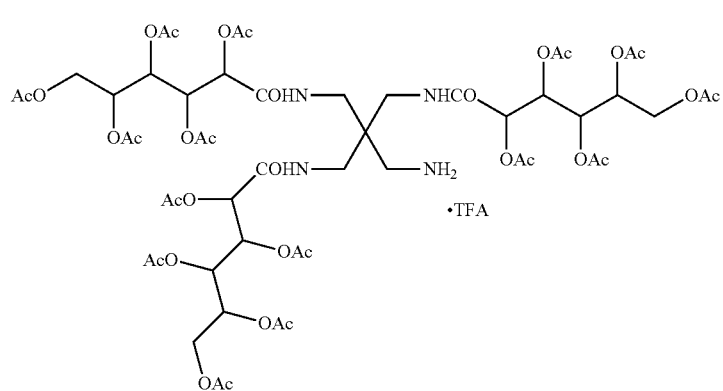
6

Compound 3 2,2-Bis(aminomethyl)-1,3-propanediamine tetrahydrochloride 1 (Zompa, L. J.; Bogucki, R. F. *J. Am. Chem. Soc.* 1966, 88, 5186-5191) (7 g; 25 mmol) was suspended in a mixture of DMF (85 mL) and TEA (12.48 mL; 90 mmol). A solution of commercially available δ-gluconolactone 2 (16 g; 90 mmol) in DMF (89 mL) was slowly added dropwise (1.5 h) at room temperature. The mixture was stirred at room temperature for two days. The reaction mixture was filtered and concentrated at reduce pressure. The residue was treated with acetonitrile to give a precipitate which was filtered and washed with acetonitrile. The solid was dried to give 3 (19 g; 28.5 mmol) as a white solid. Quantitative yield. MS: 667 (M+H).

Compound 4 Compound 3 (30.0 g, 45.0 mmol) was dissolved in DMF (450 mL) and a solution of (Boc)$_2$O (17.2 g; 65.2 mmol) in DMF (100 mL) was slowly added dropwise. Then tetramethylammonium hydroxide (8.15 g, 45.0 mmol) was added and the mixture was stirred at room temperature for 2 days. The solution was concentrated at reduced pressure. The residue was treated with CH$_2$Cl$_2$ to give a precipitate that was filtered and washed with H$_2$O (100 mL) and CH$_3$OH (100 mL). The solid was dried to give 4 (25 g; 32.6 mmol). Yield 72%.

Compound 5 To a suspension of compound 4 (10.0 g; 13.0 mmol) in Ac$_2$O (186 mL; 1.97 mol), pyridine (25.7 g; 326 mmol) was added at room temperature. The mixture was then heated to 90° C. to dissolve the reagents, then cooled at room temperature. After 1 day at room temperature, the mixture was concentrated at reduce pressure and the residue was dissolved in EtOAc (200 mL) and washed with water (200 mL) and with 10% aqueous NaHCO$_3$ (200 mL). The organic phase was dried (Na$_2$SO$_4$) and evaporated to give 5 (15 g; 10.7 mmol). Yield 82%.

Compound 6 (protected form of aminopolyol B2) TFA (3.67 g; 32.0 mmol) was added to a solution of compound 5 (4.50 g; 3.20 mmol) in CH$_2$Cl$_2$ (56 mL). After 3 days at room temperature, further TFA (1.82 g; 16.0 mmol) was added to the reaction mixture. After further 4 days at room temperature, the solvents were removed under reduced pressure and the residue was dissolved in CH$_2$Cl$_2$ (7 mL) and TFA (5.49 g; 48.0 mmol). The mixture was stirred at room temperature for 1 day, then evaporated under reduced pressure. The residue was dissolved in CH$_2$Cl$_2$ (10 mL) and evaporated. This operation was repeated two more times affording 6 (3.00 g; 2.31 mmol) as a white solid. Yield 72%.

Scheme E

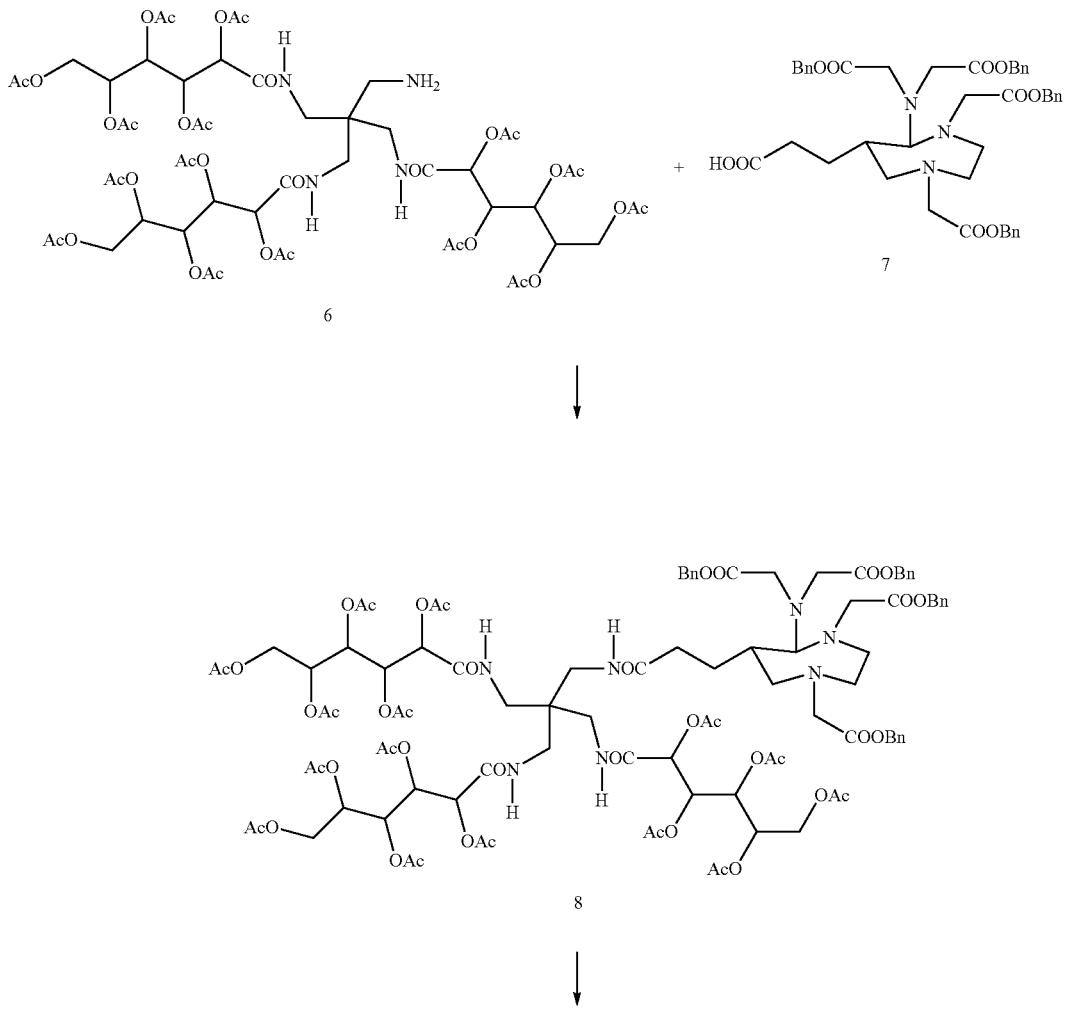

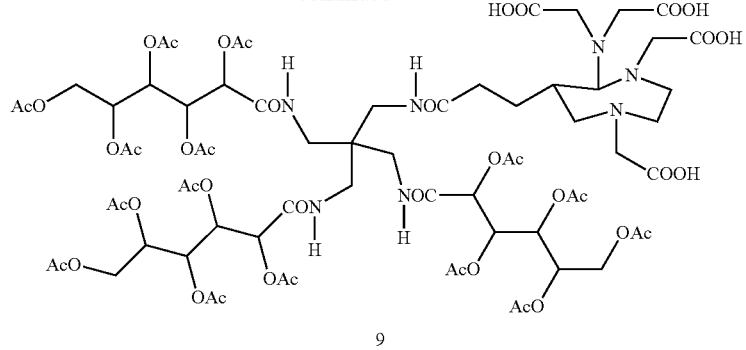

9

↓

3a

Compound 8 To a cooled mixture of acid 7 (see EXAMPLE 1) (0.45 g, 0.55 mmol) and HATU (0.23, 0.6 mmol) in DMF (3.0 mL) was added diisopropylethylamine (0.23 g, 0.32 mL, 1.8 mmol) and the mixture was stirred for 5 min. A solution of compound 6 (0.65 g, 0.5 mmol) in DMF (3.0 mL) was added to the activated acid and the solution was stirred at RT for 12 h. DMF was removed under vacuum and the thick oil obtained was treated with a saturated solution of sodium bicarbonate (2×10 mL). The obtained yellow solid was washed with water (3×10 mL) filtered and dried. The crude product obtained was purified by silica gel column chromatography using methylene chloride-methanol (95:5) to give product 8 as a foamy solid. Yield 320 mg (30%). MS: 2060.4 (M+H)

Compound 9 To a solution of compound 8 (0.32 g, 0.15 mmol) in methanol (30 mL) 10% Pd/C was added (300 mg) and the solution was hydrogenated at 45 psi for 6 h. The catalyst was removed by filtration and the methanolic solution was concentrated to give the tetra-acid 9 as a white foamy solid. Yield. 0.25 g (94%). MS: 1700.2 (M+H).

Compound 3a A saturated solution of ammonia in methanol (—25%, 5 mL) was added to the tetraacid 9 (0.25 g, 0.14 mmol) and the solution was allowed to stand at 4° C. for 48 h. The hydroxy compound 3a precipitated as a white solid. The supernatant solution was carefully decanted and the solid was washed with methanolic ammonia (2×0.5 mL) and the methanolic ammonia solution was decanted. The white solid obtained was dried under vacuum to give compound 3a. Yield 0.13 g (88%). MS: 1068.7 (M+H).

Example 3

Preparation of the Compound 2a of Formula

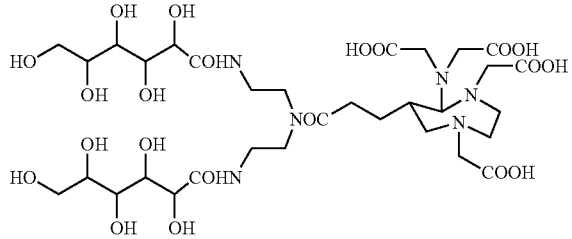

2a

The preparation includes the following steps as per scheme F

Scheme F

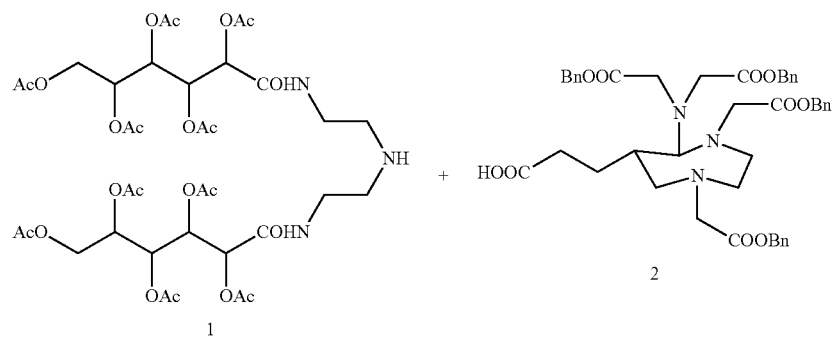

↓

-continued

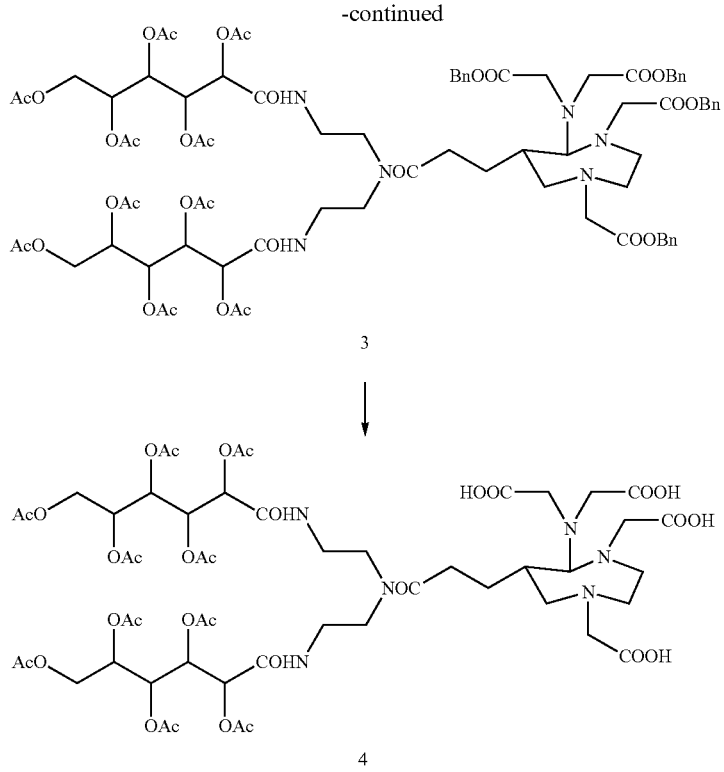

Compound 3 To a cooled mixture of acid 2 (see EXAMPLE 1) (0.65 g, 0.8 mmol) and HATU (0.342, 0.9 mmol) in DMF (3.5 mL) was added diisopropylethylamine (0.312 g, 0.43 mL, 0.24 mmol) and the mixture was stirred for 5 min. To this mixture, a solution of compound 1 (protected aminopolyol B1) (Takahashi, M. et al. *Tetrahedron Lett.* 2000, 41, 8485-8488) (0.62 g, 0.7 mmol) in DMF (3.5 mL) was added and the solution was stirred at RT for 12 h. DMF was removed under vacuum and the thick oil obtained was taken up in ethyl acetate and washed with a saturated solution of sodium bicarbonate (2×10 mL), water (2×10 mL) and dried ($Na_2SO_4$). Evaporation of ethyl acetate gave a crude product which was purified by silica gel column chromatography using methylene chloride-methanol (95:5) to give product 3 as a foamy solid. Yield 360 mg (31%). MS: 1642.1 (M+H)

Compound 4 to a solution of tetrabenzyl ester 3 (0.36 g, 0.22 mmol) in methanol (40 mL) 10% Pd/C was added (300 mg) and the solution was hydrogenated at 45 psi for 6 h. The catalyst was removed by filtration and the methanolic solution was concentrated to give the tetraacid 4 as a white foamy solid. Yield. 0.26 g (93%). MS: 1281.8 (M+H); 1303.8 (M+Na)

Compound 2a A saturated solution of ammonia in methanol (~25%, 5 mL) was added to the tetraacid 4 (0.26 g, 0.2 mmol) and the solution was allowed to stand at 4° C. for 48 h. The deacetylated product precipitated as a white solid. The methanolic ammonia solution was carefully decanted and the solid was washed with methanolic ammonia (2×0.5 mL) and the methanolic ammonia solution was decanted. The white solid obtained was dried under vacuum to give compound 2a. Yield 0.15 g (86%). MS: 861.6 (M+H).

Example 4

Preparation of the Compound 1b of Formula

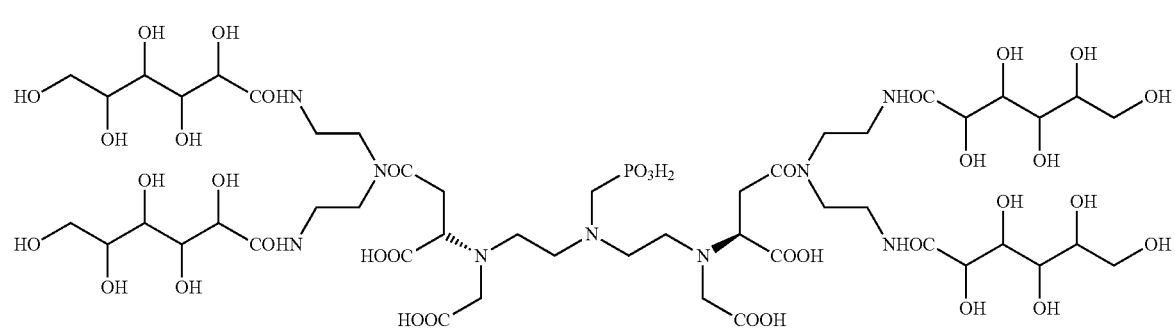

The preparation includes the following steps as per schemes G1, G2, G3 and H.

Scheme G₁

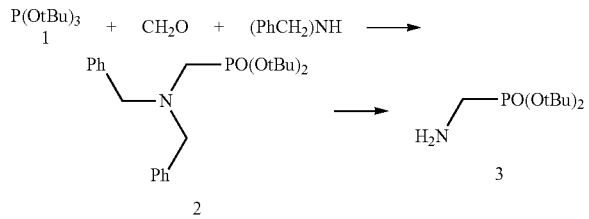

Compound 2 Paraformaldehyde (4.22 g; 140.6 mmol) was added to a solution of dibenzylamine (25.0 g; 127 mmol) in MeCN (250 ml). The suspension was heated to 80° C. for 1 hour, then the resulting solution was cooled to rt. A solution of tri-t-butyl phosphite (Cox, J. R.; Newton, M. G. *J. Org. Chem.* 1969, 34, 2600-2605) (35.2 g; 140.6 mmol) in MeCN was added dropwise over 25 min to the reaction mixture and the solution was stirred at room temperature for 22 h. The solvent was evaporated under vacuum and 0.1 N HCl (630 mL) was added to the residue. The suspension was extracted with $CH_2Cl_2$ (3×300 mL) and the combined organic phases washed with water (3×300 ml), dried ($Na_2SO_4$) and evaporated in vacuo. The crude (53.6 g) was purified by chromatography on silica gel (15:85 EtOAc/Petroleum Ether) and the desired product was obtained (33.32 g) as a white solid. Yield: 65.3%. MS: 404 (M+H)

Compound 3 Compound 2 (33.3 g; 82.7 mmol) was dissolved in MeOH (500 mL) and hydrogenated at atmospheric pressure on 10% Pd/C (3.3 g). After 2 h the mixture was filtered through Millipore Apparatus® (0.5 µm) and the solution evaporated under vacuum. The crude (18.4 g) was used without any further purification. Quantitative yield. MS: 224 (M+H).

Scheme G₂

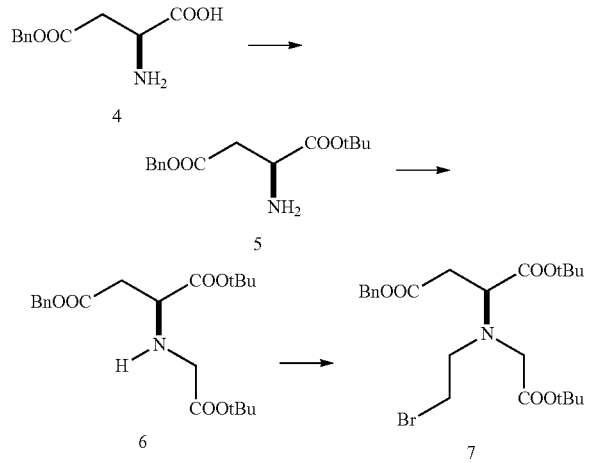

Compound 5 70% aq. $HClO_4$ (13.5 g; 0.134 mol) was dropped into a suspension of L-aspartic acid 4-(phenylmethyl) ester 4 (commercially available) (25 g; 0.112 mol) in tBuOAc (515 mL; 3.822 mol) stirred at room temperature. After 18 h at room temperature the obtained clear solution was diluted with $H_2O$ (470 mL) and the phases were separated; the aqueous phase was extracted with EtOAc (2×235 mL). The organic phases were collected and washed with 5% aq. $NaHCO_3$ (2×250 mL) and water (2×200 mL). The new aqueous phases were collected and extracted with EtOAc (3×100 mL). All organic phases were collected, dried over $Na_2SO_4$ and evaporated to obtain 5 (24.12 g) as a colourless oil. Yield 77%. MS: 280.2 (M+H), 302.2 (M+Na). Elemental Analysis (for $C_{15}H_{21}NO_4$): Calc. C 64.50; H 7.58; N 5.01. Found C 64.40; H 7.60; N 5.17.

Compound 6 A mixture of compound 5 (24.12 g; 0.086 mol), $BrCH_2CO_2tBu$ (17.68 g; 0.091 mol), MeCN (144 mL) and 2 M phosphate buffer pH 8 (72 mL) was vigorously stirred at room temperature; after 18 h the phases were separated and the organic phase was evaporated. The residue thus obtained was dissolved in EtOAc (300 mL) and washed with $H_2O$ (2×150 mL) and sat. aq. NaCl (2×150 mL). After drying over $Na_2SO_4$, the organic solution was evaporated to give a crude that was purified by flash-chromatography to give 6 (19.61 g) as a colourless oil. Yield 58%. MS: 416.2 (M+Na) Elemental Analysis (for $C_{21}H_{31}NO_6$): Calc. C 64.10; H 7.94; N 3.56. Found C 64.20; H 8.00; N 3.64.

Compound 7 Trifluoromethanesulfonic acid 2-bromo ethyl ester (Franzini, M. et al. WO 01/46207) (16 g; 0.062 mol) was slowly dropped into a solution of compound 6 (14 g; 0.036 mol) and 2,6-lutidine (12 g; 0.112 mol) in toluene (210 mL) stirred at −15° C. under inert atmosphere ($N_2$). The reaction mixture was stirred at room temperature for 20 h than diluted with water (100 mL) and extracted with EtOAc (100 mL). The organic solution was dried over $Na_2SO_4$ and evaporated to give a crude that was purified by chromatography to obtain 7 (10.35 g) as a pale yellow oil. Yield 58%.

MS: 522.3 (M+Na)

Scheme G₃

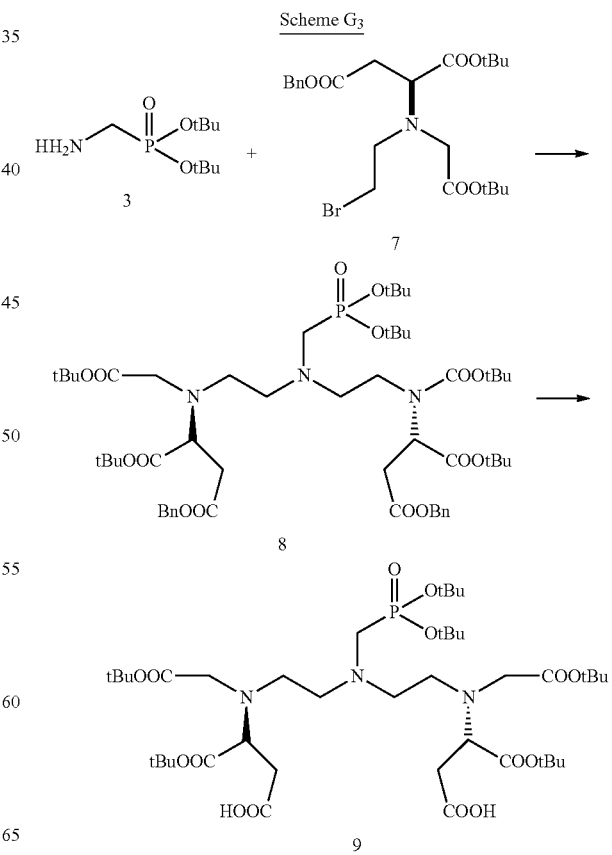

Compound 8 A solution of bromo-derivative 7 (4.11 g; 8.22 mmol) in MeCN (20 mL) was slowly dropped into an emulsion of phosphonate 3 (916 mg; 4.11 mmol) in MeCN (10 ml) and 2 M phosphate buffer (pH 8) (20 ml) over 8 hours under vigorous stirring. After 22 h, the phases were separated and the aqueous layer was extracted with EtOAc (2×30 ml). The organic phases were evaporated. The oily residue was taken up with EtOAc (20 mL), and the combined organic phases were washed with 1:1 water/brine (2×30 mL) and dried over $Na_2SO_4$. The crude was purified by silica gel chromatography. Compound 8 was obtained (1.85 g) as a yellow oil. Yield 42%. MS: 1062.8 (M+H), 1084.8 (M+Na).

Compound 9 Compound 8 (973 mg; 1.10 mmol) was dissolved in MeOH (50 ml) and hydrogenated at atmospheric pressure on 10% Pd/C (50 mg). After 30 min the reaction mixture was filtered through Millipore Apparatus® (0.5 μm filter) and the solution evaporated under vacuum. The product (725 mg) was used in the next step without any further purification. Yield 75%. MS: 881 m/z (M+H).

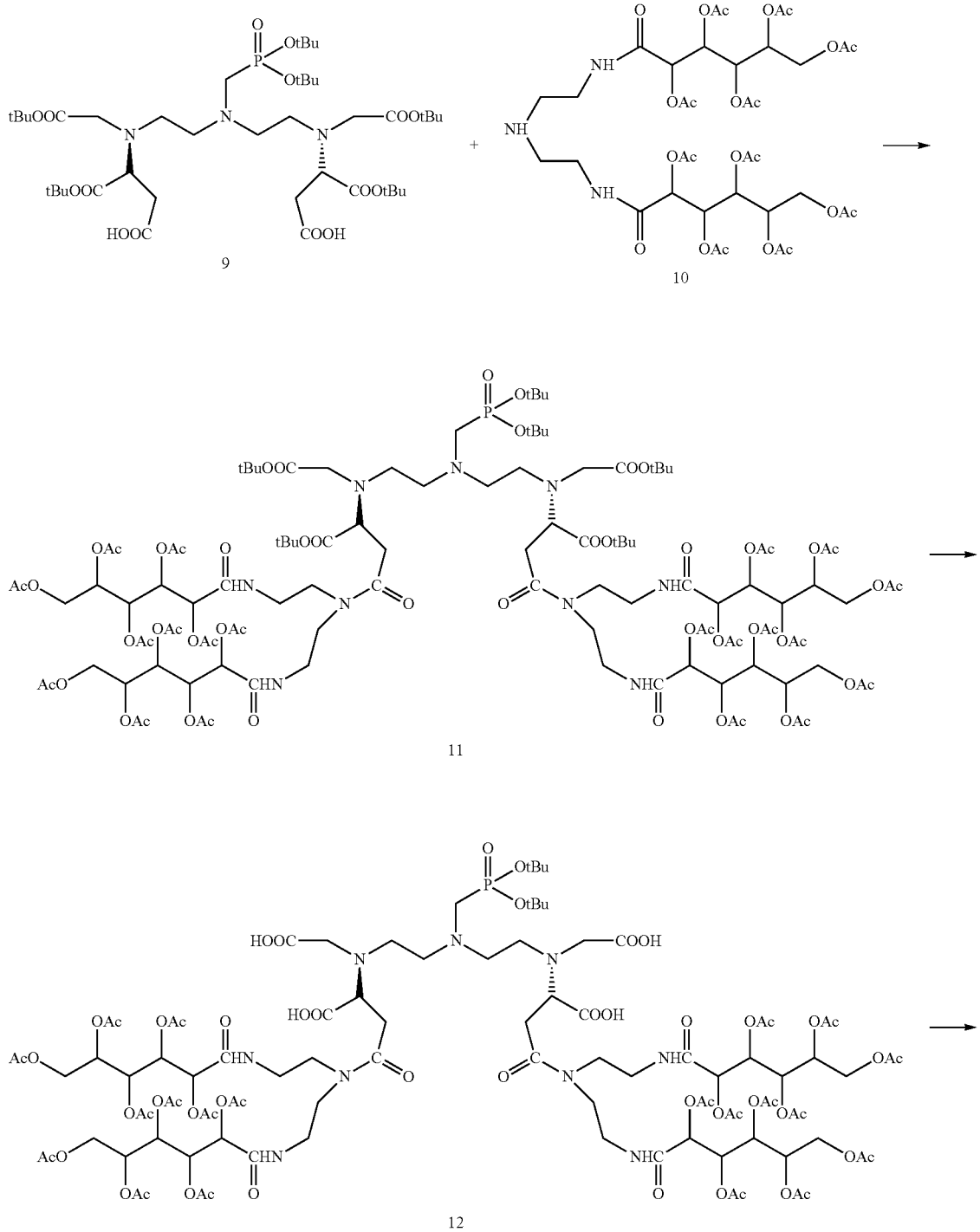

Scheme H

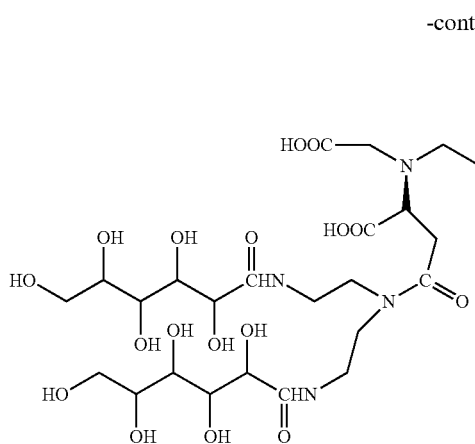

1b

Compound 11 To a solution of 9 (636 mg; 0.36 mmol) and 10 (Takahashi, M. et al. *Tetrahedron Lett.* 2000, 41, 8485-8488) (634 mg; 0.72 mmol) in dichloromethane (10 ml), HATU (274 mg; 0.72 mmol) was added and the mixture was stirred to obtain an almost clear solution. DMA (189 μL; 1.08 mmol) was added and the solution stirred at room temperature. After 26 h the mixture was washed with 1:1 water/brine (1×20 ml) and brine (1×20 ml). The aqueous layers were extracted with dichloromethane (1×20 ml) and the combined organic layers were dried over $Na_2SO_4$ and evaporated under vacuum. The crude was purified by chromatography on silica gel ($CHCl_3$/MeOH 9:1). The fractions containing the product were combined and evaporated to afford product 11 (328 mg). Yield 35%. MS: 2606.3 (M+H); 2629.1 (M+Na).

Compound 12 Compound 11 (100 mg; 0.038 mmol) was cooled with an ice bath and TFA (2 ml) was added dropwise giving a brown solution. After 30 min, the ice bath was removed and the solution was kept under stirring at rt. for 27 hours. The solvent was removed, the residue was taken up with dichloromethane (5 ml) and the solution evaporated. This procedure was repeated three times. Finally the residue was dried under vacuum pump (115 mg). Quantitative yield. MS: 2270.2 (M+H); 2309.9 (M+K).

Compound 1b To a solution of 12 (115 mg) in MeOH (0.5 ml) a 6.5% methanolic ammonia solution (2 ml) was added and the mixture was stirred at room temperature overnight. A white solid separated from the solution. The solid was filtered, suspended in 6.5% methanolic ammonia solution (4 ml) and stirred for 20 h at rt. The solid was decanted and dried in vacuo to give 1b (38 mg) as a white solid. Yield 53%. MS: 1428 (M+H).

Example 5

Preparation of the Compound 2b of Formula

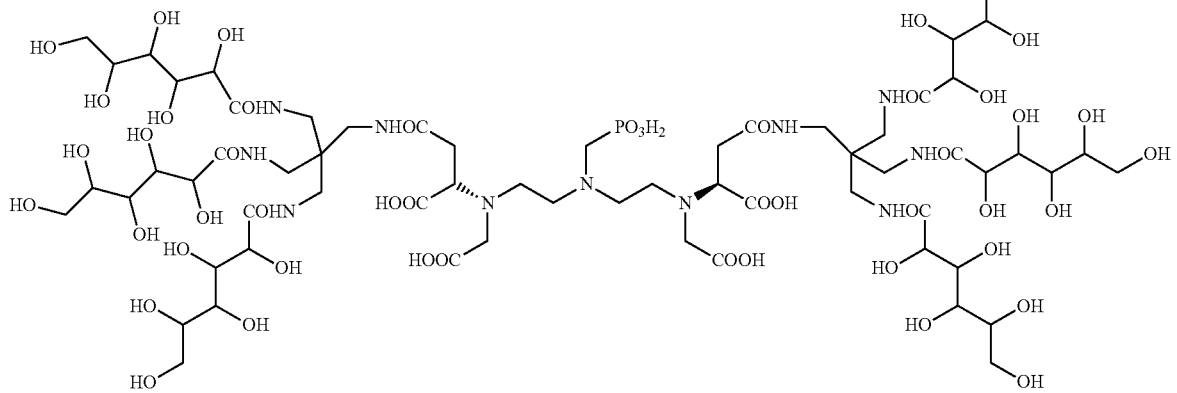

2b

The preparation of 2b include the following steps:
a) synthesis of the aminopolyol moiety according to step (a) of EXAMPLE 2;
b) synthesis of the backbone chelating structure suitably functionalized according to step (a) of EXAMPLE 4;
c) coupling reaction, carried out by operating in analogy to what reported in EXAMPLE 4, as per the following scheme I Scheme I
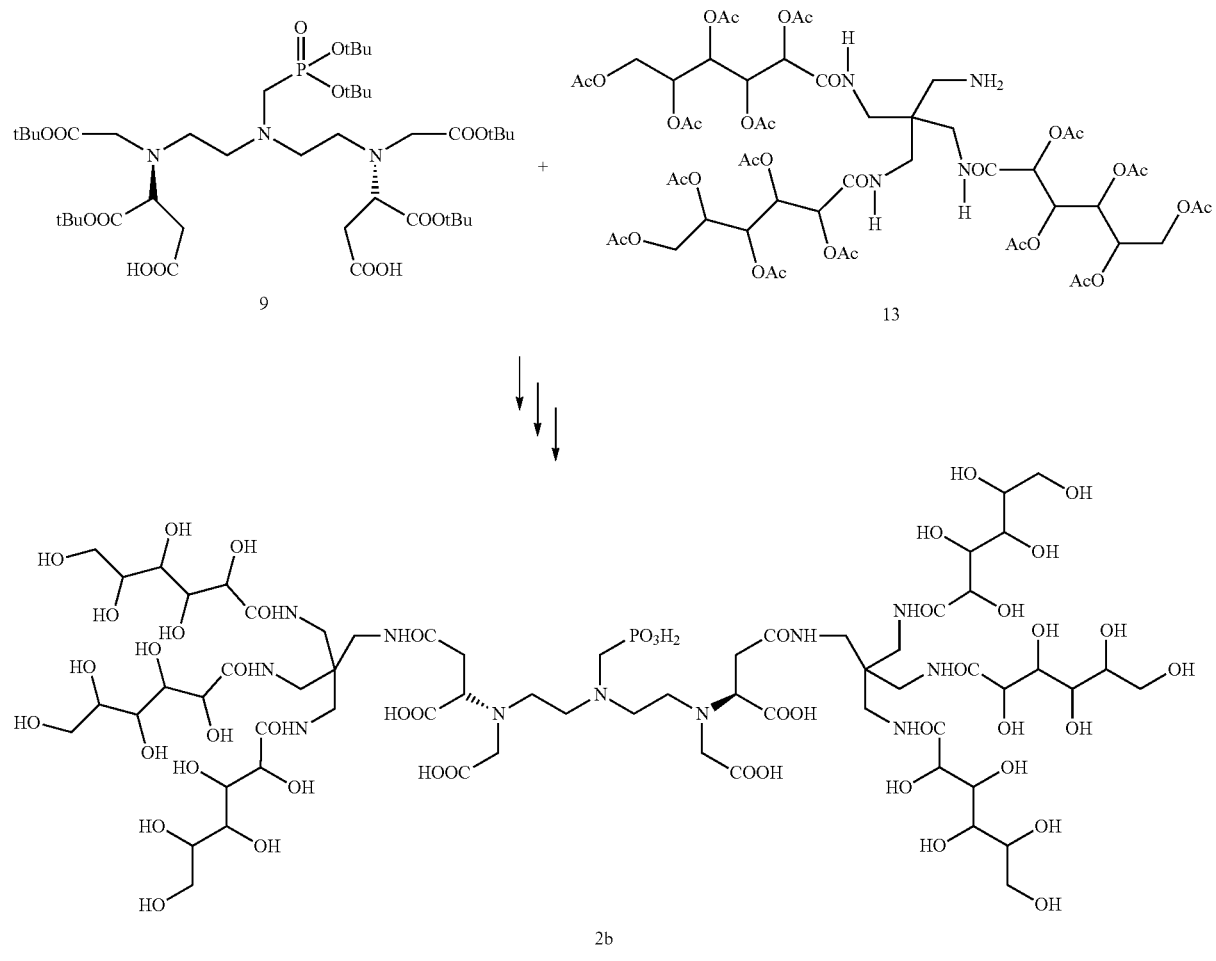
Example 6
Preparation of the Chelated Compound Gd-1c of Formula
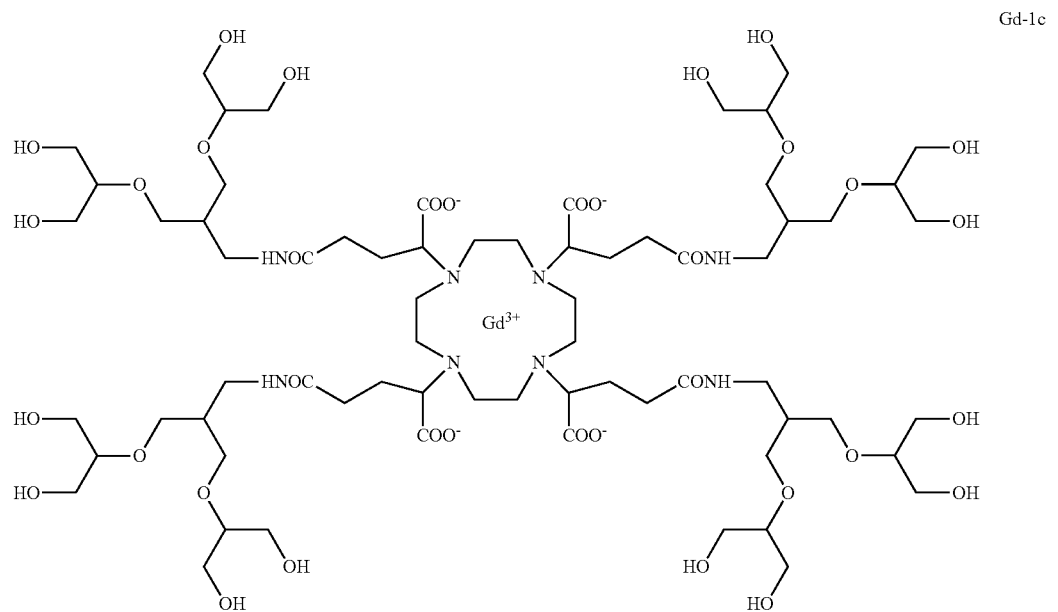

The preparation includes the following steps:
a) synthesis of the aminopolyol G1 according to the following scheme L;
b) coupling reaction according to scheme M

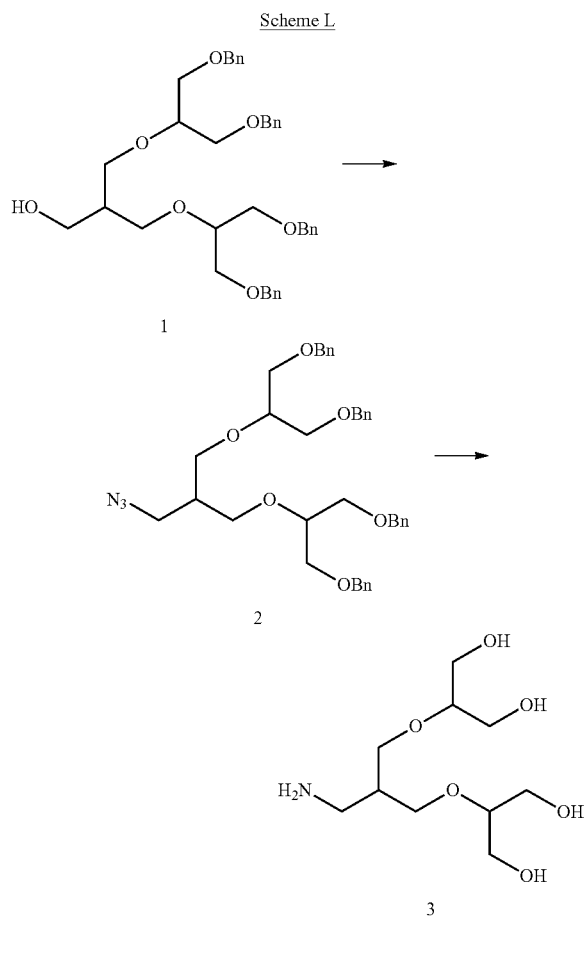

Compound 2 To a stirred solution of alcohol 1 (Grayson, S. M.; Fréchet, J. M. J. *J. Am. Chem. Soc.* 2000, 122, 10335-10344) (2.154 g, 3.50 mmol) and $Et_3N$ (1.22 mL, 8.75 mmol) in $CH_2Cl_2$ at 0° C. under an Ar atmosphere was added drop-wise methanesulfonylchloride (0.60 mL, 7.74 mmol). The reaction mixture was stirred at 0° C. for 1 h, then $H_2O$ was added (20 mL) and the mixture stirred vigorously for 10 min. The mixture was transferred to a separatory funnel and $CH_2Cl_2$ was then added (100 mL). The organic layer was then washed with 1 M HCl (100 mL), saturated $NaHCO_3$ solution (100 mL) and $H_2O$ (100 mL). The organic layer was dried ($MgSO_4$), filtered and evaporated to dryness to afford the crude mesylate (2.48 g), which was immediately used.

A suspension of crude mesylate and $NaN_3$ in DMF (20 mL) was stirred at 60° C. under an Ar atmosphere for 14 h. The solvent was then removed and the residue partitioned between $H_2O$ (100 mL) and $CH_2Cl_2$ (100 mL). The aqueous phase was further extracted with $CH_2Cl_2$ (2×100 mL), and the organics combined, dried ($MgSO_4$), filtered and evaporated to dryness. The product was purified by column chromatography ($SiO_2$:EtOAc/Hexanes 15:85) to afford the azide 2 as a clear oil (1.89 g, 84%). ES MS $[M]^+$ (calcd 662.3206) found 662.3237.

Compound 3 A suspension of azide 2 (1.89 g), 10% $Pd(OH)_2/C$ and $N_2H_4.H_2O$ in THF/EtOH was stirred at 90° C. and the progress of the reaction monitored by $ES^+$. Further 10% $Pd(OH)_2/C$ and $N_2H_4.H_2O$ were added as required. Upon completion, the reaction was filtered through a celite pad and the filtrate evaporated to dryness to afford the crude amine 3 as a slightly yellow oil (767 mg). The amine 3 was further purified by gel filtration chromatography. ES MS $[M+H]^+$ (calcd 254.1604) found 254.1597.

Scheme M

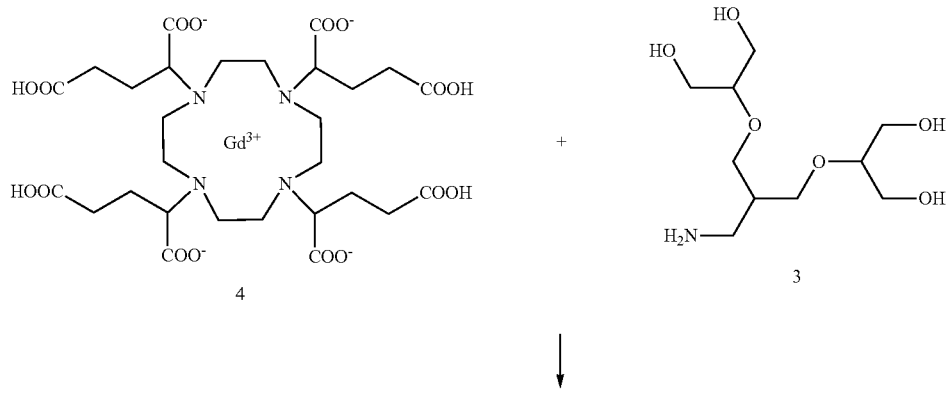

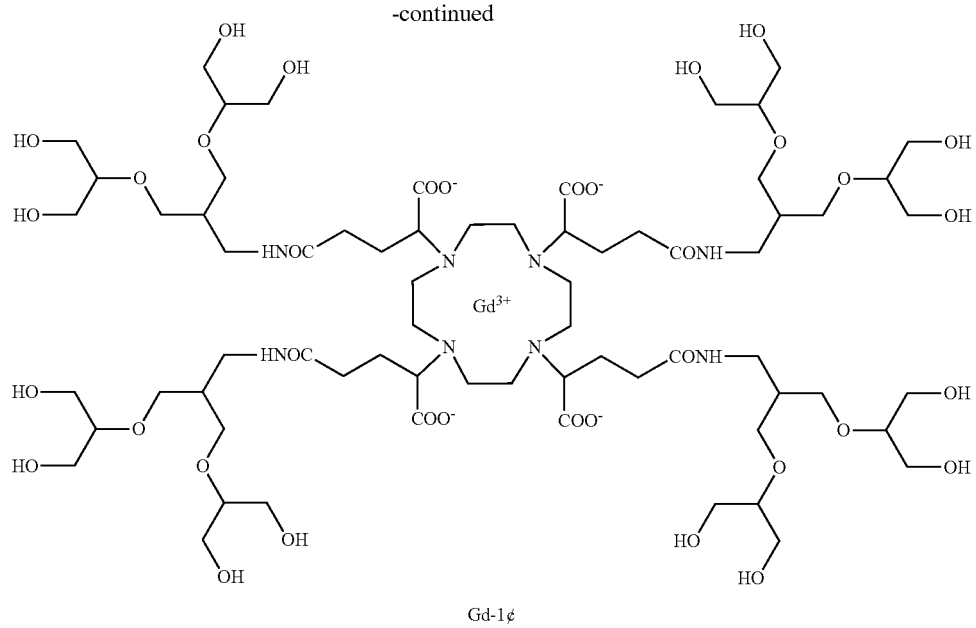

Gd-1c′

Compound Gd-1c To a solution of gadolinium complex 4 (Rousseaux, O.; Simonot, C. WO 00/71526) (20 mg) and HOBt (41 mg) in 1:1 $H_2O$/Dioxane (1.0 mL) was added EDC (60 mg) and the reaction allowed to stir for 15 min. A solution of amine 3 (70 mg) in $H_2O$ (260 μL) was added to the reaction, and the mixture allowed to stir at room temperature for 4d, during which time further EDC (60 mg) was added to the reaction. The reaction was then freeze-dried, the residue suspended in $H_2O$ (0.5 mL) and centrifuged (1500 rev/min) for 5 min. The liquid was carefully removed and freeze-dried to afford the crude as a pale brown oil (239 mg). Purification by gel-filtration chromatography afforded the pure compound Gd-1c (20 mg, 48%).

MALDI-TOF MS $[M+H]^+$=1788.7

Example 7

Preparation of the Complex Compound Gd-2c of Formula

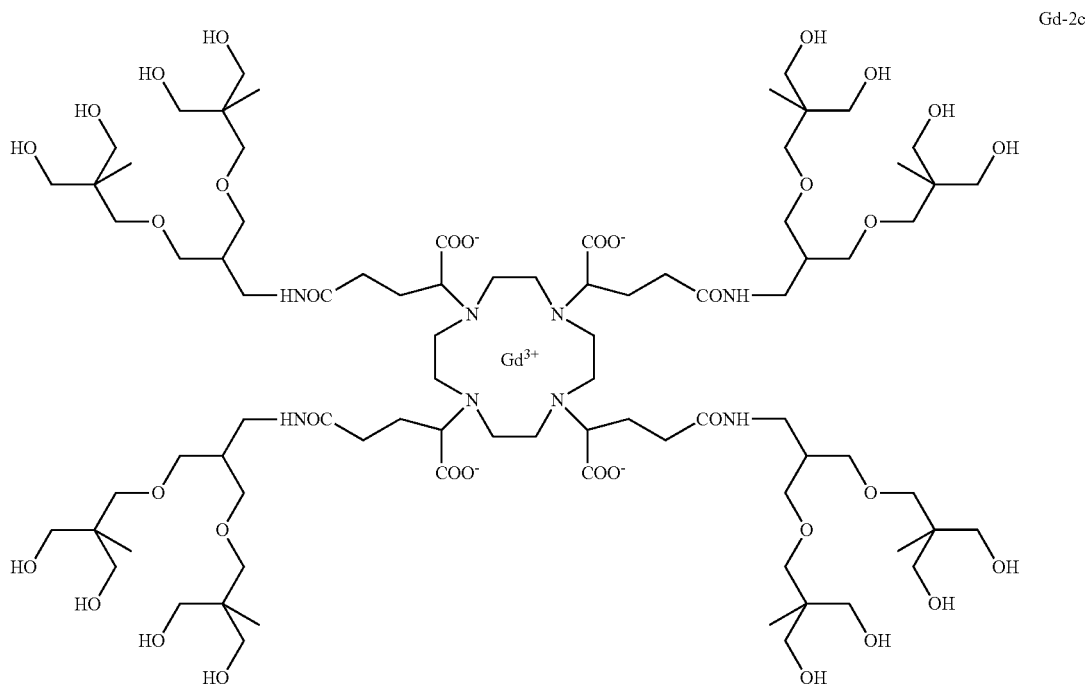

Gd-2c

The preparation includes the following steps:

a) synthesis of the aminopolyol G2 according to the following scheme N;
b) coupling reaction according to the following scheme O Scheme N

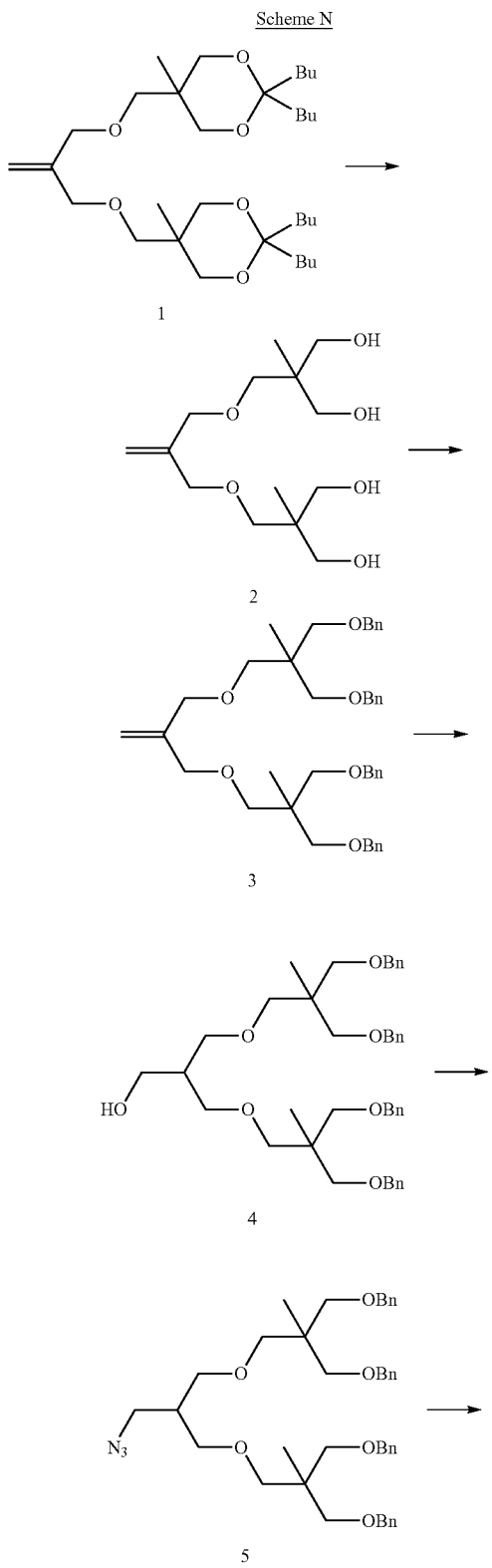

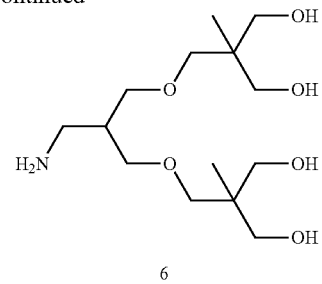

Compound 2 Compound 1 (Grayson, S. M.; Jayaraman, M.; Fréchet, J. M. J. *Chem. Commun.* 1999, 1329-1330) (6 g, 11 mmol) were taken into 2M HCl/dioxan (1:1) (100 mL) and stirred at RT for 3 h. The solvent was removed under reduced pressure and dried under vacuum to give 2 as a colourless solid (3.0 g, 93%). ES MS [M+Na]$^+$ (315).

Compound 3 Sodium hydride (0.79, 32 mol) was taken into anhydrous THF (20 mL) and the alkene 2 (2.4 g, 8.2 mmol) in THF (20 ml) was added dropwise at RT followed by benzyl bromide (5.62 g, 32 mol) in THF (30 ml). Solution was stirred at RT for 1 h and heated at reflux temperature for 72 h. Reaction was quenched with water (20 mL) and the product was extracted with diethyl ether (3×20 mL). The ether layer was dried ($K_2CO_3$) and solvent removed under vacuum to give a clear oil. The product was purified by column chromatography ($SiO_2$:ethyl acetate/hexane 20:80) to afford the desired alkene 3 as a clear oil. (5 g, 92%). ES MS [M+Na]$^+$ (675).

Compound 4 The desired alcohol 4 was prepared starting from alkene 3 by an anti-Markovnikov hydration reaction using 9-BBN (with basic peroxide work-up) according to procedures known in the art; see, as a reference, Jayaraman, M.; Freshet, J. M. J. *J. Am. Chem. Soc.* 1998, 120, 12996-12997 and Grayson, S. M.; Fréchet, J. M. J. *J. Am. Chem. Soc.* 2000, 122, 10335-10344.

ES MS [M+Na]$^+$ (693).

Compound 5 To a stirred solution of compound 4 (1.654 g, 2.46 mol) and $Et_3N$ (0.38 ml, 2.79 mol) in $CH_2Cl_2$ at 0° C. under an Argon atmosphere was added dropwise methanesulfonylchloride (0.23 mol, 3.0 mol). The reaction mixture was stirred at 0° C. for 1 h. Conversion to the mesylate was monitored using TLC and ESMS. Sodium azide in DMF (8 mL), a catalytic amount of tetrapropylammonium bromide then $H_2O$ were added and heated at 65° C. for 24 h. Solvent was removed under vacuum and the desired product was extracted using dichloromethane, dried ($MgSO_4$) and evaporated to give an oily product. The azide 5 was purified using column chromatography ($SiO_2$:EtOAc/Hexane 30:70) to give a clear oil (1.25 g, 73%). ES MS: [M+Na]$^+$ (718).

Compound 6 A solution of azide 5 (1.00 g), 10% Pd (OH)$_2$/C and few drops of hydrochloric acid in ethanol (20 mL) were stirred at RT under $H_2$ (30 psi) and the progress of the reaction monitored by ES$^+$. After 24 h the catalyst was filtered off and the solvent was removed to afford the dendramine-2 as a very pale yellow oil (0.45 g, 99%). ES MS [M+H]$^+$ (310).

Scheme O

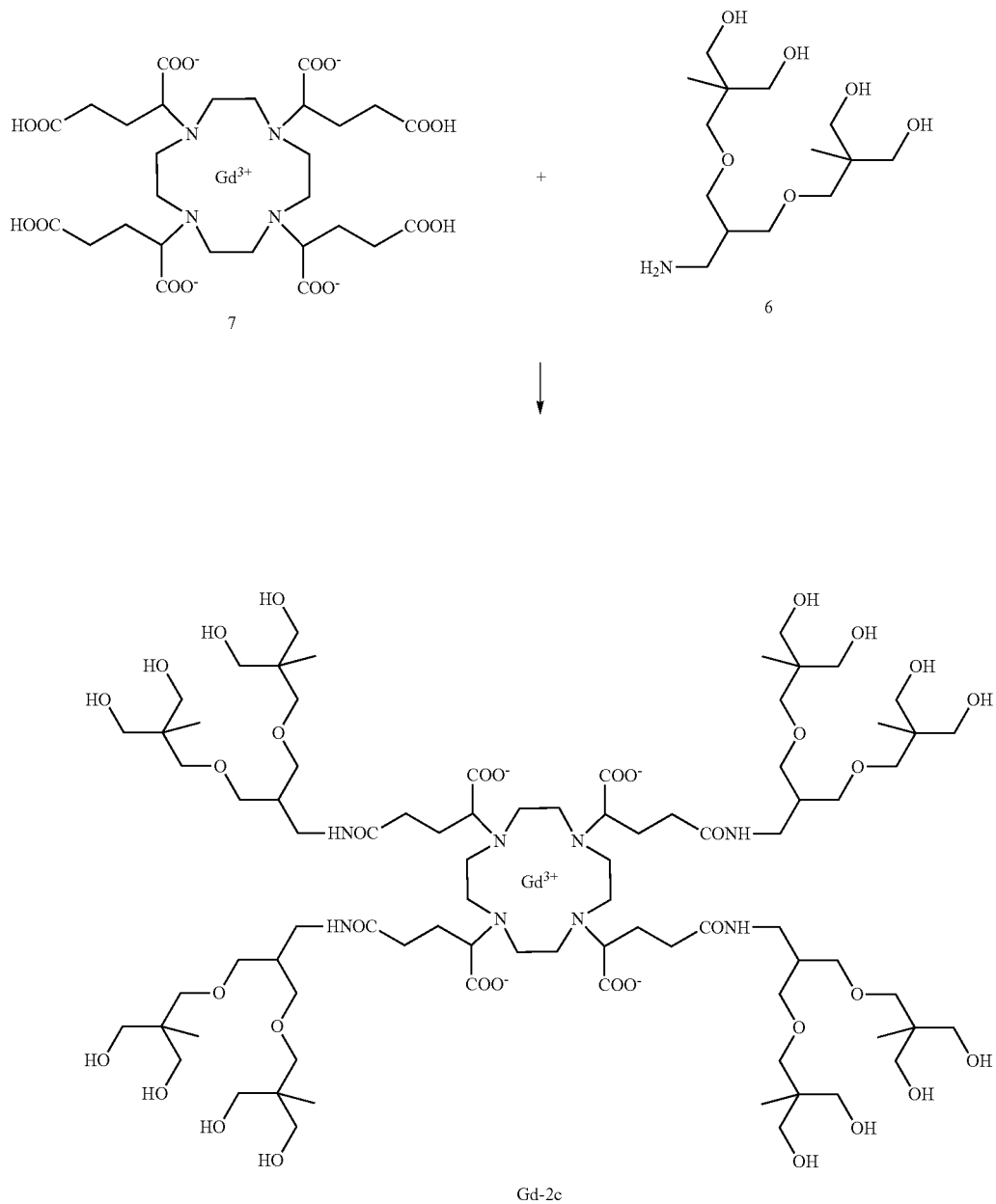

Compound Gd-2c To a solution of gadolinium complex 7 (Rousseaux, O.; Simonot, C. WO 00/71526) (30 mg) and HOBt (2 mg) in 6:4 H$_2$O/Dioxane (1.0 mL) was added EDC (54 mg) and amine 6 (87 mg). The pH of the solution was adjusted to 6.5 using a dilute solution of sodium hydroxide and stirred at RT for three days while monitoring the pH. During this period further EDC (60 mg) was added to the reaction mixture. The solution was then freeze-dried to give a yellow glass. The glass was dissolved in water (2 mL) and purified by gel-filtration chromatography to give compound Gd-2c as a colourless solid. ESMS [M]$^+$=2010.

Example 8
Preparation of the Complex Compound Gd-3c of Formula
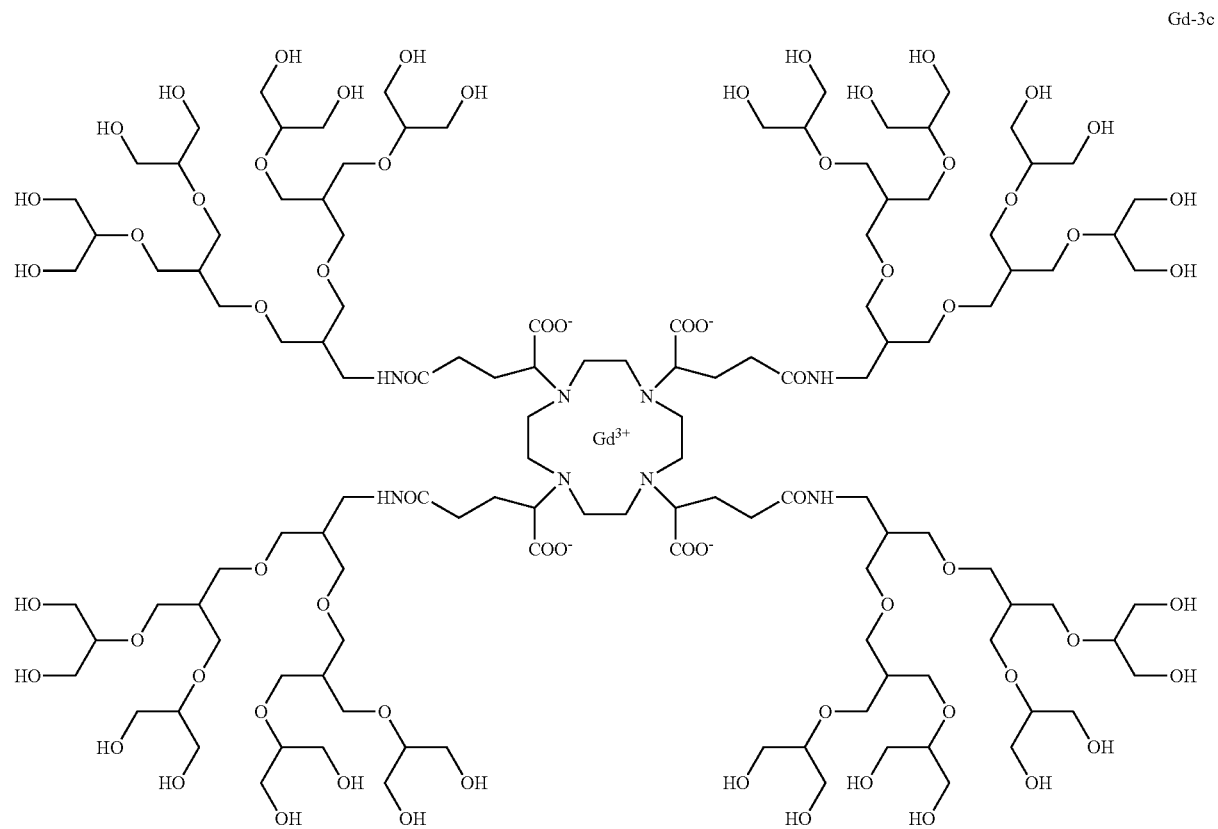
Gd-3c
The preparation includes the following steps:
a) synthesis of the aminopolyol G3 according to the following scheme P;
b) coupling reaction according to the following scheme Q
Scheme P
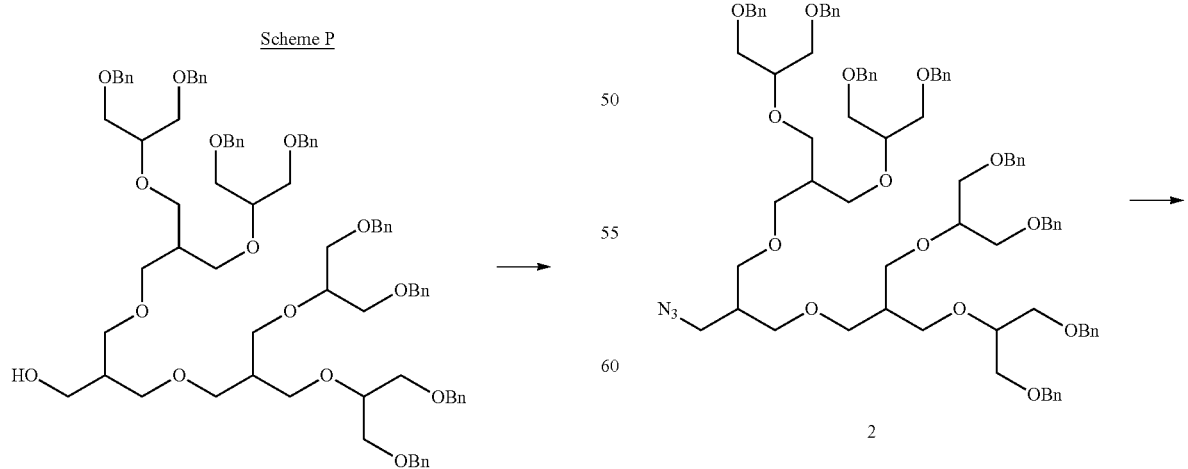

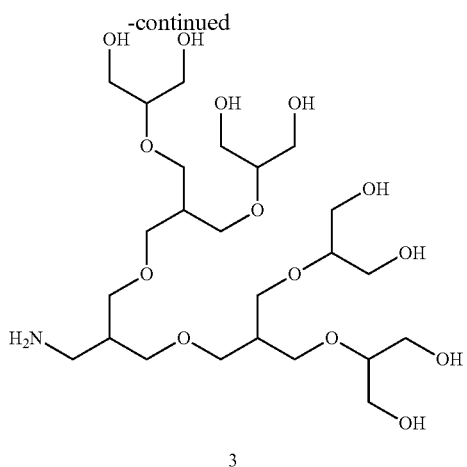

3

Compound 2 A solution of alcohol 1 (Grayson, S. M.; Fréchet, I. M. J. *J. Am. Chem. Soc.* 2000, 122, 10335-10344) (2.677 g, 2.06 mmol) and NEt₃ in CH₂Cl₂ (80 mL) was cooled to 0° C., and methanesulfonyl chloride added dropwise. The reaction mixture was stirred at 0° C. for 45 min, then H₂O was added (20 mL) and the mixture stirred vigorously for 10 min. The mixture was transferred to a separatory funnel and CH₂Cl₂ was then added (100 mL). The organic layer was then washed with 1 M HCl (50 mL), saturated NaHCO₃ solution (50 mL) and H₂O (50 mL). The organic layer was dried (MgSO₄), filtered and evaporated to dryness to afford the crude mesylate (2.934 g), which was used immediately without further purification.

A suspension of crude mesylate and NaN₃ (1.34 g, 20.6 mmol) in DMF (10 mL) was stirred at 60° C. under an argon atmosphere for 14 h. The solvent was then removed and the residue partitioned between H₂O (100 mL) and CH₂Cl₂ (100 mL). The aqueous phase was further extracted with CH₂Cl₂ (2×100 mL), and the organics combined, dried (MgSO₄), filtered and evaporated to dryness. The product was purified by column chromatography (SiO₂:EtOAc/Hexanes 20:80) to afford desired azide 2 as a clear oil (2.14 g, 78%). ES MS [M+H]⁺ (calcd 1346.9659) found 1346.9859.

Compound 3 To a suspension of azide 2 (270 mg) and 10% Pd(OH)₂/C (224 mg) in THF/EtOH (20 mL) was added 1 drop 1 M HCl. The resulting mixture was shaken under H₂ atmosphere (45 psi) for 4 d, and then filtered through a celite pad. The filtrate was evaporated to dryness to afford the crude amine as a clear oil (158 mg). The amine 3 was further purified by gel filtration chromatography. ES MS [M+H]⁺ (calcd 578.3388) found 578.3394.

Scheme Q

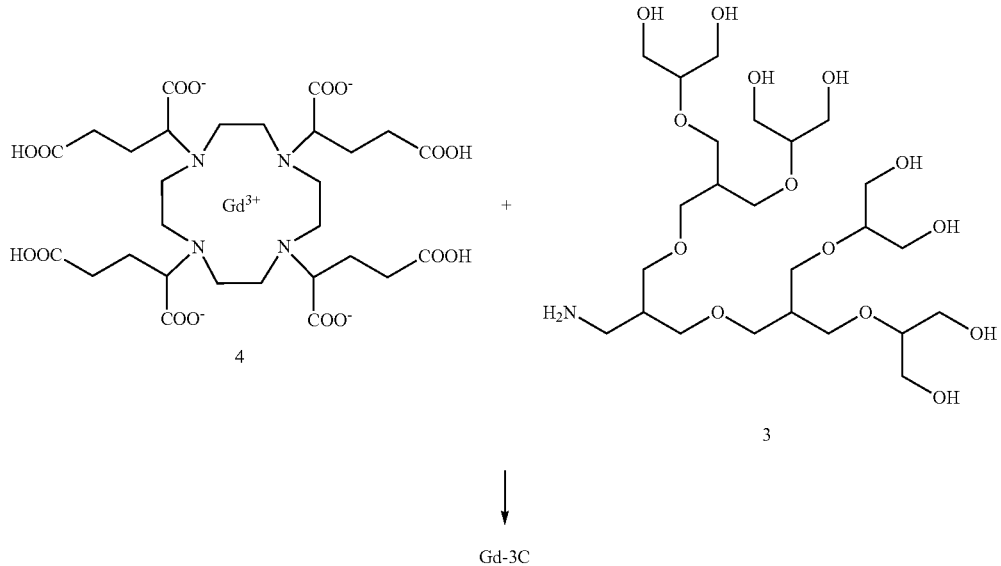

Compound Gd-3c To a suspension of gadolinium complex 4 (Rousseaux, O.; Simonot, C. WO 00/71526) (23 mg) in DMF (0.5 mL) was added O-benzotriazol-1-yl-N,N,N',N'-tetramethyluronium tetrafluoroborate (51 mg) and the mixture allowed to stir for 2 h. A solution of amine 3 (91 mg) in DMF (0.5 mL) was added to the reaction, and the mixture allowed to stir at room temperature for 5 d, during which time further O-benzotriazol-1-yl-N,N,N',N'-tetramethyluronium tetrafluoroborate (47 mg) was added to the reaction mixture. The reaction was then filtered through a syringe filter and evaporated to dryness. Purification by gel-filtration chromatography afforded the complex compound Gd-3c (25 mg, 30%). MALDI-TOF MS [M+H]⁺=3083.5.

Example 9
Preparation of the Compound Gd-4-c of Formula
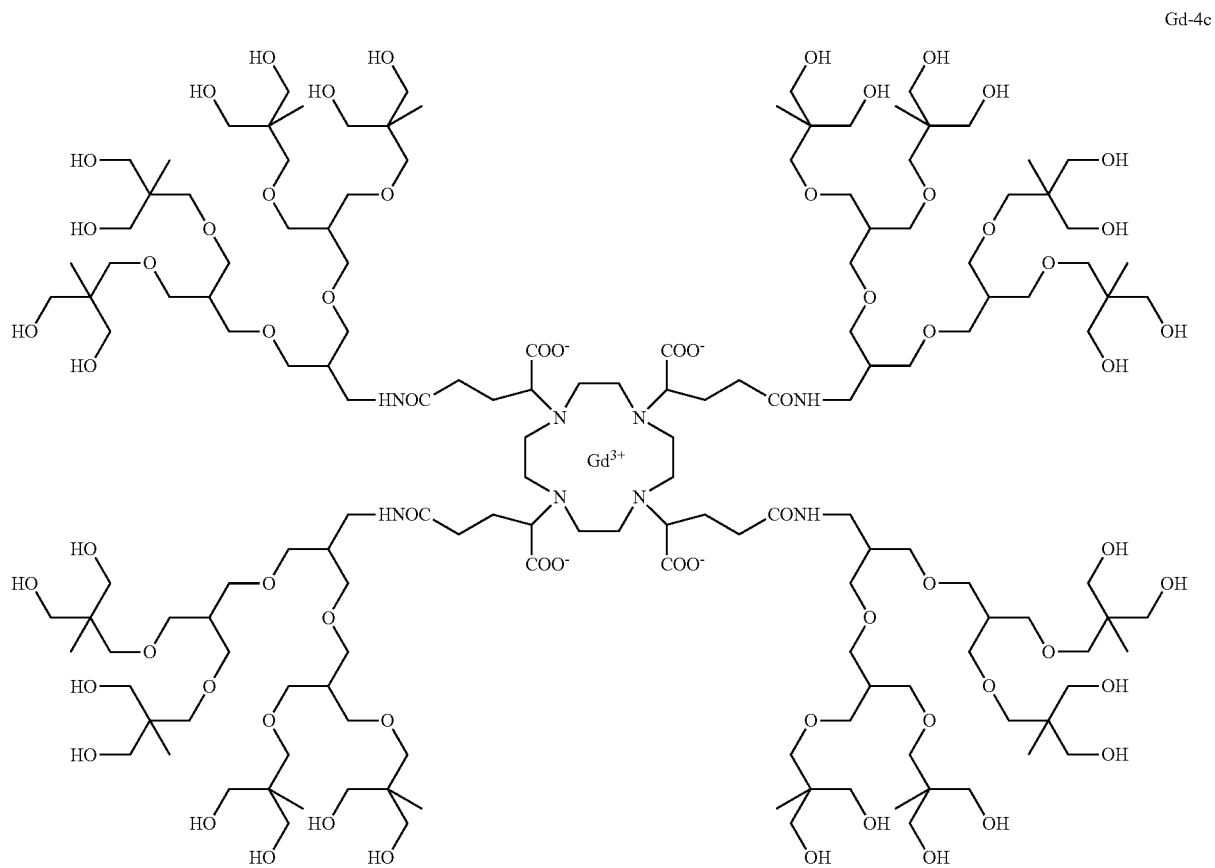
The preparation has been carried out according to the following scheme R:
Scheme R
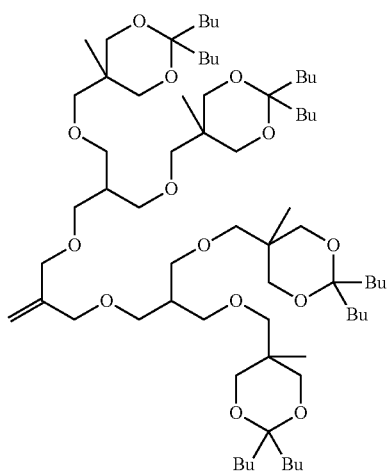
1

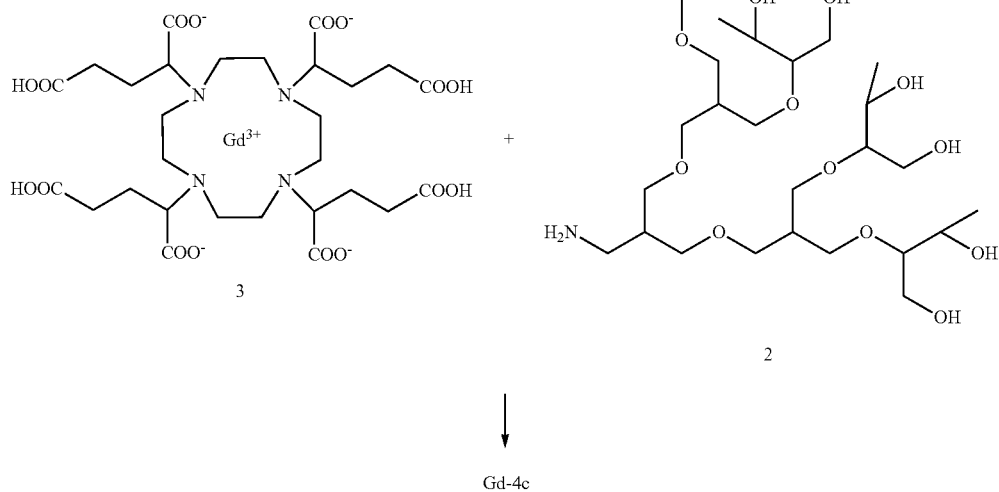

Gd-4c

Compound 2 Compound 1 (Grayson, S. M.; Jayaraman, M.; Fréchet, J. M. J. *Chem. Commun.* 1999, 1329-1330) was converted into the amine 2 by working in analogy to what reported EXAMPLE 7 (step a).

Complex compound Gd-4-c To a solution of gadolinium complex 3 (Rousseaux, O.; Simonot, C. WO 00/71526) (25 mg) in water/dioxane was added HOBt (5 mg), amine 2 (0.16 mg) and EDC (34 mg). The solution was stirred at ambient temperature and the pH adjusted to 6.5 using dilute aqueous NaOH solution.

Example 10

Preparation of the Compound 9a of Formula

The preparation includes the following steps:

a) synthesis of the backbone chelating structure suitably functionalized according to the following scheme S;

b) coupling as per the following scheme T

Scheme S

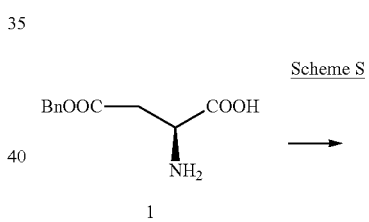

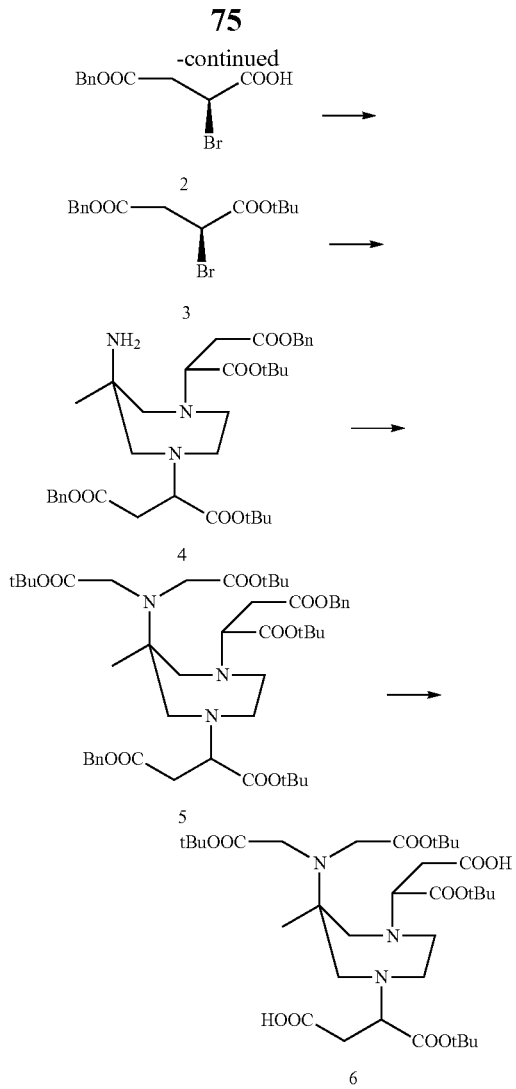

uct) (10.0 g; 44.8 mmol) and NaBr (17.1 g; 165.8 mmol) in 1 N HBr (200 mL) cooled to 0° C. After 3 h at 0° C. conc. $H_2SO_4$ (4.4 mL) was added and the solution extracted with $Et_2O$ (3×200 mL). The combined organic phases were washed with brine (2×200 mL), dried ($Na_2SO_4$) and evaporated under reduced pressure. The crude product was purified by flash chromatography to give 2 (9.3 g) as a colourless oil. Yield 73%. MS: 287.1 (M+H); 309.0 (M+Na).

Compound 3 A solution of compound 2 (9.3 g; 27.1 mmol) in t-butyl acetate (100 mL) and 70% $HClO_4$ (0.08 mL) was stirred at room temperature for 12 h. Water (300 mL) was added and the solution was extracted with ethyl acetate (3×100 mL). The combined organic phases were washed with 5% $Na_2CO_3$ (200 mL), water (200 mL) and then dried ($Na_2SO_4$) and evaporated under reduced pressure. The crude product was purified by flash chromatography to give 3 (8.4 g) as a colourless oil. Yield 90%. MS: 365.0 (M+Na).

Compound 4 A mixture of 3 (5.98 g; 17.4 mmol), 6-amino-6-methyl-perhydro-1,4-diazepine (Giovenzana G. B. et al. WO 03/008390) (0.5 g; 3.9 mmol) and $K_2CO_3$ (2.4 g; 17.4 mmol) in acetonitrile (50 mL) was stirred for 24 h. The solution was evaporated under reduced pressure and then water (100 mL) and $CHCl_3$ (100 mL) were added. The organic phase was dried ($Na_2SO_4$) and evaporated. The crude product was purified by flash chromatography to give 4 (1.3 g) as a pale yellow oil. Yield 37%. MS: 654.4 (M+H); 676.4 (M+Na).

Compound 5 t-Butyl bromoacetate (0.32 mL; 2.18 mmol) was added to a stirred solution of 4 (0.80 g; 0.87 mmol), $K_2CO_3$ (0.46 g; 3.32 mmol) and $Na_2SO_4$ (0.22 g) in acetonitrile (8 mL) cooled at 0° C. After 30 min at room temperature the solution was refluxed for 5 h and 30 min. After 14 h at room temperature, the solution was evaporated and treated with 8:2 petroleum ether/EtOAc (20 mL). The precipitate was discharged and the liquid phase evaporated to give a crude (0.90 g) that was purified by flash chromatography to give 5 (0.66 g) as a yellow oil. Yield 86%. MS: 882.8 (M+H); 904.8 (M+Na).

Compound 6 5% Pd/C (0.18 g) was added to a solution of compound 5 (0.60 g; 0.68 mmol) in absolute EtOH (50 mL). The reaction mixture was stirred under a hydrogen atmosphere for 1 h. The mixture was filtered through a Millipore® apparatus (FH 0.5 μm) and evaporated to give 6 (0.41 g) as a white solid. Yield 89%. MS: 702.6 (M+H); 724.5 (M+Na).

Compound 2 A solution of sodium nitrite (5.88 g; 85.2 mmol) in water (60 mL) was added dropwise in 30 min to a mixture of L-aspartic acid β benzyl ester (commercial prod- Scheme T

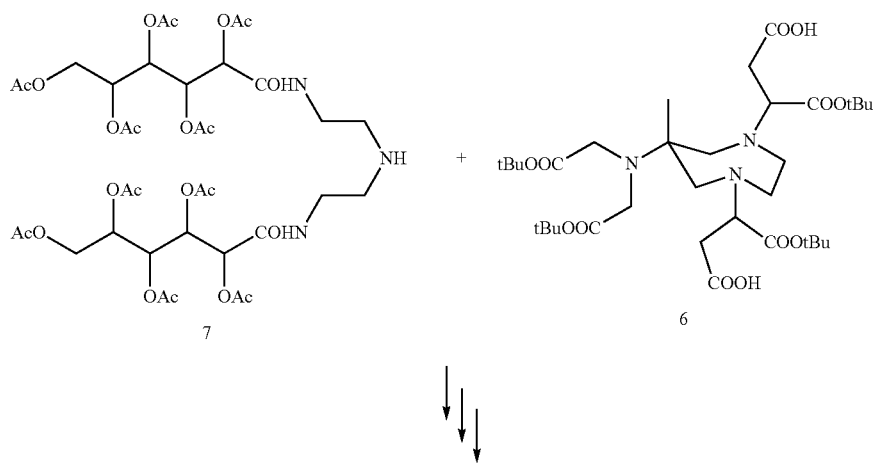

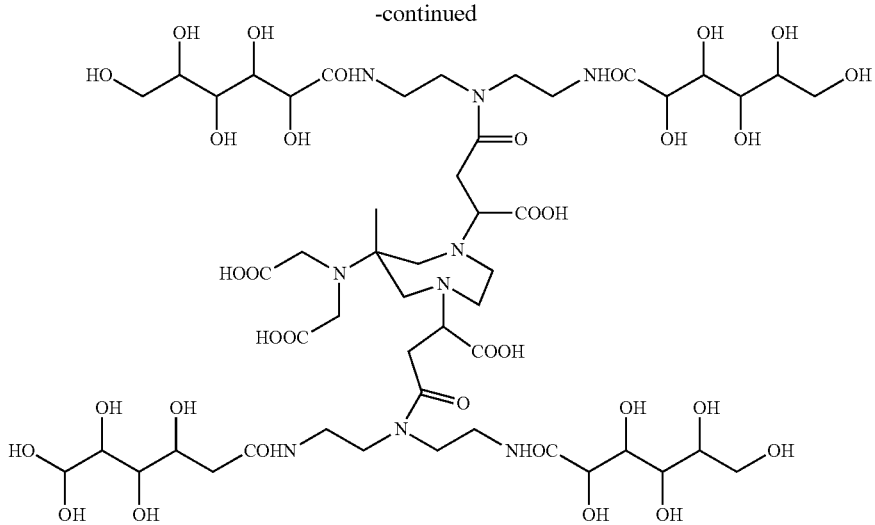
9a
Compound 9a Compound 9a was prepared by reacting the diacid 6 with the amine 7 (see EXAMPLE 3) and by working in analogy to what reported in EXAMPLE 3 (see preparation of compound 2a).
Example 11
Preparation of the Compound 10a of Formula
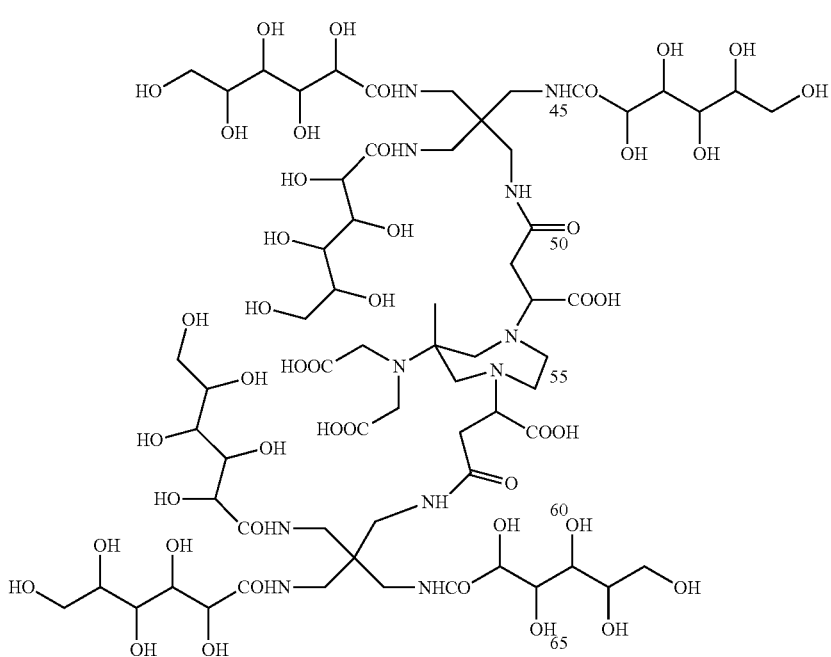
10a The compound was prepared according to the following scheme U:
Scheme U
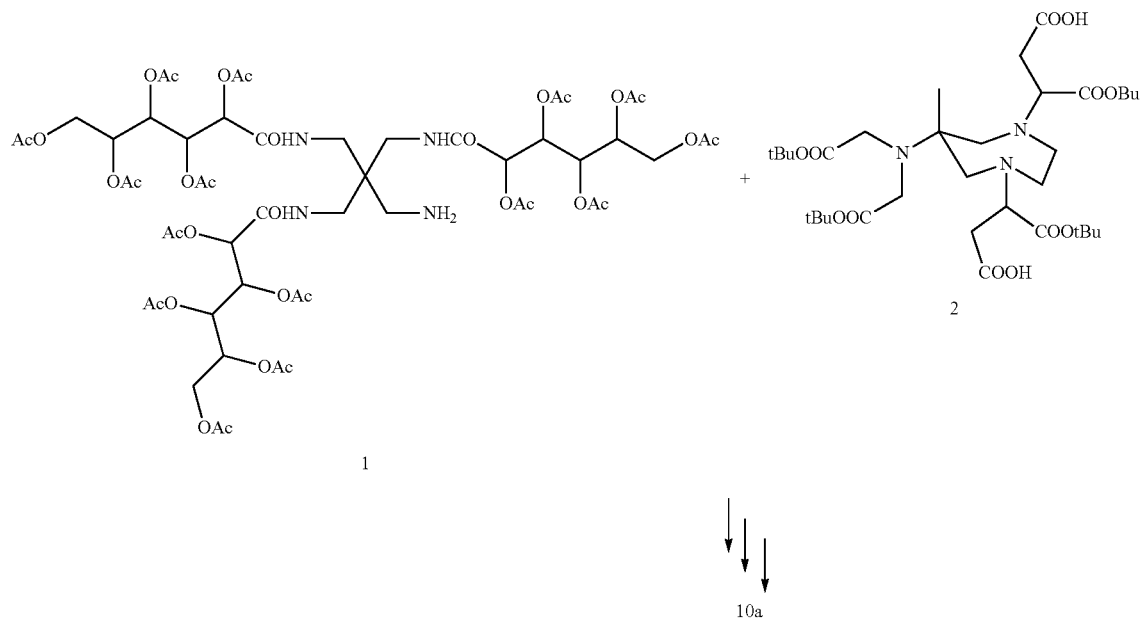
Compound 10a Compound 10a was synthesized by reacting the diacid 2 (see compound 6 of EXAMPLE 10) with the amine 1 (see EXAMPLE 2) and by working in analogy to what reported in EXAMPLE 10 (see preparation of compound 9a).
Example 12
Preparation of Compound 9b
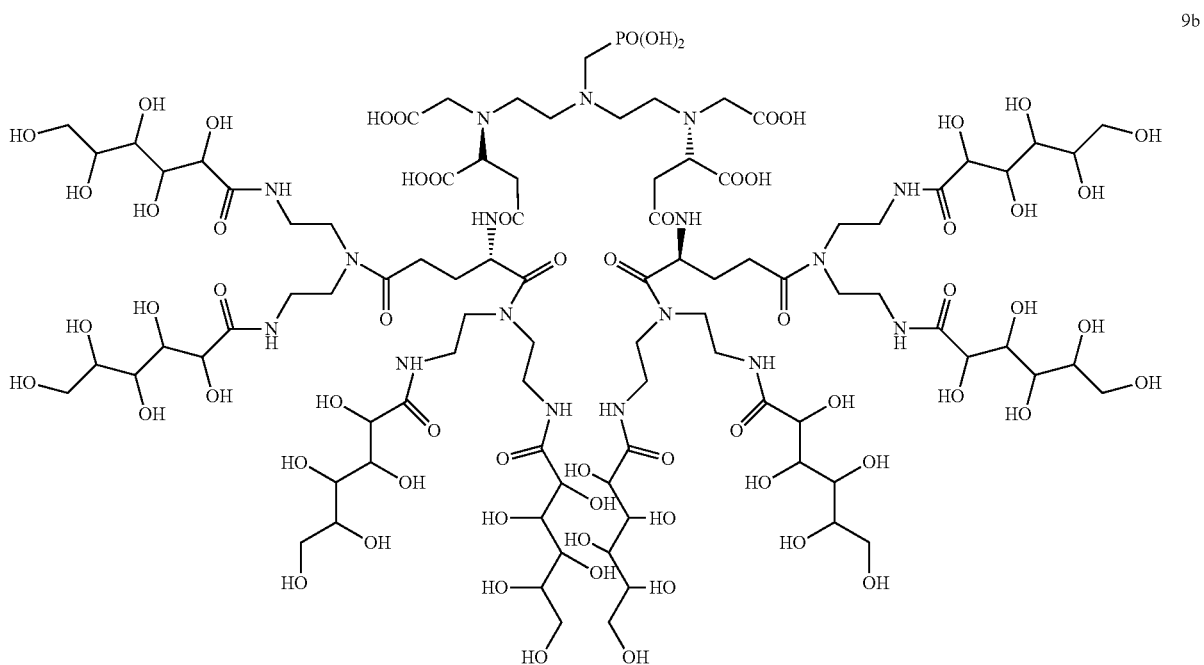

The preparation of 9b include the following steps:
a) synthesis of the aminopolyol moiety G10 as per scheme V;
b) coupling as per scheme Z
Scheme V
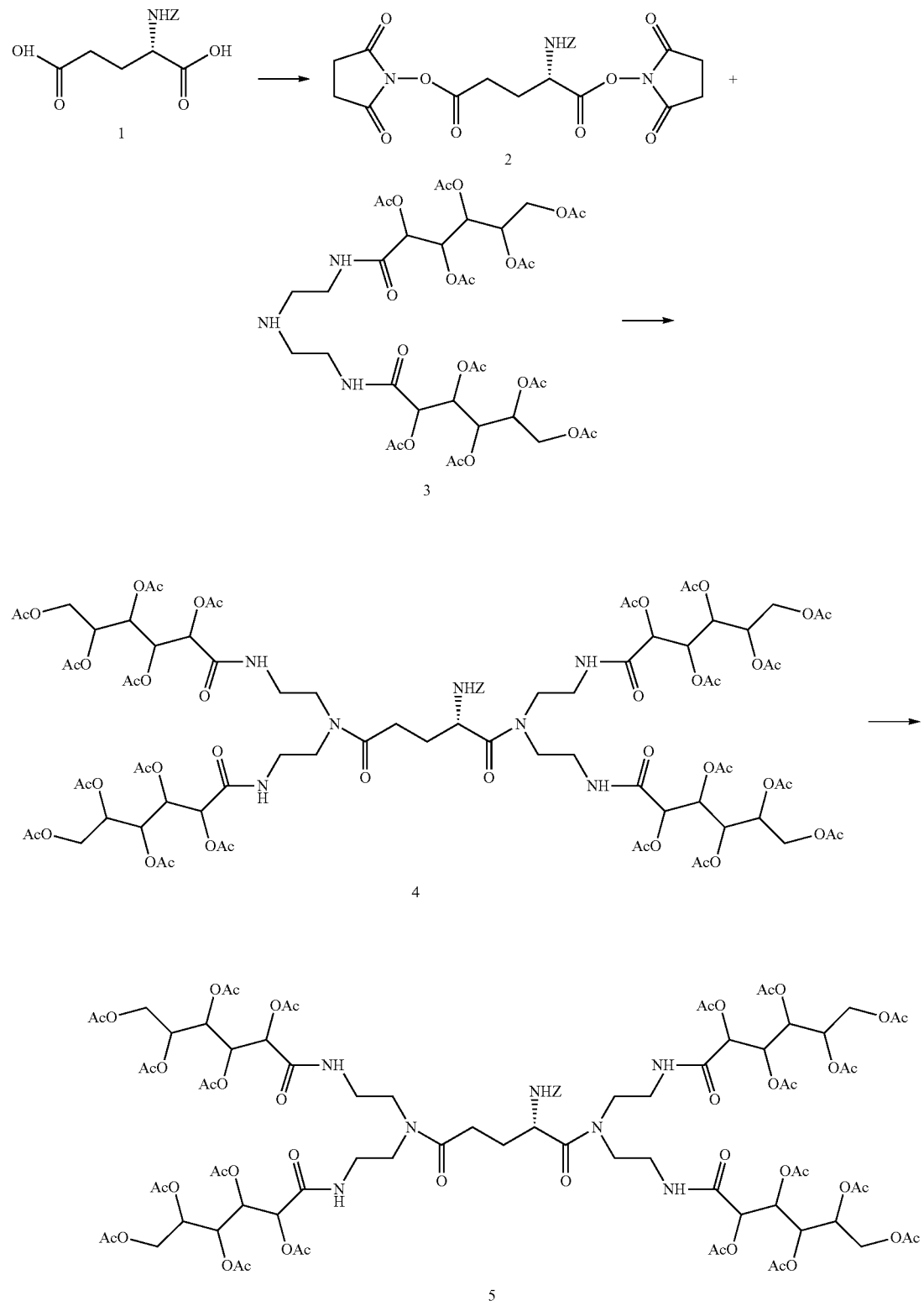

Compound 4 N-hydroxysuccinimide (1.35 g; 11.7 mmol) and diisopropylcarbodiimide (1.48 g; 11.7 mmol) were added to a suspension of 1 (1.11 g; 3.90 mmol) (commercially available) in $CH_2Cl_2$ (12 mL). After stirring at room temperature for 18 h, the suspension was filtered and evaporated under vacuum. Crude 2 (3.94 g) was dissolved in DMF (70 mL) and the amine 3 (Takahashi, M et al. *Tetrahedron Lett.* 2000, 41, 8485-8488) (6.86 g; 7.80 mmol) was added. The clear solution was stirred at 65° C. for 48 h. Another portion of 3 (1.50 g; 1.71 mmol) was added and the mixture was stirred at 65° C. for further 24 h. The solvent was removed and the crude was taken up with $CH_2Cl_2$ (200 mL) and washed with sat. aq. $NaHCO_3$ (2×50 mL) and sat. aq. $NH_4Cl$. (50 mL). The organic layer was dried over $Na_2SO_4$ and evaporated. The crude was purified by column chromatography on silica gel to afford compound 4 (3.44 g; 1.72 mmol). Yield 44%. MS: 2005.7 (M+H); 2027.7 (M+Na).

Compound 5 To a solution of compound 4 (3.44 g; 1.72 mmol) in MeOH (50 mL) 10% Pd/C (350 mg) and acetic acid (206 mg; 3.44 mmol) were added. The suspension was hydrogenated at atmospheric pressure for 4.5 h. The catalyst was removed by filtration and the solution was evaporated. The residue was dissolved in $CH_2Cl_2$ (50 mL) and washed with sat. aq. $NaHCO_3$ (2×15 mL). The organic layer was dried over $Na_2SO_4$, filtered and evaporated to obtain compound 5 (3.22 g; 1.72 mol). Quantitative yield. MS: 1870.7 (M+H).

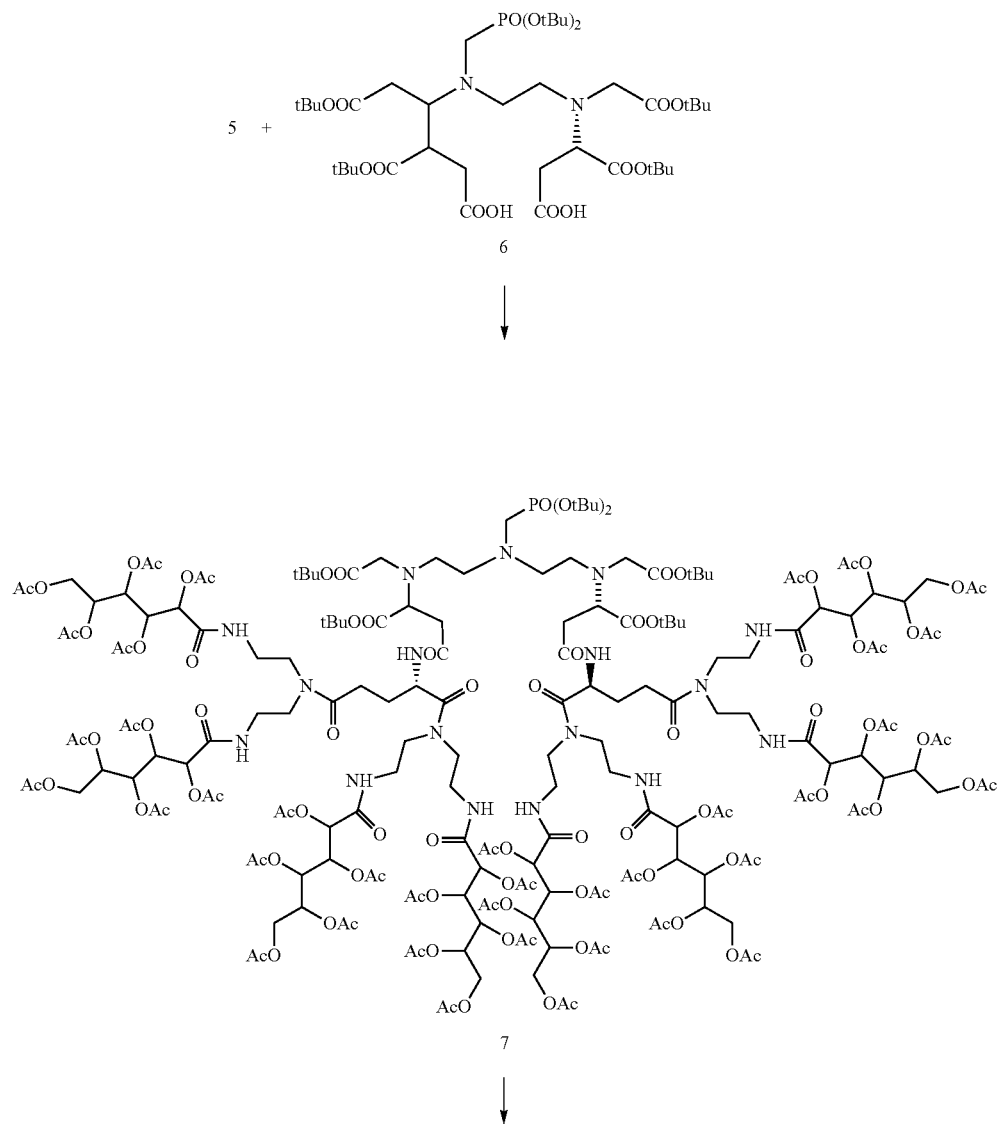

Scheme Z

-continued

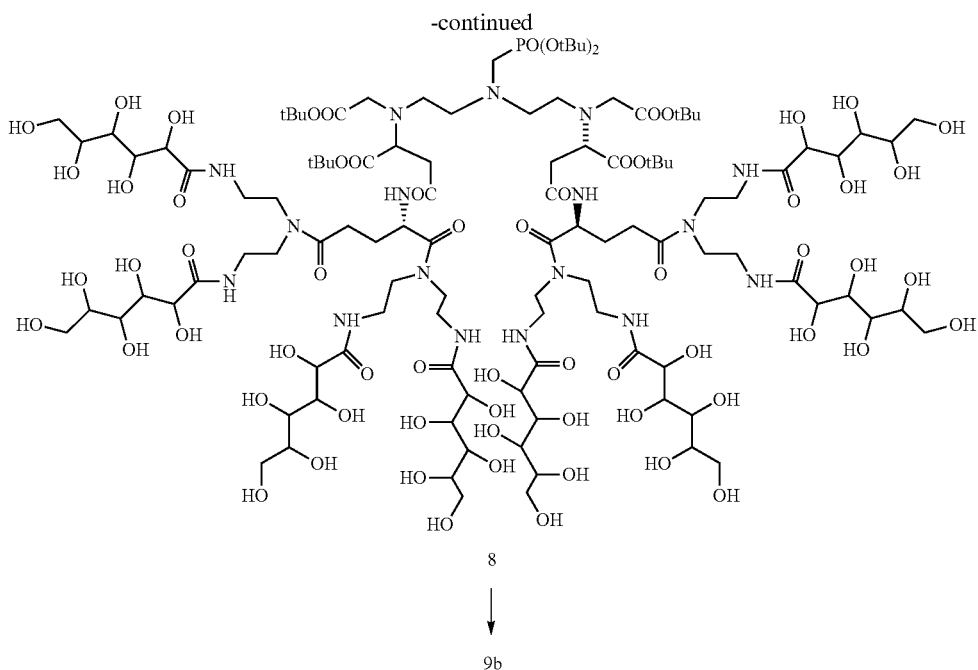

8
↓
9b

Compound 7 To a solution of diacid 6 (94.4 mg; 107 μmol), prepared as reported in EXAMPLE 4 (scheme G3) and N-methylpiperidine (26.0 μL; 214 μmol) in CH$_2$Cl$_2$ (1.0 mL) at 0° C., isobutyl chloroformate (29.2 mg; 214 μmol) was added and the solution stirred at this temperature for 20 min. Amine 5 (400 mg; 214 μmol) was added to the reaction mixture. After 1 h at 0° C. and a further hour at room temperature the mixture was diluted with CH$_2$Cl$_2$ (15 mL) and washed with sat. aq. NH$_4$Cl (2×10 mL). The organic phase was separated, dried over Na$_2$SO$_4$ and evaporated. The residue was purified by column chromatography on silica gel to give 7 (200 mg; 43.6 μmol) as a white solid. Yield 41%. MS: 4608.7 (M+Na).

Compound 8 K$_2$CO$_3$ (6.0 mg) was added to a solution of 7 (200 mg; 43.6 μmol) in MeOH (10 mL) at room temperature and the solution stirred for 10 min. A milky precipitate was afforded and more MeOH (10 mL) was added to obtain a clear solution. After 18 h the mixture was evaporated and the residue was treated with Et$_2$O (20 mL). The suspension was filtered to obtain 8 (128 mg) as a white solid. Quantitative yield. MS: 2929.4 (M+Na).

Compound 9b Compound 8 (120 mg; 41.3 μmol) was dissolved in trifluoroacetic acid (TFA) (1.5 mL) at 0° C. and the mixture allowed to warm to room temperature and stirred overnight. The mixture was evaporated, the residue taken up with fresh TFA (1.5 mL) and the solution stirred for further 5 h. The reaction mixture was evaporated and the residue treated with Et$_2$O (20 mL). The suspension was filtered to afford the tris-trifluoroacetate salt of compound 9b (120 mg) as a white solid. Quantitative yield. MS: 2593.0 (M+Na).

Example 13

Preparation of Compound 11b of Formula

11b

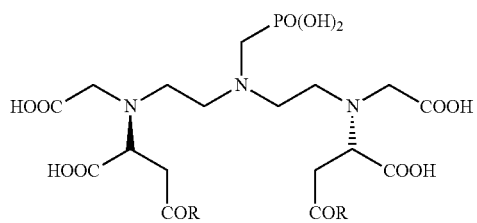

R = 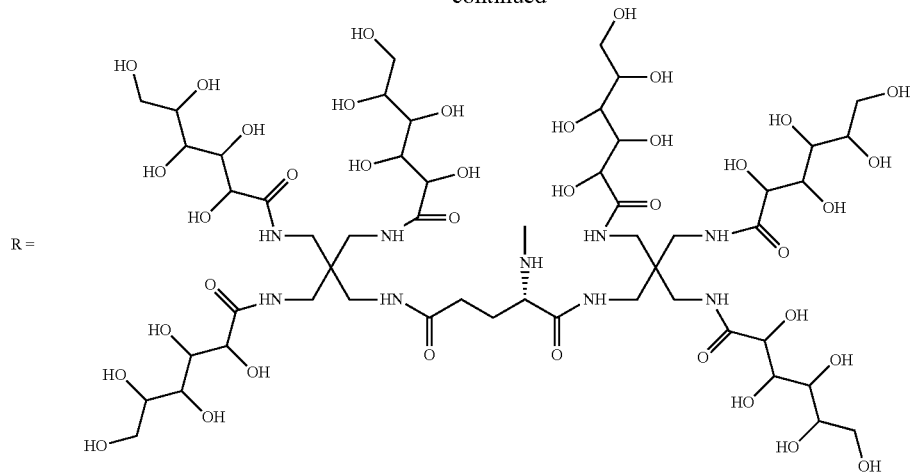
The preparation of 11b includes the following steps:
a) synthesis of the aminoplyol as per scheme Z-A;
b) coupling as per scheme Z-B.
Scheme Z-A
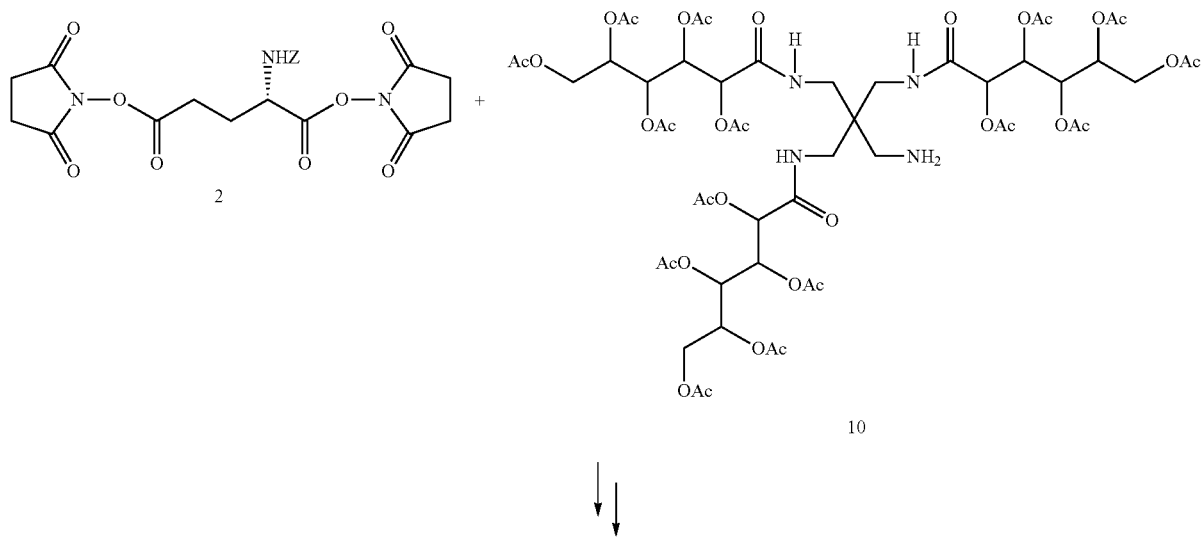

-continued

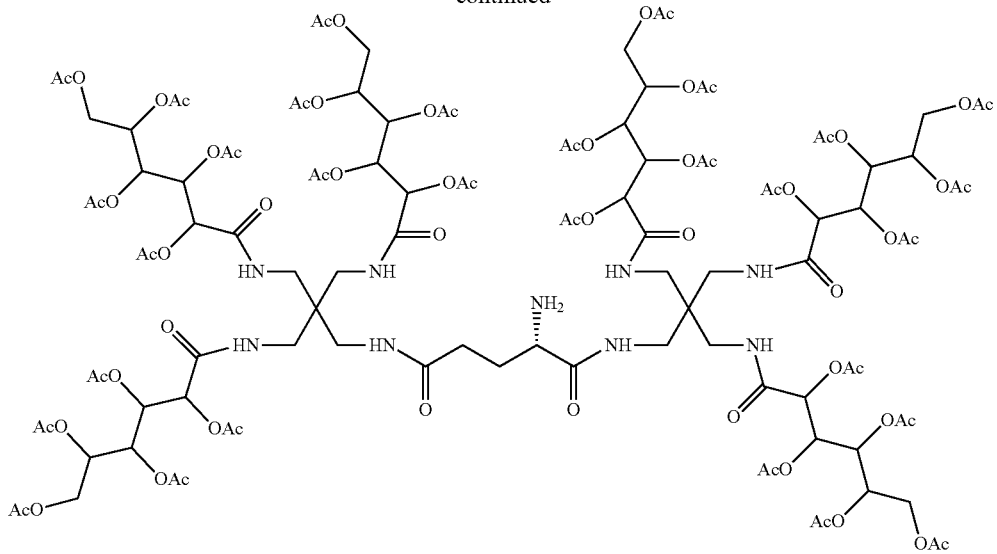

11

Compound 11 Compound 11 was prepared through intermediate 10 (see EXAMPLE 2, Scheme D), by working in analogy to what reported in EXAMPLE 12 (scheme V).

Compound 11b Compound 11b was prepared by reacting compound 11 with compound 6 (prepared as reported in EXAMPLE 4, scheme G3) and by operating in analogy to what reported in EXAMPLE 12 (scheme Z).

Example 14

Preparation of Compound 12a of Formula

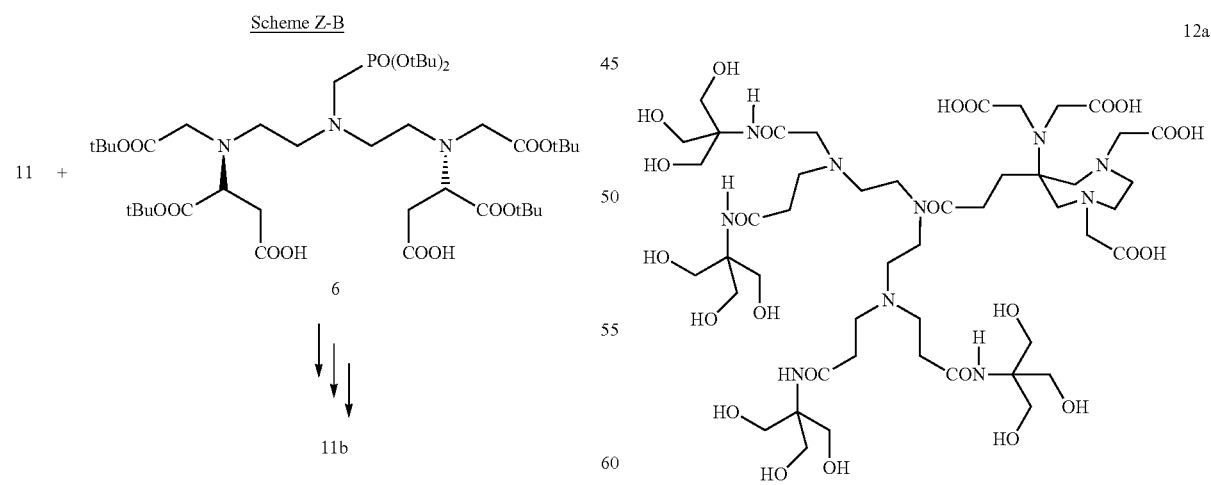

The preparation of the compound of formula 12a was carried out as per the following schemes Z-C and Z-D Scheme Z-C

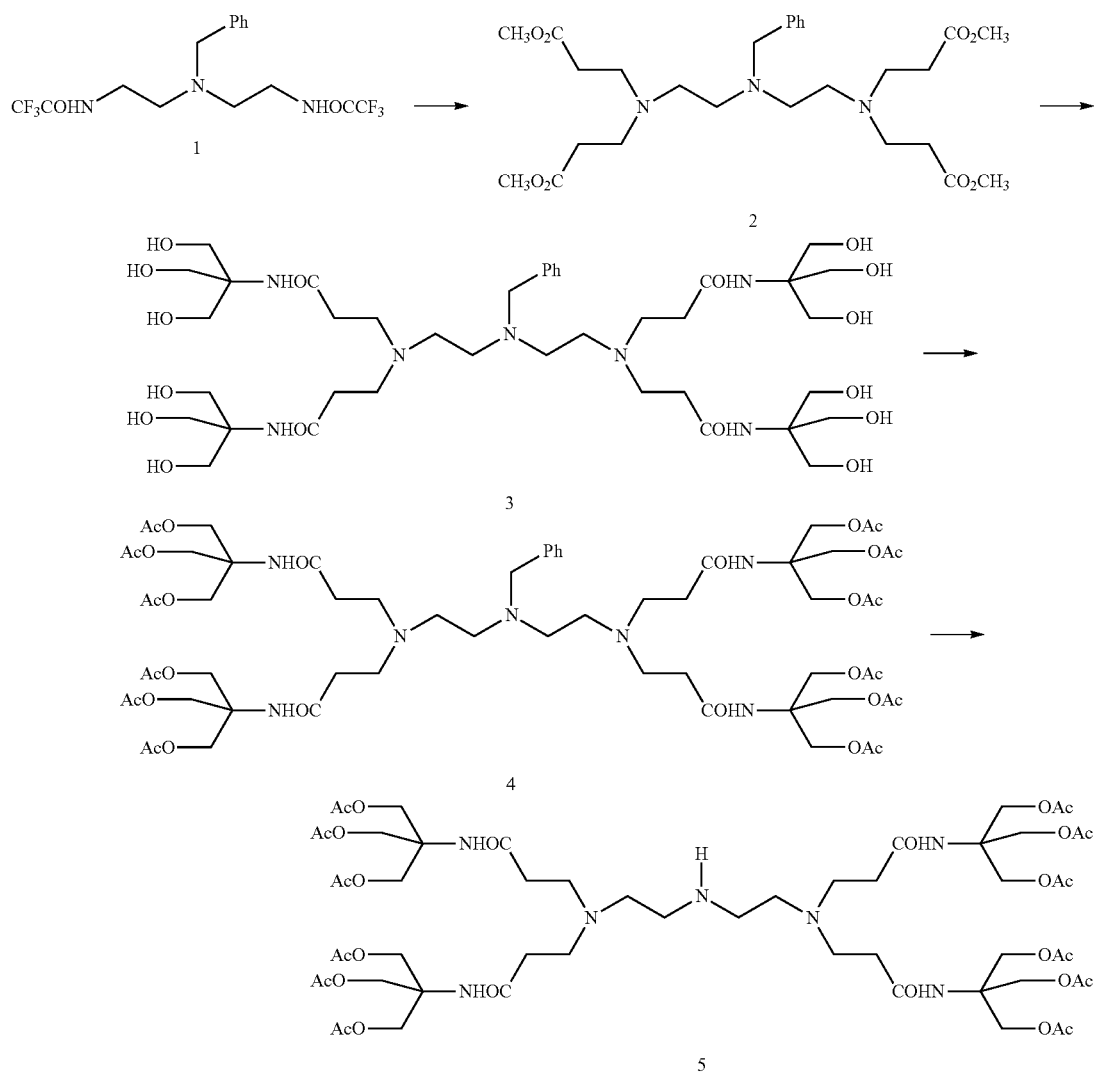

Compound 2 2M NaOH (180 mL) was added to a solution of 1 (54.0 g, 140 mmol) (U.S. Pat. No. 5,514,810) in EtOH (360 mL). The reaction mixture was stirred for 24 hours and then concentrated. The aqueous residue was evaporated to dryness by azeotropic distillation with isopropanol. The residue was taken up with MeOH (330 mL) and methyl acrylate (96.4 g, 1.12 mol) was added to the alcoholic solution. The reaction mixture was stirred for 5 days at room temperature. The solvent was evaporated and the crude was purified by column chromatography (30:1 $CH_2Cl_2$/MeOH) to afford 2 (55.7 g, 103 mmol) as a viscous oil.

Yield 74%. MS: 560.7 (M+Na).

Compound 3 A solution of 2 (14.0 g, 26.0 mmol) in DMSO (30 mL) was added to a stirred suspension of tris(hydroxymethyl)aminomethane (TRIS) (22.0 g, 182 mmol) and anhydrous $K_2CO_3$ (25.2 g, 182 mmol) in DMSO (70 mL). The reaction was stirred at 50° C. under a nitrogen atmosphere for 3 days and then more TRIS (9.44 g, 78.0 mmol) and anhydrous $K_2CO_3$ (10.8 g; 78.0 mmol) were added. The reaction mixture was stirred for further 4 days at 50° C., then filtered. The filtrate was concentrated under vacuum and the residue was purified by elution through resin Amberlite XAD 16.00 to afford 3 (15.6 g, 17.4 mmol) as a hygroscopic pale-yellow solid. Yield 67%. MS: 895.1 (M+H).

Compound 4 4-Dimethylaminopyridine (3.10 g; 25.0 mmol) and pyridine (14.0 mL; 168 mmol) were added to a solution of 3 (13.0 g; 14.0 mmol) in acetic anhydride (200 mL). The reaction mixture was stirred for 11 h at 60° C. The solution was evaporated, the residue taken up with $CHCl_3$ (300 mL) and the organic phase washed with $H_2O$ (3×50 mL). The organic layer was separated, dried over $Na_2SO_4$ and evaporated. The crude was purified by column chromatography (3:2 acetone/$CHCl_3$) to afford 4 (17.0 g; 12.0 mmol) as an oily product. Yield 86%. MS: 1421.5 (M+H).

Compound 5 To a solution of 4 (17.0 g; 12.0 mmol) in MeOH (120 mL) and AcOH (3.43 mL, 60 mmol), 10% Pd/C (1.1 g) was added and the suspension was stirred for 3 h under an hydrogen atmosphere at room temperature. After filtration the solution was evaporated under reduced pressure to give compound 5 (16.0 g; 12.0 mmol) as an oily product. Quantitative yield. MS: 1307.4 (M+H).

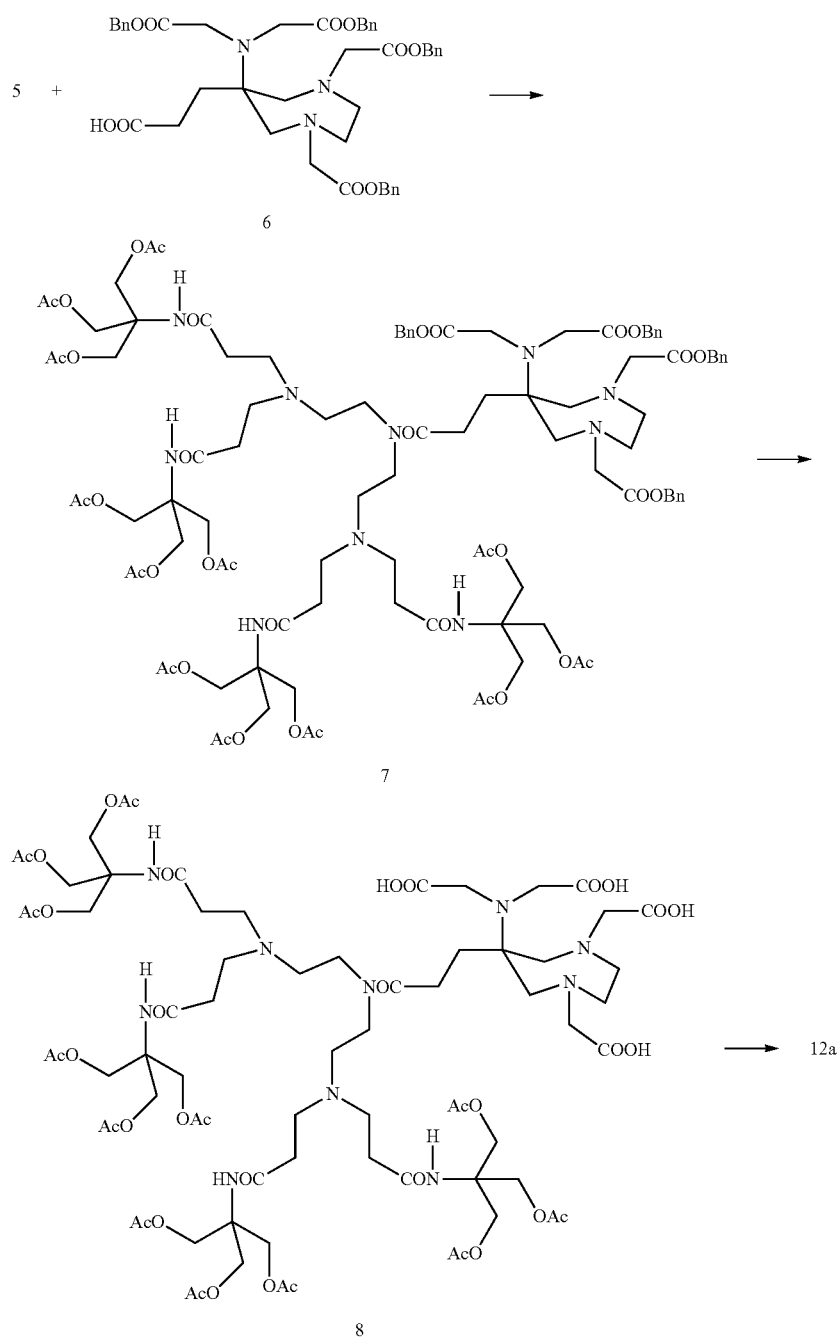

Compound 7 Diisopropylethylamine (DIEA) (130 µL, 0.77 mmol) was added to a mixture of acid 6 (300 mg, 0.38 mmol) (see EXAMPLE 3, scheme F) and HATU (180 mg, 0.46 mmol) in DMF (0.50 mL), and the mixture was stirred for 10 min at room temperature. A solution of compound 5 (500 mg, 0.38 mmol) in DMF (0.50 mL) was added to the activated acid solution and the mixture was stirred at room temperature for 15 h. DMF was removed under vacuum and the thick oil obtained was purified by column chromatography on silica gel to give product 7 (50.0 mg; 24.1 µmol) as a white solid. Yield 6.3%. MS: 2071.2 (M+H).

Compound 8 10% Pd/C (5 mg) was added to a solution of compound 7 (50.0 mg, 24.1 µmol) in MeOH (0.30 mL) and CHCl$_3$ (0.20 mL) and the solution was hydrogenated at atmospheric pressure for 48 h. The catalyst was removed by filtration and the solution was evaporated. The residue was dissolved in H$_2$O (0.50 mL) and acetonitrile (20 µL) and lyophilized to give the tetra-acid 8 (40 mg, 23 µmol) as a white solid. Quantitative yield. MS: 1710 (M+H).

Compound 12a A saturated solution of ammonia in methanol (1 mL) was added to the tetra-acid 8 (20.0 mg, 11.7 µmol) and the solution was allowed to stand at room temperature for 48 h. The reaction mixture was then evaporated and the residue dissolved in H$_2$O (500 µL) and acetonitrile (20 µL) and lyophilized to obtain compound 12a (10 mg, 8.3 µmol) as a white solid. Yield 71%. MS: 1206.5 (M+H).

Example 15
Preparation of Compound 5a of Formula 5
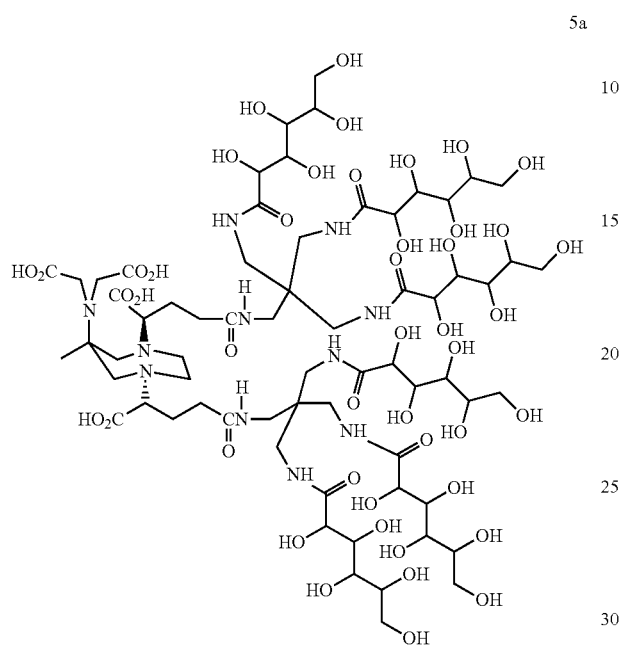
5a
The compound of formula 5a was prepared as per the following scheme Z-E:
Scheme Z-E
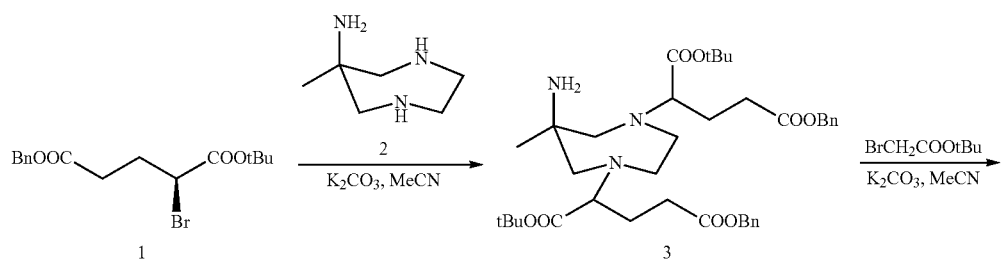
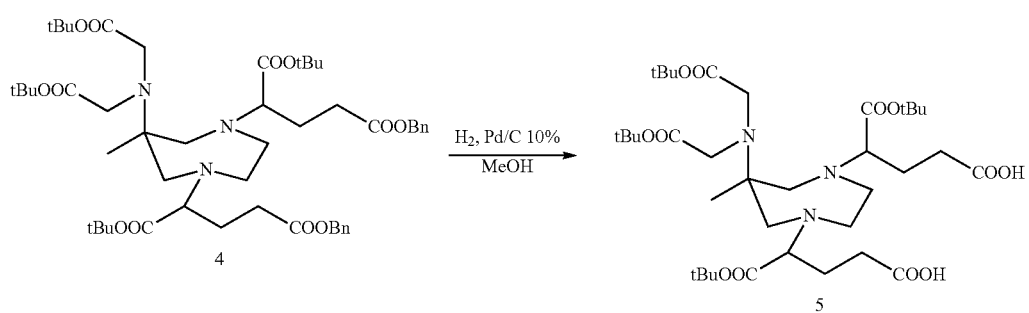

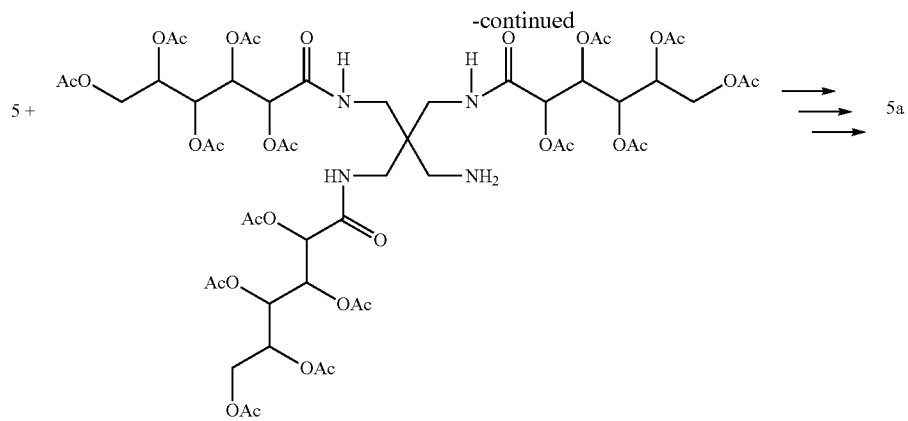

Compound 3 A mixture of 1 (see EXAMPLE 10, scheme S) (1.7 g, 4.8 mmol), 6-amino-6-methyl-perhydro-1,4-diazepine 2 (Aime, S. et al. *Inorg. Chem.* 2004, 43, 7588) (0.25 g; 1.9 mmol) and $K_2CO_3$ (0.67 g; 4.8 mmol) in MeCN (10 mL) was stirred for 72 h. The suspension was filtered and evaporated under reduced pressure. The residue was dissolved in $CH_2Cl_2$ (30 mL), then washed with water (2×20 mL) and brine (2×20 mL). After separation, the organic phase was dried ($Na_2SO_4$) and evaporated. The crude product was purified by flash chromatography to give 3 (1.1 g) as a yellow oil. Yield 85%.

Compound 4 t-Butyl bromoacetate (0.41 mL; 2.79 mmol) was added to a stirred solution of 3 (0.76 g; 1.11 mmol), $K_2CO_3$ (0.54 g; 3.90 mmol) and $Na_2SO_4$ (0.3 g) in MeCN (20 mL) cooled to 0° C. After the addition, the suspension was refluxed under nitrogen for 15 h then stirred at 60° C. for another 15 h. More t-butyl bromoacetate (0.41 mL; 2.79 mmol) was added and the reaction mixture was stirred at reflux for 8 h then at 60° C. for 15 h. The suspension was cooled to room temperature, filtered and the solvent evaporated. The residue was dissolved in $CH_2Cl_2$ (20 mL) and washed with $H_2O$ (2×10 mL) and 5% aq. $NaHCO_3$ (2×10 mL). The organic phase was dried ($Na_2SO_4$), filtered and evaporated. The crude orange oil was purified by flash chromatography to give 4 (0.65 g) as a yellow oil. Yield 64%.

Compound 5 10% Pd/C (100 mg) was added to a solution of compound 4 (0.5 g; 0.55 mmol) in MeOH (20 mL). The reaction mixture was stirred under hydrogen atmosphere for 5 h. The mixture was filtered through a Millipore® apparatus (FH 0.5 μm) and evaporated to give 5 (0.4 g) as a yellow solid. Yield 99%.

Compound 5a Compound 5a was synthesised by reacting the diacid 5 and the amine 6, prepared as per EXAMPLE 2 (scheme D), and by working in analogy to what reported in EXAMPLE 11 (scheme U).

Example 16

Preparation of Compound 1d of Formula

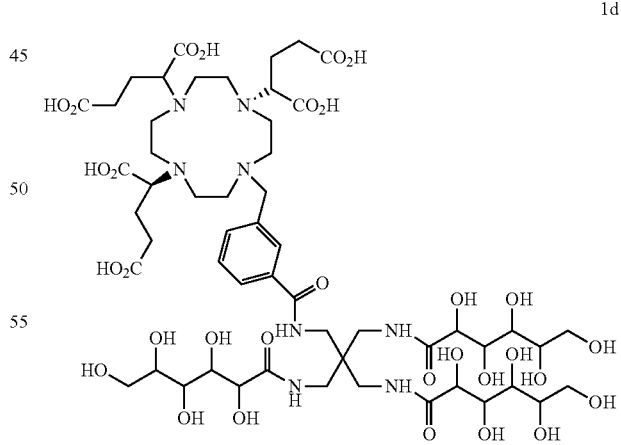

The compound 1d was prepared as per the following schemes Z-F:

Scheme Z-F
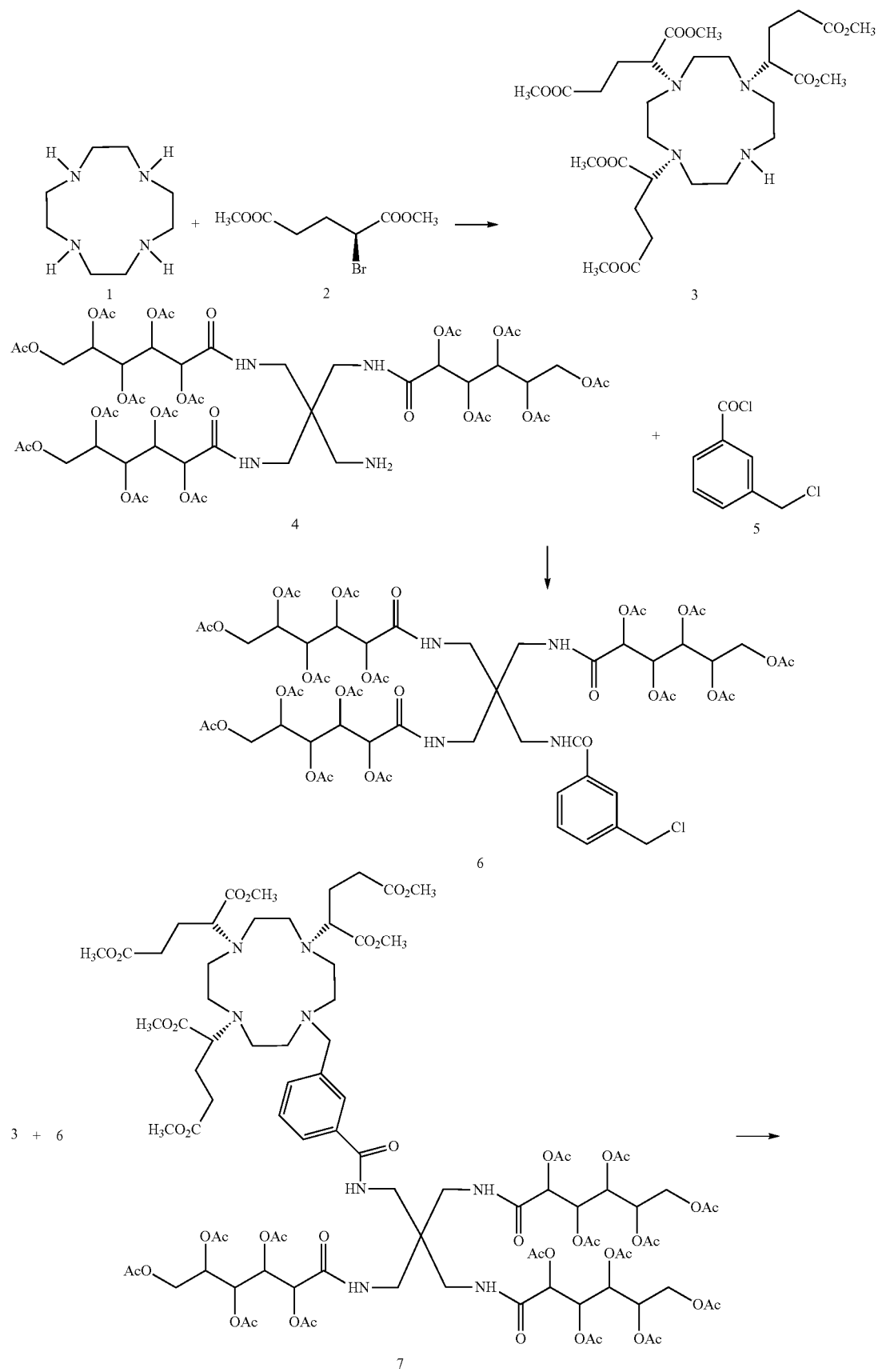

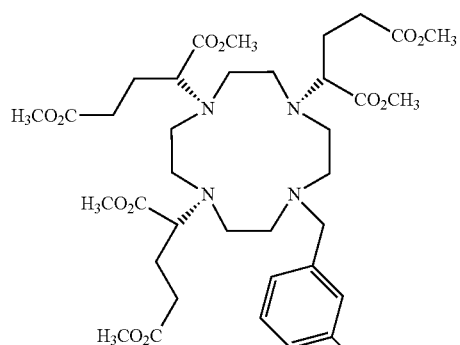

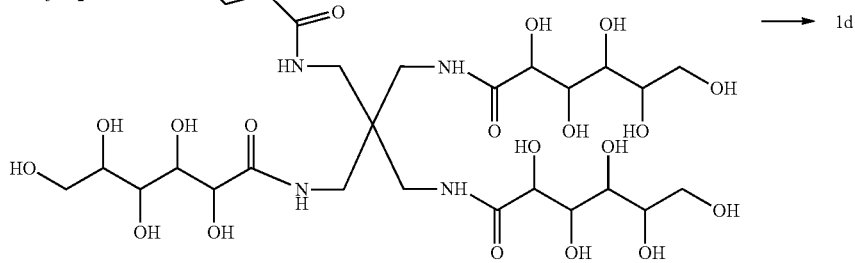

8

Compound 3 K$_2$CO$_3$ (525 mg; 3.79 mmol) and bromoderivative 2 (1.00 g; 4.18 mmol) were added to a solution of cyclen 1 (218 mg; 1.26 mmol) in anyh. acetonitrile. The suspension was heated to 60° C. for 12 hours under nitrogen atmosphere. The reaction mixture was filtered and the filtrate was diluted with CH$_2$Cl$_2$ (25 mL). The organic phase was washed with water (2×25 mL), separated, dried over Na$_2$SO$_4$ and evaporated under vacuum. The crude (770 mg) was purified by column chromatography on silica gel to afford product 3 (315 mg; 487 µmol) as a yellow oil. Yield 39%.
MS: 647.7 (M+H).

Compound 6 To a solution of amine 4 (3.00 g; 2.30 mmol), prepared as per EXAMPLE 2 (scheme D), in CH$_2$Cl$_2$ (50 mL) diisopropylethylamine (DIEA) (469 µL; 2.76 mmol) was added under nitrogen atmosphere. Chloride 5 (392 µl; 2.76 mmol) was added and the mixture was stirred at room temperature for 4 hours. The reaction mixture was washed with water (50 mL) and 0.1 N HCl (25 mL). The organic layer was separated, dried over Na$_2$SO$_4$ and evaporated under vacuum. The crude (3.42 g) was purified by column chromatography on silica gel to obtain 6 (1.39 g; 0.95 mmol) as a white solid. Yield 41%. MS: 1486.8 (M+Na).

Compound 7 A solution of 6 (847 mg; 584 µmol) in acetonitrile (15 mL) was dropped over 15 min to a suspension of compound 3 (315 mg; 490 µmol), K$_2$CO$_3$ (81.0 mg; 584 µmol) and Na$_2$SO$_4$ (50 mg) in acetonitrile (10 mL). The reaction mixture was heated to reflux for 12 hours, then filtered and the solution evaporated under vacuum. The residue was dissolved in EtOAc (50 mL) and the solution was washed with water (2×50 mL) and 5% aq. NaHCO$_3$ (2×50 mL). The organic layer was separated, dried over Na$_2$SO$_4$ and evaporated. The crude (960 mg) was purified by column chromatography on silica gel to obtain 7 (390 mg; 188 µmol) as a white solid. Yield 38%. MS: 2075.1 (M+H).

Compound 8 Compound 7 (390 mg; 188 µmol) was dissolved in MeOH (20 mL) and K$_2$CO$_3$ (24.0 mg; 0.18 mmol) was added. The suspension was stirred at room temperature for 4 hours then filtered and evaporated under vacuum to obtain 8 (256 mg; 179 µmol) as a white solid. Yield 95%. MS: 1452.5 (M+Na).

Compound 1d To a solution of compound 8 (74.0 mg; 52.0 µmol) in water (5.0 mL) at 50° C., 0.1N NaOH (3.12 mL) was added over 3 days to reach and maintain pH 11.5. The mixture was then allowed to cool to room temperature, acidified with 0.1N HCl (3.30 mL) to pH 2.5 and evaporated under vacuum. The crude was purified by elution through Amberlite XAD 16.00 resin to give the desired compound 1d (54.0 mg; 40.1 µmol). Yield 77%. MS: 1346.3 (M+H), 1368.3 (M+Na)

Example 17

Preparation of Compound 5d of Formula

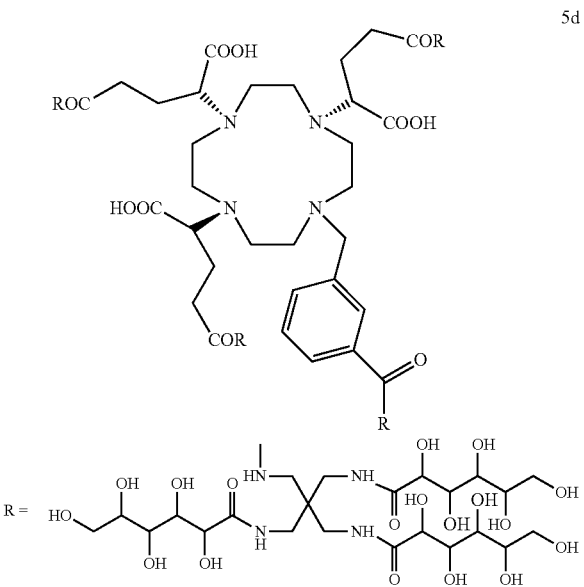

The compound of formula 5d was prepared as per the following scheme Z-G:
Scheme Z-G
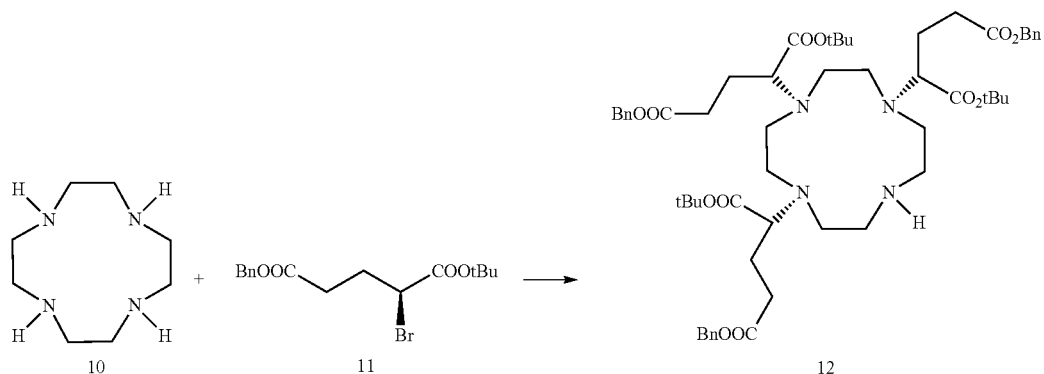
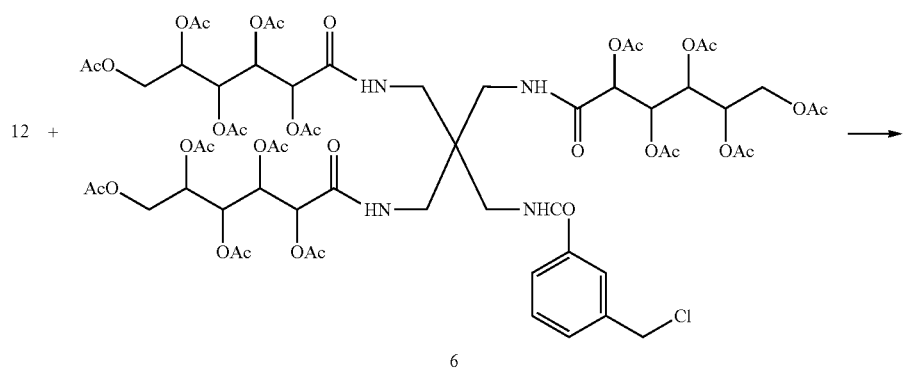
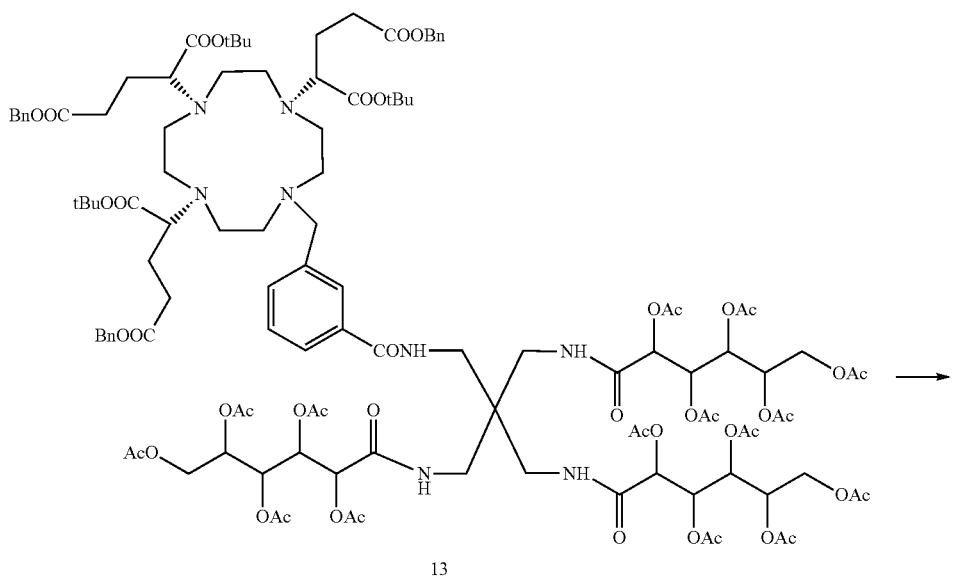

-continued
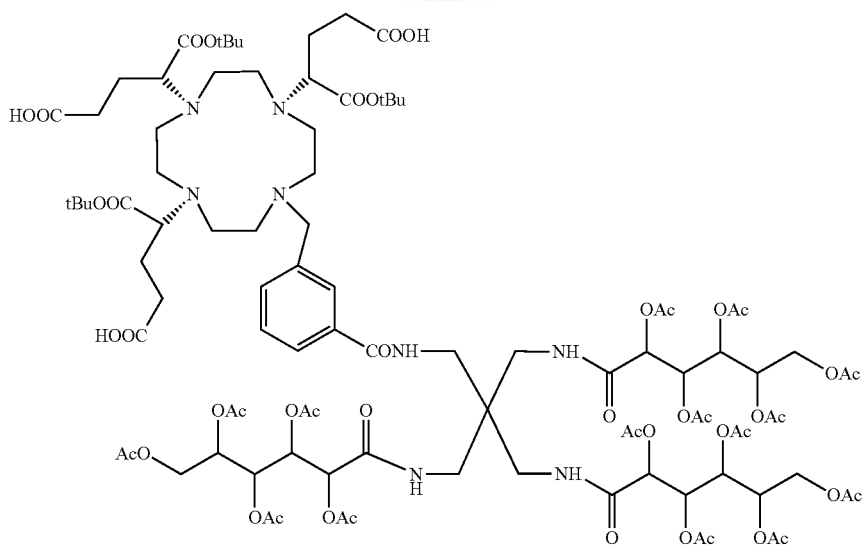
14
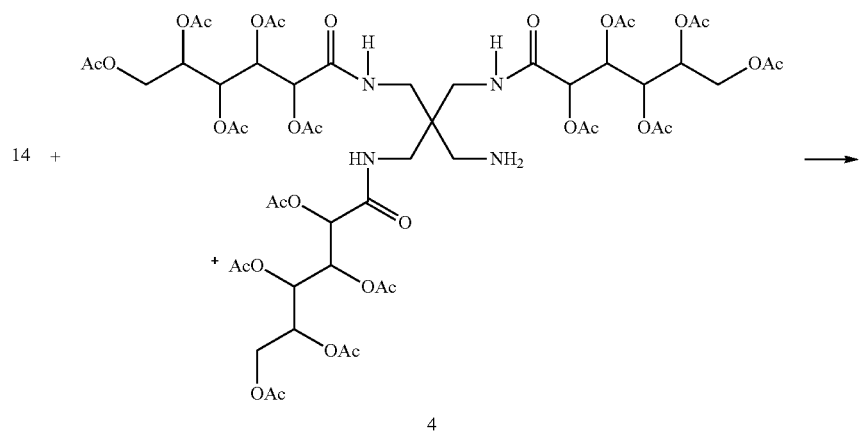
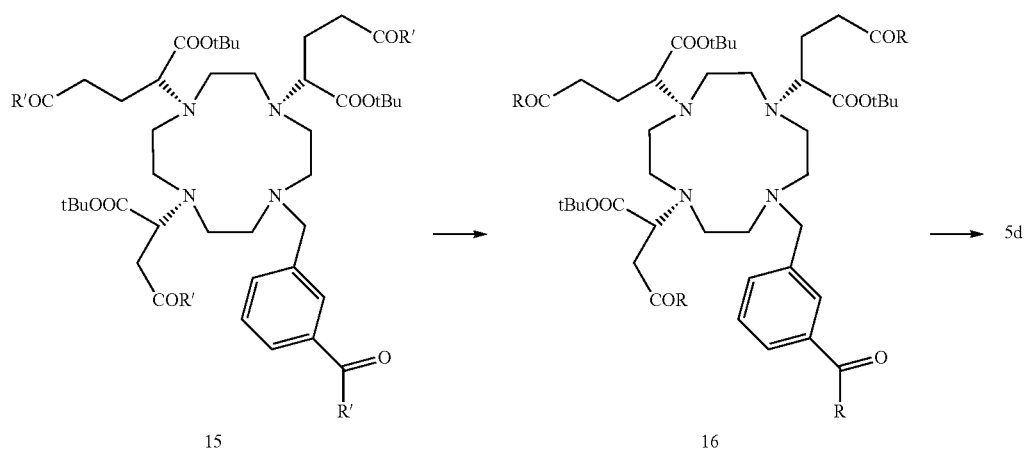

-continued

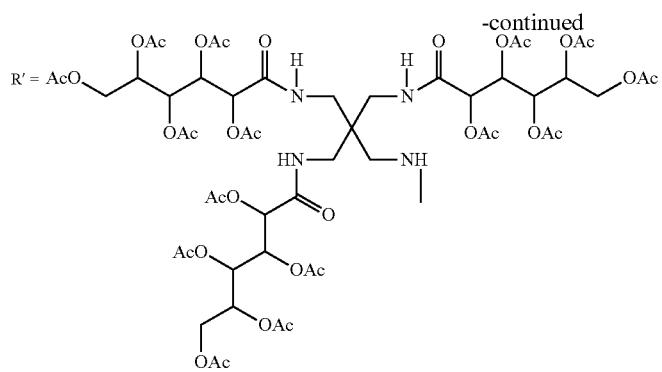

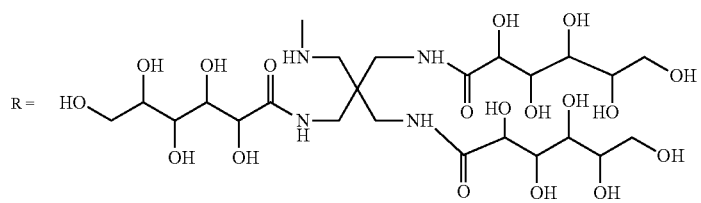

Compound 12 Compound 12 was synthesised from cyclen 10 and compound 11, prepared as per EXAMPLE 10 (scheme 6), by working in analogy to what reported in EXAMPLE 16 (scheme Z-F). Yield 84% (519 mg; 0.52 mmol). MS: 1024.3 (M+Na).

Compound 13 Compound 13 was synthesised from compounds 12 and 6 by working in analogy to what reported in EXAMPLE 16 (scheme Z-E).

Yield 84% (1.04 g; 0.43 mmol). MS: 2437.6 (M+Na).

Compound 14 Compound 13 (170 mg; 70.0 µmol) was dissolved in MeOH (10 mL) and hydrogenated at atmospheric pressure on 5% Pd/C (45 mg). After 2 hours the reaction mixture was filtered through Millipore® apparatus (0.5 µm filter) and the solution evaporated under vacuum to give compound 14 (110 mg).

Yield 73%. MS: 2167.2 (M+Na).

Compound 15 O-(7-Azabenzotriazol-1-yl)-N,N,N',N'-tetramethyluronium hexafluorophosphate (HATU) (63.0 mg; 164 µmol) and amine 4 (see EXAMPLE 2) (212 mg; 164 µmol) were added to a solution of compound 14 (110 mg; 51.0 µmol) and DIEA (58.0 µl; 0.33 mmol) in DMF (5 mL) at 0° C. The mixture was stirred at room temperature to for 48 hours under nitrogen atmosphere and then evaporated under vacuum. The residue was dissolved in CH$_2$Cl$_2$ (20 mL) and the solution washed with 5% aq. NaHCO$_3$ (20 mL) and water (20 mL). The organic layer was separated, dried over Na$_2$SO$_4$ and evaporated under vacuum. The crude was purified by column chromatography on silica gel to obtain compound 15 (128 mg; 21.4 µmol). Yield 42%. MS: 5982.7 (M+H).

Compound 16 Compound 16 was obtained by working in analogy to what reported in EXAMPLE 16 (scheme Z-F).

Yield 93% (70.0 mg; 20.0 µmol). MS: 3475.5 (M+H).

Compound 5d Compound 16 (70.0 mg; 20.0 µmol) was dissolved in trifluoroacetic acid (TFA) (1.0 mL) at 0° C. under a nitrogen atmosphere and the mixture was allowed to warm to room temperature and stirred for 18 h. The solution was evaporated, the residue taken up with fresh TFA (1.0 mL) and the solution stirred for further 5 h at room temperature. The reaction mixture was evaporated and the residue treated with Et$_2$O (20 mL). The suspension was filtered to afford the tris-trifluoroacetate salt of compound 5d (58.3 mg; 16.0 µmol) as a white solid. Yield 83%. MS: 3307.21 (M+H).

Example 18

Preparation of the Aminopolyol G11 (Protected Form) of Formula

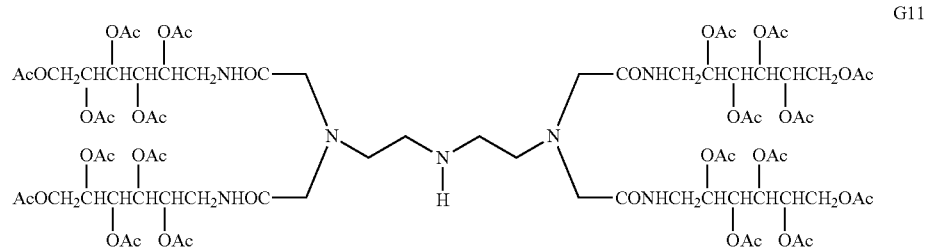

G11

The compound of formula G11, in a protected form (e.g. acylated), was prepared as per the following scheme Z-H:

Scheme Z-H

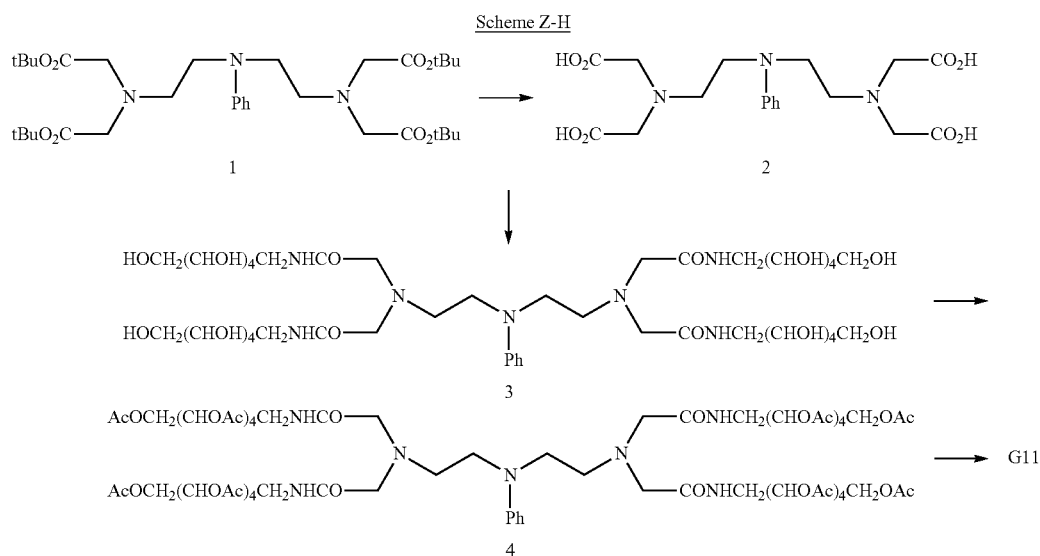

Compound 2 Trifluoroacetic acid (TFA) (0.71 mL) was added to a solution of 1 (0.50 g, 0.77 mmol) (WO 2001052899) in $CH_2Cl_2$ (5.0 mL) at room temperature. The reaction mixture was stirred for 24 hours and then concentrated. Neat TFA (5.0 mL) was added and the solution stirred 4 h longer then evaporated. The residue was taken up with $CH_2Cl_2$ (10 mL) and evaporated (operation repeated twice). The oily residue was treated with $Et_2O$ to afford the tris-trifluoroacetate of 2 (590 mg, 103 mmol) as a white solid. Quantitative yield. MS: 426.4 (M+H).

Compound 3 O-(Benzotriazol-1-yl)-N,N,N',N'-tetramethyluronium hexafluoro-phosphate (HBTU) (11.4 g; 30.0 mmol) and diisopropylethylamine (DMA) (7.65 mL; 45.0 mmol) were added to a solution of 2 (2.13 g; 5.00 mmol) (betainic form) in DMF (100 mL). After 10 min glucamine (5.43 g; 30.0 mmol) was added to the solution at room temperature and the mixture stirred for 48 h. Solvents were evaporated under vacuum and the oily residue dissolved in water and purified by elution through Amberlite XAD 16.00 resin to afford 3 (2.78 g, 2.58 mmol) as pale-yellow solid. Yield 52%. MS: 1079.2 (M+H).

Compound 4 Pyridine (10 mL) was added to a solution of 3 (1.19 g; 1.10 mmol) in acetic anhydride (10 mL) and the reaction mixture was stirred for 17 h at 60° C. The solution was evaporated, the residue taken up with $CHCl_3$ (50 mL) and the organic phase washed with $H_2O$ (3×50 mL). The organic layer was separated, dried over $Na_2SO_4$ and evaporated. The crude was purified by column chromatography (8:2:0.1 $CH_2Cl_2$/MeOH/AcOH) to afford the tris-acetate salt of 4 (1.01 g; 0.48 mmol) as an oily product. Yield 44%. MS: 1918.3 (M+H).

Compound G11 (protected) To a solution of 4 (1.01 g; 0.48 mmol) in MeOH (10 mL) and AcOH (0.25 mL), 10% Pd/C (0.10 g) was added and the suspension was stirred for 3 h under H atmosphere at room temperature. After filtration the solution was evaporated under reduced pressure, the residue taken up with $CHCl_3$ (10 mL) and the solution washed with sat. aq. $NaHCO_3$ (3×20 mL) and water (2×20 mL). The organic phase was dried and evaporated to give compound G11 (0.88 g) as off-white solid. Quantitative yield. MS: 1829.8 (M+H).

The compound of formula G11 may be used as such in the coupling reactions so as to give rise to the compounds of the invention. Alternatively, the acyl groups can be suitably removed so as to lead to free hydroxyl groups by working according to conventional methods of deprotection, for instance comprising treatment under basic conditions, as formerly reported in the examples.

Example 19

Preparation of the Aminopolyol G9 (Protected Form) of Formula

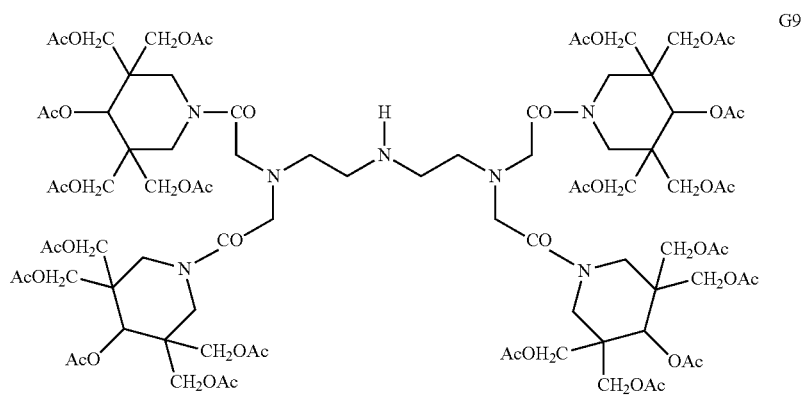

The compound of formula G9, in a protected form, was prepared as per the following scheme Z-I:

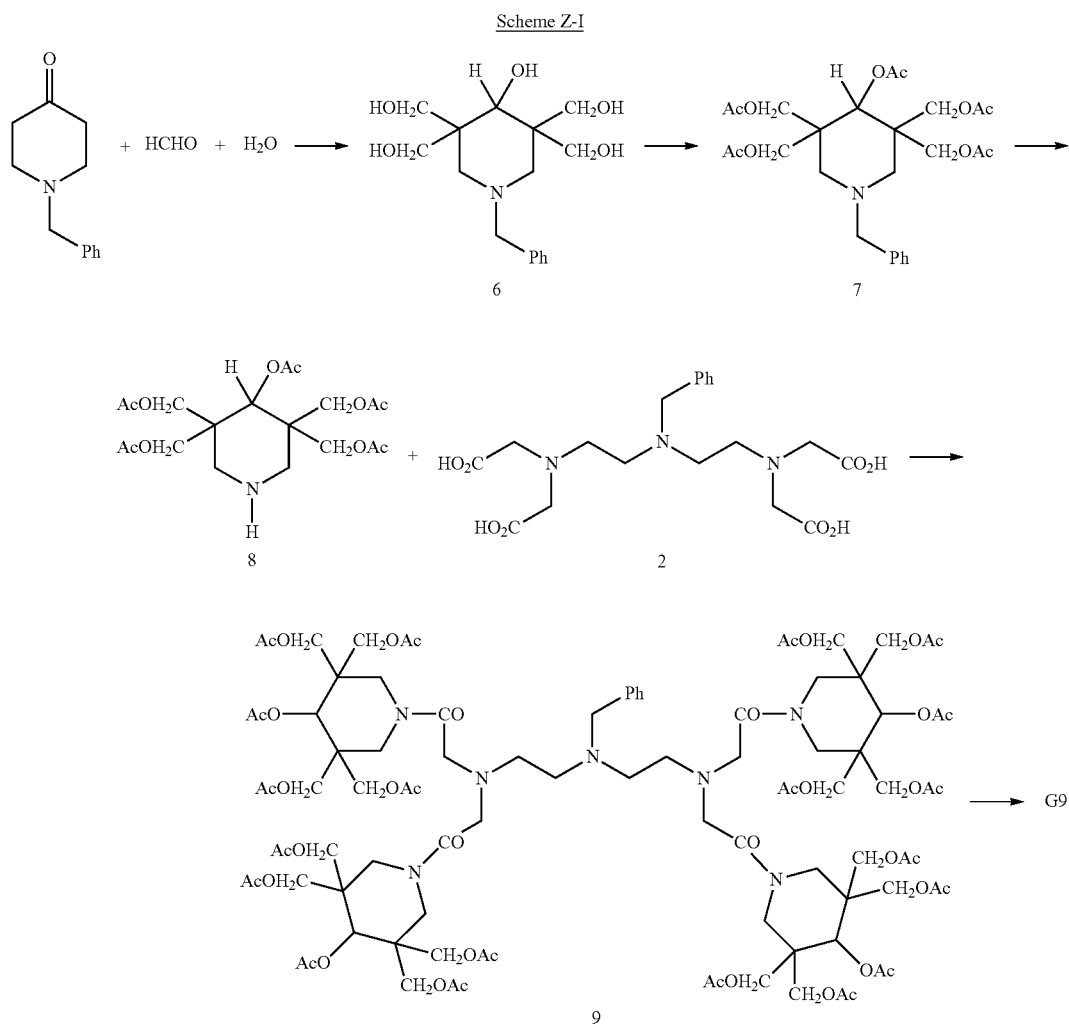

Compound 6 Compound 6 was synthesised from 1-benzyl-4-piperidone according to a procedure reported in the literature (Organic Synthesis 1951, 907).

Compound 7 Compound 6 was acetylated according to the procedure reported in EXAMPLE 18 (scheme Z-H, compound 4).

Compound 8 Compound 7 was hydrogenated according to the procedure reported in EXAMPLE 18 (scheme Z-H, compound 5).

Compound 9 Isobutyl chloroformate (1.28 g; 9.40 mmol) was added to a solution of tetra-acid 2 (see EXAMPLE 18, scheme Z-H) (1.00 g; 2.35 mmol) and N-methylpiperidine (1.14 mL; 9.40 mmol) in $CH_2Cl_2$ (10 mL) at 0° C., and the solution stirred at this temperature for 20 min. Amine 8 (4.05 g; 9.40 mmol) was added to the reaction mixture. After 1 h at 0° C. and a further hour at room temperature the mixture was diluted with $CH_2Cl_2$ (25 mL) and washed with sat. aq. $NH_4Cl$ (2×20 mL).

The organic phase was separated, dried over $Na_2SO_4$ and evaporated. The residue was purified by column chromatography on silica gel to give compound 9 (1.95 g; 0.94 mmol) as a white solid. Yield 40%. MS: 2100.8 (M+Na).

Compound G9 Compound 9 was hydrogenated according to the procedure reported in EXAMPLE 18 (scheme Z-H, preparation of compound C6).

The compound of formula G9 may be used as such in the coupling reactions so as to give rise to the compounds of the invention or suitably deprotected (see EXAMPLE 18).

Example 20

Preparation of a Compound (Herewith Below Compound 5) A-L'(H) Wherein A is a Chelating Unit of Formula (III) Bearing Protected Carboxy Groups and L' is a Linker —$CH_2$—NH—

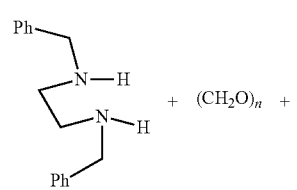

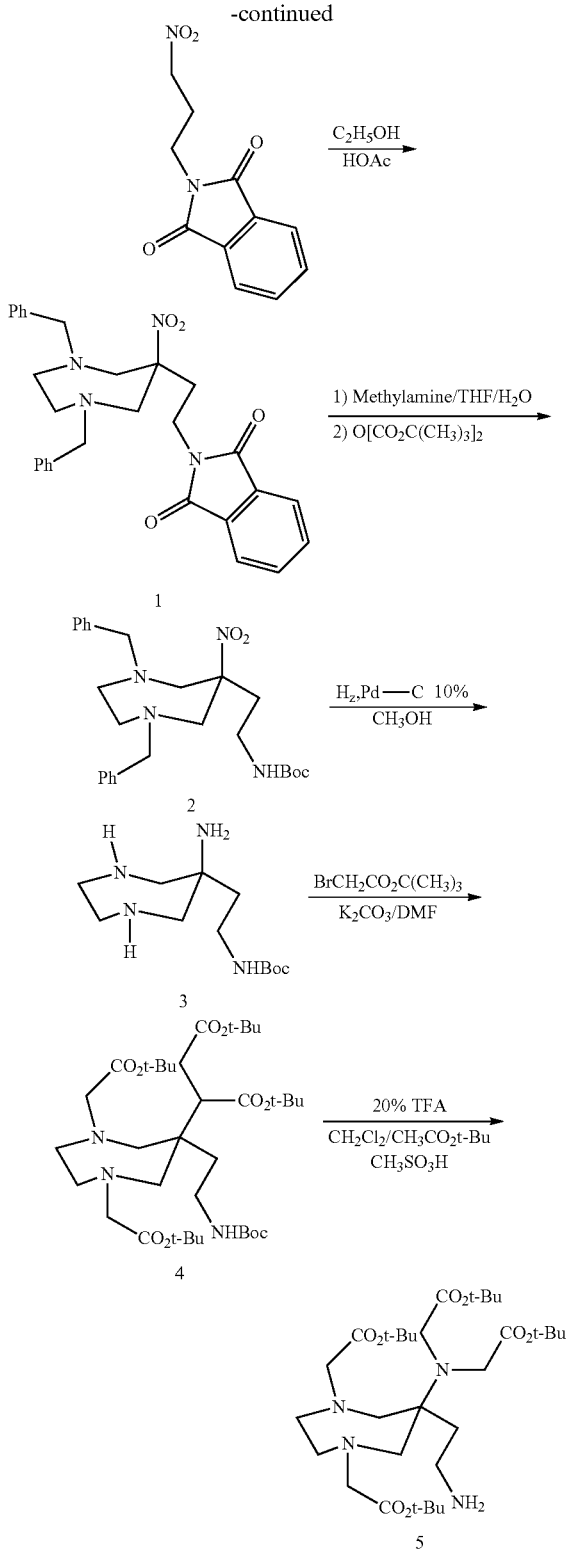

ued at 80° C. to obtain a clear solution. Paraformaldehyde (5.0 g, 166 mmol) was added to this solution in small portions over a period of 30 min and the stirring continued for 5 h at 80° C. The reaction mixture was cooled and the solid formed was filtered, washed with cold ethanol and dried under vacuum. Yield 22.0 g (88%). MS: 499.5 (M+H).

Compound 2 Phthalimido derivative 1 (21.0 g, 42.0 mmol) was added to a mixture of $CH_3NH_2$/THF (40.0 mL) $CH_3NH_2$/$H_2O$ (80 mL) and stirred at room temperature for 48 h. Excess methylamine was removed by passing a stream of nitrogen and the solvent was removed under vacuum. The solid obtained was dissolved in a mixture of tetrahydrofuran (100 mL) and water (10 mL). Di-tert-butyl dicarbonate (19.0 g, 87.0 mmol) was added to the THF-water solution and stirred for 16 h. Solvents were removed and the pasty solid obtained was dissolved in ethyl acetate (400 mL), washed with sodium chloride solution (2×200 mL) and dried ($Na_2SO_4$). Evaporation of ethyl acetate gave a yellow oil, which was purified by silica gel column chromatography using hexane-ethyl acetate (7:3). UV visible fractions were collected and evaporated to give 2, as an oil. Yield 18.20 g (92%). MS: 469.2 (M+H).

Compound 3 Pd—C 10% (750 mg) was added to a solution of the nitro compound 2 (2.0 g, 4.27 mmol) in methanol (40 mL), and the mixture was hydrogenated at 45 psi for 24 h. The catalyst was removed by filtration and methanol was removed on a rotary evaporator to give the amine 3 as a thick oil. Yield 1.0 g (91%). MS: 259.2 (M+H).

Compound 4 tert-Butyl bromoacetate (3.8 g, 2.88 mL, 19.5 mmol) was added to a mixture of the amine 3 (1.0 g, 3.87 mmol) and potassium carbonate (2.69 g, 19.5 mmol) in DMF (4 mL) and the mixture was stirred at 40° C. for 12 h. DMF was removed under vacuum and the oil obtained was dissolved in ethyl acetate (150.0 mL), washed with water and dried. ($Na_2SO_4$). Evaporation of ethyl acetate gave an oil which was purified by column chromatography using hexane-ethyl acetate (7:3). Product containing fractions (Rf 0.7) were collected and evaporated to give a thick oil. Yield 1.10 g (40%). MS: 715.5 (M+H), 737.4 (M+Na)

Compound 5 Boc derivative 4 (0.82 g 1.15 mmol) was added to a mixture of methylene chloride (5 mL), t-butyl acetate (15 mL), and TFA (4 mL) and the mixture was stirred for 10 min. Methanesulfonic acid (300 μL) in methylene chloride (1 mL) was added in portions over a period of 10 min and stirred for 12 h. The solution was neutralized by sodium bicarbonate solution and extracted with ethyl acetate. The ethyl acetate solution was washed with water and dried ($Na_2SO_4$). Evaporation of ethyl acetate gave an oil which was dried under vacuum to give a foamy solid.

Yield 0.7 g (99%). MS: 615.4 (M+H).

Example 21

Preparation of a Compound (Herewith Below Compound 8) A-L'(H) Wherein A is a Chelating Unit of Formula (III) Bearing Protected Carboxy Groups and L' is a Linker —$CH_2$—NH— Protected at the Amino Site

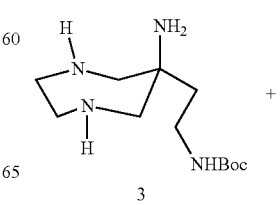

Compound 1 Acetic acid (6.0 mL) was added to a solution of N,N-dibenzylethylenediamine (12.18 g, 50.6 mmol) in ethanol (80 mL) and the solution was stirred at 60° C. for 10 min (a white solid formed which dissolved on heating to 80° C.). N-(3-nitropropyl) phthatimide[1] (11.7 g, 50.0 mmol) [([1]) Alston, T. A.; Porter, D. J. T.; Bright, H. J. *J. Enzyme Inhibition.* 1987, 212-222] was added and the stirring was contin-

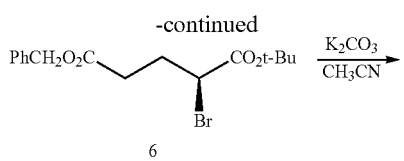

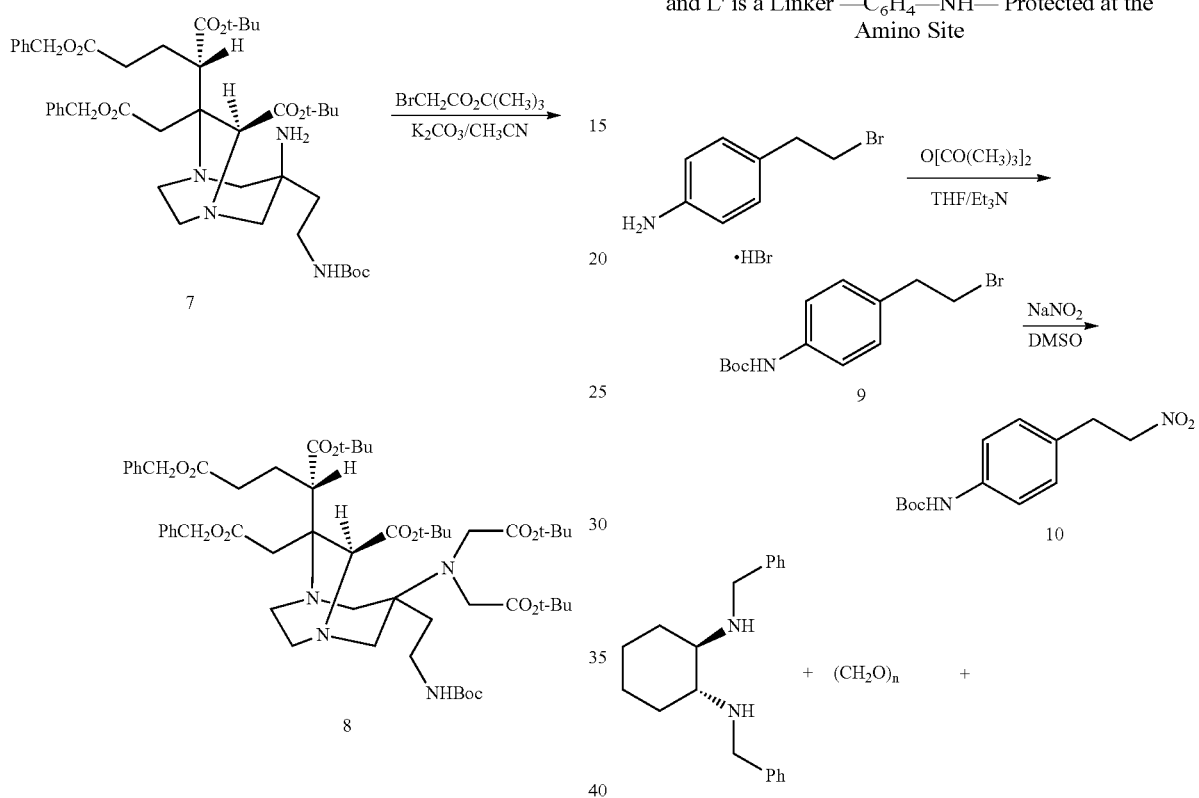

Compound 7 Bromo-ester[2] 6 (0.8 g, 2.24 mmol) [(2)Eisenwiener, K.-P.; Powell, P.; Macke, H. R. *Bioorg., Med. Chem. Lett.* 2000, 10, 2133-2135] was added to a mixture of the amine 3 (0.26 g, 1.0 mmol) and potassium carbonate (0.5 g, 3.62 mmol) in acetonitrile (4 mL) and the mixture was stirred for 8 h. The reaction mixture was filtered and acetonitrile was evaporated under vacuum. The thick oil obtained was dissolved in ethyl acetate, washed with water and dried ($Na_2SO_4$). Evaporation of ethyl acetate gave an oil which was purified by silica gel column chromatography using methylene chloride-methanol (95:5). Fractions (Rf 0.5) were collected and evaporated to give the ester 7 as an oil. Yield 0.3 g (37%). MS: 811.4 (M+H), 849.3 (M+K)

Compound 8 tert-Butyl bromoacetate (0.29 g, 0.22 mL, 1.4 mmol) was added to a mixture of the amine 7 (0.3 g, 0.37 mmol), and potassium carbonate (0.2 g, 1.45 mmol) in acetonitrile (3 mL) and the mixture was stirred at 70° C. for 24 h. Acetonitrile (15 mL) was added to the reaction mixture and filtered. Acetonitrile was removed and the oil obtained was dissolved in ethyl acetate, washed with water (2×10 mL) and dried ($Na_2SO_4$). Evaporation of the solvent gave a brown oil, which was purified by column chromatography (silica gel, hexane-ethyl acetate, 7:3). UV visible fraction (Rf 0.45) were collected and evaporated to give 8, as an oil, which solidified on standing. Yield 0.27 g (70%). MS: 1040.4 (M+H).

Example 22

Preparation of a Compound (Herewith Below Compound 13) A-L'(H) Wherein A is a Chelating Unit of Formula (IIIa) Bearing Protected Carboxy Groups and L' is a Linker —$C_6H_4$—NH— Protected at the Amino Site

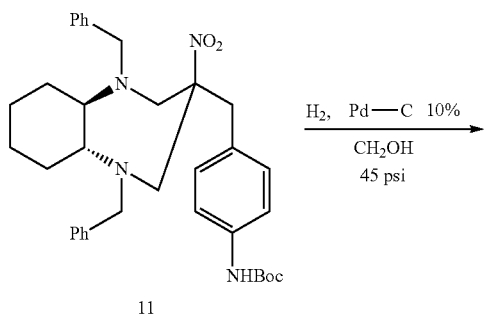

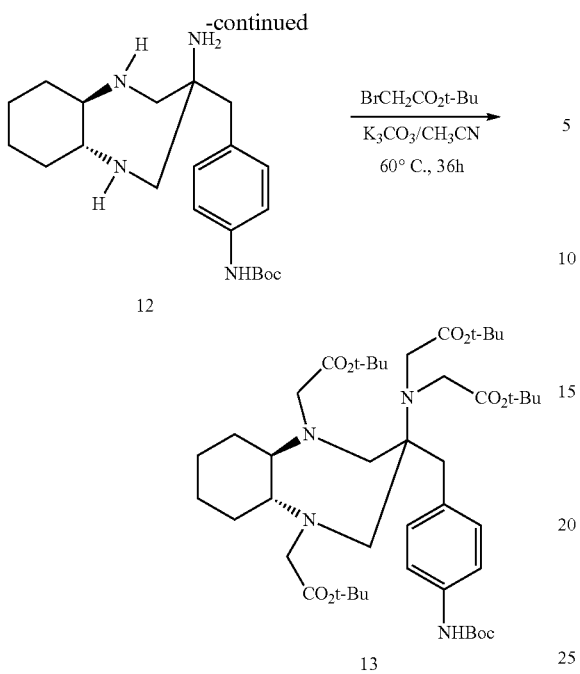

and the mixture was hydrogenated at 45 psi for 24 h at RT. The catalyst was removed by filtration and the solvent was removed under vacuum to give an oil which was used in the next step without further purification.

Yield 1.28 g (95%). MS: 375.3 (M+H), 389.4 (M+Na)

Compound 13 tert-Butyl bromoacetate (2.34 g, 1.78 mL, 12 mmol) was added to a solution of the amine 12 (0.75 g, 2.0 mmol) and potassium carbonate (1.66 g, 12.0 mmol) in DMF (4 mL) and the mixture was stirred at 70° C. for 24 h. Methylene chloride (10.0 mL) was added to the reaction mixture and filtered. The solvents were removed and the brown oil obtained was purified by silica gel column chromatography ($CH_2Cl_2$:$CH_3OH$, 95:5). UV visible fractions (Rf 0.48) were collected and evaporated to give an oil which solidified on standing. Yield 0.75 g, (45%). MS: 831.5 (M+H).

Example 23

Preparation of a Compound (Herewith Below Compound 18) A-L'(H) Wherein A is a Chelating Unit of Formula (IIIa) Bearing Protected Carboxy Groups and L' is a Linker —$CH_2$—NH—

Compound 9 Di-tert-butyl dicarbonate (30.0 g 138 mmol) was added to an ice cooled mixture of p-aminophenylethyl bromide hydrobromide[3] (36.0 g, 128 mmol) [[3]Tamai, T.; Tanaka, M.; Mukaiyama, H.; Hirabayashi, A.; Muranaka, H.; Sato. M.; Akahane, M. U.S. Pat. No. 6,353,025] and triethylamine (10 mL) and the mixture was stirred at room temperature for 24 h. Solvents were removed and the pasty solid was treated with water and extracted with ethyl acetate. Evaporation of ethyl acetate gave a solid, which was purified by column chromatography using hexane-ethyl acetate. UV visible fractions were collected and evaporated to give a white solid. Yield 34.2 g (88%). MS: 324.2 (M+Na)

Compound 10 Compound 9 (3.0 g, 10.0 mmol) was added to a mixture of sodium nitrite (1.4 g, 20.0 mmol) in DMSO (5 mL), and the mixture was stirred for 2 h. A semi-solid was formed after 30 min. After the reaction, the mixture was poured in to water and extracted with ethyl acetate. The ethyl acetate solution was washed with water and dried ($Na_2SO_4$). Evaporation of ethyl acetate gave an yellow solid, which was purified by column chromatography using hexane-ethyl acetate (7:3). UV visible fractions were collected and evaporated to give a yellow solid. Yield 1.29 g (48.5%). MS: 289.2 (M+Na)

Compound 11 Acetic acid (0.6 mL) was added to a solution of trans N,N-dibenzyl-1,2-diaminocyclohexane[4] (1.43 g, 4.85 mmol) [[4]Tye, H.; Eldred, C.; Wills, M. Tetrahedron Lett. 44, 155-158 (2002)] in ethanol (5.0 mL) and stirred at 60° C. for 10 min. Compound 10 (1.29 g, 4.84 mmol) was added to this solution and the stirring was continued at 60° C. for additional 10 min. Paraformaldehyde (0.5 g, 16.6 mmol) was added in small portions over a period of 30 min and the reaction mixture was stirred at 80° C. for 5 h. Ethanol was removed and the residue was extracted with ethyl acetate, washed with water and dried. Evaporation of ethyl acetate gave an oil, which was purified by silica gel column chromatography (hexane-ethyl acetate 7:3). UV visible fractions were collected and evaporated to give an oil. Yield 2.2 g (76%). MS: 585.3 (M+H), Compound 12 Pd—C 10% (1.0 g) was added to a warm slurry of compound 10 (2.1 g, 3.6 mmol) in methanol (40 mL)

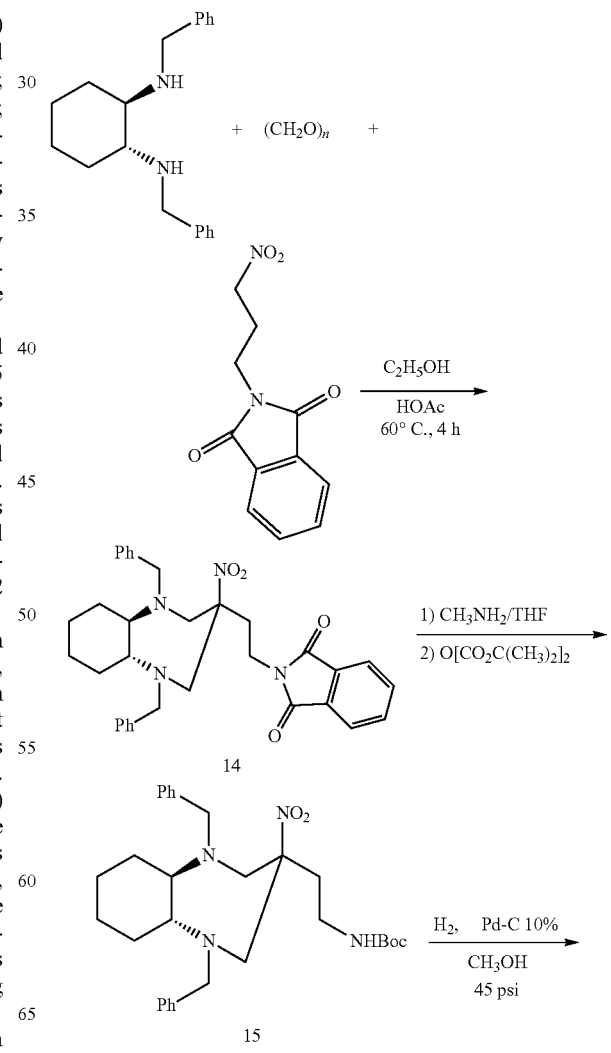

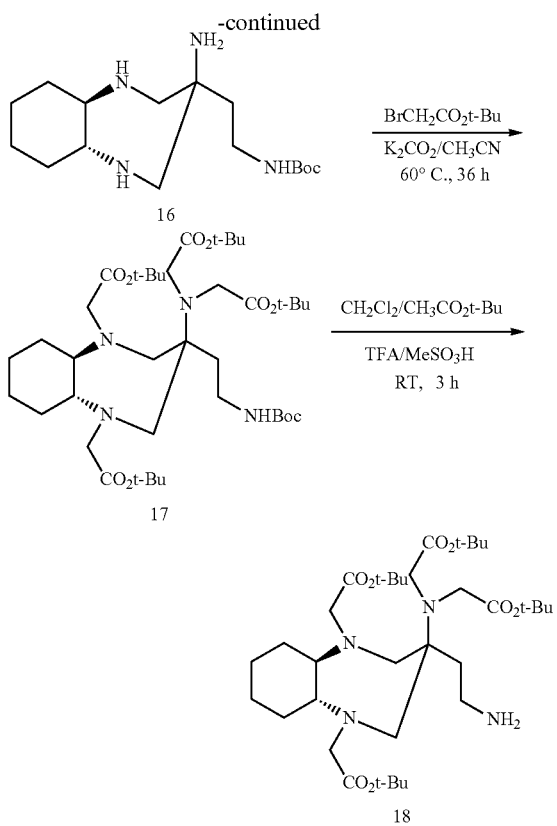

Compound 14 Acetic acid (3.60 mL) was added to a solution of trans-N,N-dibenzyl-1,2-diaminocyclohexane (8.82 g, 30.0 mmol) in ethanol (60 mL) and the solution was stirred at 60° C. for 10 min. N-(3-nitropropyl)phthalimide (7.1 g, 30.3 mmol) was added and the stirring was continued at 60° C. for additional 30 min. Paraformaldehyde (3.75 g, 126 mmol) was added to this solution in small portions over a period of 30 min and the stirring was continued for 5 h at 80° C. Ethanol was removed and the thick oil obtained was dissolved in ethyl acetate (200 mL) and the ethyl acetate solution was washed with sodium bicarbonate solution, water and dried (Na₂SO₄). Ethyl acetate solution was concentrated and the resulting oil was purified by silica gel column chromatography (7:3). Fractions (Rf 0.48) were collected and evaporated to give a thick yellow oil, which was dried under vacuum to give a foamy solid. The foamy solid obtained was dissolved in methanol (50.0 mL) and allowed to stand for 30 min. The solid formed was filtered, washed with cold ethanol and dried under vacuum. Yield 8.3 g (50.0%). MS: 553.3 (M+H).

Compound 15 Phthalimido derivative 14 (8.0 g, 14.5 mmol) was added to a mixture of 2 M solution of CH₃NH₂ in THF (75 mL) and 40% solution of CH₃NH₂ in H₂O (30 mL) and the mixture was stirred at room temperature for 48 h. Excess methylamine was removed by passing a stream of nitrogen and the solvent was removed under vacuum. The yellow solid obtained was dissolved in a mixture of tetrahydrofuran (100 mL) and water (10 mL). Di-tert-butyl Bicarbonate (8.72 g, 40.0 mmol) was added to the THF solution and stirred for 6 h. THF was removed and the pasty solid obtained was dissolved in ethyl acetate (300 mL), washed with sodium carbonate solution, then washed with sodium chloride solution (2×200 mL) and dried (Na₂SO₄). Evaporation of ethyl acetate gave an yellow oil which was purified by silica gel column chromatography using hexane-ethyl acetate (9:1, and 8:2). UV visible fractions were collected and evaporated to give 14 as an oil. The oil obtained was dissolved in methanol (50 mL) and allowed to stand for 1 h. The white solid formed was filtered and dried under vacuum. Yield 5.1 g (67.5%). MS: 523.3 (M+H).

Compound 16 Compound 14 (4.80 g, 9.2 mmol) in methanol (50 mL), was hydrogenated at 45 psi for 72 h in the presence of Pd—C 10% (2.0 g). The catalyst was removed by filtration and methanol was removed under reduced pressure to give 2.6 g (90%) of the amine 16. MS: 313.2 (M+H).

Compound 17 tert-Butyl bromoacetate (3.51 g, 2.65 mL, 18.0 mmol) was added to a slurry of potassium carbonate (2.5 g, 18.0 mmol) and amine 16 (0.93 g, 3.0 mmol) in DMF (4 mL) and the mixture was stirred at 70° C. for 24 h. Methylene chloride (10 mL) was then added to the reaction mixture and filtered. The solvents were removed and the brown oil obtained was purified by silica gel column chromatography (hexane-ethyl acetate 7:3). Fractions (Rf 0.48) were collected and evaporated to give an oil, which solidified on standing. Yield 1.1 g, (48.0%). MS: 769.5 (M+H).

Compound 18 Boc derivative 4 (1.1 g 1.43 mmol) was added to a mixture of methylene chloride (5 mL), t-butyl acetate (25 mL), and TFA (5 mL) and the mixture was stirred for 10 min. Methanesulfonic acid (400 μL) in methylene chloride (1 mL) was added in portions over a period of 10 min and the reaction was allowed to stir for 3 h. The solution was neutralized by sodium bicarbonate solution and extracted with ethyl acetate. The ethyl acetate solution was washed with water and dried (Na₂SO₄). Evaporation of ethyl acetate gave an oil, which was dried under vacuum to give a foamy solid. Yield 0.82 g (99%). MS: 669 (M+H).

Example 24

Preparation of a Compound (Herewith Below Compound 7) A-[L'(OH)]₂L''(OH) Wherein A is a Chelating Unit of Formula (III) Bearing Protected Carboxy Groups, L' is a Linker —CH₂—CH₂CO— and L'' is a Linker —CH₂CO—

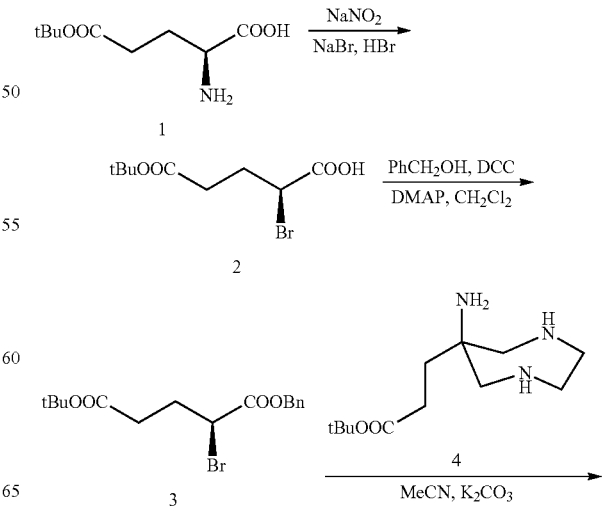

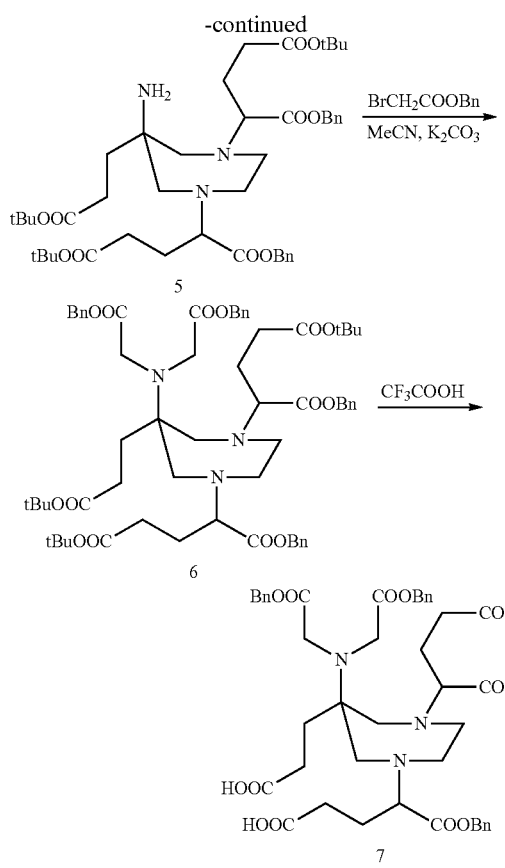

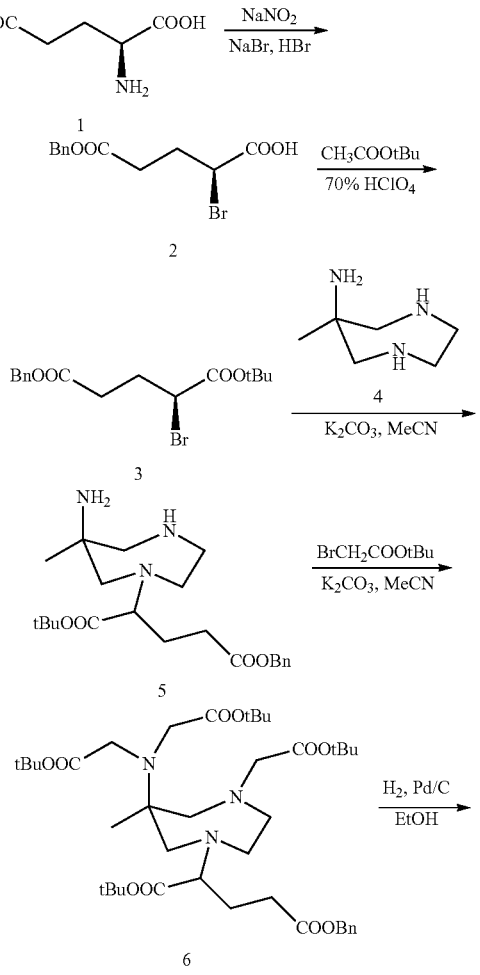

g; 2.80 mmol) and Na₂SO₄ (0.22 g) in MeCN (5 mL) cooled to 0° C. After the addition, the reaction mixture was allowed to warm to room temperature and refluxed for 6 h. Further amounts of benzyl bromoacetate (0.05 g; 0.30 mmol) and K₂CO₃ (0.04 g; 0.28 mmol) were added to the mixture that was refluxed for more 8 h. The mixture was filtered, evaporated and the residue taken up with CH₂Cl₂ (10 mL). The organic phase was washed with water (2×10 mL), dried (Na₂SO₄) and evaporated under reduced pressure. The crude was purified by column chromatography to give 6 (0.22 g) as a yellow oil. Yield 19%.

Compound 7 A solution of compound 6 (0.22 g; 0.20 mmol) in CF₃COOH (2.5 mL) was stirred at room temperature for 60 h. The mixture was then evaporated, the residue taken up with CH₂Cl₂ (10 mL) and the solution evaporated under reduced pressure. The operation was repeated two more times to afford a crude that was purified by column chromatography to give 7 (0.12 g) as a pale yellow oil. Yield 65%.

Example 25

Preparation of a Compound (Herewith Below Compound 7) A-L'(OH) Wherein A is a Chelating Unit of Formula (III) Bearing Protected Carboxy Groups and L' is a Linker —CH₂—CH₂CO—

Compound 2 A solution of NaNO₂ (1.35 g; 19.6 mmol) in water (15 mL) was added dropwise over 30 min to a mixture of L-glutamic acid 5-tbutyl ester 1 (commercial product) (2.0 g; 9.8 mmol) and KBr (4.31 g; 36.0 mmol) in 1 N HBr (45 mL) cooled to 0° C. After 3 h at 0° C. the solution was extracted with EtOAc (3×100 mL). The combined organic phases were washed with brine (80 mL), dried (Na₂SO₄) and evaporated under reduced pressure. The crude product was purified by column chromatography to give (0.53 g) 2 as a colourless oil. Yield 20%.

Compound 3 A solution of compound 2 (1.38 g; 5.2 mmol), benzyl alcohol (0.58 mL; 5.7 mmol), N,N'-dicyclohexylcarbodiimide (DCC) (1.18 g; 5.7 mmol) and 4-dimethylaminopyridine (DMAP) (0.06 g; 0.52 mmol) in CH₂Cl₂ (25 mL) was stirred at room temperature for 3 h. The precipitated dicyclohexylurea was filtered off and the filtrate was washed with 5% aq. AcOH (20 mL) and water (3×20 mL), dried (Na₂SO₄) and evaporated under reduced pressure. The crude product was purified by column chromatography to give 3 (1.31 g) as a colourless oil. Yield 71%.

Compound 5 A solution of 3 (1.30 g; 3.65 mmol) in MeCN (2 mL) was added dropwise over 5 min to a mixture of 6-amino-hexahydro-1H-1,4-diazepine-6-propanoic acid 1,1-dimethylethyl ester 4 (Example 1, Scheme B, compound 10) (0.40 g; 1.66 mmol) and K₂CO₃ (0.57 g; 4.15 mmol) in MeCN (13 mL) cooled at 0° C. The reaction mixture was allowed to warm to rt and stirred for 29 h. Salts were filtered off and the filtrate evaporated under reduced pressure. The crude product was purified by column chromatography to give 5 (0.91 g) as a yellow oil. Yield 69%.

Compound 6 Benzyl bromoacetate (0.41 mL; 2.60 mmol) was added to a mixture of 5 (0.83 g; 1.05 mmol), K₂CO₃ (0.41

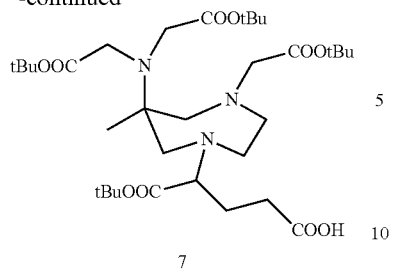

7

Compound 2 A solution of L-glutamic acid γ benzyl ester 1 (commercial product) (20 g, 84.3 mmol) in 1M HBr (400 mL) was cooled to −7° C. under mechanical stirring, then NaBr (32.1 g, 311.9 mmol) was added. A solution of NaNO$_2$ (11.05 g, 160.2 mmol) in water (40 mL) was dropped into the reaction solution in 35 min. After 1 h, conc. H$_2$SO$_4$ (10 mL) was added and the mixture was extracted with Et$_2$O (4×200 mL); the combined organic phases were washed with brine (2×150 mL), dried (Na$_2$SO$_4$) and evaporated at reduced pressure. The crude was purified by column chromatography to give the desired product 2 (13.79 g). Yield: 54%.

Compound 3 Compound 1 (13.46 g, 44.7 mmol) was dissolved in tert-butylacetate (179 mL), then 70% HClO$_4$ was added (193 μL) and the solution stirred at room temperature. Water (180 mL) was added after 24 h and the organic phase was separated, washed with water (130 mL), 5% aq. NaHCO$_3$ (130 mL) and water again (130 mL), dried (Na$_2$SO$_4$) and evaporated at reduced pressure. The crude was purified by column chromatography to give the product 3 (10.75 g). Yield: 67%.

Compound 5 A solution of bromoderivative 3 (5.5 g; 15.4 mmol) in MeCN (30 mL) was dropped in 35 min into a suspension of 6-amino-6-methyl-perhydro-1,4-diazepine 4 (Aime, S. et al. *Inorg. Chem.* 2004, 43, 7588) (6.62 g; 51.3 mmol) and K$_2$CO$_3$ (2.13 g; 15.4 mmol) in MeCN (130 mL) cooled with an ice bath. After this time, the cooling bath was removed and the reaction mixture was stirred at room temperature. After 4 h the mixture was filtered and the solvent evaporated at reduced pressure. The crude was dissolved in EtOAc (150 mL) and washed with water (3×100 mL). The organic phase was washed with diluted HBr, the aqueous phase was brought to pH 9 with 25% NH$_4$OH, then extracted with EtOAc (4×70 mL). The combined organic phases were washed with water (100 mL), dried over Na$_2$SO$_4$ and evaporated to give the product 5 (4.8 g). Yield: 77%.

Compound 6 t-Butyl bromoacetate (7.86 g, 40.3 mmol) was added to a suspension of compound 5 (4.65 g, 11.5 mmol), K$_2$CO$_3$ (6.36 g, 46 mmol) and Na$_2$SO$_4$ (1.5 g, 10.6 mmol) in MeCN (80 mL) and the mixture was heated at reflux. After 16 h the mixture was filtered and evaporated at reduced pressure. The crude was purified by flash chromatography to give the desired product 6 (7.24 g). Yield: 84%.

Compound 7 Compound 6 (572 mg, 0.77 mmol) was dissolved in EtOH (50 mL) and hydrogenated on 10% Pd/C (100 mg) at atmospheric pressure. The mixture was filtered through a Millipore® apparatus (FH 0.5 μm) and evaporated at reduced pressure to give product 7 (430 mg). Yield: 85%.

Example 26

Preparation of a Compound (Herewith Below Compound 7) A-L'(H) Wherein A is a Chelating Unit of Formula (III) Bearing Protected Carboxy Groups and L' is a Linker —(CH$_2$)$_4$—NH—

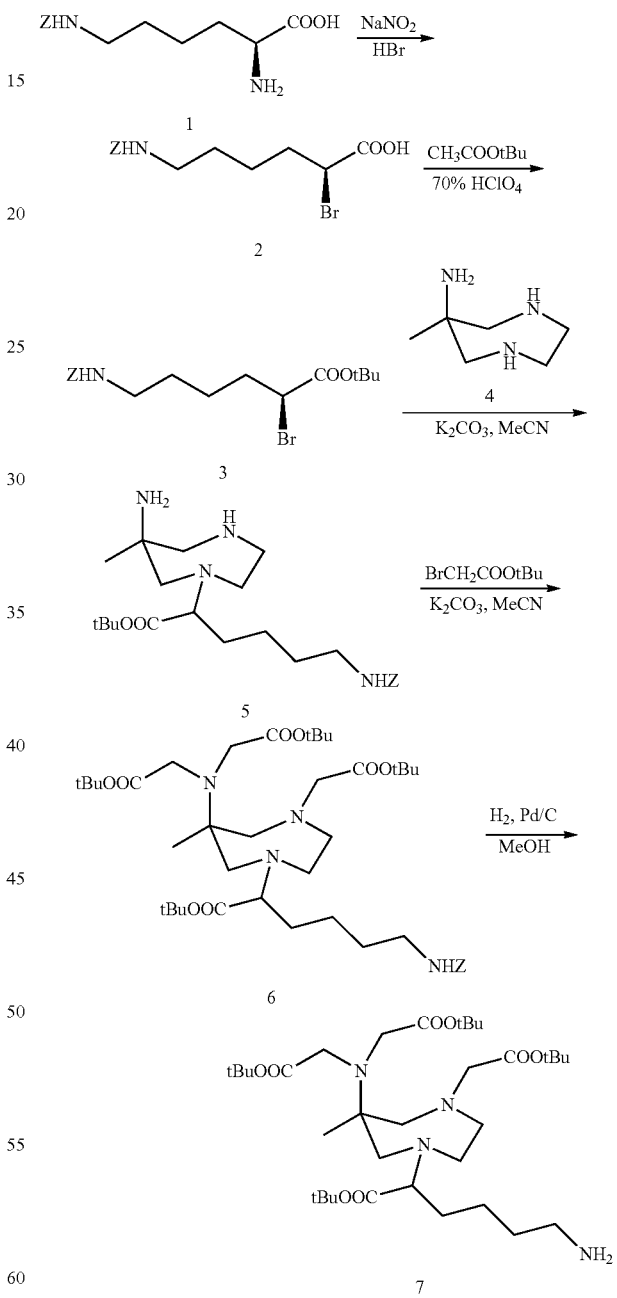

Compound 2 N$^ε$-carbobenzyloxy-L-lysine 1 (commercial product) (15 g; 0.052 mol) was dissolved in 6M HBr (45 mL) at 0° C. NaNO$_2$ (3.97 g; 0.057 mol) was added in little portions over 30 min. The reaction solution was stirred at room temperature for 2 h, then extracted with ethyl acetate (3×100 mL). The organic phase was dried (Na$_2$SO$_4$), filtered and evaporated under vacuum. The crude was purified by column chromatography to give the compound 2 (14.06 g) as an orange oil. Yield 79%.

Compound 3 70% aq. HClO$_4$ (1.5 mL) was added dropwise to a solution of the compound 2 (13 g; 0.0377 mol) in tert-butylacetate (160 mL). The reaction mixture was stirred at room temperature for 24 h. Then was washed with water (2×200 mL) and with 5% aq. NaHCO$_3$ (2×150 mL). The organic phase was dried (Na$_2$SO$_4$), filtered and evaporated under vacuum. The crude was purified by column chromatography and the product 3 (9.66 g) was obtain as a yellow oil. Yield 64%.

Compound 5 A solution of compound 3 (4.6 g; 0.115 mol) in MeCN (25 mL) was added dropwise in 30 min to a mixture of 6-amino-6-methyl-perhydro-1,4-diazepine 4 (Aime, S. et al. *Inorg. Chem.* 2004, 43, 7588) (5 g; 0.039 mol) and K$_2$CO$_3$ (1.59 g; 0.0115 mol) in MeCN (25 mL) at 0° C. The mixture was stirred at room temperature for 4 h then evaporated under vacuum. The crude was dissolved in EtOAc (25 mL) and washed with water (3×25 mL). The organic phase was dried (Na$_2$SO$_4$), filtered and evaporated under vacuum. The crude was dissolved in EtOAc (25 mL) and washed with aq. HBr. The aqueous phases were collected, the pH was brought to 9 by addition of aq. NH$_4$OH and extracted with ethyl acetate (3×100 mL). The organic phases were dried (Na$_2$SO$_4$) filtered and evaporated to give product 5 (3.3 g). Yield 64%.

Compound 6 A solution of t-butyl bromoacetate (3.8 mL) in MeCN (20 mL) was added dropwise to a stirred suspension of compound 5 (3.28 g; 7.3 mmol), K$_2$CO$_3$ (3.6 g) and Na$_2$SO$_4$ (0.5 g) in MeCN (30 mL) at 0° C. At the end of the addition the mixture was heated at reflux for 14 h. Then was filtered and evaporated under vacuum. The crude was dissolved in CH$_2$Cl$_2$ (50 mL), washed with water (50 mL) and 5% aq. NaHCO$_3$ (2×50 mL); the organic layer was dried (Na$_2$SO$_4$), filtered and evaporated under vacuum. The crude was purified by column chromatography and the product 6 (3.32 g) was obtain like a yellow oil. Yield 58%.

Compound 7 10% Pd/C (400 mg) was added to a solution of compound 7 (3.32 g; 4.2 mmol)) in MeOH (20 mL). The reaction mixture was stirred under hydrogen atmosphere for 2 h. The mixture was filtered through aMillipore® apparatus (FH 0.5 µm) and evaporated to give compound 7 (2.42 g) as a yellow oil. Yield 90%.

Example 27

Examples of Protection/Deprotection and Coupling

Within the compounds A-L'(H) of the previous examples from 20 to 26 any amino group, either as a free group or upon deprotection, can be properly coupled to a polyhydroxylated moiety, either bearing a terminal carboxy group or, alternatively, through a suitable linking group and then to an aminopolyol so as to get the compounds of the invention.

In addition, the said chelating unit bearing an amino group may be suitably coupled to a proper polyol-lactone; for a general reference see, as an example, the operative conditions being adopted in EXAMPLE 31 (e.g. condensation of a polyol-lactone with an amine) Deprotection of amino groups may be carried out according to known methods. As an example, removal of the tert-butoxycarbonyl group may be easily accomplished in acidic environment (e.g. TFA, methanesulfonic acid, in dichloromethane).

In addition to the above, compound 8 of example 21 may be suitably and selectively deprotected. As an example, the benzyloxy groups can be removed through catalytic hydrogenation (e.g. H$_2$, Pd/C 10%, methanol, 24 h) so as to get the corresponding dicarboxylic acid derivative which, in turn, may be suitably functionalized with proper aminopolyols (e.g. in the presence of HATU and diisopropylethylamine in DMF) so as to lead to the compounds of the invention.

The operative conditions to be employed in the above coupling reactions or according to any step of deprotection are all known in the art.

Example 28

Preparation of a Compound (Herewith Below Compound 25) A-L'(OH) Wherein A is a Chelating Unit of Formula (III) Bearing Carboxy Protected Groups and L' is a Linker —CH$_2$—CO—

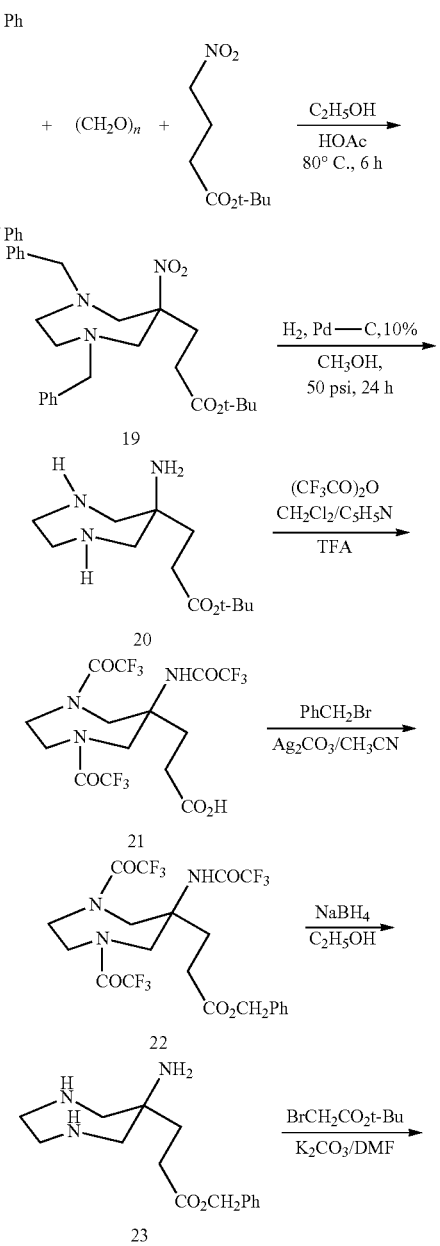

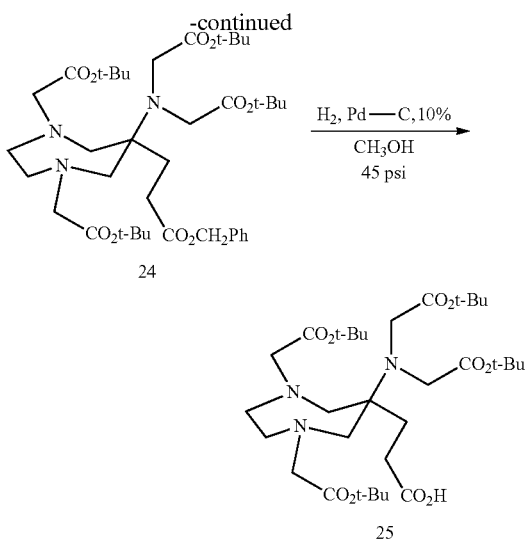

Compound 19 Acetic acid (3 mL) was added to a solution of N,N'-dibenzylethylenediamine (6.0 g, 25 mmol) in ethanol (40 mL) and the mixture was stirred at 60° C. for 10 min. 4-Nitrobutyric acid t-butyl ester (4.73 g, 25 mmol) was then added to the reaction mixture and the stirring was continued at 60° C. for additional 10 min. Paraformaldehyde (2.5 g, 83 mmol) was added in portions to the reaction mixture and the suspension was stirred at 80° C. for 5 h and at RT overnight. The dark reaction mixture was concentrated and the residue was treated with a solution of sodium bicarbonate and extracted with ethyl acetate (400 mL). The ethyl acetate solution was washed with water (2×200 mL) and dried ($Na_2SO_4$). Evaporation of ethyl acetate gave a dark thick oil. It was purified by silica gel column chromatography using methylene chloride. UV visible fractions were collected and evaporated to give a light yellow oil, which solidified on standing. Yield 8.9 g (86.5%). MS: 454.3 (M+H).

Compound 20 Pd—C 10%, (2.0 g) was added to a solution of the nitro compound 19 (4.5 g, 10 mmol) in methanol (25 mL) and the mixture was hydrogenated at 50 psi for 24 h. The catalyst was removed by filtration and the methanol was removed on a rotary evaporator. The oil obtained was dried under vacuum for 24 h to give the amine 20. Yield 2.2 g (92%). MS: 244.2 (M+H)

Compound 21 Pyridine (15.0 mL) was added to a solution of the amine 20 (3.5 g, 14.4 mmol) in methylene chloride (25.0 mL) and the mixture was cooled to −10° C. Trifluoroacetic anhydride (22.7 g, 15.25 mL, 108 mmol) in methylene chloride (25.0 mL) was added dropwise over a period of 30 min. The reaction mixture was stirred at 0° C. for 3 h and at room temperature for 12 h. Solvents were removed and the pasty mass obtained was dissolved in ethyl acetate (200 mL) and the washed with water and dried ($Na_2SO_4$). Evaporation of ethyl acetate gave an yellow oil, which was dried under vacuum to yield a foamy solid. Yield 6.92 g (90%).

Trifluoroacetic acid (15 mL) was added to a solution of the t-butyl ester (5.0 g, 9.4 mmol) in methylene chloride (10 mL) and the solution was stirred for 6 h. Solvents were removed and the resulting brown oil was dissolved in ethyl acetate, washed with water and dried ($Na_2SO_4$). Ethyl acetate solution was concentrated and the residue was dried under vacuum is to give 21 as a yellow foamy solid. Yield 4.23 g (95%). MS: 474.1 (M−H)

Compound 22 Silver carbonate (3.43 g, 12.4 mmol) was added to a solution of the acid 21 (4.2 g, 8.8 mmol) in acetonitrile (15 mL) and the mixture was stirred for 10 min. Benzyl bromide (3.42 g, 2.4 mL, 12.4 mmol) was then added to the reaction mixture and stirring was continued for 5 h. Methylene chloride (25 mL) was added to the reaction mixture and filtered. The filter cake was washed with methylene chloride (15.0 mL). The filtrate was concentrated and the brown oil obtained was purified by column chromatography (silica gel, hexane-ethyl acetate, 7:3). Fractions (Rf 0.45) were collected and evaporated to give a light yellow oil which, was dried under vacuum to give a light yellow solid. Yield 4.2 g (84%). MS: 588.1 (M+Na)

Compound 23 Sodium borohydride (0.23 g, 6.0 mmol) was added to a cooled slurry of the trifluoroacetamide 22 (0.57 g, 1.0 mmol) in absolute ethanol (5 mL), in two portions. The reaction mixture was stirred at 10° C. for 30 min and room temperature for 30 min. Ethanolic HCl was then added to the reaction mixture and the solvent was removed to give 0.72 g of the crude product. It was used in the next step without further purification. MS: 278.2 (M+H), 300.1 (M+Na)

Compound 24 tert-Butyl bromoacetate (1.17 g, 0.89 mL, 6.0 mmol) was added to a slurry of hydrochloride 23 (0.72 g, 1.0 mmol) and potassium carbonate (0.83 g, 6.0 mmol) in DMF (1 mL) and the mixture was stirred at 40° C. for 24 h. Methylene chloride (5 mL) was added to the reaction mixture and filtered. Solvents were removed under vacuum and the crude product was dissolved in ethyl acetate, washed with water, and dried ($Na_2SO_4$). Evaporation of the ethyl acetate gave an oil which, was purified by silica gel column chromatography (hexane-ethyl acetate, 7:3). Fractions (Rf 0.5) were collected and evaporated to give the benzyl ester 24 as a light yellow oil. Yield 0.12 g (17%). MS: 734.4 (M+H), 756.4 (M+Na)

Compound 25 Benzyl ester 24 (0.15 g, 0.2 mmol) in methanol (5 mL) was hydrogenated in the presence of Pd—C 10% (150 mg) at 45 psi for 6 h. The catalyst was removed by filtration and the methanolic solution was concentrated to give an oil. It was dried under vacuum to give foamy solid. Yield 0.11 g (83%). MS: 644.4 (M+H).

The title compound 25, A-L'(H), may be then coupled as previously reported through the free carboxy moiety with any suitable aminopolyol so as to get the compounds of the invention.

Example 29

Preparation of a Compound (Herewith Below Compound 30) A-L'(OH) Wherein A is a Chelating Unit of Formula (IIIa) Bearing Protected Carboxy Groups and L' is a Linker —$CH_2$—CO—

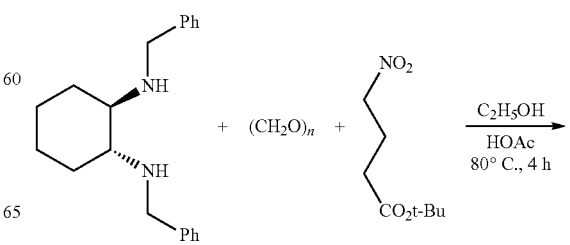

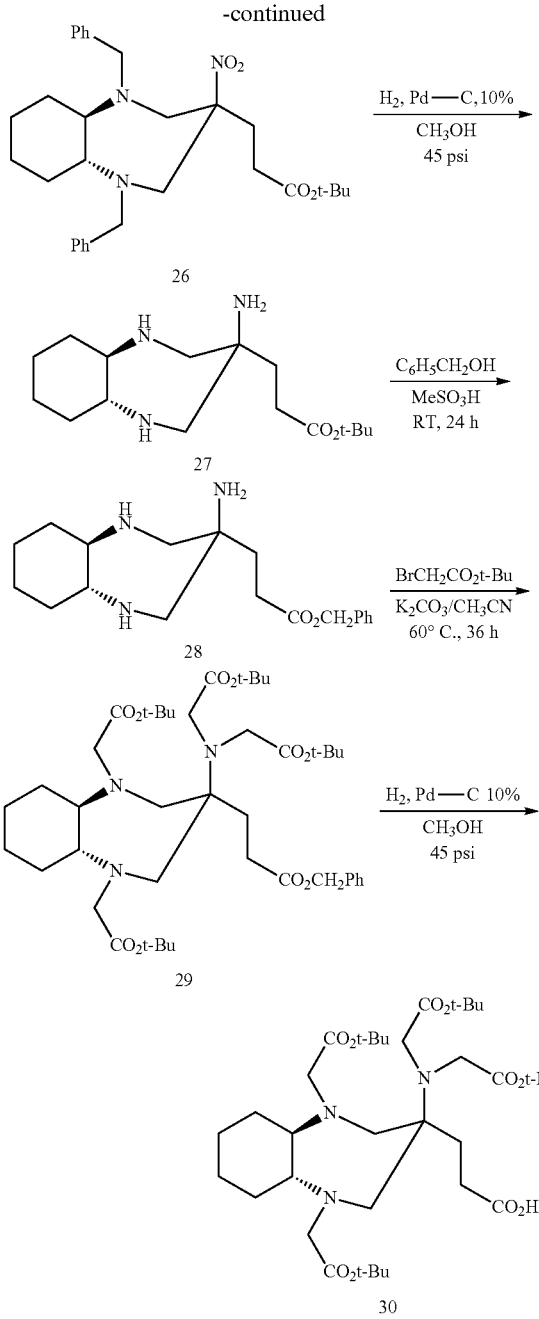

C. for 10 min. 4-Nitrobutyric acid-t-butyl ester (7.1 g, 37.5 mmol) was then added and the stirring was continued for additional 10 min. Paraformaldehyde (3.37 g, 125 mmol) was added in portions over a period of 30 min and stirred at 80° C. for 6 h. The reaction mixture was cooled and the solid formed was filtered and washed with ethanol and dried under vacuum. Yield 9.2 g (49%). MS: 508 (M+H).

Compound 27 Pd—C 10%, (2.0 g) was added to a warm solution of the nitro compound 26 (5.1 g, 10 mmol) in methanol (50 mL) and the mixture was hydrogenated at 50 psi for 24 h. The catalyst was removed by filtration and the methanol was removed to give 2.92 g (98%) of the amine 27. MS: 298 (M+H).

Compound 28 Methanesulfonic acid (1.0 mL) was added to a solution of the t-butyl ester 27 (1.0 g, 3.37 mmol) in benzyl alcohol (20 mL) and the mixture was stirred for 24 h. THF (100 mL) was added to the reaction mixture and the solid formed was filtered and triturated with THF (2×50 mL) and filtered. The crude benzylester obtained was used in the next step. Yield 1.2 g (57%). MS: 332.3 (M+H).

Compound 29 tert-Butyl bromoacetate (0.51 g, 0.39 mL, 2.6 mmol) was added to a mixture of 28 (0.15 g, 0.45 mmol) and potassium carbonate (0.5 g, 3.7 mmol) in DMF (4 mL) and the mixture was stirred for 48 h. Methylene chloride (10 mL) was added to the reaction mixture and the solvents were removed to give an oil. The oil obtained was chromatographed over silica gel using methylene chloride, then methylene chloride-methanol (95:5). Fractions containing the product (Rf 0.4) were collected and evaporated to give an oil. Yield 0.15 g (43%). MS: 788.6 (M+H), 826.4 (M+K)

Compound 30 Pd—C 10% (250 mg) was added to a solution of the benzyl ester (0.4 g, 0.19 mmol) in methanol (10 mL) and the mixture was hydrogenated at 45 psi for 6 h. The catalyst was removed by filtration and the methanolic solution was concentrated to give an oil which was dried under vacuum to give a foamy solid.

Yield 0.32 g (92%). MS: 698.4 (M+H).

The title compound 30, A-L'(H), may be then coupled as previously reported through the free carboxy moiety with any suitable aminopolyol so as to get the compounds of the invention.

Compound 26 Acetic acid (4.5 mL, 75 mmol) was added to a solution of trans-N,N-dibenzyl-1,2-diaminocyclohexane (10.87 g, 0.037 mmol) in ethanol (50 mL), and stirred at 60°

Example 30

Preparation of a Compound (Herewith Below Omega-carboxydecylAAZTA) A-L'(OH) Wherein A is a Chelating Unit of Formula (III) and L' is a Linker —$(CH_2)_8$—CO—

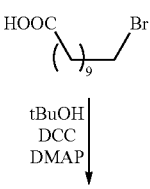

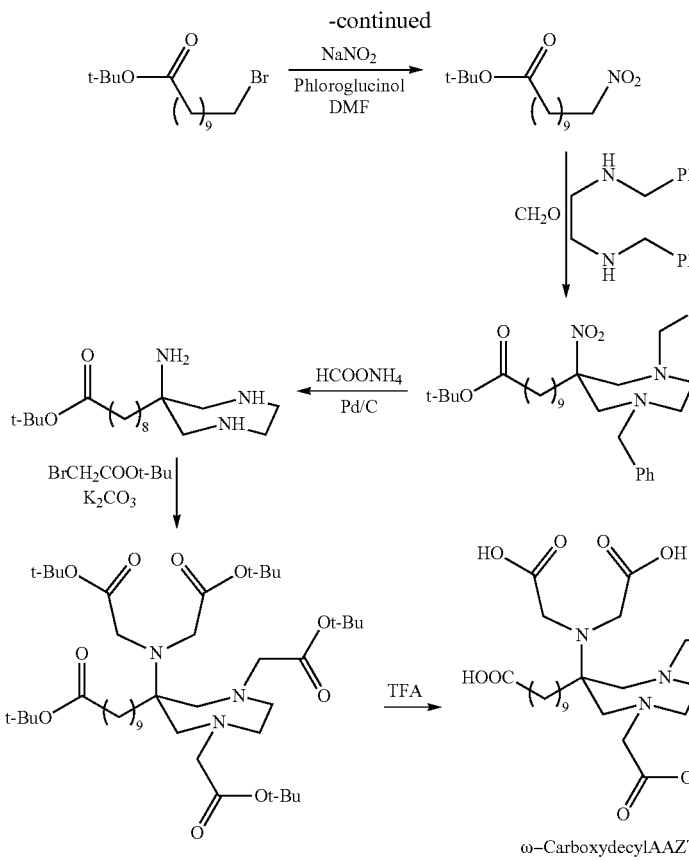

ω–CarboxydecylAAZTA

11-Bromoundecanoic acid tert-butyl ester

DCC (8.90 g, 43.4 mmol) was added to a solution of 11-bromoundecanoic acid (10.0 g, 37.7 mmol), 2-methyl-2-propanol (8.38 g, 0.113 mol) and DMAP (0.50 g, 3.77 mmol) in $CH_2Cl_2$ (60 mL). The reaction mixture was stirred for 2 days at room temperature, and the precipitated dicyclohexylurea was filtered off and washed with $CH_2Cl_2$. The filtrate and the combined washings were combined, washed with water (2×50 mL), HCl 1M (2×50 mL), $NaHCO_3$ 5% (2×50 mL) and brine (2×50 ml). The organic phase was dried ($Na_2SO_4$) and concentrated in vacuo. The crude product was purified by silica-gel column chromatography (PET/Ether 98/2) obtaining a colourless oil 3 (6.37 g, 60%).

ESI-MS: 323-321 (MH$^+$); (Calc. for $C_{15}H_{29}BrO_2$: 320 u.m.a.).

11-Nitroundecanoic acid tert-butyl ester

In a 100 ml two-neck round bottom flask 11-bromoundecanoic acid t-butyl ester (6.10 g, 19.0 mmol) was dropped into a stirred solution of $NaNO_2$ (2.60 g, 38.0 mmol) and phloroglucinol (3.10 g, 19.0 mmol) in DMF (10 ml). The reaction mixture was warmed at 50° C. and stirred for 24 h, then poured into a mixture of 40 mL of ice/water and 40 mL of PET. After separation, the aqueous phase was further extracted with PET (3×30 mL), dried ($Na_2SO_4$) and concentrated in vacuo. The crude product was purified by silica-gel column chromatography (PET/diethyl ether 95/5) obtaining a light yellow solid (2.29 g, 42%). M.p. 39-42° C. ESI-MS: 288 (MH$^+$); (Calc. for $C_{15}H_{29}NO_4$: 287 u.m.a.).

1,4-Dibenzyl-6-(10-tert-butoxycarbonyldecyl)-6-nitro-1,4-diazepane

In a 250 mL round-bottom flask N,N'-dibenzylethylenediamine diacetate (2.76 g, 7.65 mmol) and 11-nitroundecanoic acid tert-butyl ester (2.20 g, 7.65 mmol) were dissolved in 1:1 toluene/ethanol (100 mL). Paraformaldehyde (800 mg, 26.8 mmol) was added portionwise to the solution and the resulting suspension was refluxed. The mixture became homogeneous (dissolution of paraformaldehyde) and after 3 h at reflux, the mixture was cooled and evaporated in vacuo. The residue was purified by column chromatography (PET/diethyl ether 95/5) obtaining a colourless oil (2.90 g, 69%).

ESI-MS: 552 (MH$^+$); (Calc. for $C_{33}H_{49}N_3O_4$: 551 u.m.a.).

6-(10-tert-butoxycarbonyldecyl)-1,4-diazepan-6-ylamine

In a 50 ml flask, 1,4-dibenzyl-6-(10-tert-butoxycarbonyldecyl)-6-nitro-1,4-diazepane (500 mg, 0.906 mmol) was dissolved in methanol (20 mL). Pd/C 10% (200 mg, moistened with 0.2 mL water) was added followed by ammonium formate (1.14 g, 18.1 mmol). The mixture was stirred and heated to reflux until complete disappearance of starting materials. The catalyst was then removed by filtration, and the filtrate evaporated in vacuo. The residue was redissolved in dichloromethane and washed with water (2×10 mL). The organic phase was dried ($Na_2SO_4$), filtered and evaporated in vacuo to obtain the desired triaminoester (308 mg, 99.5%) as colourless oil.

ESI-MS: 364 (MNa$^+$), 342 (MH$^+$); (Calc. for $C_{19}H_{39}N_3O_2$: 341 u.m.a.).

[6-Bis(tert-butoxycarbonylmethylamino)-4-tert-butoxycarbonylmethyl-6-(10-tert-butyl decanoate)-1,4-diazepan-1-yl]acetic acid tert-butyl ester In a 100 mL round-bottom flask the triaminoester (1.16 g, 3.4 mmol) was dissolved in acetonitrile (20 mL) and $K_2CO_3$ (3.76 g, 27.2 mmol) was added. t-Butyl bromoacetate (3.31 g, 17.0 mmol) was slowly dropped into the stirred heterogeneous mixture, while maintaining the temperature <10° C. (ice bath). After the addition the mixture was heated at 60° C. with stirring until TLC showed complete conversion. The precipitate was filtered off and washed with dichloromethane; the filtrate and the washings were combined and evaporated in vacuo to give the crude product. The semisolid residue was purified by silica gel chromatography (petroleum ether/ether 8.5/1.5), obtaining the pure pentaester as a pale yellow oil (2.71 g, 37%).

ESI-MS: 820 (MNa$^+$), 798 (MH$^+$), 742 (MH$^+$–tBu); (Calc. for $C_{43}H_{79}N_3O_{10}$: 797 u.m.a.).

[6-Bis(carboxymethylamino)-4-carboxymethyl-6-(10-carboxydecyl)-1,4-diazepan-1-yl]acetic acid In a 50 mL round-bottom flask the pentaester (1.00 g, 1.25 mmol) was dissolved in trifluoroacetic acid (15 mL) and stirred at room temperature overnight. The solution was then evaporated in vacuo and the residue was dissolved in methanol (2 mL). The product was precipitated with excess diethyl ether, isolated by centrifugation, washed thoroughly with diethyl ether and dried in vacuo, obtaining the pure title compound (641 mg, 99%) as amorphous white solid. m.p. 187-190° C. (dec).

ESI-MS: 540 (MNa$^+$), 518 (MH$^+$); (Calc. for $C_{23}H_{39}N_3O_{10}$: 517 u.m.a).

Example 31

Preparation of Compound 14a (Herewith Below Referred to as Compound 50)

Compound 14a was prepared as per the following schemes Z-L and Z-M

Scheme Z-L

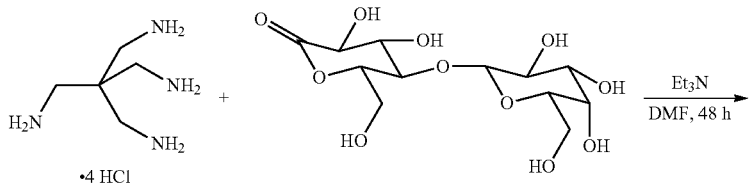

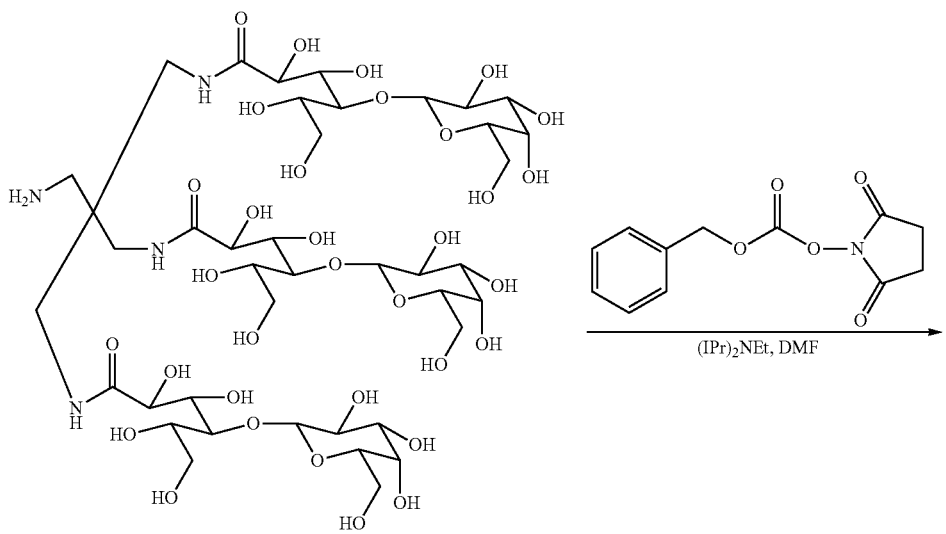

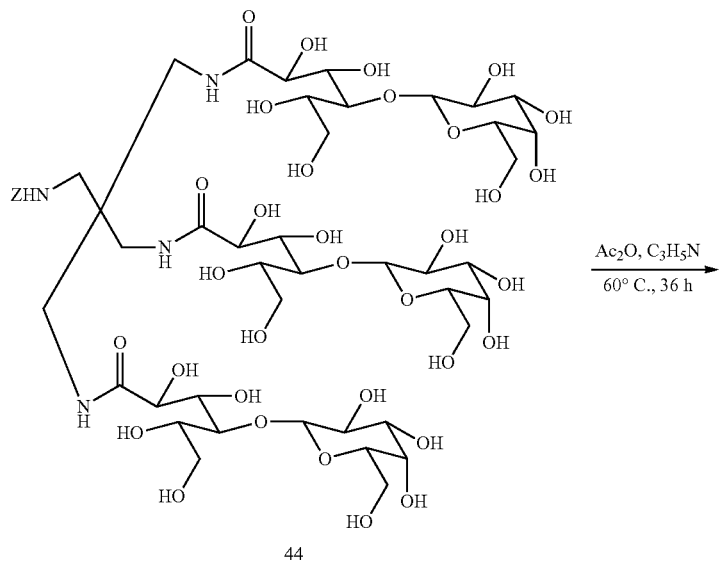
44
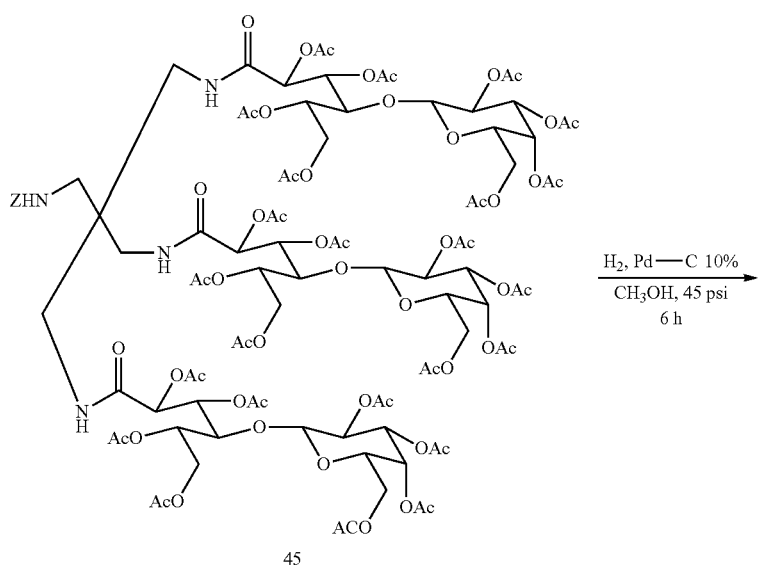
45
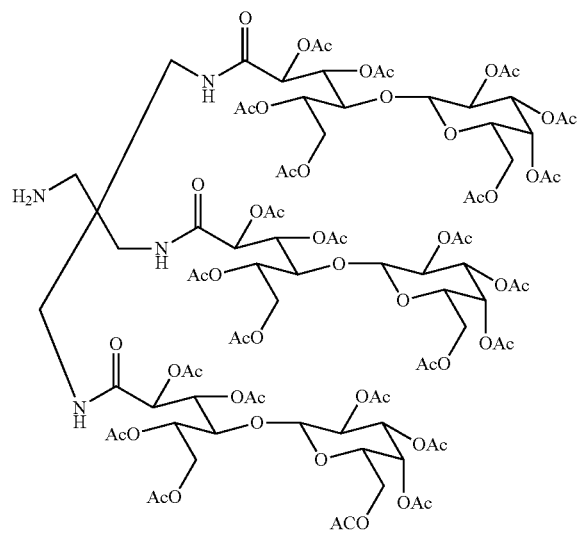
46

Compound 43 Triethylamine (1.66 g, 2.3 mL, 16.0 mmol) was added to a slurry of pentaerythrityl tetra-amine hydrochloride (1.2 g, 4.3 mmol) in DMF (25 mL) and the mixture was stirred at room temperature for 30 min. Lactanolactone[5] (5.0 g, 14.7 mmol) [[5]Guedj, C.; Pavia, A. A.; Pucci, B.; Riess, J. G.; Zarif, L. WO 94/03468] in DMF (30 ml) was added dropwise to the reaction mixture over a period of 3 h and stirred at room temperature for additional 48 h. DMF was removed under vacuum. The oily residue obtained was triturated with acetonitrile (3×100 mL) and the aceonitrile solution was decanted. The solid obtained was dried under vacuum and used in the next step without further purification. Yield 4.5 g (91%). MS: 1153.3 (M+H).

Compound 44 N-(Benzyloxycarbonyloxy) succinimide (3.75 g, 15.0 mmol) was added to a mixture of the amino-trislactonamide 43 (4.6 g, 4.0 mmol) and diisopropylethylamine (1.96 g, 2.65 mL, 15.0 mmol) in DMF (50 mL) and stirred for 24 h. DMF was removed under vacuum and the pasty solid was triturated with acetonitrile (3×100 mL) and the acetonitrile solution was discarded. The white solid obtained was dried under vacuum to give the Z-protected amino-tris-lactonamide 44. Yield 4.72 g, (92%). MS: 1287.3 (M+H).

Compound 45 Compound 44 (5.0 g, 6.3 mmol) was dissolved in a mixture of pyridine-acetic anhydride (1:1, 100 mL) and the mixture was stirred at 50° C. for 36 h. Pyridine-acetic anhydride were removed under vacuum and the dark brown oil was treated with water (500 mL) and left overnight, The orange solid formed was filtered and dissolved in ethyl acetate, washed with 10% HCl (3×100 mL), saturated sodium bicarbonate (2×100 mL) and water (2×100 mL) and dried (Na$_2$SO$_4$). Evaporation of ethyl acetate gave an orange foamy solid, which was purified by silica gel column chromatography using ethyl acetate hexane (6:4). Faintly UV visible fractions were collected and evaporated to give a light yellow solid. Yield 4.2 g (47%).

Compound 46 (protected aminopolyol G7) Pd—C 10% (300 mg) was added to a solution of 45 (0.46 g, 2.0 mmol) in methanol (20 mL) and the mixture was hydrogenated at 45 psi for 6 h. The catalyst was removed by filtration and the methanolic solution was concentrated to give 46 as a white solid. Yield 0.4 g (92%). MS: 2162.6 (M+H).

Scheme Z-M

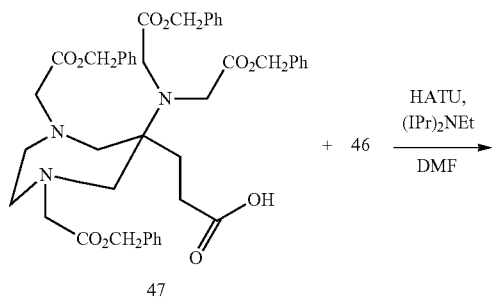

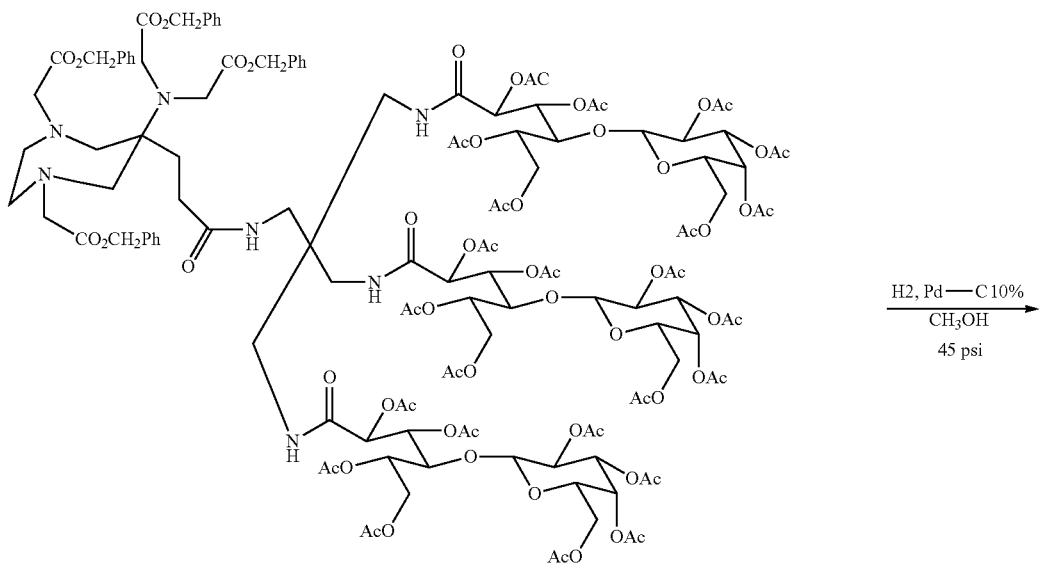

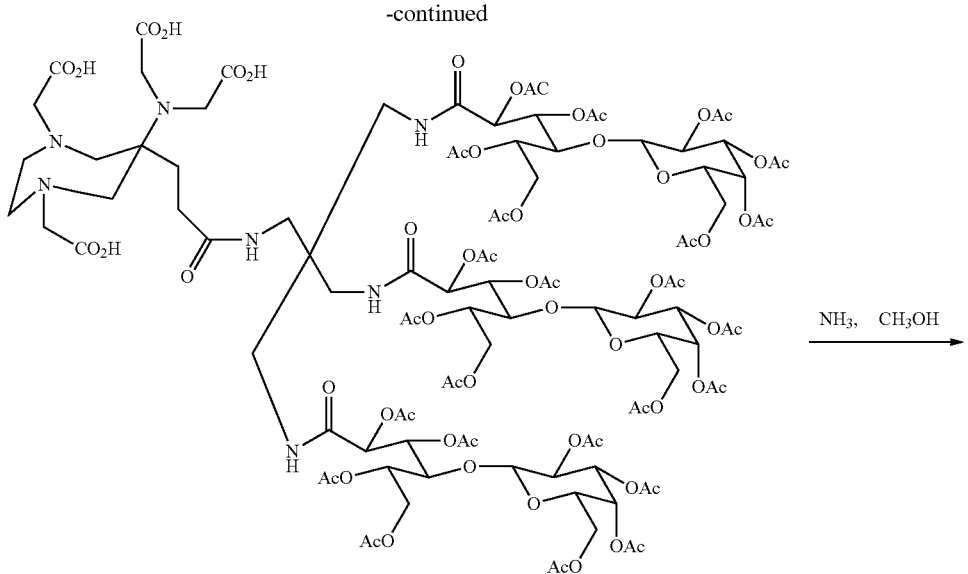

49

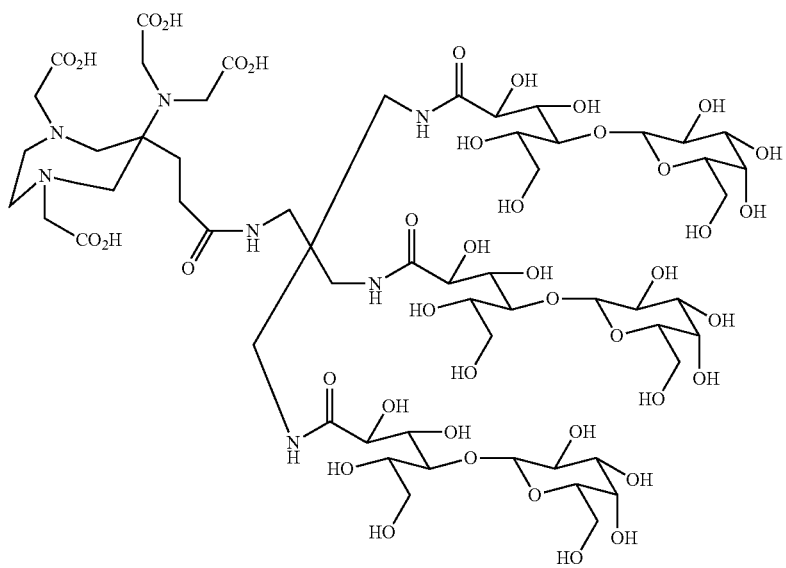

50

Compound 48 Diisopropylethylamine (0.22 g, 0.32 mL, 1.7 mmol) was added to a cooled mixture of aazta acid 47 (0.27 g, 0.35 mmol) and HATU (0.12, 0.31 mmol) in DMF (3.0 mL) and the mixture was stirred for 5 min. A solution of compound 46 (0.45 g, 0.21 mmol) in DMF (3 mL) was added to the activated aazta-acid and the solution was stirred at RT for 12 h. DMF was removed under vacuum and thick oil obtained was treated with a saturated solution of sodium bicarbonate (2×10 mL). The yellow solid obtained was filtered and dried. The crude product obtained was purified by silica gel column chromatography using methylene chloride-methanol (95:5). Product containing fractions were collected (Rf 0.5) and evaporated to give the couple product as a foamy solid. Yield 320 mg (52%). MS: 2924.6 (M+H), 1473.3 (M+211)/2

Compound 49 Pd—C 10% (50 mg) was added to a solution of tetra-benzyl ester 48 (30 mg, 0.01 mmol) in methanol (5 mL) and the solution was hydrogenated at 45 psi for 6 h. The catalyst was removed by filtration and the methanolic solution was concentrated to give the tetra-acid as a white foamy solid.

Yield 0.22 mg (88%). MS: 2563.3 (M+H), 1282.3 (M+2H)/2

Compound 50 A saturated solution of ammonia in methanol (~25%, 0.5 mL) was added to the tetra-acid 49 (20 mg, 0.008 mmol), and the solution was allowed to stand in the refrigerator for 48 h. The white solid that formed was filtered, washed with methanolic ammonia (2×0.5 mL) and dried under vacuum to give compound 50.

Yield 7.0 mg (58%). MS: 1552 (M−H), 775.7 (M−2H)/2

Example 32
Preparation of Compound 10b (Herewith Below Referred to as Compound 54)
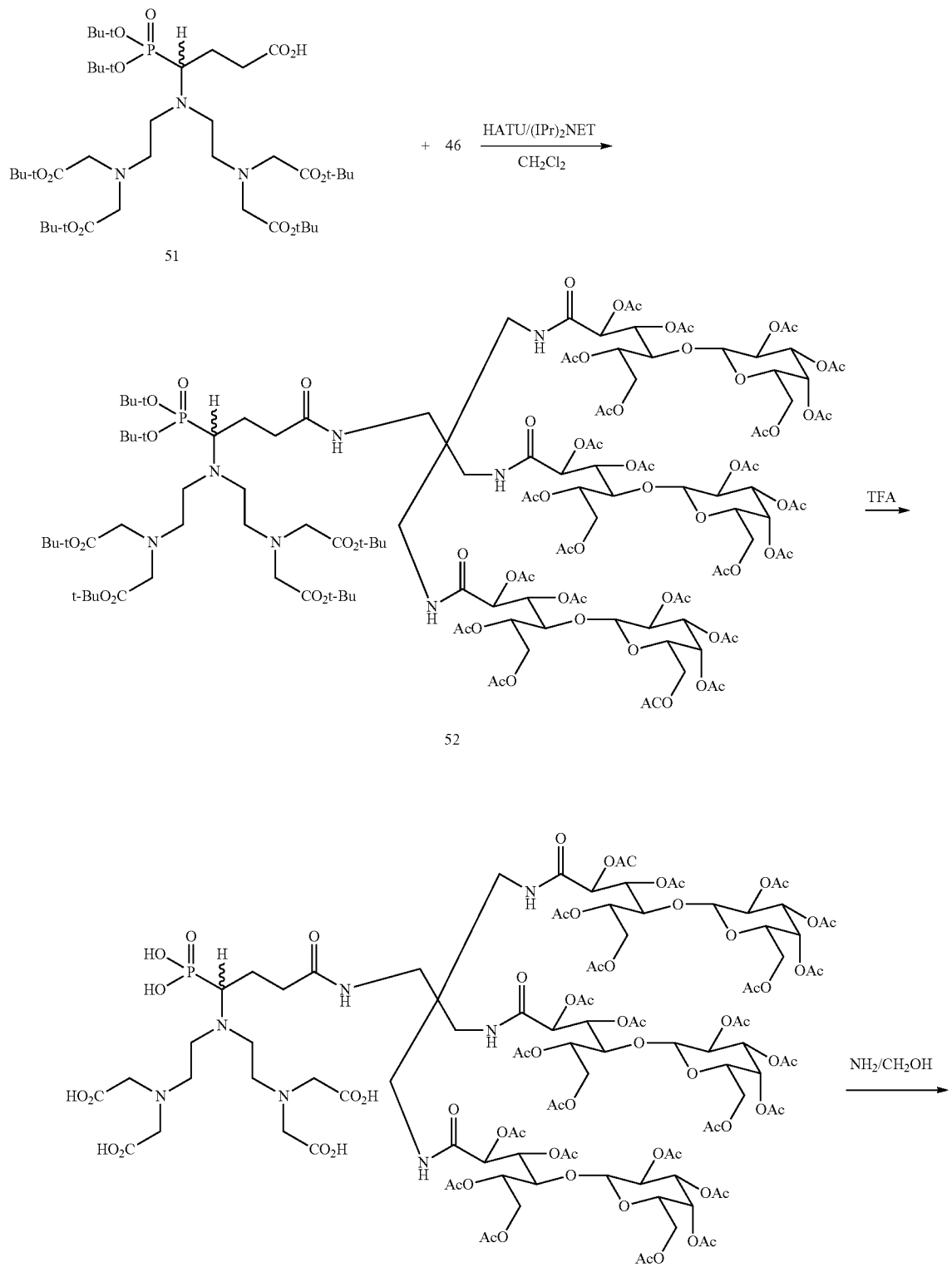

-continued

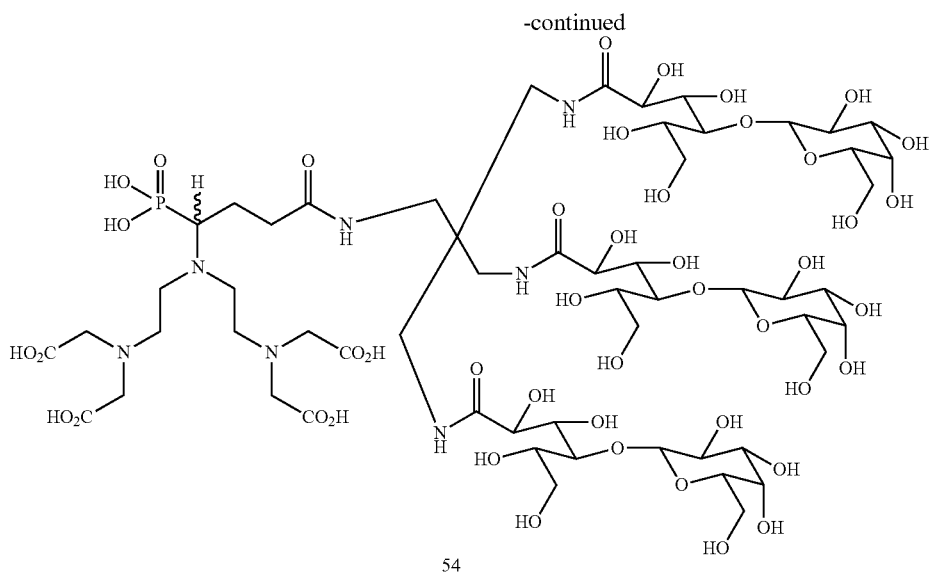

54

Compound 52 Diisopropylethylamine (35 mg, g, 45 µL, 0.27 mmol) was added to a cooled mixture of acid 47 (0.2 g, 0.24 mmol) and HATU (0.1 g, 0.26 mmol) in $CH_2Cl_2$ (2 mL) and the mixture was stirred for 5 min. A solution of compound 46 (0.43 g, 0.2 mmol) in $CH_2Cl_2$ (2 mL) was added to the activated acid and the solution was stirred at RT for 12. Methylene chloride was removed under reduced pressure and the thick oil obtained was treated with a saturated solution of sodium bicarbonate (2×10 mL). The yellow solid obtained was filtered, dried. and purified by silica gel column chromatography using methylene chloride-methanol (95:5). Product containing fractions were collected (Rf 0.5) and evaporated to give the couple product as a foamy solid. Yield 350 mg (56%). MS: 2981.9 (M+H), 1502.6 (M+Na)/2

Compound 53 TFA (0.75 mL) was added to compound 52 (30.0 mg, 01 mmol) and stirred for 8 h. TFA was removed and the resulting pasty solid was dissolved in $CH_3CN$/water (1:3, 2.0 mL) and freeze dried to give compound 53 as a white solid. Yield 23 mg (87%). MS: 2645.6 (M+H), 1323.2 (M+H)/2

Compound 54 Saturated solution of ammonia in methanol (~25%, 0.5 mL) was added to the acetate 53 (20 mg, 0.0075 mmol) and the solution was allowed to stand in the refrigerator for 48 h. The white solid formed was filtered and washed with cold methanolic ammonia (2×0.5 mL) and dried under vacuum to give compound 54. Yield 8.0 mg (66%). MS: 1634.4 (M−H), 816.8 (M−2H)/2

Example 33

Gd Complex Preparation

The paramagnetic complexes of compounds of the invention may be prepared according to well known procedures (see, for a reference, EP 230893 and EP 71564).

As a non limiting example, the preparation of the Gadolinium complex of the chelating ligand 1b (Gd-1b) is reported below.

To an aqueous solution of the compound 1b (prepared as reported in EXAMPLE 4), is added a stoichiometric equivalent of Gd—$Cl_3.6H_2O$ and 1N NaOH, keeping pH within the range 6-7. The progress of the reaction is checked by HPLC. After 18 h the solution is filtered through a Millipore® filter, nanofiltered and concentrated. The desalated solution is slowly percolated through Dowex® CCR3LB column ($Na^+$ form) to obtain the desired product.

Example 34

Relaxivity Determination

In order to best evaluate the relaxivity properties and the parameters affecting the relaxivity of the agents of the invention, some comparative tests have been performed. In a first experiment, the relaxivity of a number of Gd-based chelated compounds having different molecular weight, all derived from the following [Gd(DTPA-monophosphonate)]$^{3-}$ basic backbone structure ($r_{1p}$ at 20 MHz and 298K: 6.1 mM$^{-1}$ s$^{-1}$) of formula

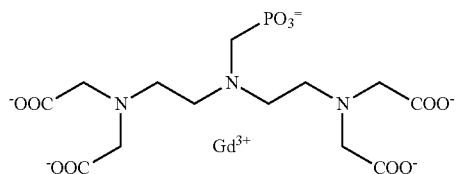

and all containing one coordinated water molecule (q=1), were compared.

Tested compounds include the Gd-complex of the chelating compounds 1b and 2b of the invention (hereinafter Gd-1b and Gd-2b) as well as a number of different derivatives of the aforementioned backbone moiety selected in order to cover a range of molecular weights of up to about 1800 Dalton. The relaxivity of all of the tested compounds were measured at 298K and 20 MHz and pH 7. The obtained values, listed in table 5 below (together with the structure of the compounds) have also been plotted against the MW of the complexes (see FIG. 1).

TABLE 5

| Compound structure | Compound code | R1p (mM-1 s-1) |
|---|---|---|
| | [Gd(DTPA-monophosphonate)]³⁻ | 6.1 |
| 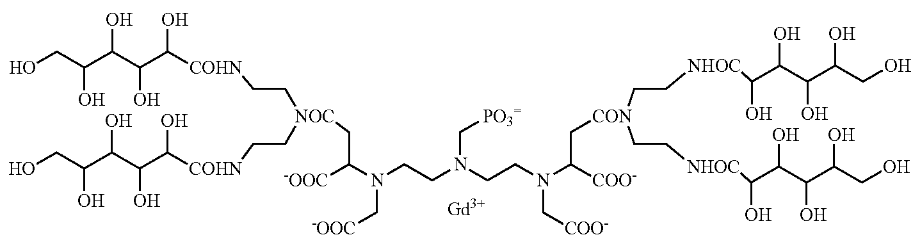 | Gb-1b | 13.5 |
| 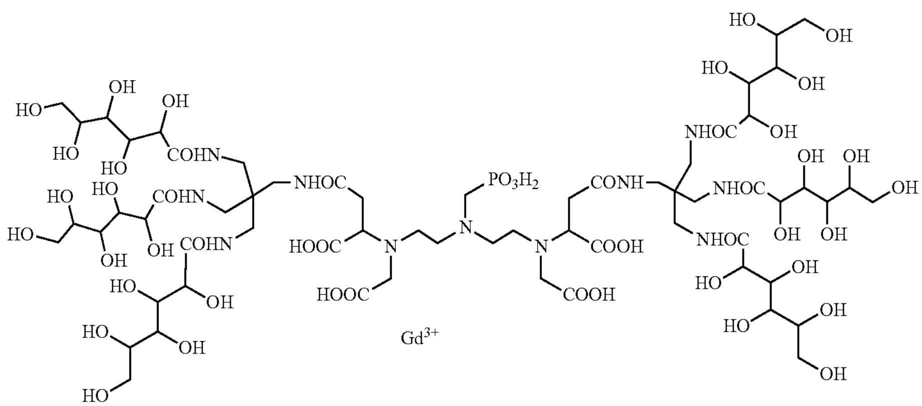 | Gb-2b | 19 |
| 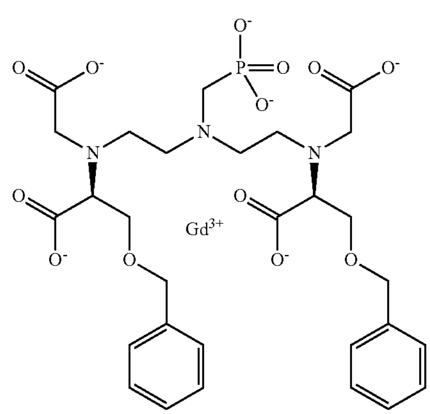 | B 22666 | 7.9 |
| 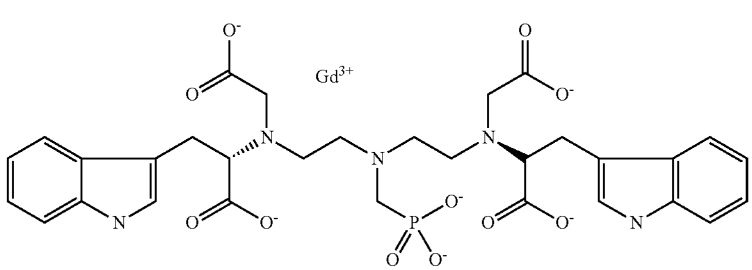 | B 22836 | 7.9 |

TABLE 5-continued

| Compound structure | Compound code | R1p (mM-1 s-1) |
|---|---|---|
| 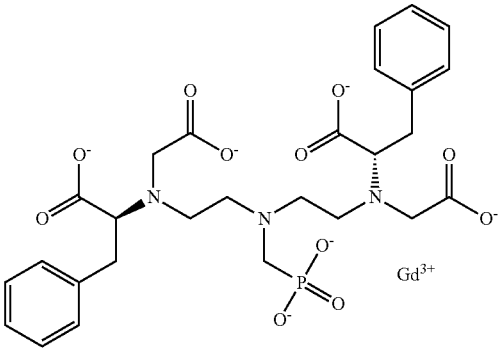 | B 22606 | 7.7 |
| 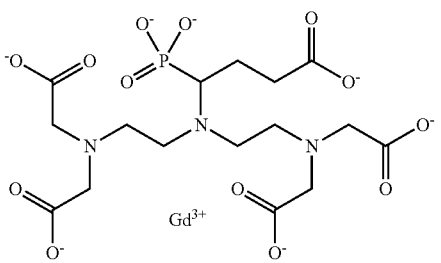 | Gd-CEMPDTTA | 7.2 |
| 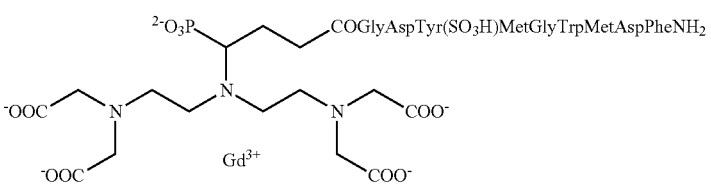 | Gd-DTPAPhosCCK8 | 11.3 |

The relaxivities of all of the tested complexes, with the exclusion of Gd-1b and Gd-2b, display a linear relationship with their MW. Gd-1b provides for an additional contribution of >2.5 mM$^{-1}$ s$^{-1}$ to the relaxivity, certainly unexpected for this compound, on the basis of its MW. To this extent, the improvement shown by the complex of compound Gd-2b is even higher.

Figure 2:
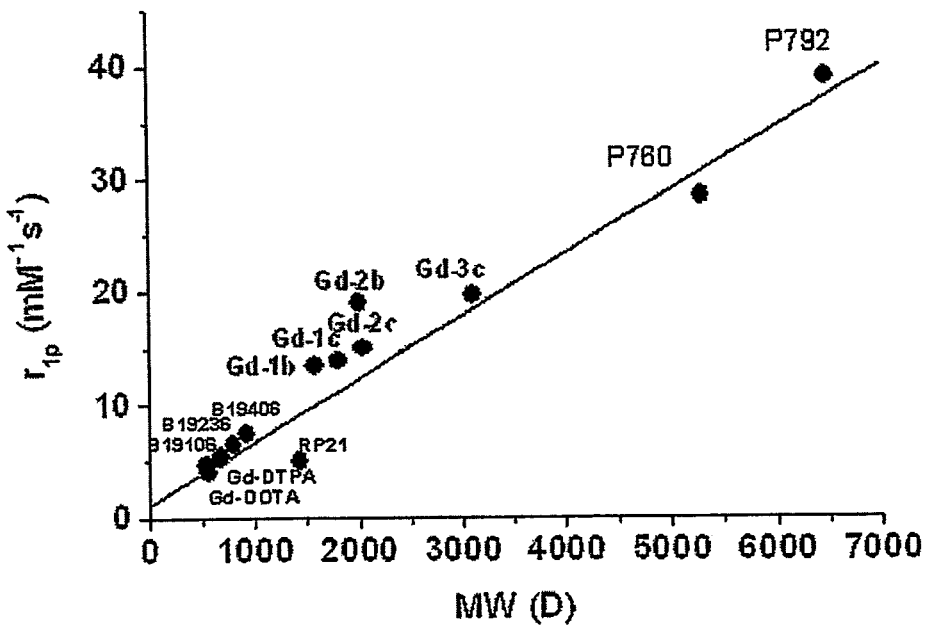
FIG. 2: Relaxivity values for structurally different q=1 Gd(III)-complexes of the invention and comparative Gd-complex compounds plotted against their molecular weight (25° C., neutral pH, 0.47 T).

A second experiment was performed to test the relaxivity of different compounds of the invention, marketed NSA, known LDA and other systems, all containing one coordinated water molecule (q=1). The data were registered at 298K and 20 MHz and pH=7, and plotted against their corresponding MW. The obtained results, included in table 6 below, are also graphically presented in FIG. 2. Relaxivity data relating to LDA P760 and P792 (LDA contrast agents) are based on literature cited below.

TABLE 6

| Compound structure | Compound code | R1p (mM-1 s-1) |
|---|---|---|
| 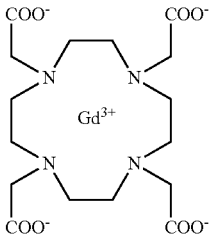 | Gd-DOTA | 4.7 |

TABLE 6-continued
| Compound structure | Compound code | R1p (mM-1 s-1) |
|---|---|---|
| 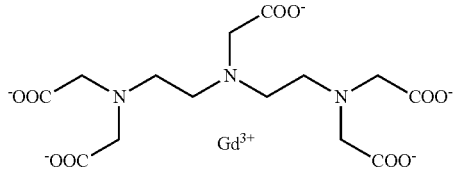 | Gd-DTPA | 4.7 |
| 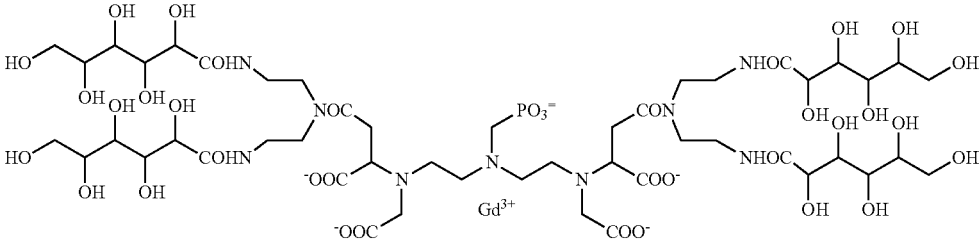 | Gd-1b | 13.5 |
| 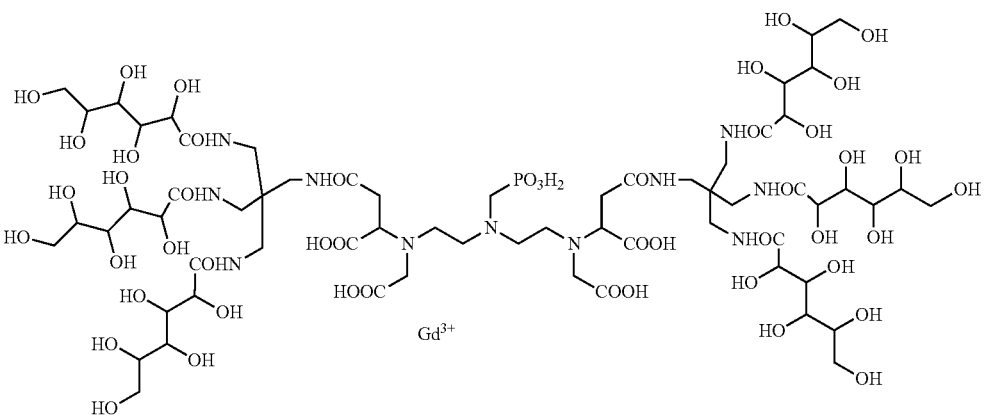 | Gd-2b | 19 |
| 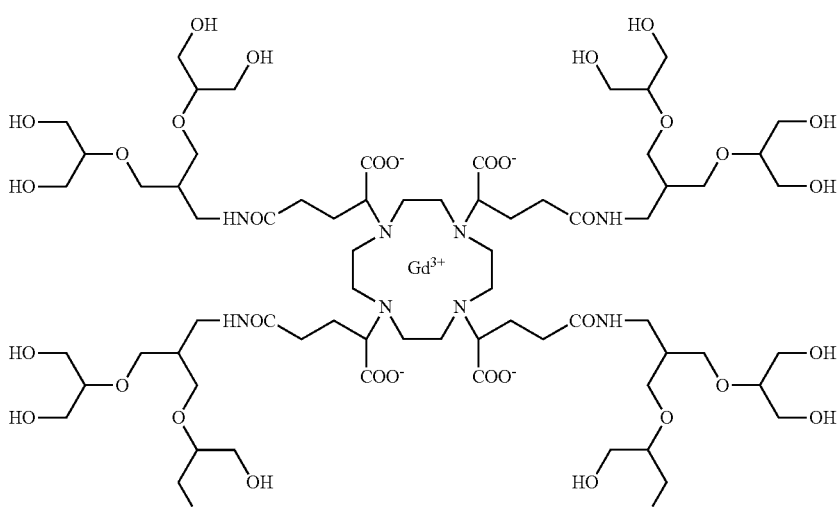 | Gd-1c | 13.84 |

TABLE 6-continued
| Compound structure | Compound code | R1p (mM-1 s-1) |
|---|---|---|
| 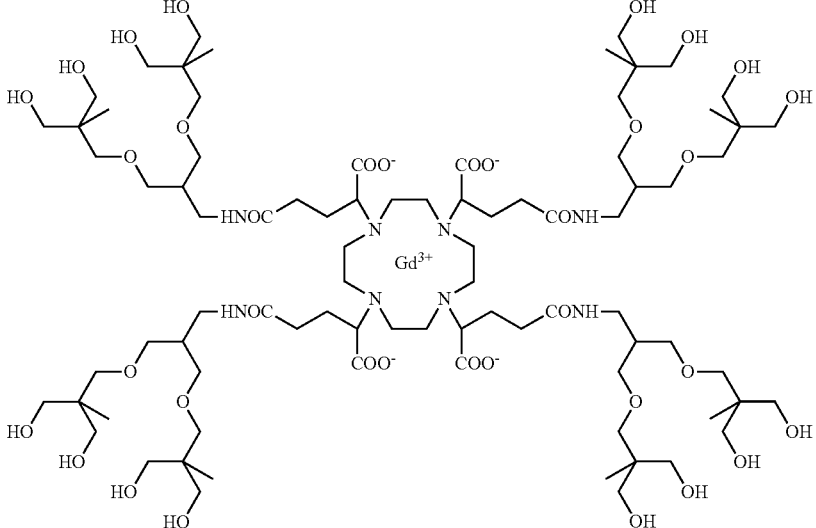 | Gd-2c | 15 |
| 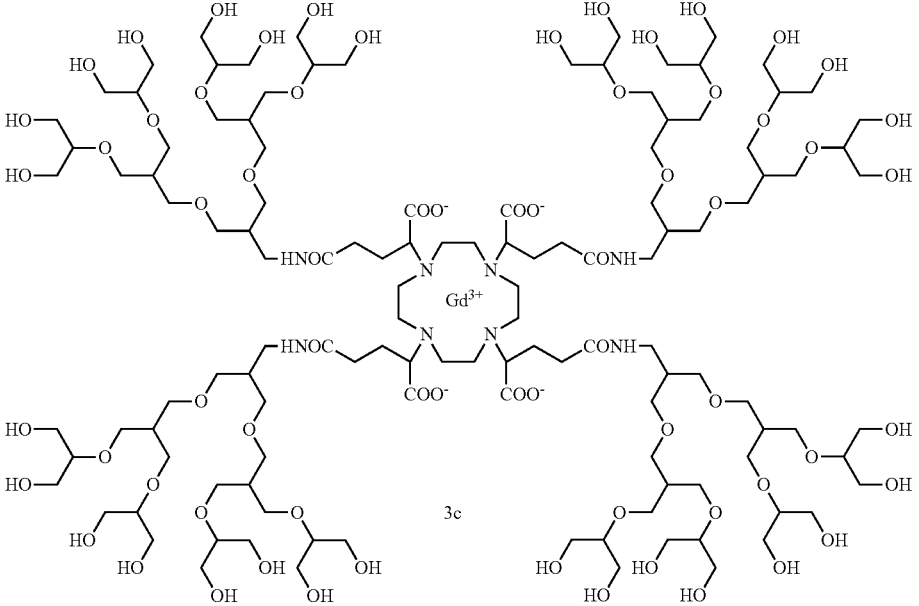 | Gd-3c | 19.6 |
| | P760[(1)] | 28.4 |
| | P792[(2)] | 39 |
| 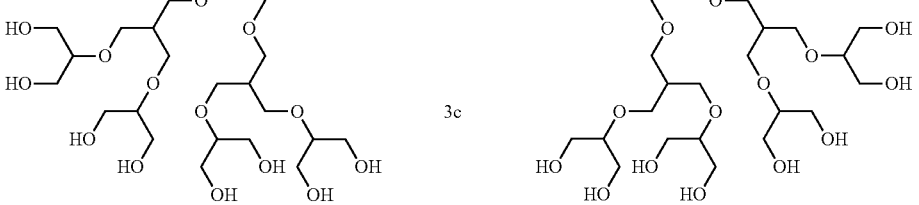 | RP21 | 5 |

TABLE 6-continued

| Compound structure | Compound code | R1p (mM-1 s-1) |
|---|---|---|
| (structure with Gd³⁺ macrocycle, two benzyloxymethyl arms) | B19236 | 6.5 |
| (structure with Gd³⁺ macrocycle, three benzyloxymethyl arms) | B19406 | 7.5 |
| (structure with Gd³⁺ macrocycle, one benzyloxymethyl arm) | B19106 | 5.5 |

[1] Vander Elst L, Port M, Raynal I, Muller RN et al. European Journal of Inorganic Chemistry, 2003, 13, 2495-2501
[2] Port M, Corot C, Rousseaux O, et al. Magnetic Resonance Materials in Physics Biology and Medicine, 2001, 12, 121-127.

Figure 3:
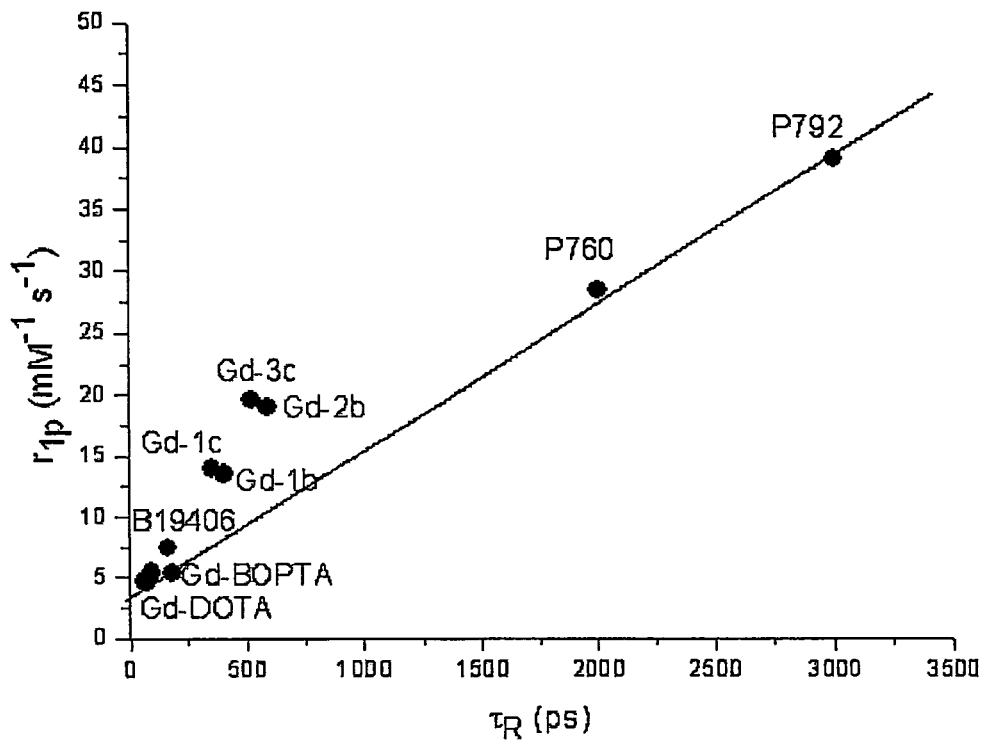
FIG. 3: Relaxivity values for structurally different q=1 Gd(III)-complexes plotted against their molecular reorientational time ($\tau_R$) (25° C., neutral pH, 0.47 T).
Figure 4:
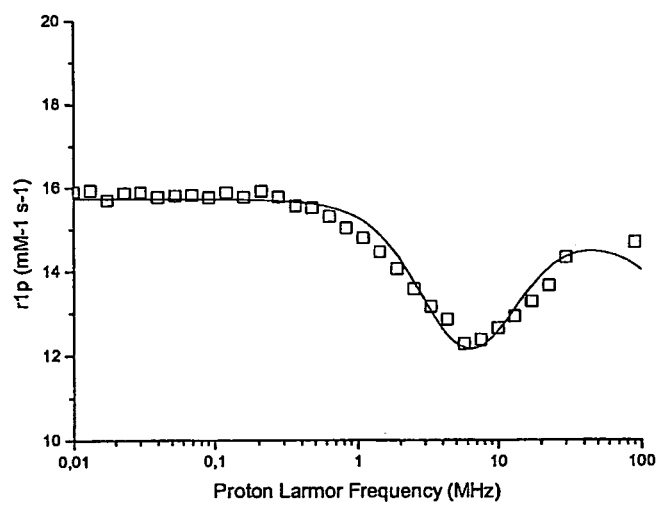
FIG. 4: $^1$H 1/T1 NMRD profile (25° C., 1 mM aqueous solution) of Gd-1b complex.
Figure 5:
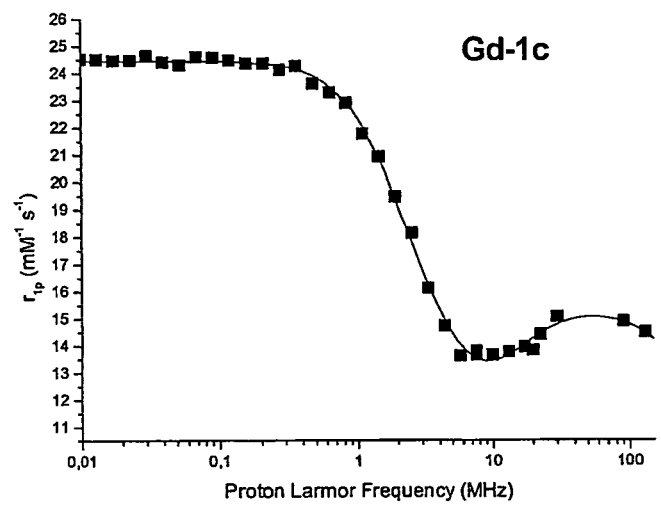
FIGS. 5 and 5 bis: $^1$H1/T1 NMRD profiles (25° C., 1 mM aqueous solution) of Gd-1c, Gd-2c and Gd-3c complexes.
Figure 5:
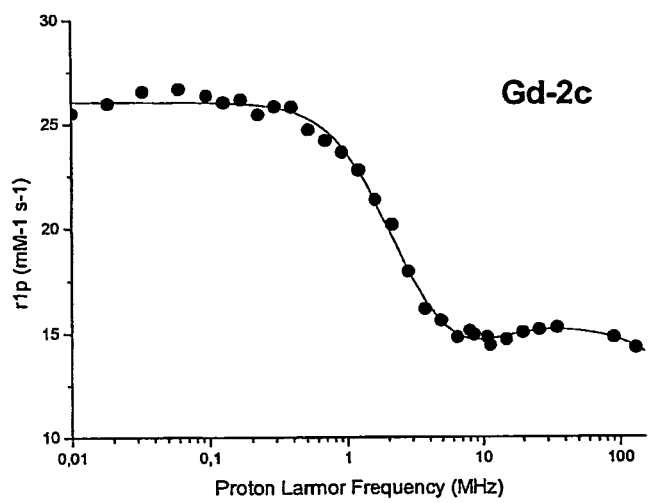

A further test was performed in which the relaxivity values $r_{1p}$, shown by the compounds of the invention as measured at 20 MHz and 298K, were plotted against the molecular reorientational values $\tau_R$ of the same compounds. Obtained result are shown in FIG. 3. The stability of the relaxivity properties shown by the compounds of the invention was tested. In a first experiment, the 1/T1 NMRD profiles for some compounds of the invention were acquired over a range of magnetic field strengths ranging from 0.01 to 130 MHz. The profile shown by the Gd-1b chelated compound of the invention is included in FIG. 4, while corresponding profiles for chelated compounds Gd-1c, Gd-2c and Gd-3c are included in FIGS. 5 and 5 bis. A comparison has been also performed for compound Gd-2b over a corresponding profile registered for GD-DTPA (Magnevist®), a marketed NSA, and for GD-DOTA-BSA, a well known blood pool agent.

The results of the comparison have shown that the compounds of the invention do possess high relaxivity and the said relaxivity is retained over a range of magnetic field strength. (see FIG. 6).

Interestingly, the relaxivity of the Gd-2b measured at 3 Tesla (and 298K) was still close to 20 mM$^{-1}$ s$^{-1}$. This clearly indicates that the relaxivity properties of Gd-2b, as a representative compound of the invention, are maintained also at field strength higher than 0.5 Tesla (ca. 20 MHz), and up to 3 Tesla. Conversely, the relaxivity improvement shown by the blood pool agent rapidly falls dawn over the same range of magnetic field strength. In addition to the above, please find below as per table 7, other relaxivity values, measured as above indicated, for some other representative compounds of the invention.

TABLE 7

| Compound structure | Compound code | R1p (mM-1 s-1) |
|---|---|---|
| 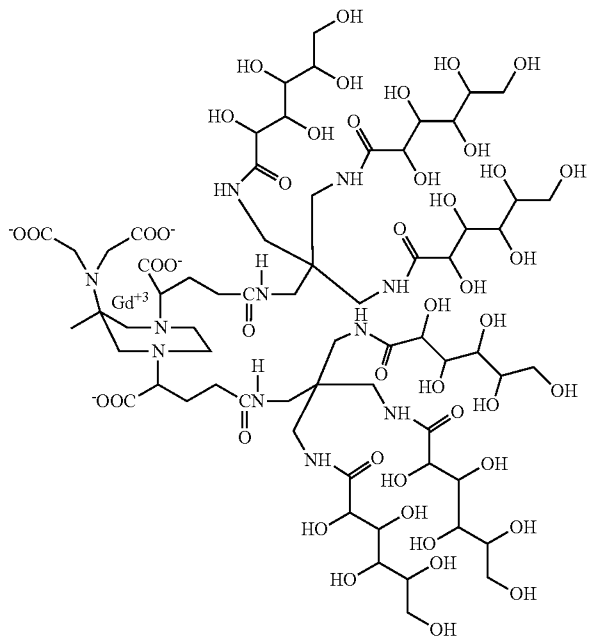 | Gd-5a | 16 |
| 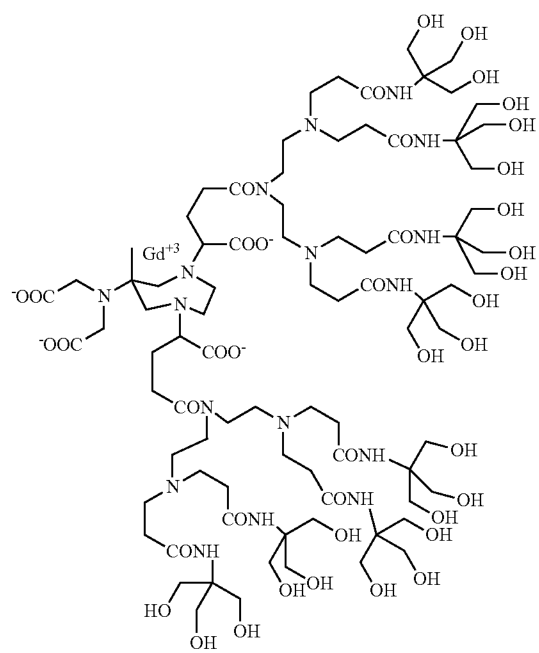 | Gd-15a | 16.7 |

TABLE 7-continued
| Compound structure | Compound code | R1p (mM-1 s-1) |
|---|---|---|
| 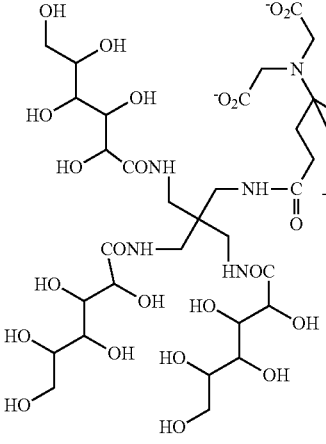 | Gd-11a | 16.1 |
| 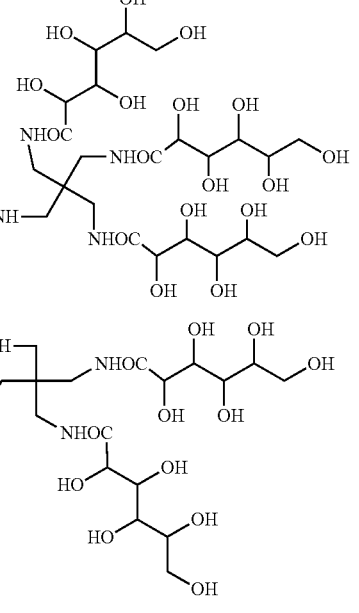 | Gd-14a | 16.1 |

TABLE 7-continued

| Compound structure | Compound code | R1p (mM-1 s-1) |
|---|---|---|
| 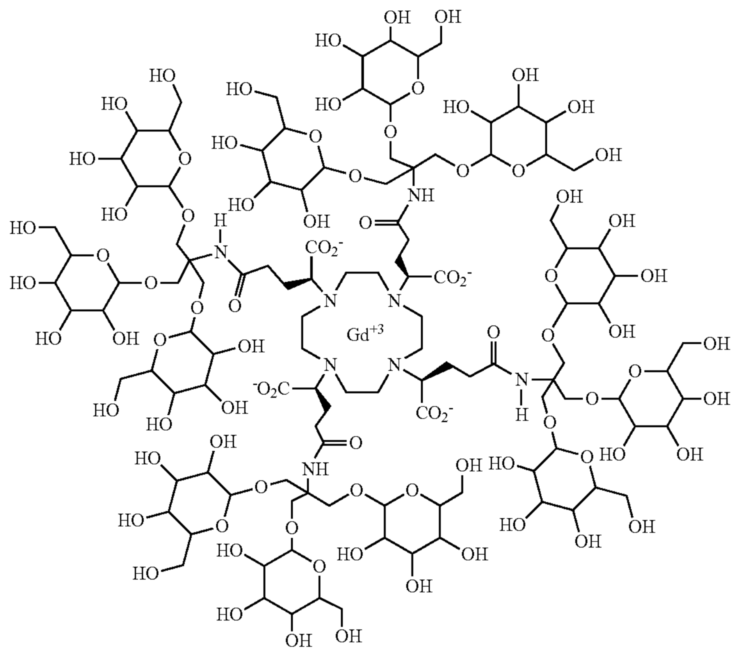 | Gd-7c | 20.4 |
| 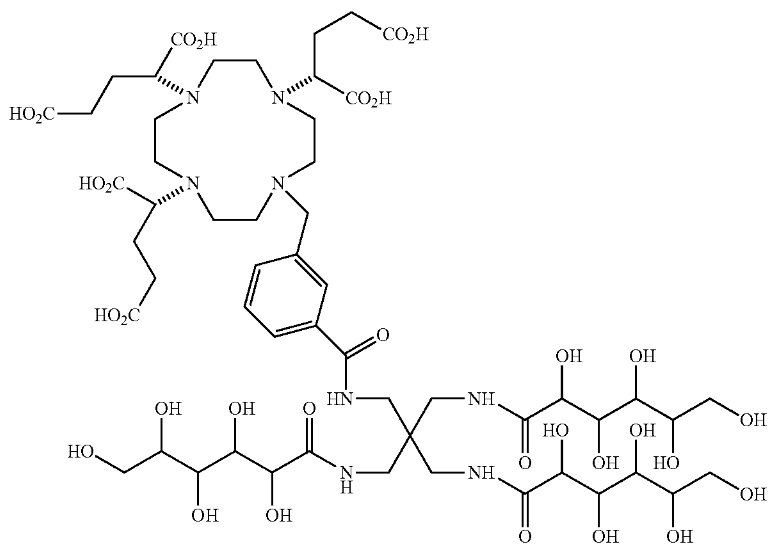 | Gd-1d | 24 |
| 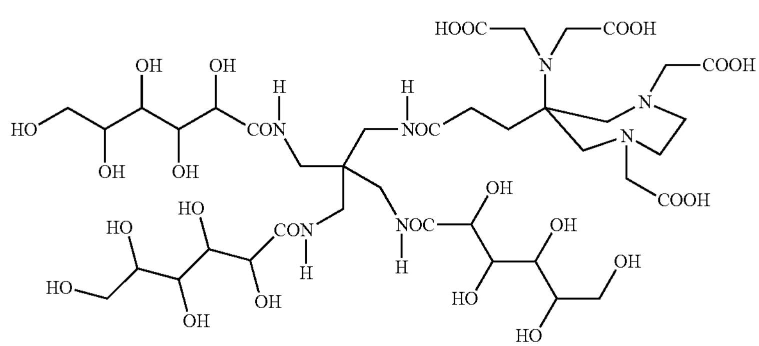 | Gd-3a | 14.0 |

Example 35

Pharmacokinetic Determination

Protocol Outline

Plasma kinetics of gadolinium after intravenous administration of Gd-based contrast agents of the invention may be tested according to the following protocol.

Introduction

Aim of this study is to evaluate the plasma kinetics of gadolinium after a single intravenous (i.v.) administration of Gd-based contrast agents to rats. The animals are treated intravenously at the dose of 0.05-0.1 mmol/kg. The rats are sacrificed at different times, up to and including 24 h after administration. Blood samples are collected and gadolinium concentration in plasma and tissue samples is determined by inductively coupled plasma atomic emission spectrometry (ICP-AES). Moreover, liver, spleen, femur and kidneys are collected to evaluate residual content of gadolinium in organs. The study is conducted by using Gd-DTPA or Pro-Hance (extracellular contrast agent) as control article for comparison of distribution data.

Materials

Test Article: A compound of the invention
Control Article Gd-DTPA (Magnevist) or ProHance
Formulation: water solution, 0.5 M
Test system: the experiment is performed on the rat because previous imaging experiments on the test article have been performed on this animal model.
Animals: rat, weight: 150-200 g Methods Experimental Procedures—Animal Treatment Water is available to the animals "ad libitum" during the experiment period. Rats are treated intravenously because this is the administration route foreseen for clinical use of the test article. The test article is administered at room temperature. The animals are inspected individually before the treatment, immediately afterwards and on several occasions during the day of dosing.

Experimental Design—Treatment Phase

The study may be performed by using 36 rats randomly allocated to each group of treatment. The test article may be administered at the dose of 0.05 or 0.1 mmol/kg. The control article may be administered at the dose of 0.1 mmol/kg.

Scheduled sacrifices (time periods) may be performed at 0 (blank), 2, 5, 10, 20, 30, 60, 120, 240, 360, 480 min and 24 h after treatment. Three rats are treated for each time of sacrifice.

1 to 2 min before the sacrifice, the animals are anaesthetized by intramuscular injection of Ketamine (Ketavet)®, 0.7 mL/kg plus Xilazine (Rompun)®, 0.35 mL/kg and exsanguinated through the carotid artery. Blood is collected into test tubes containing sodium heparin solution (5000 UI/mL) at a ratio of about 1:50 (v/v) with blood. Plasma samples are obtained after centrifugation of blood samples (15 min at 1800 g). After exsanguination, liver, kidneys, spleen, and both femurs are excised and weighed. All biological samples are stored at +4° C. until analyzed.

Assay of Gadolinium in Biological Samples—Apparatus

The assay is carried out on a Jobin-Yvon Mod 24 spectrometer operating with the following instrumental parameters: sample flow: 1 mL/min; plasma flame: 6000 to 10000° C.; wavelength: 342.247 nm; Argon flow: nebulizer 0.3 L/min, transport gas 0.2 L/min, cooling gas 12 L/min. Sample digestions are performed by a microwave system (MDS-2000 CEM Corporation).

Sample Preparation and Analytical Conditions

Plasma solutions are prepared by suspending 1 mL of plasma in 1.5 mL of nitric acid (65% v/v). Liver is dried by means of a freeze drying process and then homogenized by grinding in a mortar. Liver solutions are prepared by suspending 200 mg of tissue powder, which is accurately weighed, in 1.5 mL of nitric acid (65% v/v). Kidney solutions are prepared by suspending each kidney, accurately weighed, in 1.5 mL of nitric acid (65% v/v). Femur solutions are prepared by suspending each femur, accurately weighed, in 1.5 mL of nitric acid (65% v/v). Spleen solutions are prepared by suspending spleen, accurately weighed, in 1.5 mL of nitric acid (65% v/v). The destruction of the organic matrix is performed by subjecting this sample to a wet ashing process with a microwave oven system.

Finally, the dried residues are dissolved with 3.0 mL of HCl 5% (w/v) and then analysed by ICP-AES.

Data processing: Linearity is evaluated for three standards, ranging from 0.00 to 20 mg(Gd)/L in HCl 5% (w/v), respectively. The total content of gadolinium in the test sample is calculated by using the instrumental calibration straight line and expressed as µg(Gd)/mL.

Treatment of the Data

Presentation of results: Concentrations of gadolinium are expressed with reference to weight of tissue (µg or µmol Gd/g tissue), to the whole organ (µmol/organ) and to injected dose (% ID/organ).

For bones, the latter value is calculated assuming bone weight of 9% of the body weight. Means and standard deviations are calculated for % ID/organ.

The fraction of the injected dose in plasma at each time point is calculated assuming a plasma volume in the rat of 40 mL/kg body weight.

Statistical analysis of time courses of blood/plasma concentrations: Plasma concentrations of gadolinium as a function of time after injection of B22956/1, C(t), may be analyzed by a non-parametric method using the computer program WIN-NONLIN V2.1 (SCI Software, Lexington, KE, USA). A non-compartmental and a compartmental analysis may be performed using the average plasma concentrations from 3 animals for each time point. For $c_{max}$ and the corresponding $t_{max}$ the observed values are reported. The terminal phase elimination rate constant ($\lambda_z$) will be estimated by log-linear regression of those data points visually assessed to be in the terminal phase of the profile. The terminal elimination half life ($t_{1/2}\lambda_z$) is calculated as $t_{1/2}\lambda_z = \ln 2/\lambda_z$. Area under the plasma concentration-time curve to the last observable plasma concentration ($AUC_{(0\ to\ t)}$) is calculated from observed data using the logarithmic trapezoidal method. Total area under the plasma concentration-time curve from zero to infinity ($AUC_{(0\ to\ \infty)}$) is estimated by $AUC_{(0\ to\ \infty)} = AUC_{(0\ to\ t)} + c_t/\lambda_z$, where $c_t$ is the predicted concentration at the last quantified time point. The total plasma clearance, Cl, is estimated by $Dose/AUC_{(0\ to\ \infty)}$. The volume of distribution at steady state, $V_{dss}$, is estimated by MRT.Cl, where MRT is the mean residence time calculated as $AUC_{(0\ to\ \infty)}/AUMC_{(0\ to\ \infty)}$ and $AUMC_{(0\ to\ \infty)}$ is the first moment of the plasma concentration-time curve. The apparent volume of distribution, $V_d$, the distribution and elimination half-life is estimated also by using macroparameters of the compartmental analysis.

Example 36

Evaluation of Vascular Permeability

An in vitro permeability model in which endothelial cells are grown on porous filters has proven to be a valuable tool to evaluate the vascular permeability and the trans-vessel passage characteristics of different compounds of the invention (see, M. Corada et all. Blood, Vol. 100, n.3, pp 905-911; and C. Corot et all. Journal of Magnetic Resonance Imaging, Vol. 11, 2000, pp. 182-191).

This evaluation consists of three steps: (1) MTT assay to determine the non-toxic concentration of the test compound; (2) evaluation of the effects of the concentration selected from step 1 on cell retraction in an endothelial cell monolayer (retraction is considered as a sign of very slight and reversible cell toxicity; and (3) evaluation of the passage of the compound across the endothelial cell monolayer grown on a porous filter using the concentration selected from step 2.

Materials

Test article: compounds of the invention;

Control article: ProHance®, 0.5 M aqueous solution; Omniscan®, 0.5 M aqueous solution.

Reagents

Biologicals: Human Umbilical Vein Endothelial Cells (HUVEC) were supplied by Cambrex Bio ScienceWalkersville and mouse endothelioma H5V were supplied by Prof. Tiribelli, Centro Studi Fegato, Trieste. HUVEC is grown in Endothelial Basal Medium 2 (EBM-2) and Supplements and Growth Factors (EGM-2 Single Quots). H5V is grown in 90% DMEM medium and 10% fetal bovine serum as described in C. Garlanda et all. Proc. Natl. Acad. Sci. Vol. 91, pp 7291-7295 July 1994.

Chemicals: Penicillin/Streptomycin (10000 µg/mL), Storage: −20° C.; L-Glutamine (200 mM), Storage: −20° C.; Fetal bovine serum (FCS), Storage: −20° C.; DMEM medium, Storage: +4° C.; EBM-2 Medium, Storage: +4° C.; EGM-2 Single Quots, Storage: −20° C.; MTT (3-(4,5-dimethylthiazole-2-yl)-2,5-diphenyltetrazolium bromide), Storage: +4° C.; FITC-Dextran, P.M. about 40.000, Storage: +4° C., in the dark; Human Serum Albumin, Storage: +4° C., in the dark.

Test System

Endothelial cell monolayers were chosen because it is the most suitable in vitro model to test the in vitro permeability and extravasation of Gd-based compounds with extra-vascular properties.

Methods

Experimental Procedures

Cytotoxicity: Cells are washed two times with saline, resuspended in medium and seeded into 96-wells plates at the density of 15000 to 30000 cells/200 µL/well (depending on cell type) at least 24 hours before the MTT test.

Preparation of Test Article Working Solution: Test Articles and Controls are Diluted in Culture medium without fetal calf serum to obtain 20 mM solution.

Micro plates treatment: Starting from 24 hours after cells seeding, the test article is added to wells at the concentrations of 0.078, 0.156, 0.3125, 0.625, 1.25, 2.5, 5, 10 and 20 mM, 6 wells for each concentration.

MTT: MTT is added to each well and cells are incubated at 37° C. for 4 hours. The incubation medium is removed and the dye incorporated by living cells will be solubilized with 1:1 DMSO/Ethanol solution. The optical density of each well is determined in a micro plate reader at 570 nm Retraction Assay The transwell filters are rinsed once with medium without fetal calf serum and 600 µL of the growth medium is added in the lower compartment of the transwell.

The H5V cell is seeded on the filter in a volume of 100 µL at the density of 15000 cells/filter and into 96-wells plates at the same density and volume to monitor cell growth. Every other day the upper and lower culture medium will be changed and the cell monolayer is used for experiments at least 4 day after seeding, when the cells into the 96-wells plates are tightly confluent.

Before performing the assay, at least two transwells are colored with Crystal Violet to check the monolayer conditions.

Dextran-FITC (100 µL of 0.1 mg/mL solution) is added to the upper chamber together with the non-toxic dose of the testing compound with or without human serum albumin (3.5% w/v). Permeabilized monolayers are obtained with 4 hours of incubation with EGTA, 5 mM, before performing the assay.

For the Dextran-FITC dosage, after 30 and 60 minutes of incubation, the medium is removed from the lower and upper compartment (at least 4 transwells for each time), the samples are diluted 1:6 in PBS and the fluorescence is determined with a fluorimeter using a wavelength of 492 and 520 nm for excitation and emission, respectively.

Permeability

The filter is rinsed once with medium without fetal calf serum and 600 µL of the growth medium is added in the lower compartment of the transwell.

The H5V cells are seeded on the filter in a volume of 100 µL at the density of 15000 cells/filter and into 96-wells plates at the same density and volume to monitor cell growth. Every other day the upper and lower culture medium is changed and the cell monolayer is used for experiments at least 4 day after seeding, when the cells into the 96-wells plates are tightly confluent.

Before performing the assay, at least two transwells are colored with Crystal Violet to check the monolayer conditions. The concentration of the testing compounds with non-retraction effect resulting from retraction assay, is added to the upper chamber with and without Human serum albumin (3.5%). ProHance® is added at the same conditions and concentration. Permeabilized monolayers are obtained with 4 hours of incubation with EGTA, 5 mM, before performing the assay.

After 15 and 30 minutes of incubation, the medium is removed from the lower and upper compartment (at least 4 transwells for each time) and the Gadolinium content will be determined by Inductively Coupled Plasma-Atomic Emission Spectrometry (ICP-AES) analysis.

Data Analysis

Data are expressed as mean±standard deviation of the optical density values of each group. The parameters are compared using a parametric test (Dunnett's Test).

Figure 7:
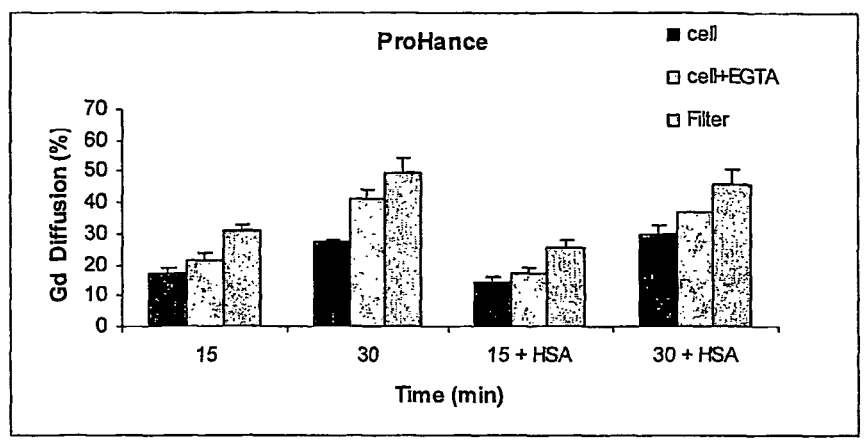
FIG. 7: Permeability assay: trans-endothelial passage of Gd-2b (1.25 mM), in comparison to ProHance®, on H5V monolayer assayed by ICP-AES (see example 36).
Figure 7:
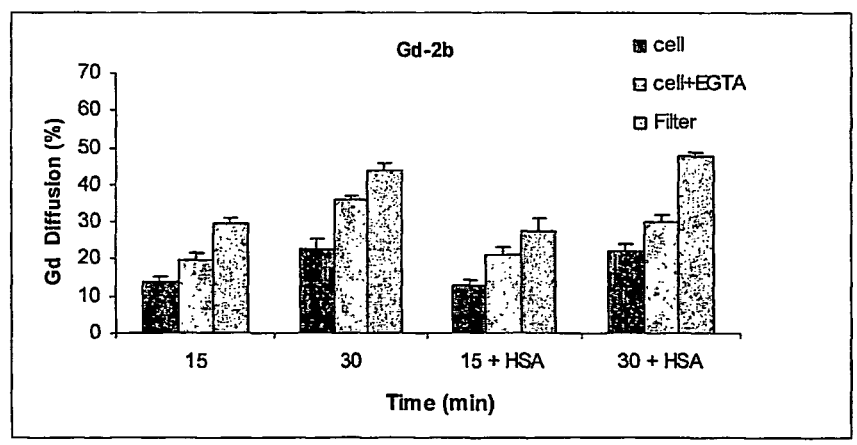

By operating as above described, a representative compound of the invention (Gd-2b) was tested to assess permeability. Collected data, as reported in FIG. 7, clearly indicate that G2-2b is endowed with extravasation properties comparable to that of ProHance®, a well known (NSA) gadolinium based paramagnetic contrast agent.

Example 37

Characterization of an Orthotopic Rat Model of Glioma Induced by C6 Cells

Magnetic resonance imaging (MRI) was used to evaluate the interest of the novel contrast agents of the invention to characterize brain tumor and to evaluate their extravasation.

The aim of this study was to develop a rat model of glioma in order to assess the efficiency of the compounds of the invention over contrast agents commonly used in central nervous system disease (MultiHance and ProHance), by using in vivo MRI. For this purpose, the tumor growth was evaluated for different number of C6 cells placed in brain of the rats.

In the group of animals inoculated with $10^6$ C6 cells, tumor size and composition at 2 weeks were more homogeneous than in the other groups. No significant difference was observed between contrast agents (CA) in the signal enhancement of the brain tumor.

This study suggests that 2 weeks after inoculation in rat of $10^6$ C6 cells in rat were the appropriate conditions in order to obtain a brain tumor at early stage of development suitable for the evaluation of new CA.

Introduction

Contrast agents are routinely used in magnetic resonance imaging (MRI) to evaluate the integrity of the cerebro-vascular system and to characterize brain lesions (Fonchy E. et al., J. of Magnetic Resonance Imaging, 2001, 14, 97-105.1). MRI is one of the most useful method for the diagnosis of brain tumor because of its ability to reveal tissue characteristics.

The aim of this study was to develop a model of glioma induced by inoculation of C6 cells in rat brain. This experimental brain tumor was monitored in vivo by MRI for both tumor growth and permeability by dynamic signal enhancement with different contrast agents (CA).

For this purpose, contrast agents with a high relaxivity were compared with standard compounds (ProHance and MultiHance) by in vivo MRI on C6 glioma rat model at early stage of tumor development (Zhang T. et al., AJNR, 2002, 23, 15-18.2).

Materials

Test Article: compounds of the invention; 0.25M aqueous solution;

Control Article: MultiHance®; ProHance® 0.5 M; both stored at room temperature.

Chemicals: Penicillin/Streptomycin (10000 mg/mL), Storage: <−20° C.; L-Glutamine (200 mM), Storage: <−20° C.; Fetal bovine serum (FBS), Storage: −20° C.; Horse serum (HS), Storage: −20° C.; Ham's F12K medium, Storage: +4° C.; Dulbecco's Phosphate Buffered Saline (PBS), Storage: room temperature.

Test System

The rat has been chosen as test system since it is a suitable model for this kind of study.

Animals: Species and strain: Wistar rat Crl(WI) BR and Fischer rat CrlBR; 38 Wistar and 12 Fischer males; Weight and age at arrival: between 106 and 151 g, 4-5 week. Supplier: Charles River Laboratories Italia S.p.A., Calco (LC), Italy.

Animal husbandry: Food: 4RF21-GLP TOP CERTIFICATE in pellets supplied by Mucedola, Settimo Milanese (MI), Italy, certified as being without estrogenic activity and with contaminant levels within the limits proposed by the Toxic Substances Control Act in the Federal Register part IV of Jul. 26, 1979. Food was available "ad libitum" until the day preceding the experiment. Water: tap water from the Milan municipal water supply, filtered through 1.0 and 0.2 μm filters. Water was available "ad libitum". Bedding material: Sano-Chip®, supplied by Charles River, certified as being without contaminant in toxic concentrations. Housing: during the quarantine period the animals were housed (up to 3 animal/cage) in Makrolon® cages (Tecniplast Gazzada, Italy). Environmental conditions: during the entire period of the study the animals were maintained in conditioned and limited access environments. The parameters were set as follows: mean relative humidity (min-max values): 55.0% (45-65%); mean temperature (min-max values): 21.0° C. (18-24° C.); Air change: 15 to 20 h−1. Lighting: controlled by automatic clock to give a daily 12 h. photoperiod.

The temperature and relative humidity data were monitored every 30 seconds and recorded every 5 minutes by a computerised data base; a daily mean value was calculated.

All the procedures involving the animals were conducted according to the national and international laws on experimental animal. No validated non-animal alternatives are known to meet the objectives of the study.

Method

Experimental Design

Cell preparation for intra-cerebral injection: C6 cells were washed two times with PBS, resuspended in 10 μL of PBS at three different concentrations ($1.10^4$; $1.10^5$; $1.10^6$) and inoculated in three groups of animals with an Hamilton syringe.

Cell preparation for subcutaneous injection: C6 cells were washed two times with saline and re-suspended in 200 μL of PBS at the following concentration: $1.10^6$, $1.5 \times 10^6$ and $1.10 \times 10^6$.

Intra-cerebral tumor inoculation: After the rat has been anesthetized, the head was shaved, disinfected and the skin incised to expose the skull. The animal was placed in a rat stereotaxic tool and the head fixed in the two ears\canals and in the upper jaw. A hole is drilled in the skull and glioma cells were injected into the right Striatum with a Hamilton syringe according to the following coordinates: 0.8 mm anterior, 3.2 mm lateral to Bregma and 4 mm ventral to bone. After cells injection, animals were monitored for neurological clinical signs onset.

Subcutaneous tumor inoculation: Cell suspension at different concentrations were subcutaneously injected in 12 Fisher and 12 Wistar male rats (4 animals per group, age ranging from 4-5 weeks).

All animals were examined for the development of tumor mass every 3-5 days starting from day 3. The tumor mass was measured by a calliper and the tumor volume was calculated as: tumor volume=(Dxd2)/2, where D=maximum diameter, d=minimum diameter.

MRI Procedure

Starting from day 7 to day 10 after C6 injection, rats were anaesthetized by intramuscular injection of a solution of tiletamine/zolazepam (Zoletil)® at a dose of 0.2 mL/kg and Xilazine (Rompun)® at a dose of 0.25 mL/kg.

The compounds of the invention and the contrast agents of reference (ProHance and Multihance) were administered intravenously at a dose of 0.1 mmol/kg (0.05 mmol/kg for B22956/1) as a single injection.

MRI acquisitions were performed in the following way:

Scout images were obtained using a T1 weighted Gradient Echo (GE) sequence for anatomical localization.

High resolution T2 weighted Fast Spin Echo (FSE) (TR/TE/TEeff=2300/30/60 ms, 4 echoes, 4 averages, pixel=281 μm, slice thickness=1.5 mm) was used in the three directions to localize and characterize the tumor, in particular necrotic areas.

High resolution axial T1 weighted Spin Echo (SE) images (TR/TE=380/13 ms, 4 averages, pixel=281 μm, slice thickness=1.5 mm) were acquired in pre and post contrast.

Successive T1 SE post contrast images were acquired every ±3 minutes up to 40 minutes after the injection. A tube of aqueous solution of $NiCl_2\text{-}6H_2O$ at 3.75 mM, placed at the level of the animal head, was used as a standard reference for signal normalization.

At the end of the experiment, animals were sacrificed by intramuscular injection of tiletamine/zolazepam (Zoletil)® 0.2 mL/kg plus Xilazine (Rompun)® 0.25 mL/kg and visual verification was done for the development of possible macroscopic brain metastases. Images were analyzed by using the SMIS scanner software. The signal enhancement was calculated from signal measurements in regions of interest (ROI) covering the whole brain tumor and of the normal brain area.

Data Analysis

Signal intensity enhancement (Enh %) was determined as:
Enh %=100*(SI post–SI pre)/SI pre
where SI pre or SI post are the mean signal intensity of the lesion measured before or after contrast agent.

Results

Intra-cerebral Tumor Characterization

In the first experiments, the tumor growth was observed by in vivo MRI in three groups of animals inoculated from 10 000 to 1 000 000 C6 cells. At 2 weeks after inoculation, no lesion was detectable in the group of $10^4$ cells whereas in the group of $10^5$ and $10^6$ the lesions were significant as shown in the FIGS. 1 and 2. For the $10^4$ cells group, the lesion increased slowly and reached a significant volume size at 4 weeks after inoculation but with a high variability between animals. An important increase in tumor volume was observed in the animals with $10^5$ and $10^6$ cells. However, in the group of $10^6$ cells, the tumor size and composition were more homogeneous than in the other groups at 2 weeks.

Subcutaneous Tumor Characterization

The implant of C6 cells in Wistar male rats resulted in the development of tumors in 100% of animals starting from day 6, but tumor presence and its volume rapidly decreased starting from day 17° after implant up to a total rejection (day). All animals were followed up to 50 days post cell inoculation without signs of tumor reappearance.

The implant of C6 cells in Fisher male rats resulted in the development of tumors in 100% of animals starting from day 3 for $10 \times 10^6$ cells and from day 5-8 for 5 and $1 \times 10^6$ cells. However, tumor presence and its volume rapidly decreased starting from day 15° after implant up to a total rejection (day 28). All animals were followed up to 35 days post cell inoculation without signs of tumor reappearance.

Contrast Enhancement

In the rats inoculated with $10^5$ and $10^6$ C6 cells, a signal enhancement of the brain tumor was observed at 2 weeks with CA; the maximum signal enhancement of the brain tumor seems to increase with tumor volume. Moreover, for big tumor, the signal enhancement appears homogeneous. No differences were found between the contrast agents tested. From these first results, the following experiments were performed on rats inoculated with $10^6$ C6 cells, and 2 weeks after, they were analyzed by in vivo MRI with the different CA.

On the T2 weighted pre contrast images, a dark area in the tumor was observed in some animals (8/15), that may correspond to a necrotic core. In these animals, with any kind of CA, the signal enhancement was not different to the other rats.

Overall the animals, no significant difference was observed between CA in the signal enhancement of the brain tumor. No enhancement was observed in normal brain tissues and also in the sham animals.

CONCLUSIONS

The orthotopical injection in the rat striatum of $1.10^6$ glioma cell resulted in a brain tumor in the 80% of animals starting from 2 weeks post cell inoculation.

In this study the optimum experimental condition were founding order to obtain a brain tumor model suitable for in vivo MRI study:
 small tumor size at early stage of development;
 detectable by in vivo MRI;
 obtained within a reasonable time (2 weeks after inoculation);
 homogeneity in tumor size and composition between animals.

In conclusion this is a useful model for the MRI imaging of the brain tumor and to evaluate the extravascular distribution of the contrast agent.

Moreover, the subcutaneous C6 injection both in an inbred and outbred rat strain did not result in a stable model of tumor. In fact, tumors developed in 100% of animals but their presence and volume rapidly decreased starting up to a total rejection. For this reasons, the eterothopical C6 implant is not suitable for imaging studies.

Throughout the foregoing description of the invention, various patents, articles, and other publications have been cited or referenced. The entire contents of each patent, article and other publication is hereby incorporated by reference into the subject application.

The invention claimed is:

1. A compound of formula (III)

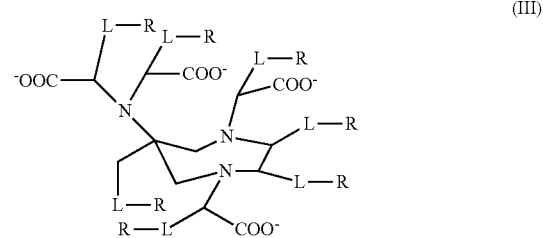

(III)

wherein:

R is, independently, H or a $C_2$-$C_{70}$ aminopolyol moiety comprising a straight or branched alkyl chain substituted by from 2 to 30 hydroxyl groups, said chain being optionally interrupted by one or more groups selected from —O—, —NH—, —N<, —CO—, —CONH—, —NHCO—, —CON< or >NCO—; and optionally substituted by one or more $C_4$-$C_{10}$ cyclic units;

L is, independently, a direct bond or a divalent straight or branched linker moiety between R and the rest of the molecule, comprising at most 20 carbon atoms;

together with the corresponding protonated forms of the carboxy (—COOH) groups; or a physiologically acceptable salt of such ligand;

with the proviso that at least one of the R groups is other than H.

2. A compound according to claim 1 of formula

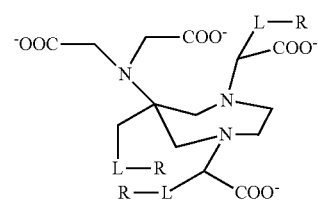

wherein R and L are as defined in claim 1, together with the corresponding protonated forms of the carboxy (—COOH) groups.

3. A compound according to claim 2

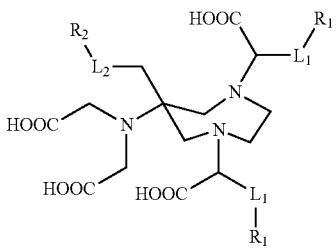

wherein:
1a) $L_1$ is a direct bond, $L_2$ is —$CH_2CO$—, $R_1$ is H, and $R_2$ is group A2;
2a) $L_1$ is a direct bond, $L_2$ is —$CH_2CO$—, $R_1$ is H, and $R_2$ is group B1;
3a) $L_1$ is a direct bond, $L_2$ is —$CH_2CO$—, $R_1$ is H, and $R_2$ is group B2;
4a) $L_1$ is —$CH_2CH_2CO$—, $L_2$ is a direct bond, $R_1$ is group B1, and $R_2$ is H;
5a) $L_1$ is —$CH_2CH_2CO$—, $L_2$ is a direct bond, $R_1$ is group B2, and $R_2$ is H;
6a) $L_1$ is —$CH_2CH_2CO$—, $L_2$ is a direct bond, $R_1$ is group G3, and $R_2$ is H;
7a) $L_1$ is —$CH_2CH_2CO$—, $L_2$ is —$CH_2CO$—, $R_1$ is group B1, and $R_2$ is group B1;
8a) $L_1$ is —$CH_2CH_2CO$—, $L_2$ is —$CH_2CO$—, $R_1$ is group G3, and $R_2$ is group G3;
9a) $L_1$ is —$CH_2CO$—, $L_2$ is a direct bond, $R_1$ is group B1, and $R_2$ is H;
10a) $L_1$ is —$CH_2CO$—, $L_2$ is a direct bond, $R_1$ is group B2, and $R_2$ is H;
11a) $L_1$ is —$CH_2CH_2CO$—, $L_2$ is —$CH_2CO$—, $R_1$ is group B2, and $R_2$ is group B2;
12a) $L_1$ is a direct bond, $L_2$ is —$CH_2CO$—, $R_1$ is H, and $R_2$ is group C1;
13a) $L_1$ is —$CH_2CH_2CO$—, $L_2$ is a direct bond, $R_1$ is group B2, and $R_2$ is H;
14a) $L_1$ is a direct bond, $L_2$ is —$CH_2CO$—, $R_1$ is H, and $R_2$ is group G7;
15a) $L_1$ is —$CH_2CH_2CO$—, $L_2$ is a direct bond, $R_1$ is group C1, and $R_2$ is H;
and wherein any group A, B, C, G is as defined in claim 10; and the physiologically acceptable salts thereof.

4. A compound according to any one of claims 1 or 2 wherein L represents a direct bond or a linker comprising at most 15 carbon atoms.

5. A compound according to claim 4 wherein L represents a direct bond or a linker of formula

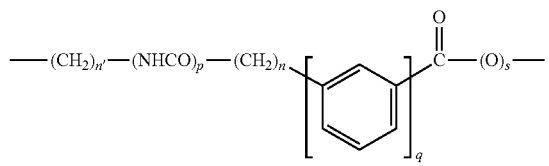

wherein
n and n' are, independently, 0 or an integer from 1 to 4,
p, q and s are, independently, 0 or 1.

6. A compound according to claim 5 wherein L represents a direct bond or a linker of formula

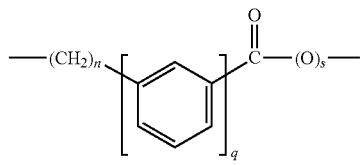

wherein n, q and s are as defined in claim 5.

7. A compound according to any one of claims 1 or 2 wherein, within the meanings for R, any $C_4$-$C_{10}$ cyclic unit is, independently, a carbocyclic or heterocyclic ring optionally substituted by one or more groups selected from hydroxy, hydroxymethyl and amino.

8. A compound according to claim 7 wherein the carbocyclic or heterocyclic ring is selected from

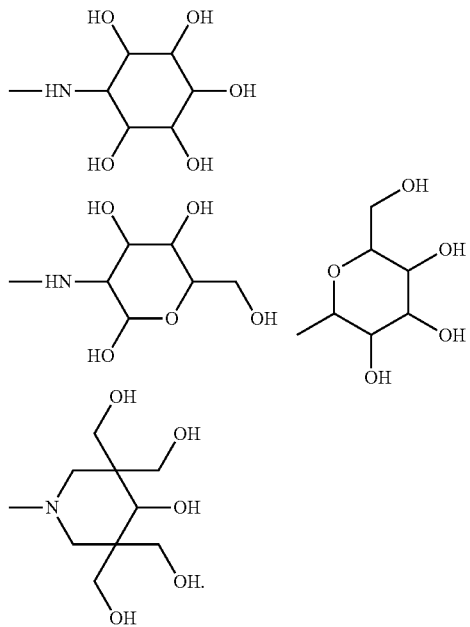

9. A compound according to any one of claims 1 or 2 wherein each R is, independently, H or is selected from:
—NH—$(CH_2)_{0-2}$—C[$(CH_2)_{1-2}$—O-Q]$_3$;
—NH—$(CH_2)_{1-2}$—CON[$(CH_2)_{1-3}$—CONH—C[$(CH_2)_{1-2}$—O-Q]$_3$]$_2$;
—N[$(CH_2)_{1-4}$—NHCO—$(CHOH)_4$—$CH_2OH$]$_2$;
—NH—$(CH_2)_{0-2}$—C[$(CH_2)_{1-4}$—NHCO—$(CHOH)_4$—$CH_2OH$]$_3$;
—N[$(CH_2)_{1-4}$—N[$(CH_2)_{1-4}$—$COY$]$_2$]$_2$;
—NH—C[$(CH_2)_{1-4}$—$COY$]$_3$;
—NH—C[$(CH_2)_{1-2}$—O—$(CH_2)_{1-3}$—$COY$]$_3$;
—NH—CH($COY$)[$(CH_2)_{1-2}$—$COY$];
—NH—$(CH_2)_{1-2}$—CH[$(CH_2)_{1-2}$—O—$(CH_2)_{0-2}$—C($R_1$)($CH_2OH$)$_2$]$_2$;
—NH—$(CH_2)_{1-2}$—CH[$(CH_2)_{1-2}$—O—$(CH_2)_{1-2}$—CH[$(CH_2)_{1-2}$—O—cont.     —$(CH_2)_{0-2}$—C($R_1$)($CH_2OH$)$_2$]$_2$]$_2$;
—NH—$(CH_2)_{1-2}$—CH[$(CH_2)_{1-2}$—O—$(CH_2)_{1-2}$—CH[$(CH_2)_{1-2}$—O—cont.     —$(CH_2)_{1-2}$—CH[$(CH_2)_{1-2}$—O—$(CH_2)_{0-2}$—C($R_1$)($CH_2OH$)$_2$]$_2$]$_2$]$_2$;

wherein
Q is a group of formula
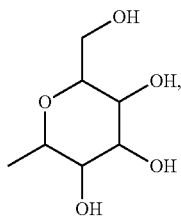
$R_1$ is H or methyl; and
Y is selected, independently, from
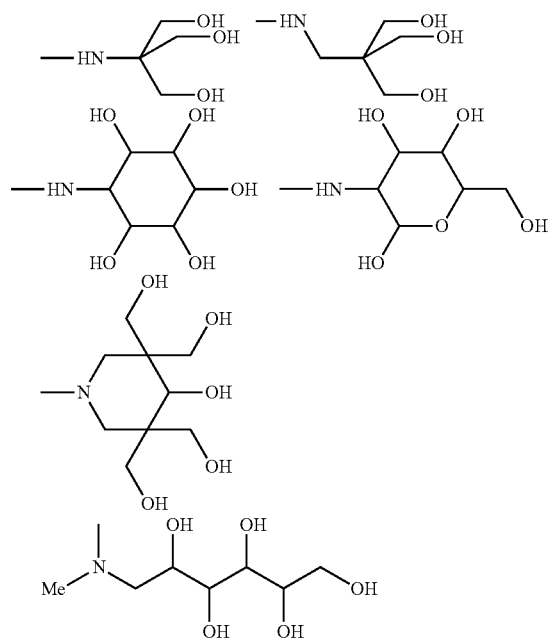
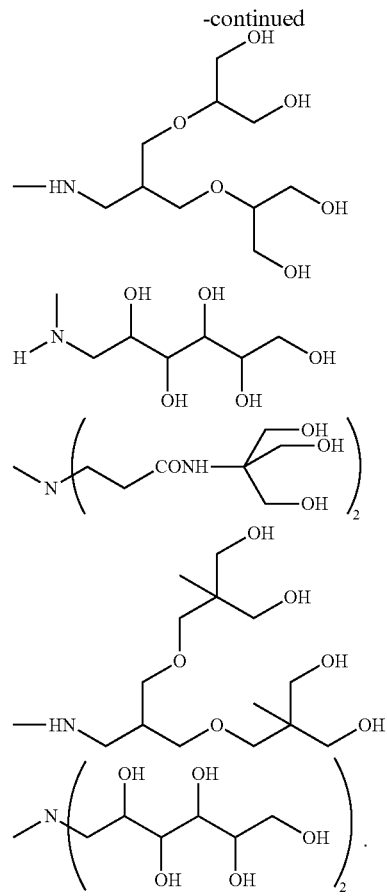
10. A compound according to claim 9 wherein each R, independently, is H or is selected from the group of formula: A1 to A2, B1 to B3, G1 to G11, C1 to C11, D1 to D11, E1 to E11 and F1 to F11
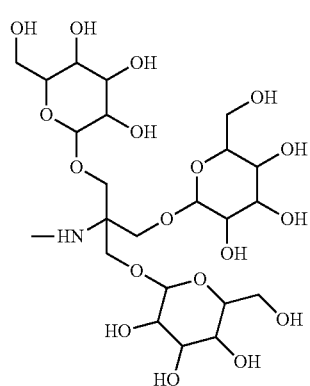
A1
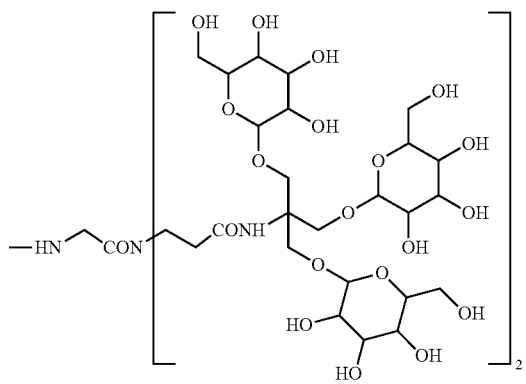
A2
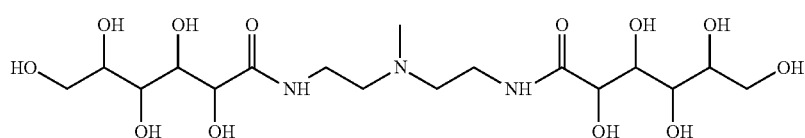
B1

173 174
-continued
B2 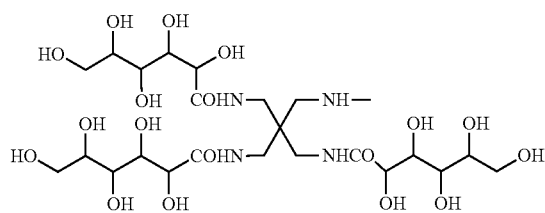 B3 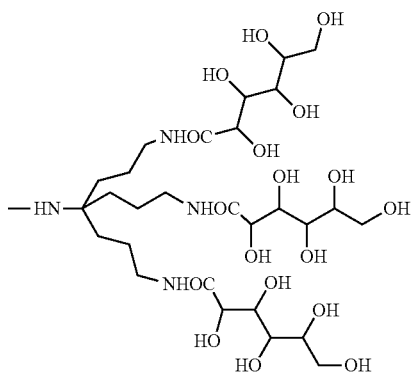
G1 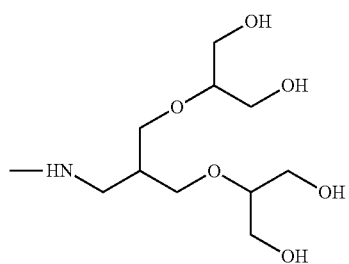 G2 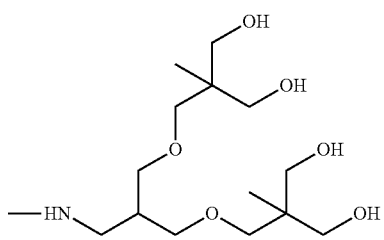
G3 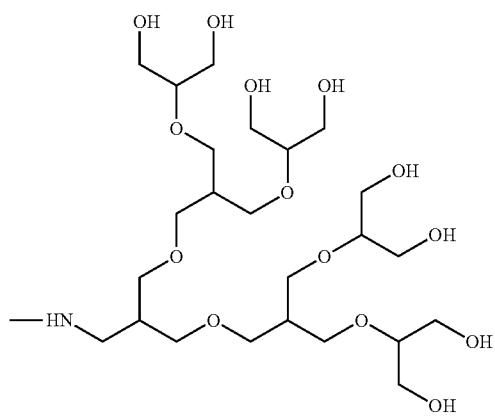 G4 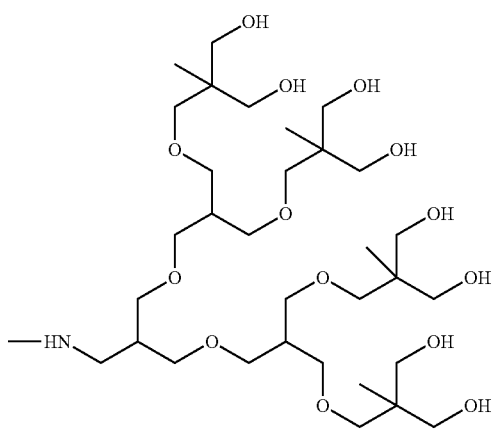
G5 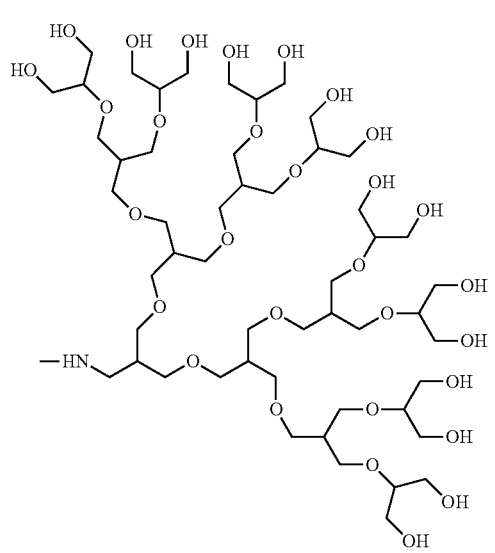 G6 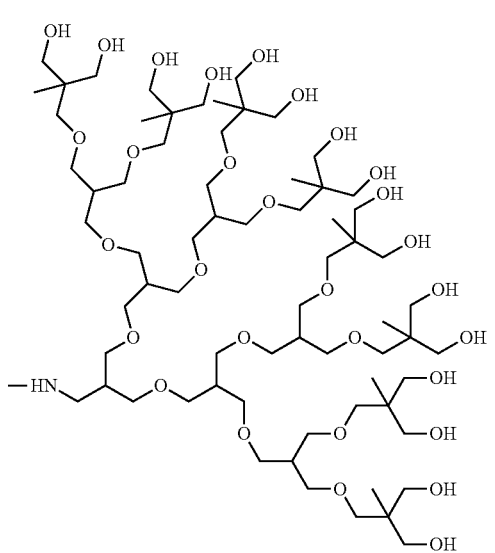

-continued
G7
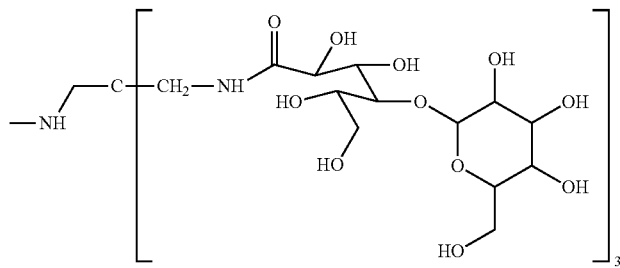
G8
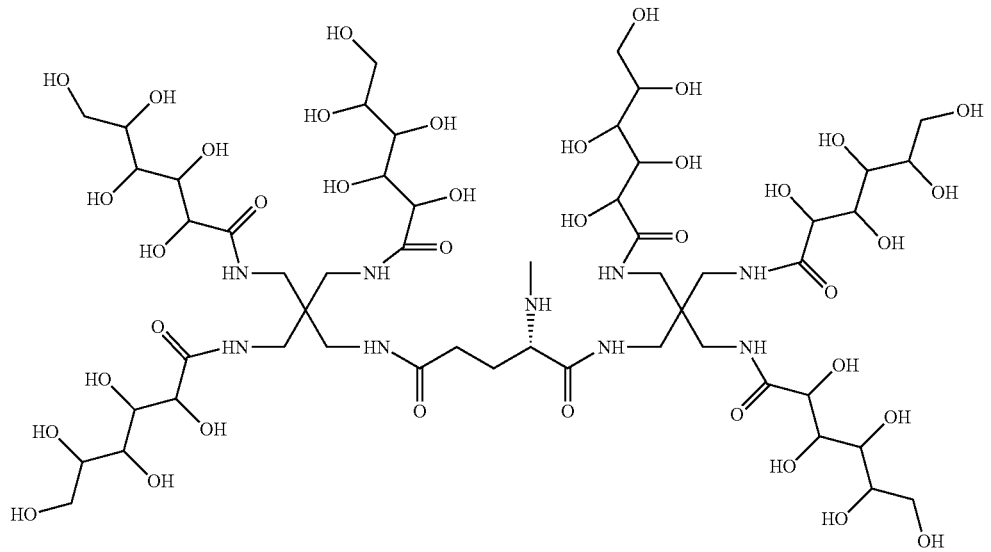
G9
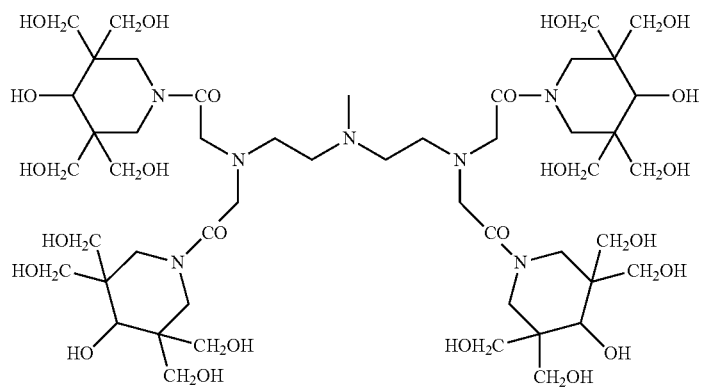
G10
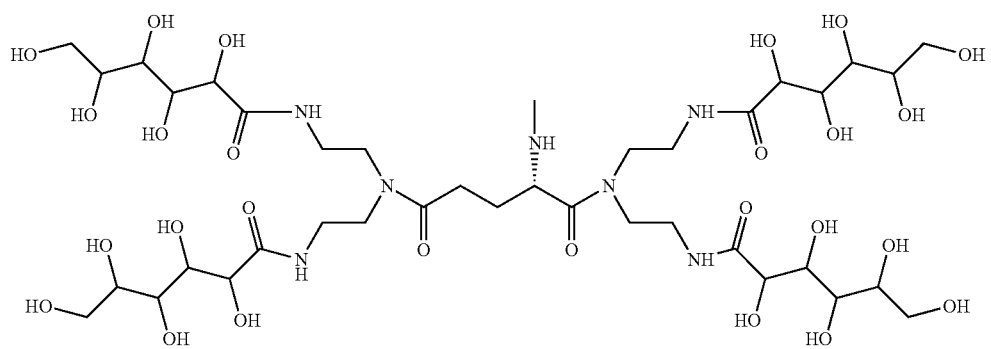

G11
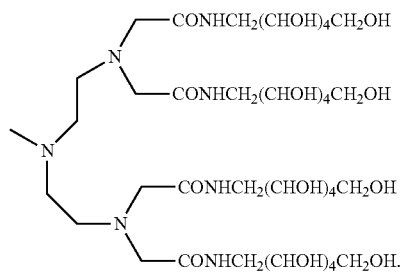
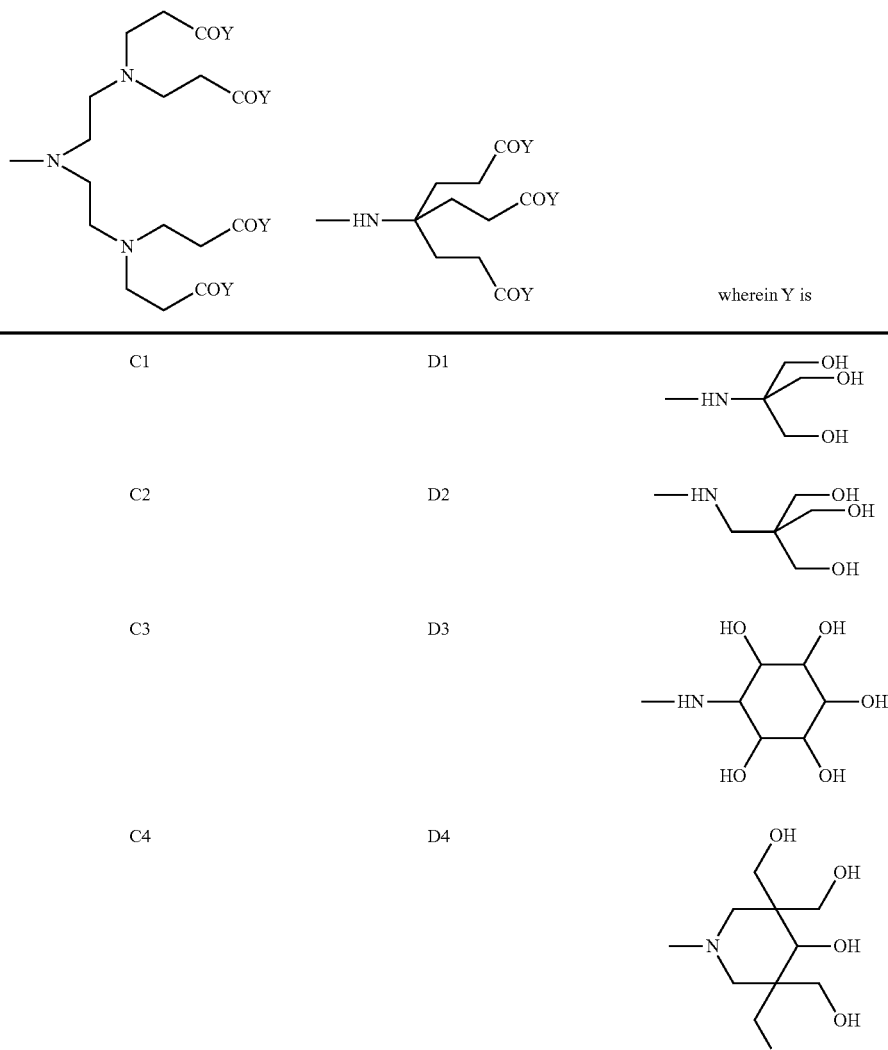
wherein Y is
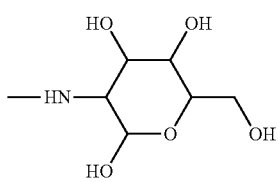

-continued
| | | |
|---|---|---|
| C6 | D6 | 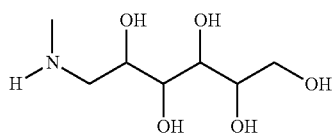 |
| C7 | D7 | 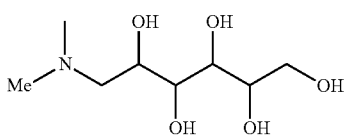 |
| C8 | D8 | 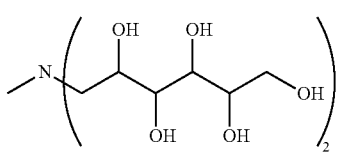 |
| C9 | D9 | 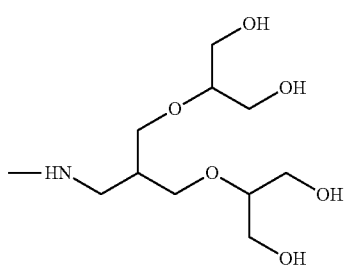 [SMILES: CNCC(COC(CO)CO)COC(CO)CO] |
| C10 | D10 | 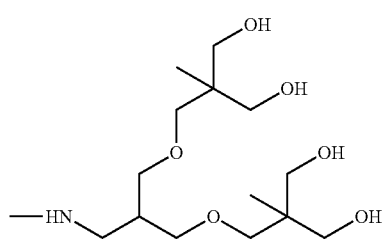 [SMILES: CNCC(COCC(C)(CO)CO)COCC(C)(CO)CO] |
| C11 | D11 | 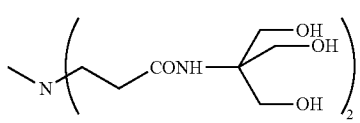 |
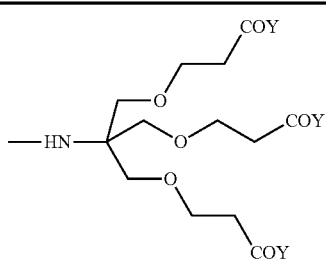 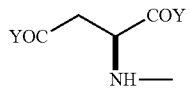 wherein Y is
| | | |
|---|---|---|
| E1 | F1 | 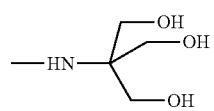 |
| E2 | F2 | 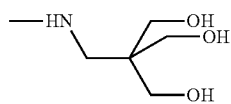 |

| | | |
|---|---|---|
| E3 | F3 | 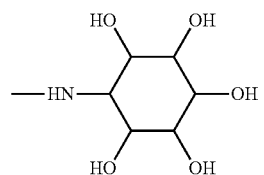 |
| E4 | F4 | 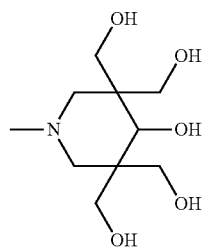 [SMILES: CN1CC(CO)(CO)C(O)C(CO)(CO)C1] |
| E5 | F5 | 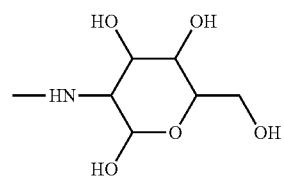 |
| E6 | F6 | 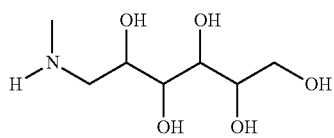 |
| E7 | F7 | 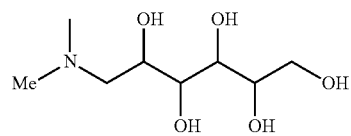 |
| E8 | F8 | 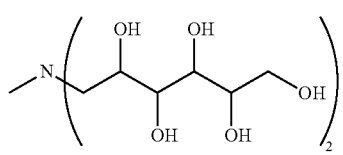 |
| E9 | F9 | 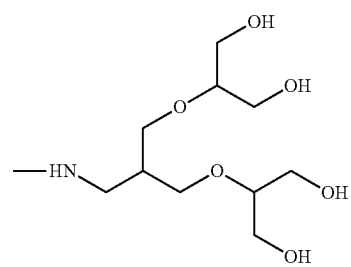 [SMILES: CNCC(COC(CO)CO)COC(CO)CO] |
| E10 | F10 | 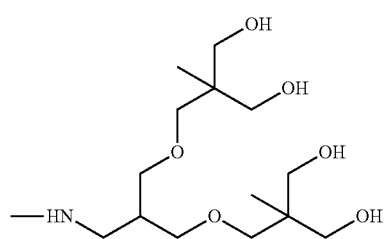 [SMILES: CNCC(COCC(C)(CO)CO)COCC(C)(CO)CO] |

| E11 | F11 |
|---|---|
| | 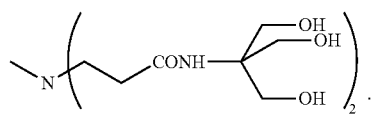 |

11. A compound according to any one of claims 1 or 2 and any physiologically acceptable salt thereof, as a chelated complex with a bivalent or trivalent paramagnetic metal ion selected from $Fe^{2+}$, $Fe^{3+}$, $Cu^{2+}$, $Cr^{3+}$, $Eu^{3+}$, $Dy^{3+}$, $La^{3+}$, $Yb^{3+}$, $Mn^{2+}$, $Mn^{3+}$ and $Gd^{3+}$.

12. A compound according to claim 11 wherein the paramagnetic metal ion is $Gd^{3+}$.

13. A chelated complex of a compound according to claim 11, for diagnostic use.

14. A pharmaceutical composition for diagnostic use comprising an effective amount of a chelated complex of a compound according to claim 11, together with optional carriers, diluents and excipients.

15. A pharmaceutical composition according to claim 14 comprising a Gd chelated complex of a compound of formula (III).

16. A method of imaging a human or animal body organ or tissue by use of MRI, said method comprising administering a pharmaceutical composition of claim 14 to the human or animal body, and imaging said human or animal body by use of MRI.

17. A compound according to any one of claims 1 or 2, wherein the physiologically acceptable salt is an acid or basic addition salt selected from: alkali or alkaline-earth metals such as potassium, sodium, calcium or magnesium; organic bases such as ethanolamine, diethanolamine, morpholine, glucamine, N-methylglucamine, and N,N-dimethylglucamine; anions of inorganic or organic acids such as chloride, bromide, iodide, sulfate, acetate, succinate, citrate, fumarate, maleate, oxalate; and cations and anions of amino acids such as taurine, glycine, lysine, arginine, ornithine or of aspartic and glutamic acid.

* * * * *